United States Patent
Tuna et al.

(10) Patent No.: US 11,548,948 B2
(45) Date of Patent: Jan. 10, 2023

(54) FC BINDING FRAGMENTS COMPRISING A PD-L1 ANTIGEN-BINDING SITE

(71) Applicant: F-STAR BETA LIMITED, Cambridge (GB)

(72) Inventors: Mihriban Tuna, Cambridge (GB); Francisca Wollerton Van Horck, Cambridge (GB); Ryan Fiehler, Cambridge (GB); Mustapha Faroudi, Cambridge (GB); Frederick Akele, Cambridge (GB); Fadi Badr, Cambridge (GB); Cyril Privezentzev, Cambridge (GB)

(73) Assignee: F-star Therapeutics Limited, Cambridge (GB)

( * ) Notice: Subject to any disclaimer, the term of this patent is extended or adjusted under 35 U.S.C. 154(b) by 80 days.

(21) Appl. No.: 16/955,450

(22) PCT Filed: Dec. 19, 2018

(86) PCT No.: PCT/EP2018/085834
§ 371 (c)(1),
(2) Date: Jun. 18, 2020

(87) PCT Pub. No.: WO2019/121906
PCT Pub. Date: Jun. 27, 2019

(65) Prior Publication Data
US 2021/0139590 A1    May 13, 2021

Related U.S. Application Data

(60) Provisional application No. 62/657,195, filed on Apr. 13, 2018, provisional application No. 62/607,686, filed on Dec. 19, 2017.

(51) Int. Cl.
*C07K 16/28* (2006.01)
*A61K 39/395* (2006.01)

(52) U.S. Cl.
CPC .... *C07K 16/2827* (2013.01); *C07K 2317/524* (2013.01); *C07K 2317/526* (2013.01); *C07K 2317/53* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,909,459 A | 9/1975 | Friese et al. |
| 3,967,230 A | 6/1976 | Kamigaito et al. |
| 4,004,183 A | 1/1977 | Oki et al. |
| 6,380,664 B1 | 4/2002 | Pollner |
| 7,592,426 B2 | 9/2009 | Ebel et al. |
| 8,911,732 B2 | 12/2014 | Dennis et al. |
| 9,567,399 B1 | 2/2017 | Campbell et al. |
| 9,617,338 B1 | 4/2017 | Campbell et al. |
| 10,090,646 B2 | 10/2018 | Takaoka et al. |
| 10,205,305 B2 | 2/2019 | Uegaki et al. |
| 10,233,258 B2 | 3/2019 | Akamatsu et al. |
| 11,214,618 B2 | 1/2022 | Tuna et al. |
| 11,214,620 B2 | 1/2022 | Campbell et al. |
| 2003/0030355 A1 | 2/2003 | Honda |
| 2009/0055944 A1 | 2/2009 | Korman et al. |
| 2012/0276104 A1 | 11/2012 | Woisetschlager |
| 2014/0004121 A1 | 1/2014 | Fanslow, III et al. |
| 2015/0214697 A1 | 7/2015 | Yoshida et al. |
| 2015/0259420 A1 | 9/2015 | Triebel et al. |
| 2016/0043531 A1 | 2/2016 | Firstenberg et al. |
| 2016/0244528 A1 | 8/2016 | Gray et al. |
| 2018/0175592 A1 | 6/2018 | Uegaki et al. |
| 2018/0339031 A1 | 11/2018 | Masternak et al. |
| 2019/0106494 A1 | 4/2019 | Wang et al. |
| 2019/0202920 A1 | 7/2019 | Tuna et al. |
| 2019/0256602 A1 | 8/2019 | Campbell et al. |
| 2019/0330344 A1 | 10/2019 | Tuna et al. |
| 2019/0338049 A1 | 11/2019 | Tuna et al. |
| 2020/0407446 A1* | 12/2020 | Mccourt ................ A61P 35/00 |
| 2021/0238299 A1 | 8/2021 | Pechouckova et al. |
| 2021/0277134 A1 | 9/2021 | Lakins et al. |

(Continued)

FOREIGN PATENT DOCUMENTS

| | | |
|---|---|---|
| EP | 2407487 A1 | 1/2012 |
| EP | 2546268 A1 | 1/2013 |

(Continued)

OTHER PUBLICATIONS

[No Author Listed] F-star Alpha: A new asset centric company. Retrieved from http://www.onenucleus.com/media/Events/LSLS/11%20feb%202014/Jane%20Dancer.pdf on Jan. 8, 2015. 15 pages.

(Continued)

*Primary Examiner* — Ilia I Ouspenski
(74) *Attorney, Agent, or Firm* — Wolf, Greenfield & Sacks, P.C.

(57) ABSTRACT

The application relates to specific binding members which bind to programmed death-ligand (PD-L1). The specific binding members preferably comprise a PD-L1 antigen-binding site located in structural loops of a constant domain of the specific binding member. The specific binding members find application, for example, in the treatment of cancer, as well as infectious diseases, inflammation, diseases and conditions associated with inflammation, and inflammatory diseases.

21 Claims, 16 Drawing Sheets
Specification includes a Sequence Listing.

(56) References Cited

U.S. PATENT DOCUMENTS

| | | |
|---|---|---|
| 2021/0301022 A1 | 9/2021 | Wollerton et al. |
| 2021/0309753 A1 | 10/2021 | Tuna et al. |
| 2021/0355228 A1 | 11/2021 | Lakins et al. |
| 2022/0048996 A1 | 2/2022 | Tuna et al. |
| 2022/0049007 A1 | 2/2022 | Lakins et al. |
| 2022/0185890 A1 | 6/2022 | Tuna et al. |
| 2022/0185894 A1 | 6/2022 | Campbell et al. |

FOREIGN PATENT DOCUMENTS

| | | |
|---|---|---|
| EP | 2905030 A1 | 8/2015 |
| JP | S51-046628 A | 4/1976 |
| JP | 2003-022886 A | 1/2003 |
| JP | 2012-500006 A | 1/2012 |
| JP | 2017-010741 A | 1/2017 |
| WO | WO 2006/072620 A1 | 7/2006 |
| WO | WO 2009/000006 A1 | 12/2008 |
| WO | WO 2009/068204 A1 | 6/2009 |
| WO | WO 2009/132876 A1 | 11/2009 |
| WO | WO 2010/019570 A2 | 2/2010 |
| WO | WO 2010/111282 A1 | 9/2010 |
| WO | WO 2014/004549 A2 | 1/2014 |
| WO | WO 2014/008218 A1 | 1/2014 |
| WO | WO 2014/140180 A1 | 9/2014 |
| WO | WO 2015/048312 A1 | 4/2015 |
| WO | WO 2015/138920 A1 | 9/2015 |
| WO | WO 2015/198312 A1 | 12/2015 |
| WO | WO 2015/200119 A1 | 12/2015 |
| WO | WO 2016/028672 A1 | 2/2016 |
| WO | WO 2016/177802 A1 | 11/2016 |
| WO | WO 2016/185016 A1 | 11/2016 |
| WO | WO 2016/200782 A1 | 12/2016 |
| WO | WO 2017/009456 A1 | 1/2017 |
| WO | WO 2017/015560 A2 | 1/2017 |
| WO | WO 2017/025498 A1 | 2/2017 |
| WO | WO 2017/052241 A1 | 3/2017 |
| WO | WO 2017/062888 A1 | 4/2017 |
| WO | WO 2017/077085 A2 | 5/2017 |
| WO | WO 2017/087589 A2 | 5/2017 |
| WO | WO 2017/087901 A2 | 5/2017 |
| WO | WO 2017/123650 A2 | 7/2017 |
| WO | WO 2017/182672 A1 | 10/2017 |
| WO | WO 2017/205738 A1 | 11/2017 |
| WO | WO 2017/220569 A1 | 12/2017 |
| WO | WO 2018/017673 A1 | 1/2018 |
| WO | WO 2017/220990 A9 | 3/2018 |
| WO | WO 2018/056821 A1 | 3/2018 |
| WO | WO 2018/060480 A1 | 4/2018 |
| WO | WO 2018/127610 A1 | 7/2018 |
| WO | WO 2018/222711 A2 | 12/2018 |
| WO | WO 2019/025545 A1 | 2/2019 |

OTHER PUBLICATIONS

Bacac et al., Abstract 1494: CEA TCB: A novel head-to-tail 2:1 T cell bispecific antibody for treatment of CEA-positive solid tumors. Oncoimmunology. Aug. 2016; 5(Abstract): e1203498. Epub Jun. 24, 2016. doi: 10.1080/2162402X.2016.1203498.

Goding et al., Combination of adoptive cell transfer, anti-PD-L1 and anti-LAG-3 antibodies for the treatment of recurrent tumors: better with more. OncoImmunology. Oct. 22, 2013;2(8):e25050-1-e25050-3.

Hasenhindl et al., Creating stable stem regions for loop elongation in Fcabs—insights from combining yeast surface display, in silico loop reconstruction and molecular dynamics simulations. Biochim Biophys Acta. 2014;1844(9):1530-1540. doi:10.1016/j.bbapap.2014.04.020.

Hasenhindl et al., Stability assessment on a library scale: a rapid method for the evaluation of the commutability and insertion of residues in C-terminal loops of the CH3 domains of IgG1-Fc. Protein Eng Des Sel. 2013;26(10):675-682.

Jing et al., Combined immune checkpoint protein blockade and low dose whole body irradiation as immunotherapy for myeloma. Journal of Immunotherapy of Cancer, doi: 10.1186/S40425-014-0043-Z. Jan. 20, 2015. 15 pages.

Kraman et al., A LAG-3/PD-L1 bispecific antibody inhibits tumor growth in two syngeneic colon carcinoma models. Journal of ImmunoTherapy of Cancer. 2016;4(Suppl 1):82(abstract P124).

Kraman et al., A LAG-3/PD-L1 bispecific antibody inhibits tumor growth in two syngeneic colon carcinoma models. Retrieved from http://www.f-star.com/media/73722/A-LAG-3-PD-L1-bispecific-antibody-inhibits-tumour-growth-in-two-syngeneic-colon-carcinoma-models.pdf. Nov. 9-13, 2016. 1 page.

Lundqvist et al., 31st Annual Meeting and Associated Programs of the Society for Immunotherapy of Cancer (SITC 2016): Part One. Journal for Immunotherapy of Cancer. Nov. 16, 2016;4(1):74(abstract P124).

Vilgelm et al., Combinatorial approach to cancer immunotherapy: strength in numbers. Journal of Leukocyte Biology. 2016;100(2):275-90. Epub Jun. 2, 2016.

Wozniak-Knopp et al., et al. Introducing antigen-binding sites in structural loops of immunoglobulin constant domains: Fc fragments with engineered HER2/neu-binding sites and antibody properties. Protein Eng Des Sel. 2010;23(4):289-297. doi:10.1093/protein/gzq005.

Xu et al, In vitro characterization of five humanized OKT3 effector function variant antibodies. Cell Immunol. Feb. 25, 2000;200(1):16-26.

[No Author Listed] Abstract for CHI Immuno-Oncology Summit Europe. Mar. 18-22, 2019. 1 page. PDR303.

[No Author Listed] F-Star Modular Bispecific Antibodies. Summary for ATLAS deck. Presented at JP Morgan. Jan. 2017. 1 page. PDR159.

[No Author Listed] First-in-Class bispecific antibodies for cancer immunotherapy. Presentation at Takeda. Dec. 13, 2016. 24 pages. PDR160.

[No Author Listed], FS118 First in Human Study in Patients With Advanced Malignancies. Sponsored by F-star Therapeutics Limited. Clinical Trial. Retreived from https://clinicaltrials.gov/ct2/show/NCT03440437. Feb. 22, 2018. 7 pages.

[No Author Listed], Pipeline Overview: F-star is developing a pipeline of bispecific antibodies focused on oncology and immuno-oncology. F-Start website update. Sep. 2016. 2 pages. PDR 126.

Ascierto et al., Initial efficacy of anti-lymphocyte activation gene-3 (anti-LAG-3:BMS-986016) in combination with nivolumab (nivo) in pts with melanoma (MEL) previously treated with anti-PD-1/PD-L1 therapy. J Clin Oncology. May 20, 2017;35(15):9520-9520. Abstract only. doi: 10.1200/JCO.2017.35.15_suppl.9520. EPub May 30, 2017.

Asgarov et al., A new anti-mesothelin antibody targets selectively the membrane-associated form. MAbs. Apr. 2017;9(3):567-577. doi: 10.1080/19420862.2017.1288770.

Berg et al., Biochemistry. 5th ed. New York. 2002. Accessible at https://www.ncbi.nlm.nih.gov/books/NBK22358/section5.5. Accessed Jun. 9, 2021. 4 pages.

Bernett et al., Abstract P122: Multiple bispecific checkpoint combinations enhance T cell activity. J Immunother Cancer. 2016;4(Suppl 1):P122. 2 pages.

Bernett et al., Multiple bispecific checkpoint combinations enhance T cell activity. Xencor Poster Presentation. 2016. 1 page.

Bodhankar et al., PD-L1 Monoclonal Antibody Treats Ischemic Stroke by Controlling Central Nervous System Inflammation. Stroke. Oct. 2015;46(10):2926-34. doi: 10.1161/STROKEAHA.115.010592. Epub Aug. 25, 2015.

Borlak et al., Immune-mediated liver injury of the cancer therapeutic antibody catumaxomab targeting EpCAM, CD3 and Fc? receptors. Oncotarget. May 10, 2016;7(19):28059-74. doi: 10.18632/oncotarget.8574.

Brewis, Development of an anti-PD-L1 Fcab. Presentation. Human Antibodies and Hybrodomas Conference. Oct. 22, 2018. PDR 312.

Brewis, Identification of a PD-L1 binding Fcab: a potent inhibitor of immunosuppressive signals. Abstract. Huamn Antibodies and Hybridomas 2018. Jun. 11, 2018. 1 page. PDR282.

(56) References Cited

OTHER PUBLICATIONS

Brewis, The use of bispecific antibodies to modulate anti-tumour immune responses. Oral Presentation at ELRIG—Research and Innovation. Mar. 29, 2017. 33 pages. PDR177.

Brewis, The use of bispecific antibodies to modulate anti-tumour immune responses. Oral Presentation at PEPtalk. Jan. 12, 2017. 26 pages. PDR163.

Burova et al., Abstract 1484: Combined treatment with anti-LAG-3 and anti-PD-1 fully human monoclonal antibodies inhibits tumor growth in immunocompetent double-humanized LAG-3/PD-1 mice. Proceedings: AACR 107th Annual Meeting 2016. Apr. 16-20, 2016. New Orleans, LA. doi: 10.1158/1538-7445.AM2016-1484. Published Jul. 2016. 8 pages.

Burova et al., Abstract P195: A novel anti-human LAG-3 antibody in combination with anti-human PD-1 (REGN2810) shows enhanced anti-tumor activity in PD-1 x LAG-3 dual-humanized mice and favorable pharmacokinetic and safety profiles in cynomolgus monkey. J Immunother Cancer. 2016;4(Suppl 1):P195. 2 pages.

Camisaschi et al., LAG-3 expression defines a subset of CD4(+)CD25(high)Foxp3(+) regulatory T cells that are expanded at tumor sites. J Immunol. Jun. 1, 2010;184(11):6545-51. doi: 10.4049/jimmunol.0903879. Epub Apr. 26, 2010.

Cemerski et al., T cell activation and anti-tumor efficacy of anti-LAG-3 antibodies is independent of LAG-3-MHCII blocking capacity. Poster Presentation. 30th Annual Meeting and Associated Programs of the Society for Immunotherapy of Cancer (SITC 2015). National Harbor, MD. Nov. 4-8, 2015. 1 page.

Chen et al., Molecular mechanisms of T cell co-stimulation and co-inhibition. Nat Rev Immunol. Apr. 2013;13(4):227-42. doi: 10.1038/nri3405. Epub Mar. 8, 2013. Erratum in: Nat Rev Immunol. Jul. 2013;13(7):542.

Chester et al., 4-1BB agonism: adding the accelerator to cancer immunotherapy. Cancer Immunol Immunother. Oct. 2016;65(10):1243-8. doi: 10.1007/s00262-016-1829-2. Epub Mar. 31, 2016.

Chester et al., Dual antibody therapy to harness the innate anti-tumor immune response to enhance antibody targeting of tumors. Curr Opin Immunol. Apr. 2015;33:1-8. doi: 10.1016/j.coi.2014.12.010. Epub Jan. 7, 2015.

Chiu et al., Antibody Structure and Function: The Basis for Engineering Therapeutics. Antibodies (Basel). Dec. 3, 2019;8(4):55. doi: 10.3390/antib8040055.

Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.

Davies, Analytical challenges for next generation biologies. Oral Presentation at Waters Biopharma Mini-Seminar. May 24, 2017. 20 pages. PDR191.

Davies, Bispecific Antibodies: New Opportunities for Novel Therapies. Oral Presentation at Bioprocess UK 2016. Nov. 26, 2016. 14 pages. PDR 135.

Davies, Overcoming the Manufacturing Challenges for Bisepcific mAbs. Oral Presentation at 5th Annual Cell Culture and Bioprocessing Congress. Nov. 6, 2016. 16 pages. PDR142.

Davies, Overcoming the Manufacturing Challenges for Bisepcific mAbs. Oral Presentation at Biopronet 3rd Annual Scientific Symposium. Oct. 20, 2016. 16 pages. PDR136.

Daxini et al., Vasculitis associated with immune checkpoint inhibitors—a systematic review. Clin Rheumatol. Sep. 2018;37(9):2579-2584. doi: 10.1007/s10067-018-4177-0. Epub Jun. 19, 2018.

Demeure et al., T Lymphocytes infiltrating various tumour types express the MHC class II ligand lymphocyte activation gene-3 (LAG-3): role of LAG-3/MHC class II interactions in cellcell contacts. Eur J Cancer. Sep. 2001;37(13):1709-18. doi: 10.1016/s0959-8049(01)00184-8.

Deng et al., LAG-3 confers poor prognosis and its blockade reshapes antitumor response in head and neck squamous cell carcinoma. Oncoimmunology. Oct. 7, 2016;5(11):e1239005. doi: 10.1080/2162402X.2016.1239005.

Doody et al., Abstract B091: a LAG-3/PD-L1 bispecific antibody inhibits tumor growth in two syngeneic colon carcinoma models. Second CRI-CIMT-EATI-AACR International Cancer Immunotherapy Conference: Translating Science into Survival. Sep. 25-28, 2016. New York, NY. doi: 10.1158/23/26-6066.IMM2016-B091. Published Nov. 2016. 8 pages.

Doody, An anti-murine LAG-3/PD-L1 bispecific antibody which modulates T cell activity and inhibits tumour growth. Oral Presentation at 2nd Annual Advances in Immuno-Oncology Congress. May 16, 2017. 17 pages. PDR188.

Doody, In vivo Efficacy of bispecific antibodies targeting two immmune-modulatory receptors. Oral Presentation at PEGS Europe. Nov. 4, 2016. 16 pages. PDR144.

Everett et al., A LAG-3/PD-L1 bispecific antibody inhibits tumour growth in two syngeneic colon carcinoma models. Poster Presentation. AACR Tumor Immunology and Immunotherapy. Oct. 21, 2016. 1 page. PDR137.

Everett et al., Abstract PR06: A LAG-3/PD-L1 bispecific antibody inhibits tumour growth in two syngeneic colon carcinoma models. AACR Special Conference on Tumor Immunology and Immunotherapy. Oct. 20-23, 2016. Boston, MA. Doi: 10.1158/2326-6074.TUMIMM16-PR06. Published Mar. 2017. 8 pages.

Everett, A LAG-3/PD-L1 Bispecific Antibody Inhibits Tumour Growth in Two Syngeneic Colon Carcinoma Models. Oral Presentation at AACR Tumor Immunology and Immunotherapy. Boston, MA. Oct. 20-23, 2016. 5 pages. PDR141.

F-STAR, First-in-Class Bispecific Antibodies for Cance Immunotherapy. Jul. 2016. Presentation. 14 pages. PDR119.

Faroudi et al., Abstract 2399: LAG-3/PD-L1 mAb2 can overcome PD-L1-mediated compensatory upregulation of LAG-3 induced by single-agent checkpoint blockade. Proceedings: AACR Annual Meeting 2019; Mar. 29-Apr. 3, 2019. Atlanta, GA. Doi: 10.1158/1538-7445.AM2019-2399. Published Jul. 2019. 4 pages.

Fiehler, Development of an anti-PD-L1 Fcab. Presentation. European Antibody Congress. Oct. 29, 2018. 26 pages. PDR312.

Foy et al., Poxvirus-Based Active Immunotherapy with PD-1 and LAG-3 Dual Immune Checkpoint Inhibition Overcomes Compensatory Immune Regulation, Yielding Complete Tumor Regression in Mice. PLoS One. Feb. 2, 20164;11(2):e0150084. doi: 10.1371/journal.pone.0150084.

Gandhi et al., Expression of LAG-3 by tumor-infiltrating lymphocytes is coincident with the suppression of latent membrane antigen-specific CD8+ T-cell function in Hodgkin lymphoma patients. Blood. Oct. 1, 2006;108(7):2280-9. doi: 10.1182/blood-2006-04-015164. Epub Jun. 6, 2006.

Gliddon, Pushing all the buttons: innovating in immuno-oncology with mAb. Oral Presentation at Phacilitate Immunotherapy World 2017. Jan. 18, 2017. 11 pages. PDR165.

Grosso et al., Programmed death-ligand 1 (PD-L1) expression in various tumor types. J Immunother Cancer. 2013;1(Suppl 1):P53. http://www.immunotherapyofcancer.org/content/1/S1/P53. 1 page.

Haines et al., Abstract 4714: Blockade of LAG-3 amplifies immune activation signatures and augments curative antitumor responses to anti-PD-1 therapy in immune competent mouse models of cancer. Proceedings: AACR Annual Meeting 2017. Apr. 1-5, 2017. Washington, DC. doi: 10.1158/1538-7445.AM2017-4714. Published Jul. 2017. 8 pages.

Herbst et al., Predictive correlates of response to the anti-PD-L1 antibody MPDL3280A in cancer patients. Nature. Nov. 27, 2014;515(7528):563-7. doi: 10.1038/nature14011. Author Manuscript.

Hid Cadena et al., Checks and Balances in Autoimmune Vasculitis. Front Immunol. Feb. 22, 2018;9:315. doi: 10.3389/fimmu.2018.00315.

Horn et al., CD3xPDL1 bi-specific T cell engager (BiTE) simultaneously activates T cells and NKT cells, kills PDL1+ tumor cells, and extends the survival of tumor-bearing humanized mice. Oncotarget. Aug. 3, 2017;8(35):57964-57980. doi: 10.18632/oncotarget.19865.

Huang et al., Abstract PR03: Combinatorial blockade of PD-1, CTLA-4, and LAG-3 pathways inhibits murine ovarian tumor growth. Abstracts: AACR Special Conference: Advances in Ovarian

(56) References Cited

OTHER PUBLICATIONS

Cancer Research: Exploiting Vulnerabilites. Oct. 17-20, 2015. Orlando, FL. doi: 10.1158/1557-3265.OVCA15-PR03. Published Jan. 2016. 8 pages.

Iwai et al., Involvement of PD-L1 on tumor cells in the escape from host immune system and tumor immunotherapy by PD-L1 blockade. Proc Natl Acad Sci U S A. Sep. 17, 2002;99(19):12293-7. doi: 10.1073/pnas.192461099. Epub Sep. 6, 2002.

Jochems et al., Analyses of functions of an anti-PD-L1/TGF?R2 bispecific fusion protein (M7824). Oncotarget. Sep. 8, 2017;8(43):75217-75231. doi: 10.18632/oncotarget.20680.

Kehry et al., Abstract 271: Targeting PD-1, TIM-3 and LAG-3 in combination for improved immunotherapy combinations. AACR 106th Annual Meeting. Apr. 18-22, 2015. Philadelphia, PA. doi: 10.1158/1538-7445.AM2015-271. 8 pages.

Klooster et al., Abstract B088: Generation of immuno-modulatory receptor binding bispecific antibodies to modulate tumor immunity. Second CRI-CIMT-EATI-AACR International Cancer Immunotherapy Conference: Translating Science into Survival. Sep. 25-28, 2016. New York, NY. doi: 10.1158/2326-6066.IMM2016-B088. 4 pages.

Koopmans et al., A novel bispecific antibody for EGFR-directed blockade of the PD-1/PD-L1 immune checkpoint. Oncoimmunology. May 31, 2018;7(8):e1466016. doi: 10.1080/2162402X.2018.1466016.

Kraman et al., A LAG-3/PD-L1 bispecific antibody inhibits tmour growth in two syngeneic colon carcinoma models. Poster Presentation. BSI/NVVI Congress. Dec. 6, 2016. 1 page. PDR153.

Kraman et al., A LAG-3/PD-L1 bispecific antibody inhibits tumour growth in two syngeneic colon carcinoma models. Abstract B091. Poster Presentation. CRI-CIMT-EATI-AACR Cancer Immunotherapy Conference. Sep. 26, 2016. 1 page. PDR129.

Kraman et al., A LAG-3/PD-L1 bispecific antibody inhibits tumour growth in two syngeneic colon carcinoma models. Poster 003. Poster Presentation. 2nd Annual Advances in ImmunoOncology Congress. May 15, 2017. 1 page. PDR185.

Kraman et al., A LAG-3/PD-L1 bispecific antibody inhibits tumour growth in two syngeneic colon carcinoma models. Poster 1103. Poster Presentation. Keystone Symposium—Cancer Immunology and Immunotherapy. Mar. 19, 2017. 1 page. PDR174.

Kraman et al., A LAG-3/PD-L1 bispecific antibody inhibits tumour growth in two syngeneic colon carcinoma models. Poster 128. Poster Presentation at SITC. Nov. 9, 2016. 1 page. PDR143.

Kraman et al., A LAG-3/PD-L1 bispecific antibody inhibits tumour growth in two syngeneic colon carcinoma models. Poster 5651. Poster Presentation. AACR Annual Meeting. Apr. 1, 2017. 1 page. PDR176.

Kraman et al., A Lag-3/PD-L1 bispecific antibody inhibits tumour growth in two syngeneic colon carcinoma models. Poster Presentation. International Conference on Human & Translational Immunology. Sep. 16, 2016. 1 page. PDR123.

Kraman et al., A LAG-3/PD-L1 bispecific antibody inhibits tumour growth in two syngeneic coon carcinoma models. Poster 3005. Poster Presentation. Keystome Symposium—Biobetters and Next-Generation Biologies. Jan. 22-26, 2017. 1 page. PDR164.

Kraman et al., Abstract 5651:A LAG-3/PD/L1 bispecific antibody inhibits tumor growth in two syngeneic colon carcinoma models. AACR Annual Meeting 2017. Apr. 1-5, 2017. Washington, DC. Doi: 10.1158/1538-7445.AM2017-5651. 8 pages.

Kraman et al., FS118, a Bispecific Antibody Targeting LAG-3 and PD-L1, Enhances T-Cell Activation Resulting in Potent Antitumor Activity. Clin Cancer Res. Jul. 1, 2020;26(13):3333-3344. doi: 10.1158/1078-0432.CCR-19-3548. Epub Apr. 16, 2020.

La Motte-Mohs et al., Abstract 3217: MGD013, a bispecific PD-1 x LAG-3 Dual-Affinity Re-Targeting (DART®) protein with T-cell immunomodulatory activity for cancer treatment. AACR 107th Annual Meeting. Apr. 16-20, 2016. New Orleans, LA. Doi: 10.1158/1538-7445.AM2016-3217. 8 pages.

La Motte-Mohs et al., MGD013, a bispecific PD-1 x LAG-3 Dual-Affinity Re-Targeting (DART®) protein with T-cell immunomodulatory activity for cancer treatment. Poster Presentation. 2016. http://ir.macrogenics.com/events.cfm. 1 page.

Lakins et al., A Novel CD137/PD-L1 Bispecific Antibody Modulates the Tumour Microenvironmentby Activating CD8+ T cells and Results in Tumour Growth Inhibition. F-Star Poster. Nov. 7, 2018. 1 page. Retrieved from https://www.f-star.com/media/87488/201811-SITC-2018-F-star-FS222-Poster-ONLINE.pdf.

Larkin et al., Combined Nivolumab and Ipilimumab or Monotherapy in Untreated Melanoma. N Engl J Med. Jul. 2, 2015;373(1):23-34. doi: 10.1056/NEJMoal504030. Epub May 31, 2015. Erratum in: N Engl J Med. Nov. 29, 2018;379(22):2185.

Lee et al., 4-1BB and OX40 dual costimulation synergistically stimulate primary specific CD8 T cells for robust effector function. J Immunol. Sep. 1, 2004;173(5):3002-12. doi: 10.4049/jimmunol.173.5.3002.

Leung et al., A HER2-specific Modified Fc Fragment (Fcab) Induces Antitumor Effects Through Degradation of HER2 and Apoptosis. Mol Ther. Nov. 2015;23(11):1722-1733. doi: 10.1038/mt.2015.127. Epub Aug. 3, 2015. Erratum in: Mol Ther. Nov. 2015;23(11):1794.

Levitan, Amgen Halts Rilotumumab Development Due to Increased Death Signal. Cancer Network. Nov. 26, 2014. Retrieved from www.cancernetwork.com/view/amgen-halts-rilotumumab-development-due-increased-death-signal. 3 pages.

Liu et al., Dual Targeting of Innate and Adaptive Checkpoints on Tumor Cells Limits Immune Evasion. Cell Rep. Aug. 21, 2018;24(8):2101-2111. doi: 10.1016/j.celrep.2018.07.062.

Lobner et al., Engineered IgG1-Fc—one fragment to bind them all. Immunol Rev. Mar. 2016;270(1):113-31. doi: 10.1111/imr.12385.

Lobner et al., Two-faced Fcab prevents polymerization with VEGF and reveals thermodynamics and the 2.15 Å crystal structure of the complex. MAbs. Oct. 2017;9(7):1088-1104. doi: 10.1080/19420862.2017.1364825. Epub Aug. 17, 2017.

McCourt et al., KY1055; a novel ICOS/PD-L1 bispecific antibody, enhance T cell activation and delivers potent monotherapy antitumour response in vivo. Abstract. CIMT 2018. Feb. 28, 2018. 1 page. PDR245.

McCourt et al., KY1055; a novel ICOS/PD-L1 bispecific antibody, enhance T cell activation and delivers potent monotherapy antitumour response in vivo. Poster Presentation. CIMT Conference. May 9, 2018. 1 page. PDR 264.

McCourt et al., KY1055; a novel ICOS/PD-L1 bispecific antibody, enhance T cell activation and delivers potent monotherapy antitumour response in vivo. Presentation. CIMT Conference. May 9, 2018. 13 pages. PDR265.

Michaelson et al., Anti-tumor activity of stability-engineered IgG-like bispecific antibodies targeting TRAIT-R2 and LTbetaR. MAbs. Mar.-Apr. 2009;1(2):128-41. doi: 10.4161/mabs.1.2.7631. Epub Mar. 11, 2009.

Munoz-Olaya, Development of an anti-PD-L1Fcab. Presentation. PEGS Lisbon. Nov. 16, 2018. 24 pages. PDR321.

Nalivaiko et al., A Recombinant Bispecific CD20xCD95 Antibody With Superior Activity Against Normal and Malignant B-cells. Mol Ther. Feb. 2016;24(2):298-305. doi: 10.1038/mt.2015.209. Epub Nov. 19, 2015.

Pavlidou et al., Simultaneous costimulatory T-cell engagement and checkpoint inhibition by PRS-344/ONC0055, a 4-1BB/PD-L1 bispecific compound for tumor localized activation of the immune system. SITC 2018. Poster Presentation. 2018. 1 page.

Powles et al., MPDL3280A (anti-PD-L1) treatment leads to clinical activity in metastatic bladder cancer. Nature. Nov. 27, 2014;515(7528):558-62. doi: 10.1038/nature13904.

Qui et al., CD 134 plus CD 137 dual costimulation induces Eomesodermin in CD4 T cells to program cytotoxic Th1 differentiation. J Immunol. Oct. 1, 2011;187(7):3555-64. doi: 10.4049/jimmunol.1101244. Epub Aug. 31, 2011.

Ramelet et al., Beneficial outcome of combination therapy with 4-1BB targeting antibody. Eur J Cancer. Nov. 29, 2016;69(Suppl 1):S96-S97.

Sainson et al., KY1055, a novel ICOS/PD-L1 bispecific antibody, efficiently enhances T cell activation and delivers a potent antitumour response in vivo. Abstract. AACR. Jan. 22, 2018. 1 page. PDR236.

(56) References Cited

OTHER PUBLICATIONS

Sainson et al., KY1055, a novel ICOS/PD-L1 bispecific antibody, efficiently enhances T cell activation and delivers a potent anti-tumour response in vivo. Poster Presentation. AACR 2018. Apr. 4, 2018. 1 page. PDR254.
Sallin et al., The anti-lymphoma activities of anti-CD137 monoclonal antibodies are enhanced in Fc?RIII(−/−) mice. Cancer Immunol Immunother. Sep. 2014;63(9):947-58. doi: 10.1007/s00262-014-1567-2. Epub Jun. 14, 2014.
Schlothauer et al., Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016.
Shindo et al., Combination immunotherapy with 4-IBB activation and PD-1 blockade enhances antitumor efficacy in a mouse model of subcutaneous tumor. Anticancer Res. Jan. 2015;35(1):129-36.
Strauss et al., Phase I Trial of M7824 (MSB0011359C), a Bifunctional Fusion Protein Targeting PD-L1 and TGF?, in Advanced Solid Tumors. Clin Cancer Res. Mar. 15, 2018;24(6):1287-1295. doi: 10.1158/1078-0432.CCR-17-2653. Epub Jan. 3, 2018.
Tuna, Identification of a PD-L1 binding FCAB: a potent inhibitor of immunosuppressive signals. Abstract. European Antibody Congress. May 3, 2018. 1 page. PDR270.
Tuna, The use of bispecific antibodies to modulate anti-tumour immune responses. Oral Presentation at 10th Annual Proteins and Antibodies Congress. Apr. 24, 2017. 26 pages. PDR183.
Vanamee et al., Structural principles of tumor necrosis factor superfamily signaling. Sci Signal. Jan. 2, 2018;11(511):eaao4910. doi: 10.1126/scisignal.aao4910. 12 pages.
Weismann, A LAG-3/PD-L1 Bispecific Antibody Inhibits Tumour Growth in Two Syngeneic Colon Carcinoma Models. International Conference on Human and Translational Immunology. Rhodes, Greece. Sep. 16-21, 2016. Presentation. 6 pages. PDR128.
Wherry, T cell exhaustion. Nat Immunol. Jun. 2011;12(6):492-9. doi: 10.1038/ni.2035.
Wilton, KY1055, a bispecific mAb2 targeting ICOS and PD-L1. Presentation. Feb. 21, 2018. 17 pages. PDR238.
Wolchok et al., Nivolumab plus ipilimumab in advanced melanoma. N Engl J Med. Jul. 11, 2013;369(2):122-33. doi: 10.1056/NEJMoa1302369. Epub Jun. 2, 2013. Erratum in: N Engl J Med. Nov. 29, 2018;379(22):2185. Author Manuscript.
Woo et al., Immune inhibitory molecules LAG-3 and PD-1 synergistically regulate T-cell function to promote tumoral immune escape. Cancer Res. Feb. 15, 2012;72(4):917-27. doi: 10.1158/0008-5472.CAN-11-1620. Epub Dec. 20, 2011.
Workman et al., Negative regulation of T cell homeostasis by lymphocyte activation gene-3 (CD223). J Immunol. Jan. 15, 2005;174(2):688-95. doi: 10.4049/jimmunol.174.2.688.
Workman et al., The CD4-related molecule, LAG-3 (CD223), regulates the expansion of activated T cells. Eur J Immunol. Apr. 2003;33(4):970-9. doi: 10.1002/eji.200323382.
Wozniak-Knopp et al., Designing Fcabs: well-expressed and stable high affinity antigen-binding Fc fragments. Protein Eng Des Sel. Sep. 1, 2017;30(9):657-671. doi: 10.1093/protein/gzx042.
Wydro, Bispecific antibodies: new opportunities for novel therapies. Oral Presentation at 7th Annual Biologies Symposium. Mar. 1, 2017. 24 pages. PDR172.
Wykes et al., Immune checkpoint blockade in infectious diseases. Nat Rev Immunol. Feb. 2018;18(2):91-104. doi: 10.1038/nri.2017.112. Epub Oct. 9, 2017.
Yap et al., A first-in-human phase I study of FS118, an anti-LAG-3/PD-L1 bispecific antibody in patients with solid tumors that have progressed on prior PD-1/PD-L1 therapy. Journal of Clinical Oncology. May 2, 20196;37(15_suppl). 4 pages.
Zhang et al., Structural basis of a novel PD-L1 nanobody for immune checkpoint blockade. Cell Discov. Mar. 7, 2017;3:17004. doi: 10.1038/celldisc.2017.4.
U.S. Appl. No. 17/534,315, filed Nov. 23, 2021, Tuna et al.
U.S. Appl. No. 17/533,230, filed Nov. 23, 2021, Campbell et al.
U.S. Appl. No. 17/259,634, filed Jan. 12, 2021, Munoz-Olaya et al.
U.S. Appl. No. 17/259,680, filed Jan. 12, 2021, Pechouckova et al.
U.S. Appl. No. 17/259,677, filed Jan. 12, 2021, Munoz-Olaya et al.
U.S. Appl. No. 17/259,754, filed Jan. 12, 2021, Lakins et al.
U.S. Appl. No. 17/259,642, filed Jan. 12, 2021, Wollerton et al.
U.S. Appl. No. 17/259,714, filed Jan. 12, 2021, Tuna et al.
U.S. Appl. No. 17/259,791, filed Jan. 12, 2021, Lakins et al.
U.S. Appl. No. 17/259,796, filed Jan. 12, 2021, Tuna et al.
U.S. Appl. No. 17/610,873, filed Nov. 12, 2021, Morrow.
Asgarov et al., A new anti-mesothelin antibody targets selectively the membrane-associated form. MAbs. Apr. 2017;9(3):Supplementary Data, doi: 10.1080/19420862.2017.1288770. 6 pages.
Awuah et al., Reduced Shedding of Surface Mesothelin Improves Efficacy of Mesothelin-Targeting Recombinant Immunotoxins. Mol Cancer Ther. Jul. 2016;15(7):1648-55. doi: 10.1158/1535-7163.MCT-15-0863. Epub May 18, 2016.
Del Bano et al., A Bispecific Antibody-Based Approach for Targeting Mesothelin in Triple Negative Breast Cancer. Front Immunol. Jul. 10, 2019; 10:1593. doi: 10.3389/fimmu.2019.01593.
Hassan et al., Mesothelin Immunotherapy for Cancer: Ready for Prime Time? J Clin Oncol. Dec. 2016;34(34):4171-4179. doi: 10.1200/JCO.2016.68.3672. Epub Oct. 31, 2016.
Hassan et al., Phase II clinical trial of amatuximab, a chimeric antimesothelin antibody with pemetrexed and cisplatin in advanced unresectable pleural mesothelioma. Clin Cancer Res. Dec. 1, 2014;20(23):5927-36. doi: 10.1158/1078-0432.CCR-14-0804. Epub Sep. 17, 2014.
Ho et al., A novel high-affinity human monoclonal antibody to mesothelin. Int J Cancer. May 1, 2011;128(9):2020-30. doi: 10.1002/ijc.25557.
Ma et al., Recognition of mesothelin by the therapeutic antibody MORAb-009: structural and mechanistic insights. J Biol Chem. Sep. 28, 2012;287(40):33123-31. doi: 10.1074/jbc.M112.381756. Epub Jul. 11, 2012.
Tang et al., A human single-domain antibody elicits potent antitumor activity by targeting an epitope in mesothelin close to the cancer cell surface. Mol Cancer Ther. Apr. 2013;12(4):416-26. doi: 10.1158/1535-7163.MCT-12-0731. Epub Jan. 31, 2013.
Zhao et al., Novel Antibody Therapeutics Targeting Mesothelin in Solid Tumors. Clin Cancer Drugs. Oct. 2016;3(2):76-86. doi: 10.2174/2212697X03666160218215744.

* cited by examiner

| | AB loop (14-18) | | | | | | CD loop (45.1-78) | | | | | | | | | EF loop (92-101) | | | | | | | | | |
|---|---|---|---|---|---|---|---|---|---|---|---|---|---|---|---|---|---|---|---|---|---|---|---|---|---|
| IMGT position | 14 | 15 | 16 | 17 | 18 | 38 | 45.1 | 45.2 | 45.3 | 45.4 | 77 | 78 | 84.1 | 85.3 | 92 | 93 | 94 | 95 | 96 | 97 | 98 | 99 | 100 | 101 | 113 |
| Consecutive numbering (IMGT exon numbering) | 18 | 19 | 20 | 21 | 22 | 38 | 46 | 47 | 48 | 49 | 50 | 51 | 58 | 63 | 73 | 74 | 75 | 76 | 77 | 78 | 79 | 80 | 81 | 82 | 93 |
| WT Fcab | L | T | K | N | Q | A | Q | P | E | N | N | Y | L | S | D | K | S | R | W | Q | Q | G | N | V | H |
| FS17-33 | Q | S | G | Y | W | A | Q | P | E | N | N | Y | L | S | S | N | W | R | W | Q | M | G | D | ? | H |
| FS17-33-37 | Q | V | G | Y | W | A | Q | P | E | N | N | Y | L | S | S | N | W | R | W | Q | M | D | D | ? | H |
| FS17-33-116 | ? | S | G | Y | W | V | E | P | Q | Y | W | A | L | S | S | N | W | R | W | Q | M | D | D | ? | H |
| FS17-33-288 | ? | S | G | Y | W | V | E | P | Q | Y | W | A | L | S | S | N | W | R | W | Q | I | D | D | ? | H |
| FS17-33-289 | ? | S | G | Y | W | V | E | P | Q | Y | W | A | L | S | S | N | W | R | W | Q | L | D | D | ? | H |
| FS17-33-296 | ? | S | G | Y | W | A | E | P | Q | Y | W | A | L | S | S | N | W | R | W | Q | V | D | D | ? | H |
| FS17-33-334 | ? | T | G | Y | W | A | E | P | Q | Y | W | A | L | S | S | N | W | R | W | Q | L | D | D | ? | H |
| FS17-33-449 | ? | E | G | Y | W | A | E | P | Q | Y | W | A | L | S | S | N | W | R | W | Q | L | D | D | V | H |
| FS17-33-451 | ? | E | G | Y | W | A | E | P | Q | Y | W | A | P | T | S | N | W | R | W | Q | L | D | D | V | H |
| FS17-33-488 | ? | T | G | Y | W | A | E | P | Q | Y | W | A | L | S | S | N | W | R | W | Q | L | G | D | A | R |
| FS17-33-539 | ? | E | G | Y | W | A | E | P | Q | Y | W | A | L | S | S | N | W | R | W | Q | L | G | D | V | R |
| FS17-33-548 | ? | E | G | Y | W | A | E | P | Q | Y | W | A | L | S | S | N | W | R | W | Q | L | G | D | V | H |

| IMGT | IMGT exon numbering | EU numbering | Kabat numbering | Amino Acid (WT) |
|---|---|---|---|---|
| 1.4 | 1 | 341 | 361 | G |
| 1.3 | 2 | 342 | 363 | Q |
| 1.2 | 3 | 343 | 364 | P |
| 1.1 | 4 | 344 | 365 | R |
| 1 | 5 | 345 | 366 | E |
| 2 | 6 | 346 | 367 | P |
| 3 | 7 | 347 | 368 | Q |
| 4 | 8 | 348 | 369 | V |
| 5 | 9 | 349 | 370 | Y |
| 6 | 10 | 350 | 371 | T |
| 7 | 11 | 351 | 372 | L |
| 8 | 12 | 352 | 373 | P |
| 9 | 13 | 353 | 374 | P |
| 10 | 14 | 354 | 375 | S |
| 11 | 15 | 355 | 376 | R |
| 12 | 16 | 356 | 377 | D |
| 13 | 17 | 357 | 378 | E |
| 14 | 18 | 358 | 381 | L |
| 15 | 19 | 359 | 382 | T |
| 16 | 20 | 360 | 383 | K |
| 17 | 21 | 361 | 384 | N |
| 18 | 22 | 362 | 385 | Q |
| 19 | 23 | 363 | 386 | V |
| 20 | 24 | 364 | 387 | S |
| 21 | 25 | 365 | 388 | L |
| 22 | 26 | 366 | 389 | T |
| 23 | 27 | 367 | 390 | C |
| 24 | 28 | 368 | 391 | L |
| 25 | 29 | 369 | 392 | V |
| 26 | 30 | 370 | 393 | K |
| 27 | 31 | 371 | 394 | G |
| 28 | 32 | 372 | 395 | F |
| 29 | 33 | 373 | 396 | Y |
| 30 | 34 | 374 | 397 | P |
| 35 | 35 | 375 | 398 | S |
| 36 | 36 | 376 | 399 | D |
| 37 | 37 | 377 | 400 | I |
| 38 | 38 | 378 | 401 | A |
| 39 | 39 | 379 | 402 | V |
| 40 | 40 | 380 | 405 | E |
| 41 | 41 | 381 | 406 | W |
| 42 | 42 | 382 | 407 | E |
| 43 | 43 | 383 | 408 | S |
| 44 | 44 | 384 | 410 | N |
| 45 | 45 | 385 | 411 | G |
| 45.1 | 46 | 386 | 414 | Q |
| 45.2 | 47 | 387 | 415 | P |
| 45.3 | 48 | 388 | 416 | E |
| 45.4 | 49 | 389 | 417 | N |
| 77 | 50 | 390 | 418 | N |
| 78 | 51 | 391 | 419 | Y |
| 79 | 52 | 392 | 420 | K |
| 80 | 53 | 393 | 421 | T |

| IMGT | IMGT exon numbering | EU numbering | Kabat numbering | Amino Acid (WT) |
|---|---|---|---|---|
| 81 | 54 | 394 | 422 | T |
| 82 | 55 | 395 | 423 | P |
| 83 | 56 | 396 | 424 | P |
| 84 | 57 | 397 | 425 | V |
| 84.1 | 58 | 398 | 426 | L |
| 84.2 | 59 | 399 | 427 | D |
| 84.3 | 60 | 400 | 428 | S |
| 84.4 | 61 | 401 | 430 | D |
| 85.4 | 62 | 402 | 433 | G |
| 85.3 | 63 | 403 | 434 | S |
| 85.2 | 64 | 404 | 435 | F |
| 85.1 | 65 | 405 | 436 | F |
| 85 | 66 | 406 | 437 | L |
| 86 | 67 | 407 | 438 | Y |
| 87 | 68 | 408 | 439 | S |
| 88 | 69 | 409 | 440 | K |
| 89 | 70 | 410 | 441 | L |
| 90 | 71 | 411 | 442 | T |
| 91 | 72 | 412 | 443 | V |
| 92 | 73 | 413 | 444 | D |
| 93 | 74 | 414 | 445 | K |
| 94 | 75 | 415 | 446 | S |
| 95 | 76 | 416 | 447 | R |
| 96 | 77 | 417 | 448 | W |
| 97 | 78 | 418 | 449 | Q |
| 98 | 79 | 419 | 450 | Q |
| 99 | 80 | 420 | 451 | G |
| 100 | 81 | 421 | 452 | N |
| 101 | 82 | 422 | 453 | V |
| 102 | 83 | 423 | 454 | F |
| 103 | 84 | 424 | 455 | S |
| 104 | 85 | 425 | 456 | C |
| 105 | 86 | 426 | 457 | S |
| 106 | 87 | 427 | 458 | V |
| 107 | 88 | 428 | 459 | M |
| 108 | 89 | 429 | 460 | H |
| 109 | 90 | 430 | 461 | E |
| 110 | 91 | 431 | 462 | A |
| 112 | 92 | 432 | 463 | L |
| 113 | 93 | 433 | 464 | H |
| 114 | 94 | 434 | 465 | N |
| 115 | 95 | 435 | 466 | H |
| 116 | 96 | 436 | 467 | Y |
| 117 | 97 | 437 | 468 | T |
| 118 | 98 | 438 | 469 | Q |
| 119 | 99 | 439 | 470 | K |
| 120 | 100 | 440 | 471 | S |
| 121 | 101 | 441 | 472 | L |
| 122 | 102 | 442 | 473 | S |
| 123 | 103 | 443 | 474 | L |
| 124 | 104 | 444 | 475 | S |
| 125 | 105 | 445 | 476 | P |
| 129 | CHS 106 | 446 | 477 | G |
| 130 | CHS 107 | 447 | 478 | K |

| Clone ID | CH3 domain sequence |
|---|---|
| WT Fcab | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| FS17-33 | GQPREPQVYTLPPSRDEQSGYWVSLTCLVKGFYPSDIAVEWESNGQPENNYKTTPPVLDSDGSFFLYSKLTVSNWRWQMGD~FSCSVMHEALHNHYTQKSLSLSPGK |
| FS17-33-37 | GQPREPQVYTLPPSRDEQVGYWVSLTCLVKGFYPSDIAVEWESNGQPENNYKTTPPVLDSDGSFFLYSKLTVSNWRWQMDD~FSCSVMHEALHNHYTQKSLSLSPGK |
| FS17-33-116 | GQPREPQVYTLPPSRDE~SGYWVSLTCLVKGFYPSDIVVEWESNGEPQYWAKTTPPVLDSDGSFFLYSKLTVSNWRWQMDD~FSCSVMHEALHNHYTQKSLSLSPGK |
| FS17-33-288 | GQPREPQVYTLPPSRDE~SGYWVSLTCLVKGFYPSDIAVEWESNGEPQYWAKTTPPVLDSDGSFFLYSKLTVSNWRWQIDD~FSCSVMHEALHNHYTQKSLSLSPGK |
| FS17-33-289 | GQPREPQVYTLPPSRDE~SGYWVSLTCLVKGFYPSDIVVEWESNGEPQYWAKTTPPVLDSDGSFFLYSKLTVSNWRWQLDD~FSCSVMHEALHNHYTQKSLSLSPGK |
| FS17-33-296 | GQPREPQVYTLPPSRDE~SGYWVSLTCLVKGFYPSDIVVEWESNGEPQYWAKTTPPVLDSDGSFFLYSKLTVSNWRWQVDD~FSCSVMHEALHNHYTQKSLSLSPGK |
| FS17-33-334 | GQPREPQVYTLPPSRDE~SGYWVSLTCLVKGFYPSDIAVEWESNGEPQYWAKTTPPVLDSDGSFFLYSKLTVSNWRWQLDD~FSCSVMHEALHNHYTQKSLSLSPGK |
| FS17-33-449 | GQPREPQVYTLPPSRDE~TGYWVSLTCLVKGFYPSDIVVEWESNGEPQYWAKTTPPVLDSDGSFFLYSKLTVSNWRWQLDDVFSCSVMHEALHNHYTQKSLSLSPGK |
| FS17-33-451 | GQPREPQVYTLPPSRDE~EGYWVSLTCLVKGFYPSDIAVEWESNGEPQYWAKTTPPVLDSDGSFFLYSKLTVSNWRWQLDDVFSCSVMHEALHNHYTQKSLSLSPGK |
| FS17-33-488 | GQPREPQVYTLPPSRDE~EGYWVSLTCLVKGFYPSDIAVEWESNGEPQYWAKTTPPVPDSDGTFFLYSKLTVSNWRWQLGDAFSCSVMHEALRNHYTQKSLSLSPGK |
| FS17-33-539 | GQPREPQVYTLPPSRDE~TGYWVSLTCLVKGFYPSDIAVEWESNGEPQYWAKTTPPVLDSDGSFFLYSKLTVSNWRWQLGDVFSCSVMHEALRNHYTQKSLSLSPGK |
| FS17-33-548 | GQPREPQVYTLPPSRDE~EGYWVSLTCLVKGFYPSDIAVEWESNGEPQYWAKTTPPVLDSDGSFFLYSKLTVSNWRWQLGDVFSCSVMHEEALHNHYTQKSLSLSPGK |

Figure 1 continued

SEQUENCE LISTING

<160> NUMBER OF SEQ ID NOS: 82

<210> SEQ ID NO 1
<211> LENGTH: 5
<212> TYPE: PRT
<213> ORGANISM: Artificial Sequence
<220> FEATURE:
<223> OTHER INFORMATION: WT Fcab CH3 domain AB loop

<400> SEQUENCE: 1

Leu Thr Lys Asn Gln
1               5

<210> SEQ ID NO 2
<211> LENGTH: 6
<212> TYPE: PRT
<213> ORGANISM: Artificial Sequence
<220> FEATURE:
<223> OTHER INFORMATION: WT Fcab CH3 domain CD loop

<400> SEQUENCE: 2

Gln Pro Glu Asn Asn Tyr
1               5

<210> SEQ ID NO 3
<211> LENGTH: 10
<212> TYPE: PRT
<213> ORGANISM: Artificial Sequence
<220> FEATURE:
<223> OTHER INFORMATION: WT Fcab CH3 domain EF loop

<400> SEQUENCE: 3

Asp Lys Ser Arg Trp Gln Gln Gly Asn Val
1               5                   10

<210> SEQ ID NO 4
<211> LENGTH: 107
<212> TYPE: PRT
<213> ORGANISM: Artificial Sequence
<220> FEATURE:
<223> OTHER INFORMATION: WT Fcab CH3 domain

<400> SEQUENCE: 4

Gly Gln Pro Arg Glu Pro Gln Val Tyr Thr Leu Pro Pro Ser Arg Asp
1               5                   10                  15

```
Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 5
<211> LENGTH: 110
<212> TYPE: PRT
<213> ORGANISM: Artificial Sequence
<220> FEATURE:
<223> OTHER INFORMATION: CH2 domain of the WT Fcab, FS17-33, and
      FS17-33-37/116/288/289/296/334/449/451/488/539/548 with LALA
      mutation

<400> SEQUENCE: 5

```
Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 6
<211> LENGTH: 110
<212> TYPE: PRT
<213> ORGANISM: Artificial Sequence
<220> FEATURE:
<223> OTHER INFORMATION: CH2 domain of the WT Fcab, FS17-33, and
      FS17-33-37/116/288/289/296/334/449/451/488/539/548 without LALA
      mutation

<400> SEQUENCE: 6

```
Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80
```

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 7
<211> LENGTH: 6
<212> TYPE: PRT
<213> ORGANISM: Artificial Sequence
<220> FEATURE:
<223> OTHER INFORMATION: truncated hinge region of the WT Fcab, FS17-33,
      and FS17-33-37/116/288/289/296/334/449/451/488/539/548

<400> SEQUENCE: 7

Thr Cys Pro Pro Cys Pro
1               5

<210> SEQ ID NO 8
<211> LENGTH: 223
<212> TYPE: PRT
<213> ORGANISM: Artificial Sequence
<220> FEATURE:
<223> OTHER INFORMATION: WT Fcab with LALA mutation

<400> SEQUENCE: 8

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 9
<211> LENGTH: 223
<212> TYPE: PRT
<213> ORGANISM: Artificial Sequence
<220> FEATURE:
<223> OTHER INFORMATION: WT Fcab without LALA mutation

```
<400> SEQUENCE: 9

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65              70                  75                  80

Val Leu Thr Val Leu His Gln Asp Trp Leu Asn Gly Lys Glu Tyr Lys
            85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
            165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220

<210> SEQ ID NO 10
<211> LENGTH: 4
<212> TYPE: PRT
<213> ORGANISM: Artificial Sequence
<220> FEATURE:
<223> OTHER INFORMATION: Consensus sequences of Fcab
      FS17-33-116/288/289/296/334/449/451 CH3 domain AB loop
<220> FEATURE:
<221> NAME/KEY: MISC_FEATURE
<222> LOCATION: (1)..(1)
<223> OTHER INFORMATION: X = V, S, T, or E

<400> SEQUENCE: 10

Xaa Gly Tyr Trp
1

<210> SEQ ID NO 11
<211> LENGTH: 6
<212> TYPE: PRT
<213> ORGANISM: Artificial Sequence
<220> FEATURE:
<223> OTHER INFORMATION: Consensus sequences of Fcab
      FS17-33-116/288/289/296/334/449/451 CH3 domain CD loop

<400> SEQUENCE: 11

Glu Pro Gln Tyr Trp Ala
1               5

<210> SEQ ID NO 12
```

```
<211> LENGTH: 10
<212> TYPE: PRT
<213> ORGANISM: Artificial Sequence
<220> FEATURE:
<223> OTHER INFORMATION: Consensus sequences of Fcab
      FS17-33-116/288/289/296/334/449/451 CH3 domain EF loop
<220> FEATURE:
<221> NAME/KEY: MISC_FEATURE
<222> LOCATION: (7)..(7)
<223> OTHER INFORMATION: X = M, I, L, or V
<220> FEATURE:
<221> NAME/KEY: MISC_FEATURE
<222> LOCATION: (10)..(10)
<223> OTHER INFORMATION: X = V or absent

<400> SEQUENCE: 12

Ser Asn Trp Arg Trp Gln Xaa Asp Asp Xaa
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Fcab FS17-33 CH3 domain AB loop

<400> SEQUENCE: 13

Gln Ser Gly Tyr Trp
1               5

<210> SEQ ID NO 14
<211> LENGTH: 9
<212> TYPE: PRT
<213> ORGANISM: Artificial Sequence
<220> FEATURE:
<223> OTHER INFORMATION: Fcab FS17-33 CH3 domain EF loop

<400> SEQUENCE: 14

Ser Asn Trp Arg Trp Gln Met Gly Asp
1               5

<210> SEQ ID NO 15
<211> LENGTH: 106
<212> TYPE: PRT
<213> ORGANISM: Artificial Sequence
<220> FEATURE:
<223> OTHER INFORMATION: Fcab FS17-33 CH3 domain

<400> SEQUENCE: 15

Gly Gln Pro Arg Glu Pro Gln Val Tyr Thr Leu Pro Pro Ser Arg Asp
1               5                   10                  15

Glu Gln Ser Gly Tyr Trp Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Ser Asn Trp Arg Trp Gln Met Gly
65                  70                  75                  80

Asp Phe Ser Cys Ser Val Met His Glu Ala Leu His Asn His Tyr Thr
                85                  90                  95

Gln Lys Ser Leu Ser Leu Ser Pro Gly Lys
            100                 105

<210> SEQ ID NO 16
```

```
<211> LENGTH: 222
<212> TYPE: PRT
<213> ORGANISM: Artificial Sequence
<220> FEATURE:
<223> OTHER INFORMATION: Fcab FS17-33 with LALA mutation

<400> SEQUENCE: 16

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Gln Ser Gly Tyr Trp Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Ser Asn Trp Arg
            180                 185                 190

Trp Gln Met Gly Asp Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 17
<211> LENGTH: 222
<212> TYPE: PRT
<213> ORGANISM: Artificial Sequence
<220> FEATURE:
<223> OTHER INFORMATION: Fcab FS17-33 without LALA mutation

<400> SEQUENCE: 17

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
```

```
                100                 105                 110
Ser Lys Ala Lys Gly Gln Pro Arg Glu Pro Gln Val Tyr Thr Leu Pro
            115                 120                 125

Pro Ser Arg Asp Glu Gln Ser Gly Tyr Trp Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Ser Asn Trp Arg
            180                 185                 190

Trp Gln Met Gly Asp Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 18
<211> LENGTH: 5
<212> TYPE: PRT
<213> ORGANISM: Artificial Sequence
<220> FEATURE:
<223> OTHER INFORMATION: Fcab FS17-33-37 CH3 domain AB loop

<400> SEQUENCE: 18

Gln Val Gly Tyr Trp
1               5

<210> SEQ ID NO 19
<211> LENGTH: 9
<212> TYPE: PRT
<213> ORGANISM: Artificial Sequence
<220> FEATURE:
<223> OTHER INFORMATION: Fcab FS17-33-37 CH3 domain EF loop

<400> SEQUENCE: 19

Ser Asn Trp Arg Trp Gln Met Asp Asp
1               5

<210> SEQ ID NO 20
<211> LENGTH: 106
<212> TYPE: PRT
<213> ORGANISM: Artificial Sequence
<220> FEATURE:
<223> OTHER INFORMATION: Fcab FS17-33-37 CH3 domain

<400> SEQUENCE: 20

Gly Gln Pro Arg Glu Pro Gln Val Tyr Thr Leu Pro Pro Ser Arg Asp
1               5                   10                  15

Glu Gln Val Gly Tyr Trp Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Ser Asn Trp Arg Trp Gln Met Asp
65                  70                  75                  80

Asp Phe Ser Cys Ser Val Met His Glu Ala Leu His Asn His Tyr Thr
                85                  90                  95

Gln Lys Ser Leu Ser Leu Ser Pro Gly Lys
            100                 105
```

<210> SEQ ID NO 21
<211> LENGTH: 222
<212> TYPE: PRT
<213> ORGANISM: Artificial Sequence
<220> FEATURE:
<223> OTHER INFORMATION: Fcab FS17-33-37 with LALA mutation

<400> SEQUENCE: 21

```
Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Gln Val Gly Tyr Trp Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Ser Asn Trp Arg
            180                 185                 190

Trp Gln Met Asp Asp Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 22
<211> LENGTH: 222
<212> TYPE: PRT
<213> ORGANISM: Artificial Sequence
<220> FEATURE:
<223> OTHER INFORMATION: Fcab FS17-33-37 without LALA mutation

<400> SEQUENCE: 22

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
```

```
                85                  90                  95
Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Gln Val Gly Tyr Trp Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Ser Asn Trp Arg
            180                 185                 190

Trp Gln Met Asp Asp Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 23
<211> LENGTH: 4
<212> TYPE: PRT
<213> ORGANISM: Artificial Sequence
<220> FEATURE:
<223> OTHER INFORMATION: Fcab FS17-33-116 CH3 domain AB loop

<400> SEQUENCE: 23

Ser Gly Tyr Trp
1

<210> SEQ ID NO 24
<211> LENGTH: 105
<212> TYPE: PRT
<213> ORGANISM: Artificial Sequence
<220> FEATURE:
<223> OTHER INFORMATION: Fcab FS17-33-116 CH3 domain

<400> SEQUENCE: 24

Gly Gln Pro Arg Glu Pro Gln Val Tyr Thr Leu Pro Pro Ser Arg Asp
1               5                   10                  15

Glu Ser Gly Tyr Trp Val Ser Leu Thr Cys Leu Val Lys Gly Phe Tyr
            20                  25                  30

Pro Ser Asp Ile Val Val Glu Trp Glu Ser Asn Gly Glu Pro Gln Tyr
        35                  40                  45

Trp Ala Lys Thr Thr Pro Pro Val Leu Asp Ser Asp Gly Ser Phe Phe
    50                  55                  60

Leu Tyr Ser Lys Leu Thr Val Ser Asn Trp Arg Trp Gln Met Asp Asp
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys
            100                 105

<210> SEQ ID NO 25
<211> LENGTH: 221
<212> TYPE: PRT
<213> ORGANISM: Artificial Sequence
<220> FEATURE:
<223> OTHER INFORMATION: Fcab FS17-33-116 with LALA mutation

<400> SEQUENCE: 25
```

```
Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
        50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Asp Glu Ser Gly Tyr Trp Val Ser Leu Thr Cys Leu Val
        130                 135                 140

Lys Gly Phe Tyr Pro Ser Asp Ile Val Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
            180                 185                 190

Gln Met Asp Asp Phe Ser Cys Ser Val Met His Glu Ala Leu His Asn
        195                 200                 205

His Tyr Thr Gln Lys Ser Leu Ser Leu Ser Pro Gly Lys
210                 215                 220

<210> SEQ ID NO 26
<211> LENGTH: 221
<212> TYPE: PRT
<213> ORGANISM: Artificial Sequence
<220> FEATURE:
<223> OTHER INFORMATION: Fcab FS17-33-116 without LALA mutation

<400> SEQUENCE: 26

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
        50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Asp Glu Ser Gly Tyr Trp Val Ser Leu Thr Cys Leu Val
        130                 135                 140
```

-continued

```
Lys Gly Phe Tyr Pro Ser Asp Ile Val Val Glu Trp Glu Ser Asn Gly
145                 150                 155                 160

Glu Pro Gln Tyr Trp Ala Lys Thr Thr Pro Val Leu Asp Ser Asp
                165                 170                 175

Gly Ser Phe Phe Leu Tyr Ser Lys Leu Thr Val Ser Asn Trp Arg Trp
            180                 185                 190

Gln Met Asp Asp Phe Ser Cys Ser Val Met His Glu Ala Leu His Asn
        195                 200                 205

His Tyr Thr Gln Lys Ser Leu Ser Leu Ser Pro Gly Lys
    210                 215                 220

<210> SEQ ID NO 27
<211> LENGTH: 9
<212> TYPE: PRT
<213> ORGANISM: Artificial Sequence
<220> FEATURE:
<223> OTHER INFORMATION: Fcab FS17-33-288 CH3 domain EF loop

<400> SEQUENCE: 27

Ser Asn Trp Arg Trp Gln Ile Asp Asp
1               5

<210> SEQ ID NO 28
<211> LENGTH: 105
<212> TYPE: PRT
<213> ORGANISM: Artificial Sequence
<220> FEATURE:
<223> OTHER INFORMATION: FS17-33-288 CH3 domain

<400> SEQUENCE: 28

Gly Gln Pro Arg Glu Pro Gln Val Tyr Thr Leu Pro Pro Ser Arg Asp
1               5                   10                  15

Glu Ser Gly Tyr Trp Val Ser Leu Thr Cys Leu Val Lys Gly Phe Tyr
            20                  25                  30

Pro Ser Asp Ile Val Val Glu Trp Glu Ser Asn Gly Glu Pro Gln Tyr
            35                  40                  45

Trp Ala Lys Thr Thr Pro Pro Val Leu Asp Ser Asp Gly Ser Phe Phe
50                  55                  60

Leu Tyr Ser Lys Leu Thr Val Ser Asn Trp Arg Trp Gln Ile Asp Asp
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys
            100                 105

<210> SEQ ID NO 29
<211> LENGTH: 221
<212> TYPE: PRT
<213> ORGANISM: Artificial Sequence
<220> FEATURE:
<223> OTHER INFORMATION: Fcab FS17-33-288 with LALA mutation

<400> SEQUENCE: 29

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45
```

```
Val Lys Phe Asn Trp Tyr Val Asp Gly Val Glu Val His Asn Ala Lys
 50                  55                  60
Thr Lys Pro Arg Glu Glu Gln Tyr Asn Ser Thr Tyr Arg Val Val Ser
 65                  70                  75                  80
Val Leu Thr Val Leu His Gln Asp Trp Leu Asn Gly Lys Glu Tyr Lys
                 85                  90                  95
Cys Lys Val Ser Asn Lys Ala Leu Pro Ala Pro Ile Glu Lys Thr Ile
                100                 105                 110
Ser Lys Ala Lys Gly Gln Pro Arg Glu Pro Gln Val Tyr Thr Leu Pro
                115                 120                 125
Pro Ser Arg Asp Glu Ser Gly Tyr Trp Val Ser Leu Thr Cys Leu Val
                130                 135                 140
Lys Gly Phe Tyr Pro Ser Asp Ile Val Val Glu Trp Glu Ser Asn Gly
145                 150                 155                 160
Glu Pro Gln Tyr Trp Ala Lys Thr Thr Pro Pro Val Leu Asp Ser Asp
                165                 170                 175
Gly Ser Phe Phe Leu Tyr Ser Lys Leu Thr Val Ser Asn Trp Arg Trp
                180                 185                 190
Gln Ile Asp Asp Phe Ser Cys Ser Val Met His Glu Ala Leu His Asn
                195                 200                 205
His Tyr Thr Gln Lys Ser Leu Ser Leu Ser Pro Gly Lys
                210                 215                 220

<210> SEQ ID NO 30
<211> LENGTH: 221
<212> TYPE: PRT
<213> ORGANISM: Artificial Sequence
<220> FEATURE:
<223> OTHER INFORMATION: Fcab FS17-33-288 without LALA mutation

<400> SEQUENCE: 30

Thr Cys Pro Pro Cys Pro Ala Pro Glu Leu Leu Gly Gly Pro Ser Val
  1               5                  10                  15
Phe Leu Phe Pro Pro Lys Pro Lys Asp Thr Leu Met Ile Ser Arg Thr
                 20                  25                  30
Pro Glu Val Thr Cys Val Val Asp Val Ser His Glu Asp Pro Glu
                 35                  40                  45
Val Lys Phe Asn Trp Tyr Val Asp Gly Val Glu Val His Asn Ala Lys
 50                  55                  60
Thr Lys Pro Arg Glu Glu Gln Tyr Asn Ser Thr Tyr Arg Val Val Ser
 65                  70                  75                  80
Val Leu Thr Val Leu His Gln Asp Trp Leu Asn Gly Lys Glu Tyr Lys
                 85                  90                  95
Cys Lys Val Ser Asn Lys Ala Leu Pro Ala Pro Ile Glu Lys Thr Ile
                100                 105                 110
Ser Lys Ala Lys Gly Gln Pro Arg Glu Pro Gln Val Tyr Thr Leu Pro
                115                 120                 125
Pro Ser Arg Asp Glu Ser Gly Tyr Trp Val Ser Leu Thr Cys Leu Val
                130                 135                 140
Lys Gly Phe Tyr Pro Ser Asp Ile Val Val Glu Trp Glu Ser Asn Gly
145                 150                 155                 160
Glu Pro Gln Tyr Trp Ala Lys Thr Thr Pro Pro Val Leu Asp Ser Asp
                165                 170                 175
Gly Ser Phe Phe Leu Tyr Ser Lys Leu Thr Val Ser Asn Trp Arg Trp
                180                 185                 190
```

Gln Ile Asp Asp Phe Ser Cys Ser Val Met His Glu Ala Leu His Asn
            195                 200                 205

His Tyr Thr Gln Lys Ser Leu Ser Leu Ser Pro Gly Lys
    210                 215                 220

<210> SEQ ID NO 31
<211> LENGTH: 9
<212> TYPE: PRT
<213> ORGANISM: Artificial Sequence
<220> FEATURE:
<223> OTHER INFORMATION: Fcab FS17-33-289 CH3 domain EF loop

<400> SEQUENCE: 31

Ser Asn Trp Arg Trp Gln Leu Asp Asp
1               5

<210> SEQ ID NO 32
<211> LENGTH: 105
<212> TYPE: PRT
<213> ORGANISM: Artificial Sequence
<220> FEATURE:
<223> OTHER INFORMATION: Fcab FS17-33-289 CH3 domain

<400> SEQUENCE: 32

Gly Gln Pro Arg Glu Pro Gln Val Tyr Thr Leu Pro Pro Ser Arg Asp
1               5                   10                  15

Glu Ser Gly Tyr Trp Val Ser Leu Thr Cys Leu Val Lys Gly Phe Tyr
            20                  25                  30

Pro Ser Asp Ile Val Val Glu Trp Glu Ser Asn Gly Glu Pro Gln Tyr
        35                  40                  45

Trp Ala Lys Thr Thr Pro Pro Val Leu Asp Ser Asp Gly Ser Phe Phe
    50                  55                  60

Leu Tyr Ser Lys Leu Thr Val Ser Asn Trp Arg Trp Gln Leu Asp Asp
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys
            100                 105

<210> SEQ ID NO 33
<211> LENGTH: 221
<212> TYPE: PRT
<213> ORGANISM: Artificial Sequence
<220> FEATURE:
<223> OTHER INFORMATION: Fcab FS17-33-289 with LALA mutation

<400> SEQUENCE: 33

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile

-continued

```
                100                 105                 110
Ser Lys Ala Lys Gly Gln Pro Arg Glu Pro Gln Val Tyr Thr Leu Pro
            115                 120                 125

Pro Ser Arg Asp Glu Ser Gly Tyr Trp Val Ser Leu Thr Cys Leu Val
        130                 135                 140

Lys Gly Phe Tyr Pro Ser Asp Ile Val Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
            180                 185                 190

Gln Leu Asp Asp Phe Ser Cys Ser Val Met His Glu Ala Leu His Asn
        195                 200                 205

His Tyr Thr Gln Lys Ser Leu Ser Leu Ser Pro Gly Lys
    210                 215                 220
```

<210> SEQ ID NO 34
<211> LENGTH: 221
<212> TYPE: PRT
<213> ORGANISM: Artificial Sequence
<220> FEATURE:
<223> OTHER INFORMATION: Fcab FS17-33-289 without LALA mutation

<400> SEQUENCE: 34

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Ser Gly Tyr Trp Val Ser Leu Thr Cys Leu Val
    130                 135                 140

Lys Gly Phe Tyr Pro Ser Asp Ile Val Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
            180                 185                 190

Gln Leu Asp Asp Phe Ser Cys Ser Val Met His Glu Ala Leu His Asn
        195                 200                 205

His Tyr Thr Gln Lys Ser Leu Ser Leu Ser Pro Gly Lys
    210                 215                 220
```

<210> SEQ ID NO 35
<211> LENGTH: 9
<212> TYPE: PRT

<210> SEQ ID NO 35
<211> LENGTH: 8
<212> TYPE: PRT
<213> ORGANISM: Artificial Sequence
<220> FEATURE:
<223> OTHER INFORMATION: Fcab FS17-33-296 CH3 domain EF loop

<400> SEQUENCE: 35

Ser Asn Trp Arg Trp Gln Val Asp
1               5

<210> SEQ ID NO 36
<211> LENGTH: 105
<212> TYPE: PRT
<213> ORGANISM: Artificial Sequence
<220> FEATURE:
<223> OTHER INFORMATION: Fcab FS17-33-296 CH3 domain

<400> SEQUENCE: 36

Gly Gln Pro Arg Glu Pro Gln Val Tyr Thr Leu Pro Pro Ser Arg Asp
1               5                   10                  15

Glu Ser Gly Tyr Trp Val Ser Leu Thr Cys Leu Val Lys Gly Phe Tyr
                20                  25                  30

Pro Ser Asp Ile Val Val Glu Trp Glu Ser Asn Gly Glu Pro Gln Tyr
            35                  40                  45

Trp Ala Lys Thr Thr Pro Pro Val Leu Asp Ser Asp Gly Ser Phe Phe
    50                  55                  60

Leu Tyr Ser Lys Leu Thr Val Ser Asn Trp Arg Trp Gln Val Asp Asp
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys
            100                 105

<210> SEQ ID NO 37
<211> LENGTH: 221
<212> TYPE: PRT
<213> ORGANISM: Artificial Sequence
<220> FEATURE:
<223> OTHER INFORMATION: Fcab FS17-33-296 with LALA mutation

<400> SEQUENCE: 37

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
    115                 120                 125

Pro Ser Arg Asp Glu Ser Gly Tyr Trp Val Ser Leu Thr Cys Leu Val
130                 135                 140

Lys Gly Phe Tyr Pro Ser Asp Ile Val Val Glu Trp Glu Ser Asn Gly
145                 150                 155                 160

Glu Pro Gln Tyr Trp Ala Lys Thr Thr Pro Val Leu Asp Ser Asp
                165                 170                 175

Gly Ser Phe Phe Leu Tyr Ser Lys Leu Thr Val Ser Asn Trp Arg Trp
            180                 185                 190

Gln Val Asp Asp Phe Ser Cys Ser Val Met His Glu Ala Leu His Asn
        195                 200                 205

His Tyr Thr Gln Lys Ser Leu Ser Leu Ser Pro Gly Lys
    210                 215                 220

<210> SEQ ID NO 38
<211> LENGTH: 221
<212> TYPE: PRT
<213> ORGANISM: Artificial Sequence
<220> FEATURE:
<223> OTHER INFORMATION: Fcab FS17-33-296 without LALA mutation

<400> SEQUENCE: 38

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Ser Gly Tyr Trp Val Ser Leu Thr Cys Leu Val
    130                 135                 140

Lys Gly Phe Tyr Pro Ser Asp Ile Val Val Glu Trp Glu Ser Asn Gly
145                 150                 155                 160

Glu Pro Gln Tyr Trp Ala Lys Thr Thr Pro Val Leu Asp Ser Asp
                165                 170                 175

Gly Ser Phe Phe Leu Tyr Ser Lys Leu Thr Val Ser Asn Trp Arg Trp
            180                 185                 190

Gln Val Asp Asp Phe Ser Cys Ser Val Met His Glu Ala Leu His Asn
        195                 200                 205

His Tyr Thr Gln Lys Ser Leu Ser Leu Ser Pro Gly Lys
    210                 215                 220

<210> SEQ ID NO 39
<211> LENGTH: 105
<212> TYPE: PRT
<213> ORGANISM: Artificial Sequence
<220> FEATURE:
<223> OTHER INFORMATION: Fcab FS17-33-334 CH3 domain

<400> SEQUENCE: 39

Gly Gln Pro Arg Glu Pro Gln Val Tyr Thr Leu Pro Pro Ser Arg Asp
1               5                   10                  15

Glu Ser Gly Tyr Trp Val Ser Leu Thr Cys Leu Val Lys Gly Phe Tyr

```
                    20                  25                  30

Pro Ser Asp Ile Ala Val Glu Trp Glu Ser Asn Gly Glu Pro Gln Tyr
        35                  40                  45

Trp Ala Lys Thr Thr Pro Pro Val Leu Asp Ser Asp Gly Ser Phe Phe
 50                  55                  60

Leu Tyr Ser Lys Leu Thr Val Ser Asn Trp Arg Trp Gln Leu Asp Asp
 65                  70                  75                  80

Phe Ser Cys Ser Val Met His Glu Ala Leu His Asn His Tyr Thr Gln
                 85                  90                  95

Lys Ser Leu Ser Leu Ser Pro Gly Lys
            100                 105

<210> SEQ ID NO 40
<211> LENGTH: 221
<212> TYPE: PRT
<213> ORGANISM: Artificial Sequence
<220> FEATURE:
<223> OTHER INFORMATION: Fcab FS17-33-334 with LALA mutation

<400> SEQUENCE: 40

Thr Cys Pro Pro Cys Pro Ala Pro Glu Ala Ala Gly Gly Pro Ser Val
 1               5                  10                  15

Phe Leu Phe Pro Pro Lys Pro Lys Asp Thr Leu Met Ile Ser Arg Thr
                20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Ser Gly Tyr Trp Val Ser Leu Thr Cys Leu Val
        130                 135                 140

Lys Gly Phe Tyr Pro Ser Asp Ile Ala Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
                180                 185                 190

Gln Leu Asp Asp Phe Ser Cys Ser Val Met His Glu Ala Leu His Asn
            195                 200                 205

His Tyr Thr Gln Lys Ser Leu Ser Leu Ser Pro Gly Lys
        210                 215                 220

<210> SEQ ID NO 41
<211> LENGTH: 221
<212> TYPE: PRT
<213> ORGANISM: Artificial Sequence
<220> FEATURE:
<223> OTHER INFORMATION: Fcab FS17-33-334 without LALA mutation

<400> SEQUENCE: 41
```

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Asp Glu Ser Gly Tyr Trp Val Ser Leu Thr Cys Leu Val
        130                 135                 140

Lys Gly Phe Tyr Pro Ser Asp Ile Ala Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
                180                 185                 190

Gln Leu Asp Asp Phe Ser Cys Ser Val Met His Glu Ala Leu His Asn
            195                 200                 205

His Tyr Thr Gln Lys Ser Leu Ser Leu Ser Pro Gly Lys
    210                 215                 220

<210> SEQ ID NO 42
<211> LENGTH: 4
<212> TYPE: PRT
<213> ORGANISM: Artificial Sequence
<220> FEATURE:
<223> OTHER INFORMATION: Fcab FS17-33-449 CH3 domain AB loop

<400> SEQUENCE: 42

Thr Gly Tyr Trp
1

<210> SEQ ID NO 43
<211> LENGTH: 10
<212> TYPE: PRT
<213> ORGANISM: Artificial Sequence
<220> FEATURE:
<223> OTHER INFORMATION: Fcab FS17-33-449 CH3 domain EF loop

<400> SEQUENCE: 43

Ser Asn Trp Arg Trp Gln Leu Asp Asp Val
1               5                   10

<210> SEQ ID NO 44
<211> LENGTH: 106
<212> TYPE: PRT
<213> ORGANISM: Artificial Sequence
<220> FEATURE:
<223> OTHER INFORMATION: Fcab FS17-33-449 CH3 domain

<400> SEQUENCE: 44

Gly Gln Pro Arg Glu Pro Gln Val Tyr Thr Leu Pro Pro Ser Arg Asp

```
                1               5                   10                  15
Glu Thr Gly Tyr Trp Val Ser Leu Thr Cys Leu Val Lys Gly Phe Tyr
                20                  25                  30

Pro Ser Asp Ile Ala Val Glu Trp Glu Ser Asn Gly Glu Pro Gln Tyr
                35                  40                  45

Trp Ala Lys Thr Thr Pro Pro Val Leu Asp Ser Asp Gly Ser Phe Phe
 50                  55                  60

Leu Tyr Ser Lys Leu Thr Val Ser Asn Trp Arg Trp Gln Leu Asp Asp
 65                  70                  75                  80

Val Phe Ser Cys Ser Val Met His Glu Ala Leu His Asn His Tyr Thr
                85                  90                  95

Gln Lys Ser Leu Ser Leu Ser Pro Gly Lys
                100                 105
```

<210> SEQ ID NO 45
<211> LENGTH: 222
<212> TYPE: PRT
<213> ORGANISM: Artificial Sequence
<220> FEATURE:
<223> OTHER INFORMATION: Fcab FS17-33-449 with LALA mutation

<400> SEQUENCE: 45

```
Thr Cys Pro Pro Cys Pro Ala Pro Glu Ala Ala Gly Gly Pro Ser Val
 1               5                  10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
                35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Arg Asp Glu Thr Gly Tyr Trp Val Ser Leu Thr Cys Leu Val
130                 135                 140

Lys Gly Phe Tyr Pro Ser Asp Ile Ala Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
                180                 185                 190

Gln Leu Asp Asp Val Phe Ser Cys Ser Val Met His Glu Ala Leu His
                195                 200                 205

Asn His Tyr Thr Gln Lys Ser Leu Ser Leu Ser Pro Gly Lys
    210                 215                 220
```

<210> SEQ ID NO 46
<211> LENGTH: 222
<212> TYPE: PRT
<213> ORGANISM: Artificial Sequence
<220> FEATURE:
<223> OTHER INFORMATION: Fcab FS17-33-449 without LALA mutation

<400> SEQUENCE: 46

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Thr Gly Tyr Trp Val Ser Leu Thr Cys Leu Val
130                 135                 140

Lys Gly Phe Tyr Pro Ser Asp Ile Ala Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
            180                 185                 190

Gln Leu Asp Asp Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 47
<211> LENGTH: 4
<212> TYPE: PRT
<213> ORGANISM: Artificial Sequence
<220> FEATURE:
<223> OTHER INFORMATION: Fcab FS17-33-451 CH3 domain AB loop

<400> SEQUENCE: 47

Glu Gly Tyr Trp
1

<210> SEQ ID NO 48
<211> LENGTH: 106
<212> TYPE: PRT
<213> ORGANISM: Artificial Sequence
<220> FEATURE:
<223> OTHER INFORMATION: Fcab FS17-33-451 CH3 domain

<400> SEQUENCE: 48

Gly Gln Pro Arg Glu Pro Gln Val Tyr Thr Leu Pro Pro Ser Arg Asp
1               5                   10                  15

Glu Glu Gly Tyr Trp Val Ser Leu Thr Cys Leu Val Lys Gly Phe Tyr
            20                  25                  30

Pro Ser Asp Ile Ala Val Glu Trp Glu Ser Asn Gly Glu Pro Gln Tyr
        35                  40                  45

Trp Ala Lys Thr Thr Pro Pro Val Leu Asp Ser Asp Gly Ser Phe Phe
    50                  55                  60

Leu Tyr Ser Lys Leu Thr Val Ser Asn Trp Arg Trp Gln Leu Asp Asp
65                  70                  75                  80

Val Phe Ser Cys Ser Val Met His Glu Ala Leu His Asn His Tyr Thr
                85                  90                  95

Gln Lys Ser Leu Ser Leu Ser Pro Gly Lys
            100                 105

<210> SEQ ID NO 49
<211> LENGTH: 222
<212> TYPE: PRT
<213> ORGANISM: Artificial Sequence
<220> FEATURE:
<223> OTHER INFORMATION: Fcab FS17-33-451 with LALA mutation

<400> SEQUENCE: 49

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Glu Gly Tyr Trp Val Ser Leu Thr Cys Leu Val
130                 135                 140

Lys Gly Phe Tyr Pro Ser Asp Ile Ala Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
            180                 185                 190

Gln Leu Asp Asp Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 50
<211> LENGTH: 222
<212> TYPE: PRT
<213> ORGANISM: Artificial Sequence
<220> FEATURE:
<223> OTHER INFORMATION: Fcab FS17-33-451 without LALA mutation

<400> SEQUENCE: 50

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu

```
                35                  40                  45
Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Glu Gly Tyr Trp Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
            180                 185                 190

Gln Leu Asp Asp Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 51
<211> LENGTH: 448
<212> TYPE: PRT
<213> ORGANISM: Artificial Sequence
<220> FEATURE:
<223> OTHER INFORMATION: heavy chain of the IgG1 4420 antibody with LALA
      mutation

<400> SEQUENCE: 51

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

-continued

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 52
<211> LENGTH: 219
<212> TYPE: PRT
<213> ORGANISM: Artificial Sequence
<220> FEATURE:
<223> OTHER INFORMATION: light chain of the IgG1 4420 antibody with LALA
      mutation

<400> SEQUENCE: 52

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95
```

Thr His Val Pro Trp Thr Phe Gly Gly Gly Thr Lys Leu Glu Ile Lys
             100                 105                 110

Arg Thr Val Ala Ala Pro Ser Val Phe Ile Phe Pro Pro Ser Asp Glu
             115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
             180                 185                 190

Lys His Lys Val Tyr Ala Cys Glu Val Thr His Gln Gly Leu Ser Ser
             195                 200                 205

Pro Val Thr Lys Ser Phe Asn Arg Gly Glu Cys
             210                 215

<210> SEQ ID NO 53
<211> LENGTH: 446
<212> TYPE: PRT
<213> ORGANISM: Artificial Sequence
<220> FEATURE:
<223> OTHER INFORMATION: heavy chain of the HelD1.3 antibody with LALA
      mutation

<400> SEQUENCE: 53

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe

```
              225                 230                 235                 240
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 54
<211> LENGTH: 214
<212> TYPE: PRT
<213> ORGANISM: Artificial Sequence
<220> FEATURE:
<223> OTHER INFORMATION: light chain of the HelD1.3 antibody with LALA
      mutation

<400> SEQUENCE: 54

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
                35                  40                  45

Tyr Asn Ala Lys Thr Leu Ala Asp Gly Val Pro Ser Arg Phe Ser Gly
50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 55
<211> LENGTH: 460
<212> TYPE: PRT
<213> ORGANISM: Artificial Sequence
<220> FEATURE:
<223> OTHER INFORMATION: heavy chain of the MSL109 antibody with LALA mutation

<400> SEQUENCE: 55

```
Glu Glu Gln Val Leu Glu Ser Gly Gly Gly Leu Val Lys Pro Gly Gly
1               5                   10                  15

Ser Leu Arg Leu Ser Cys Ala Ala Ser Gly Phe Thr Phe Ser Pro Tyr
            20                  25                  30

Ser Val Phe Trp Val Arg Gln Ala Pro Gly Lys Gly Leu Glu Trp Val
        35                  40                  45

Ser Ser Ile Asn Ser Asp Ser Thr Tyr Lys Tyr Tyr Ala Asp Ser Val
    50                  55                  60

Lys Gly Arg Phe Thr Ile Ser Arg Asp Asn Ala Glu Asn Ser Ile Phe
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Tyr Ala Phe Ser Ser Gly Ser Leu Ser Asp
            100                 105                 110

Tyr Tyr Tyr Gly Leu Asp Val Trp Gly Gln Gly Thr Thr Val Ile Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Ala Ala Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285
```

```
Asn Trp Tyr Val Asp Gly Val Glu Val His Asn Ala Lys Thr Lys Pro
            290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
            355                 360                 365

Asp Glu Leu Thr Lys Asn Gln Val Ser Leu Thr Cys Leu Val Lys Gly
370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
    450                 455                 460

<210> SEQ ID NO 56
<211> LENGTH: 219
<212> TYPE: PRT
<213> ORGANISM: Artificial Sequence
<220> FEATURE:
<223> OTHER INFORMATION: light chain of the MSL109 antibody with LALA
      mutation

<400> SEQUENCE: 56

Asp Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Tyr Leu Asp Trp Tyr Val Gln Lys Pro Gly Gln Ser
        35                  40                  45

Pro Gln Leu Leu Ile Tyr Leu Ala Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Val Gly Val Tyr Tyr Cys Met Gln Ala
                85                  90                  95

Leu Gln Ile Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

```
                180             185                  190
Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 57
<211> LENGTH: 448
<212> TYPE: PRT
<213> ORGANISM: Artificial Sequence
<220> FEATURE:
<223> OTHER INFORMATION: heavy chain of the S70 antibody with LALA
      mutation

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 58
<211> LENGTH: 214
<212> TYPE: PRT
<213> ORGANISM: Artificial Sequence
<220> FEATURE:
<223> OTHER INFORMATION: light chain of the S70 antibody with LALA
      mutation

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 59
```

```
<211> LENGTH: 448
<212> TYPE: PRT
<213> ORGANISM: Artificial Sequence
<220> FEATURE:
<223> OTHER INFORMATION: heavy chain of the S1 antibody with LALA
      mutation

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
```

```
                    370                 375                 380
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 60
<211> LENGTH: 214
<212> TYPE: PRT
<213> ORGANISM: Artificial Sequence
<220> FEATURE:
<223> OTHER INFORMATION: light chain of the S1 antibody with LALA
      mutation

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Phe Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 290
<212> TYPE: PRT
<213> ORGANISM: Homo sapiens

<400> SEQUENCE: 61

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
```

-continued

```
                20                  25                  30
Gly Ser Asn Met Thr Ile Glu Cys Lys Phe Pro Val Glu Lys Gln Leu
            35                  40                  45
Asp Leu Ala Ala Leu Ile Val Tyr Trp Glu Met Glu Asp Lys Asn Ile
    50                  55                  60
Ile Gln Phe Val His Gly Glu Glu Asp Leu Lys Val Gln His Ser Ser
65                  70                  75                  80
Tyr Arg Gln Arg Ala Arg Leu Leu Lys Asp Gln Leu Ser Leu Gly Asn
                85                  90                  95
Ala Ala Leu Gln Ile Thr Asp Val Lys Leu Gln Asp Ala Gly Val Tyr
            100                 105                 110
Arg Cys Met Ile Ser Tyr Gly Gly Ala Asp Tyr Lys Arg Ile Thr Val
                115                 120                 125
Lys Val Asn Ala Pro Tyr Asn Lys Ile Asn Gln Arg Ile Leu Val Val
            130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
                195                 200                 205
Cys Thr Phe Arg Arg Leu Asp Pro Glu Glu Asn His Thr Ala Glu Leu
            210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
            260                 265                 270
Gly Ile Gln Asp Thr Asn Ser Lys Lys Gln Ser Asp Thr His Leu Glu
            275                 280                 285
Glu Thr
    290

<210> SEQ ID NO 62
<211> LENGTH: 290
<212> TYPE: PRT
<213> ORGANISM: Artificial Sequence
<220> FEATURE:
<223> OTHER INFORMATION: murine PD-L1

<400> SEQUENCE: 62

Met Arg Ile Phe Ala Gly Ile Ile Phe Thr Ala Cys Cys His Leu Leu
1               5                   10                  15
Arg Ala Phe Thr Ile Thr Ala Pro Lys Asp Leu Tyr Val Val Glu Tyr
                20                  25                  30
Gly Ser Asn Val Thr Met Glu Cys Arg Phe Pro Val Glu Arg Glu Leu
            35                  40                  45
Asp Leu Leu Ala Leu Val Val Tyr Trp Glu Lys Glu Asp Glu Gln Val
    50                  55                  60
Ile Gln Phe Val Ala Gly Glu Glu Asp Leu Lys Pro Gln His Ser Asn
65                  70                  75                  80
Phe Arg Gly Arg Ala Ser Leu Pro Lys Asp Gln Leu Leu Lys Gly Asn
```

```
                85                  90                  95
Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
            115                 120                 125

Lys Val Asn Ala Pro Tyr Arg Lys Ile Asn Gln Arg Ile Ser Val Asp
        130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
            195                 200                 205

Thr Phe Trp Arg Ser Gln Pro Gly Gln Asn His Thr Ala Glu Leu Ile
        210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
            275                 280                 285

Glu Thr
    290

<210> SEQ ID NO 63
<211> LENGTH: 290
<212> TYPE: PRT
<213> ORGANISM: Artificial Sequence
<220> FEATURE:
<223> OTHER INFORMATION: cynomolgus PD-L1

<400> SEQUENCE: 63

Met Arg Ile Phe Ala Val Phe Ile Phe Thr Ile Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Thr Ser Leu Ile Val Tyr Trp Glu Met Glu Asp Lys Asn Ile
        50                  55                  60

Ile Gln Phe Val His Gly Glu Asp Leu Lys Val Gln His Ser Asn
65                  70                  75                  80

Tyr Arg Gln Arg Ala Gln Leu Leu Lys Asp Gln Leu Ser Leu Gly Asn
                85                  90                  95

Ala Ala Leu Arg Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
```

```
            145                 150                 155                 160
Pro Lys Ala Glu Val Ile Trp Thr Ser Ser Asp His Gln Val Leu Ser
                    165                 170                 175

Gly Lys Thr Thr Thr Thr Asn Ser Lys Arg Glu Glu Lys Leu Leu Asn
            180                 185                 190

Val Thr Ser Thr Leu Arg Ile Asn Thr Thr Ala Asn Glu Ile Phe Tyr
            195                 200                 205

Cys Ile Phe Arg Arg Leu Asp Pro Glu Glu Asn His Thr Ala Glu Leu
            210                 215                 220

Val Ile Pro Glu Leu Pro Leu Ala Leu Pro Pro Asn Glu Arg Thr His
225                 230                 235                 240

Leu Val Ile Leu Gly Ala Ile Phe Leu Leu Leu Gly Val Ala Leu Thr
                    245                 250                 255

Phe Ile Phe Tyr Leu Arg Lys Gly Arg Met Met Asp Met Lys Lys Cys
                    260                 265                 270

Gly Ile Arg Val Thr Asn Ser Lys Lys Gln Arg Asp Thr Gln Leu Glu
                    275                 280                 285

Glu Thr
    290

<210> SEQ ID NO 64
<211> LENGTH: 288
<212> TYPE: PRT
<213> ORGANISM: Homo sapiens

<400> SEQUENCE: 64

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                    165                 170                 175

Leu Leu Gly Ser Leu Val Leu Leu Val Trp Val Leu Ala Val Ile Cys
                    180                 185                 190

Ser Arg Ala Ala Arg Gly Thr Ile Gly Ala Arg Arg Thr Gly Gln Pro
                    195                 200                 205

Leu Lys Glu Asp Pro Ser Ala Val Pro Val Phe Ser Val Asp Tyr Gly
            210                 215                 220
```

```
Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
        260                 265                 270

Ser Ala Gln Pro Leu Arg Pro Glu Asp Gly His Cys Ser Trp Pro Leu
    275                 280                 285

<210> SEQ ID NO 65
<211> LENGTH: 288
<212> TYPE: PRT
<213> ORGANISM: Homo sapiens

<400> SEQUENCE: 65

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 66
<211> LENGTH: 306
<212> TYPE: PRT
<213> ORGANISM: Artificial Sequence
```

<220> FEATURE:
<223> OTHER INFORMATION: mouse CD80

<400> SEQUENCE: 66

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
            260                 265                 270

Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
    290                 295                 300

Phe Leu
305

<210> SEQ ID NO 67
<211> LENGTH: 448
<212> TYPE: PRT
<213> ORGANISM: Artificial Sequence
<220> FEATURE:
<223> OTHER INFORMATION: heavy chain of the Ipilimumab antibody without
      LALA mutation

<400> SEQUENCE: 67

Gln Val Gln Leu Val Glu Ser Gly Gly Gly Val Val Gln Pro Gly Arg
1               5                   10                  15

-continued

```
Ser Leu Arg Leu Ser Cys Ala Ala Ser Gly Phe Thr Phe Ser Ser Tyr
         20                  25                  30
Thr Met His Trp Val Arg Gln Ala Pro Gly Lys Gly Leu Glu Trp Val
         35                  40                  45
Thr Phe Ile Ser Tyr Asp Gly Asn Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Ile Tyr Tyr Cys
                 85                  90                  95
Ala Arg Thr Gly Trp Leu Gly Pro Phe Asp Tyr Trp Gly Gln Gly Thr
             100                 105                 110
Leu Val Thr Val Ser Ser Ala Ser Thr Lys Gly Pro Ser Val Phe Pro
         115                 120                 125
Leu Ala Pro Ser Ser Lys Ser Thr Ser Gly Gly Thr Ala Ala Leu Gly
     130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                 165                 170                 175
Ser Ser Gly Leu Tyr Ser Leu Ser Ser Val Val Thr Val Pro Ser Ser
             180                 185                 190
Ser Leu Gly Thr Gln Thr Tyr Ile Cys Asn Val Asn His Lys Pro Ser
         195                 200                 205
Asn Thr Lys Val Asp Lys Lys Val Glu Pro Lys Ser Cys Asp Lys Thr
     210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                 245                 250                 255
Thr Pro Glu Val Thr Cys Val Val Val Asp Val Ser His Glu Asp Pro
             260                 265                 270
Glu Val Lys Phe Asn Trp Tyr Val Asp Gly Val Glu Val His Asn Ala
         275                 280                 285
Lys Thr Lys Pro Arg Glu Glu Gln Tyr Asn Ser Thr Tyr Arg Val Val
     290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                 325                 330                 335
Ile Ser Lys Ala Lys Gly Gln Pro Arg Glu Pro Gln Val Tyr Thr Leu
             340                 345                 350
Pro Pro Ser Arg Asp Glu Leu Thr Lys Asn Gln Val Ser Leu Thr Cys
         355                 360                 365
Leu Val Lys Gly Phe Tyr Pro Ser Asp Ile Ala Val Glu Trp Glu Ser
     370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                 405                 410                 415
Arg Trp Gln Gln Gly Asn Val Phe Ser Cys Ser Val Met His Glu Ala
             420                 425                 430
Leu His Asn His Tyr Thr Gln Lys Ser Leu Ser Leu Ser Pro Gly Lys
```

-continued

<210> SEQ ID NO 68
<211> LENGTH: 215
<212> TYPE: PRT
<213> ORGANISM: Artificial Sequence
<220> FEATURE:
<223> OTHER INFORMATION: light chain of the Ipilimumab antibody without
     LALA mutation

<400> SEQUENCE: 68

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 69
<211> LENGTH: 15
<212> TYPE: PRT
<213> ORGANISM: Homo sapiens

<400> SEQUENCE: 69

Glu Pro Lys Ser Cys Asp Lys Thr His Thr Cys Pro Pro Cys Pro
1               5                   10                  15

<210> SEQ ID NO 70
<211> LENGTH: 10
<212> TYPE: PRT
<213> ORGANISM: Artificial Sequence
<220> FEATURE:
<223> OTHER INFORMATION: Fcab FS17-33-488 CH3 domain EF loop

<400> SEQUENCE: 70

Ser Asn Trp Arg Trp Gln Leu Gly Asp Ala
1               5                   10

```
<210> SEQ ID NO 71
<211> LENGTH: 106
<212> TYPE: PRT
<213> ORGANISM: Artificial Sequence
<220> FEATURE:
<223> OTHER INFORMATION: Fcab FS17-33-488 CH3 domain

<400> SEQUENCE: 71

Gly Gln Pro Arg Glu Pro Gln Val Tyr Thr Leu Pro Pro Ser Arg Asp
1               5                   10                  15

Glu Glu Gly Tyr Trp Val Ser Leu Thr Cys Leu Val Lys Gly Phe Tyr
            20                  25                  30

Pro Ser Asp Ile Ala Val Glu Trp Glu Ser Asn Gly Glu Pro Gln Tyr
        35                  40                  45

Trp Ala Lys Thr Thr Pro Pro Val Pro Asp Ser Asp Gly Thr Phe Phe
    50                  55                  60

Leu Tyr Ser Lys Leu Thr Val Ser Asn Trp Arg Trp Gln Leu Gly Asp
65                  70                  75                  80

Ala Phe Ser Cys Ser Val Met His Glu Ala Leu Arg Asn His Tyr Thr
                85                  90                  95

Gln Lys Ser Leu Ser Leu Ser Pro Gly Lys
            100                 105

<210> SEQ ID NO 72
<211> LENGTH: 222
<212> TYPE: PRT
<213> ORGANISM: Artificial Sequence
<220> FEATURE:
<223> OTHER INFORMATION: Fcab FS17-33-488 with LALA mutation

<400> SEQUENCE: 72

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Glu Gly Tyr Trp Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Glu Pro Gln Tyr Trp Ala Lys Thr Thr Pro Pro Val Pro Asp Ser Asp
                165                 170                 175

Gly Thr Phe Phe Leu Tyr Ser Lys Leu Thr Val Ser Asn Trp Arg Trp
            180                 185                 190

Gln Leu Gly Asp Ala Phe Ser Cys Ser Val Met His Glu Ala Leu Arg
        195                 200                 205
```

-continued

```
Asn His Tyr Thr Gln Lys Ser Leu Ser Leu Ser Pro Gly Lys
    210                 215                 220
```

<210> SEQ ID NO 73
<211> LENGTH: 222
<212> TYPE: PRT
<213> ORGANISM: Artificial Sequence
<220> FEATURE:
<223> OTHER INFORMATION: Fcab FS17-33-488 without LALA mutation

<400> SEQUENCE: 73

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Glu Gly Tyr Trp Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Glu Pro Gln Tyr Trp Ala Lys Thr Thr Pro Pro Val Pro Asp Ser Asp
                165                 170                 175

Gly Thr Phe Phe Leu Tyr Ser Lys Leu Thr Val Ser Asn Trp Arg Trp
            180                 185                 190

Gln Leu Gly Asp Ala Phe Ser Cys Ser Val Met His Glu Ala Leu Arg
        195                 200                 205

Asn His Tyr Thr Gln Lys Ser Leu Ser Leu Ser Pro Gly Lys
    210                 215                 220
```

<210> SEQ ID NO 74
<211> LENGTH: 10
<212> TYPE: PRT
<213> ORGANISM: Artificial Sequence
<220> FEATURE:
<223> OTHER INFORMATION: Fcab FS17-33-539 CH3 domain EF loop

<400> SEQUENCE: 74

```
Ser Asn Trp Arg Trp Gln Leu Gly Asp Val
1               5                   10
```

<210> SEQ ID NO 75
<211> LENGTH: 106
<212> TYPE: PRT
<213> ORGANISM: Artificial Sequence
<220> FEATURE:
<223> OTHER INFORMATION: Fcab FS17-33-539 CH3 domain

<400> SEQUENCE: 75

```
Gly Gln Pro Arg Glu Pro Gln Val Tyr Thr Leu Pro Pro Ser Arg Asp
1               5                   10                  15

Glu Thr Gly Tyr Trp Val Ser Leu Thr Cys Leu Val Lys Gly Phe Tyr
            20                  25                  30

Pro Ser Asp Ile Ala Val Glu Trp Glu Ser Asn Gly Glu Pro Gln Tyr
            35                  40                  45

Trp Ala Lys Thr Thr Pro Pro Val Leu Asp Ser Asp Gly Ser Phe Phe
50                  55                  60

Leu Tyr Ser Lys Leu Thr Val Ser Asn Trp Arg Trp Gln Leu Gly Asp
65                  70                  75                  80

Val Phe Ser Cys Ser Val Met His Glu Ala Leu Arg Asn His Tyr Thr
                85                  90                  95

Gln Lys Ser Leu Ser Leu Ser Pro Gly Lys
            100                 105
```

<210> SEQ ID NO 76
<211> LENGTH: 222
<212> TYPE: PRT
<213> ORGANISM: Artificial Sequence
<220> FEATURE:
<223> OTHER INFORMATION: Fcab FS17-33-539 with LALA mutation

<400> SEQUENCE: 76

```
Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Thr Gly Tyr Trp Val Ser Leu Thr Cys Leu Val
130                 135                 140

Lys Gly Phe Tyr Pro Ser Asp Ile Ala Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
            180                 185                 190

Gln Leu Gly Asp Val Phe Ser Cys Ser Val Met His Glu Ala Leu Arg
            195                 200                 205

Asn His Tyr Thr Gln Lys Ser Leu Ser Leu Ser Pro Gly Lys
    210                 215                 220
```

<210> SEQ ID NO 77
<211> LENGTH: 222
<212> TYPE: PRT
<213> ORGANISM: Artificial Sequence
<220> FEATURE:

<223> OTHER INFORMATION: Fcab FS17-33-539 without LALA mutation

<400> SEQUENCE: 77

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
            85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Thr Gly Tyr Trp Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
            180                 185                 190

Gln Leu Gly Asp Val Phe Ser Cys Ser Val Met His Glu Ala Leu Arg
        195                 200                 205

Asn His Tyr Thr Gln Lys Ser Leu Ser Leu Ser Pro Gly Lys
    210                 215                 220

<210> SEQ ID NO 78
<211> LENGTH: 10
<212> TYPE: PRT
<213> ORGANISM: Artificial Sequence
<220> FEATURE:
<223> OTHER INFORMATION: Fcab FS17-33-548 CH3 domain EF loop

<400> SEQUENCE: 78

Ser Asn Trp Arg Trp Gln Leu Gly Asp Val
1               5                   10

<210> SEQ ID NO 79
<211> LENGTH: 106
<212> TYPE: PRT
<213> ORGANISM: Artificial Sequence
<220> FEATURE:
<223> OTHER INFORMATION: Fcab FS17-33-548 CH3 domain

<400> SEQUENCE: 79

Gly Gln Pro Arg Glu Pro Gln Val Tyr Thr Leu Pro Pro Ser Arg Asp
1               5                   10                  15

Glu Glu Gly Tyr Trp Val Ser Leu Thr Cys Leu Val Lys Gly Phe Tyr
            20                  25                  30

Pro Ser Asp Ile Ala Val Glu Trp Glu Ser Asn Gly Glu Pro Gln Tyr
        35                  40                  45

Trp Ala Lys Thr Thr Pro Pro Val Leu Asp Ser Asp Gly Ser Phe Phe

```
                    50                  55                  60
Leu Tyr Ser Lys Leu Thr Val Ser Asn Trp Arg Trp Gln Leu Gly Asp
 65                  70                  75                  80

Val Phe Ser Cys Ser Val Met His Glu Ala Leu His Asn His Tyr Thr
                     85                  90                  95

Gln Lys Ser Leu Ser Leu Ser Pro Gly Lys
                100                 105

<210> SEQ ID NO 80
<211> LENGTH: 222
<212> TYPE: PRT
<213> ORGANISM: Artificial Sequence
<220> FEATURE:
<223> OTHER INFORMATION: Fcab FS17-33-548 with LALA mutation

<400> SEQUENCE: 80

Thr Cys Pro Pro Cys Pro Ala Pro Glu Ala Ala Gly Gly Pro Ser Val
  1               5                  10                  15

Phe Leu Phe Pro Pro Lys Pro Lys Asp Thr Leu Met Ile Ser Arg Thr
                 20                  25                  30

Pro Glu Val Thr Cys Val Val Val Asp Val Ser His Glu Asp Pro Glu
             35                  40                  45

Val Lys Phe Asn Trp Tyr Val Asp Gly Val Glu Val His Asn Ala Lys
         50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Glu Gly Tyr Trp Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Glu Pro Gln Tyr Trp Ala Lys Thr Thr Pro Pro Val Leu Asp Ser Asp
                165                 170                 175

Gly Ser Phe Phe Leu Tyr Ser Lys Leu Thr Val Ser Asn Trp Arg Trp
            180                 185                 190

Gln Leu Gly Asp Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 81
<211> LENGTH: 222
<212> TYPE: PRT
<213> ORGANISM: Artificial Sequence
<220> FEATURE:
<223> OTHER INFORMATION: Fcab FS17-33-548 without LALA mutation

<400> SEQUENCE: 81

Thr Cys Pro Pro Cys Pro Ala Pro Glu Leu Leu Gly Gly Pro Ser Val
  1               5                  10                  15

Phe Leu Phe Pro Pro Lys Pro Lys Asp Thr Leu Met Ile Ser Arg Thr
                 20                  25                  30
```

```
Pro Glu Val Thr Cys Val Val Asp Val Ser His Glu Asp Pro Glu
            35              40              45

Val Lys Phe Asn Trp Tyr Val Asp Gly Val Glu Val His Asn Ala Lys
    50              55              60

Thr Lys Pro Arg Glu Glu Gln Tyr Asn Ser Thr Tyr Arg Val Val Ser
65              70              75              80

Val Leu Thr Val Leu His Gln Asp Trp Leu Asn Gly Lys Glu Tyr Lys
                85              90              95

Cys Lys Val Ser Asn Lys Ala Leu Pro Ala Pro Ile Glu Lys Thr Ile
                100             105             110

Ser Lys Ala Lys Gly Gln Pro Arg Glu Pro Gln Val Tyr Thr Leu Pro
            115             120             125

Pro Ser Arg Asp Glu Glu Gly Tyr Trp Val Ser Leu Thr Cys Leu Val
130             135             140

Lys Gly Phe Tyr Pro Ser Asp Ile Ala Val Glu Trp Glu Ser Asn Gly
145             150             155             160

Glu Pro Gln Tyr Trp Ala Lys Thr Thr Pro Pro Val Leu Asp Ser Asp
                165             170             175

Gly Ser Phe Phe Leu Tyr Ser Lys Leu Thr Val Ser Asn Trp Arg Trp
                180             185             190

Gln Leu Gly Asp Val Phe Ser Cys Ser Val Met His Glu Ala Leu His
            195             200             205

Asn His Tyr Thr Gln Lys Ser Leu Ser Leu Ser Pro Gly Lys
            210             215             220

<210> SEQ ID NO 82
<211> LENGTH: 110
<212> TYPE: PRT
<213> ORGANISM: Artificial Sequence
<220> FEATURE:
<223> OTHER INFORMATION: CH2 domain with LALA mutation and P114A
      mutation

<400> SEQUENCE: 82

Ala Pro Glu Ala Ala Gly Gly Pro Ser Val Phe Leu Phe Pro Pro Lys
1               5               10              15

Pro Lys Asp Thr Leu Met Ile Ser Arg Thr Pro Glu Val Thr Cys Val
            20              25              30

Val Val Asp Val Ser His Glu Asp Pro Glu Val Lys Phe Asn Trp Tyr
            35              40              45

Val Asp Gly Val Glu Val His Asn Ala Lys Thr Lys Pro Arg Glu Glu
    50              55              60

Gln Tyr Asn Ser Thr Tyr Arg Val Val Ser Val Leu Thr Val Leu His
65              70              75              80

Gln Asp Trp Leu Asn Gly Lys Glu Tyr Lys Cys Lys Val Ser Asn Lys
                85              90              95

Ala Leu Ala Ala Pro Ile Glu Lys Thr Ile Ser Lys Ala Lys
            100             105             110
```

FC BINDING FRAGMENTS COMPRISING A PD-L1 ANTIGEN-BINDING SITE

RELATED APPLICATIONS

This Application is a national stage filing under 35 U.S.C. § 371 of International Patent Application Serial No. PCT/EP2018/085834, filed Dec. 19, 2018, which claims priority under 35 U.S.C. § 119(e) to U.S. Provisional Application No. 62/657,195, filed Apr. 13, 2018, and U.S. Provisional Application No. 62/607,686, filed Dec. 19, 2017, the entire content of which are incorporated herein by reference in their entireties.

FIELD OF THE INVENTION

The present invention relates to specific binding members which bind to programmed death-ligand 1 (PD-L1). The specific binding members preferably comprise a PD-L1 antigen-binding site located in structural loops of a constant domain of the specific binding member. The specific binding members of the invention find application, for example, in the treatment of cancer, as well as infectious diseases and inflammation.

BACKGROUND TO THE INVENTION

Programmed cell death 1 (PD-1) and its ligands PD-L1 (CD274, B7-H1) and PD-L2 (B7-DC) deliver inhibitory signals that regulate the balance between T cell activation, tolerance, and immunopathology. PD-L1 is constitutively or transiently expressed on multiple immune cell types and certain tumour cells.

PD-L1 is a type I transmembrane protein with two Ig-like domains within the extracellular region, a transmembrane domain and a short cytoplasmic domain. The complete human PD-L1 sequence can be found under UniProt accession no. Q9NZQ7. The cytoplasmic domain has no known signal transduction motif suggesting that there is no signaling by PD-L1 on interaction of the ligand with its receptor. The molecular weight of human PD-L1 is 40 kDa (290 amino acids) and it shares 70% and 93% amino acid identity with the murine and cynomolgus orthologs of PD-L1, respectively.

Human PD-L1 binds to its receptor PD-1 with an affinity ($K_D$) of 770 nM. PD-1 is expressed on activated T cells, B cells and myeloid cells, and modulates activation or inhibition of cellular immune responses. Binding of PD-L1 to PD-1 delivers an inhibitory signal, reducing cytokine production and proliferation of T cells. Consequently, PD-L1 expression by cells can mediate protection against cytotoxic T lymphocyte (CTL) killing and is a regulatory mechanism that dampens chronic immune responses during viral infections. Cancer, as a chronic and pro-inflammatory disease, subverts this immune-protective pathway through up-regulation of PD-L1 expression to evade the host immune response. In the context of an active immune response, IFNγ also upregulates the expression of PD-L1.

PD-L1 also mediates immune suppression through interaction with another protein, B7.1 (also known as CD80), blocking its ability to deliver one of the secondary signals of activation on T cells through CD28.

PD-L1 expression has been shown in a wide variety of solid tumours. Of 654 samples examined in one study, spanning 19 tumours from different sites, 14% were PD-L1 positive. The highest PD-L1 positive frequencies were seen in head and neck (31%), cervical (29%), cancer of unknown primary origin (CUP; 28%), glioblastoma multiforme (GBM; 25%), bladder cancer (21%), oesophageal cancer (20%), triple negative (TN) breast cancer (18%), and hepatocarcinoma (15%) (Grosso et al, 2013). Tumour-associated expression of PD-L1 has been shown to confer immune resistance and potentially protect tumour cells from T cell mediated apoptosis.

Therapies targeting PD-L1 have shown excellent results in murine in vivo studies. In the B16 murine model of melanoma, treatment with anti-PD-L1 combined with either GVAX or FVAX vaccination strategies resulted in a significant effect both on survival (30 days for control vs 52 days for PD-L1-treated) and percentage of tumour-free (5%) animals upon conclusion of the study (Curran et al., 2010). Anti-PD-L1 therapy has also been used to study the mechanism of immune suppression in the P815 murine mastoma model. P815 cells injected into mice normally trigger a strong immune response, which results in their rejection. When PD-L1 is expressed on P815 cells, these cells escape immune attack, which in turn can be negated through administration of anti-PD-L1 antibodies (Iwai et al, 2002). It is evident that targeting the PD-1/PD-L1 axis in immunogenic human cancers (Herbst et al., 2014) results in a survival advantage through stimulation of an anti-cancer immune response (Wolchok et al., 2013; Larkin et al., 2015).

Clinical trials have shown the clinical benefit of targeting PD-L1 in patients leading to the approval of three anti-PD-L1 targeting monoclonal antibodies to date.

Atezolizumab (Tecentriq™) is a humanised IgG1 antibody which binds to PD-L1. It is in clinical trials as a monotherapy and also in combination with other biologic and/or small molecule therapies for treatment of solid cancers, including colorectal cancer, breast cancer, non-small-cell lung cancer, small cell lung cancer, bladder cancer, and renal cell carcinoma.

Avelumab (Bavencio™) is a fully human IgG1 antibody which binds to PD-L1 and is undergoing clinical testing in a number of cancers including bladder cancer, gastric cancer, head and neck cancer, mesothelioma, non-small-cell lung carcinoma, ovarian cancer, renal cancer, Merkel-cell carcinoma, and metastatic urothelial carcinoma (UC).

Durvalumab (Imfinzi™) is a human IgG1 antibody which binds to PD-L1 and is being tested in clinical trials alone or in combination with tremelimumab in squamous cell carcinoma of the head and neck, bladder cancer, pancreatic cancer and with other biologic and small molecules in trials for additional solid cancers such as gastric cancers, melanoma and unresectable hepatocellular carcinoma.

Durvalumab has been approved for the treatment of patients with locally advanced or metastatic urothelial carcinoma and unresectable stage III NSCLC.

Further anti-PD-L1 antibodies, including BMS-936559 (NCT00729664), have been tested in clinical trials, and others are in preclinical testing.

Infectious diseases show many parallels with oncology. It is thought that the role of PD-L1 in immune regulation could be harnessed to maximise the immune response against pathogens. Immunomodulation in infectious disease is an emerging area of medicine and early reviews suggest that PD-L1 blockade may improve biological responses to infection, in particular, helping to counteract T cell exhaustion, manage immune-mediated clearance, and generate long-term immunity (Wykes, M. N. and Lewin, S. R., 2018).

Furthermore, recent studies also suggest that the PD-1/PD-L1 pathway may be a therapeutic target for the treatment of inflammation, diseases and conditions associated with inflammation, and inflammatory diseases, such as stroke and stroke-related inflammation (Bodhankar et al., 2015), and vascular inflammation or vasculitis, e.g., medium and large vessel vasculitis, or vasculitis of the central and/or peripheral nervous system (Hid Cadena et al., 2018 and Daxini et al., 2018).

Whilst there are various anti-PD-L1 therapeutics in development, current data shows that overall treatment with existing anti-PD-L1 monotherapies results in a response in less than 50% of cancer patients. The spectrum and severity of reported adverse reactions differs between antibodies in clinical testing. To increase the objective response rate (ORR), and/or seek to reduce adverse effects, anti-PD-L1 antibodies may be combined with other biologics, such as antibodies against other checkpoint regulators, as well as with small molecule therapies and other immune system activating approaches, such as tumour vaccines.

Thus, there remains a need in the art for additional molecules which can target PD-L1 and which find application in cancer therapy.

In addition, there also remains a need in the art for additional molecules which can target PD-L1 and which find application in the treatment of infectious diseases.

Furthermore, there also remains a need in the art for additional molecules which can target PD-L1 and which find application in the treatment of inflammation, diseases and conditions associated with inflammation, and inflammatory diseases.

STATEMENTS OF INVENTION

The present inventors have prepared a number of specific binding members comprising a non-native binding site for PD-L1 in the CH3 domain of the specific binding members. These specific binding members were isolated through an initial screen of a naïve CH3 domain phage library, followed by a complex programme of iterative rounds of mutagenesis, screening and selection to isolate variants of the specific binding members initially selected which had improved activity and affinity for PD-L1.

The present inventors found that specific binding members, identified from an initial affinity maturation programme following the initial screen of the naïve CH3 domain phage library, showed increased affinity for PD-L1, as well as increased blocking of the interaction between PD-L1 and its ligand PD-1. However, the selected specific binding members unexpectedly had very weak activity in a T cell activation assay.

Following additional rounds of mutagenesis, screening and selection, the inventors identified specific binding members which not only had high affinity for PD-L1 but also excellent activity in a T cell activation assay. These specific binding members surprisingly comprised CH3 domains which had a deletion in the AB structural loop sequence (located at either residue 14, 15 or 16 of the AB structural loop). The deletion is thought to be an artefact resulting from accidentally truncated mutagenesis primers. Specific binding members comprising such deletions in their structural loop regions are usually removed during the selection process, as deletions rarely result in specific binding members which retain antigen-binding activity. However, as a result of the particular sequence of mutagenesis approaches employed by the present inventors, this truncated AB loop sequence, which was not identified following mutagenesis of the AB loop, is thought to have been present in the output pool from the selections as a rare clone or lower affinity binder. When this truncated AB structural loop sequence was shuffled with the other structural loops, it became the dominant AB structural loop sequence, suggesting a strong contribution of this deletion to the antigen-binding activity and/or structure of the specific binding members following the shuffling of the structural loop sequences. Specific binding members comprising such a deletion in their AB structural loop would not have been identified if a more directed shuffle approach had been employed by the inventors, where the most promising sequences identified from the AB structural loop selections are combined with the most promising sequences from the CD structural loop selections. The inventors found that restoring the deleted residue in the AB structural loop unexpectedly resulted in a significant reduction in the affinity of the resulting specific binding members for PD-L1, demonstrating that the deletion in the AB loop is important for binding to PD-L1.

Further rounds of mutagenesis, screening and selection were performed by the inventors in order to remove potential manufacturing sequence liabilities and to improve the biophysical properties of the selected specific binding members.

The above approach allowed the present inventors to identify a large number of specific binding members which comprise a binding site for PD-L1 in their CH3 domain, and which showed excellent binding to PD-L1, and were either shown, or are expected, to have high activity in T cell activation assays. Based on these characteristics, it is expected that the specific binding members of the invention will find application in the treatment of human cancers, as well as infectious diseases, inflammation, diseases and conditions associated with inflammation, and inflammatory diseases, through inhibition of PD-L1.

The specific binding members were also shown to have a high affinity for cynomolgus PD-L1, which is comparable to the affinity for human PD-L1 and is expected to be useful in the evaluation of the properties of the specific binding members in cynomolgus monkey disease models. The reason for this is that the results obtained are more likely to be predictive of the effects of the specific binding member in human patients than when a specific binding member having a higher variability in its affinity for human and cynomolgus PD-L1 is tested in cynomolgus monkey models.

Thus, in a first aspect the present invention provides a specific binding member which binds to PD-L1, and comprises a PD-L1 antigen-binding site located in a constant domain, such as CL, CH1, CH2 or CH3 domain, preferably a CH1, CH2 or CH3 domain, most preferably a CH3 domain of the specific binding member.

The PD-L1 binding site of the specific binding member of the invention preferably comprises:
  (i) a first sequence located in the AB structural loop at positions 14 to 18 of the CH3 domain, wherein the specific binding member comprises an amino acid deletion at position 14, 15 or 16 of the CH3 domain, and wherein the first sequence consists of:
    (a) amino acid sequence SGYW (SEQ ID NO: 23), or
    (b) a variant of SEQ ID NO: 23, wherein
    the serine (S) is substituted with amino acid A, E, F, G, H, I, L, P, R, T, V, or Y, and/or
    the glycine (G) is substituted with amino acid A, D, E, F, H, K, L, N, P, R, T, V, or Y;
  (ii) a second sequence located in the CD structural loop at positions 45.1 to 78 of the CH3 domain, wherein the second sequence consists of:
    (a) amino acid sequence EPQYWA (SEQ ID NO: 11), or
    (b) a variant of SEQ ID NO: 11, wherein the glutamic acid (E) is substituted with amino acid A, G, H, I, L, N, Q, R, S, or W, and/or the proline (P) is substituted with amino acid A, D, E, G, H, N, Q, W, or Y, and/or the glutamine (Q) is substituted with amino acid H, or N, and/or the tyrosine (Y) is substituted with amino acid A, D, H, T, or V, and/or the alanine (A) is substituted with amino acid D, E, G, L, R, S, or W; and (iii) a third sequence located in the EF structural loop at positions 92 to 100 of the CH3 domain, wherein the third sequence consists of:
(a) amino acid sequence SNWRWQMDD (SEQ ID NO: 19), or
(b) a variant of SEQ ID NO: 19, wherein
the serine (S) at position 92 is substituted with amino acid A, or G, and/or
the asparagine (N) at position 93 is substituted with amino acid A, E, F, G, H, I, K, L, Q, R, S, T, or Y, and/or
the glutamine (Q) at position 97 is substituted with amino acid A, D, E, F, G, H, K, L, N, R, S, or V, and/or
the methionine (M) at position 98 is substituted with amino acid F, I, L, V, W, or Y, and/or
the aspartic acid (D) at position 99 is substituted with amino acid E, A, I, L, R, S, T, V, W, or Y, and/or
the aspartic acid (D) at position 100 is substituted with amino acid A, E, F, I, K, L, N, R, V, W, or Y; and
wherein the amino acid at position 101 of the CH3 domain is valine (V) or is absent;

wherein the amino acid residue numbering is according to the ImMunoGeneTics (IMGT) numbering scheme.

The present invention therefore provides:

[1] A specific binding member which binds to PD-L1, and comprises a PD-L1 antigen-binding site located in a CH3 domain of the specific binding member, wherein the PD-L1 binding site comprises:
(i) a first sequence located in the AB structural loop at positions 14 to 18 of the CH3 domain, wherein the specific binding member comprises an amino acid deletion at position 14, 15 or 16 of the CH3 domain,
(ii) a second sequence located in the CD structural loop at positions 45.1 to 78 of the CH3 domain, and
(iii) a third sequence located in the EF structural loop at positions 92 to 100 of the CH3 domain.

[2] A specific binding member according to [1], wherein the first sequence consists of amino acid sequence SGYW (SEQ ID NO: 23), or a variant thereof.

[3] A specific binding member according to [1] or [2], wherein the second sequence consists of amino acid sequence EPQYWA (SEQ ID NO: 11), or a variant thereof.

[4] A specific binding member according to any one of [1] to [3], wherein the third sequence consists of amino acid sequence SNWRWQMDD (SEQ ID NO: 19), or a variant thereof.

[5] A specific binding member according to any one of [1] to [4], wherein the first sequence consists of a variant of SEQ ID NO: 23, in which the serine (S) is substituted with amino acid A.

[6] A specific binding member according to any one of [1] to [4], wherein the first sequence consists of a variant of SEQ ID NO: 23, in which the serine (S) is substituted with amino acid E.

[7] A specific binding member according to any one of [1] to [4], wherein the first sequence consists of a variant of SEQ ID NO: 23, in which the serine (S) is substituted with amino acid F.

[8] A specific binding member according to any one of [1] to [4], wherein the first sequence consists of a variant of SEQ ID NO: 23, in which the serine (S) is substituted with amino acid G.

[9] A specific binding member according to any one of [1] to [4], wherein the first sequence consists of a variant of SEQ ID NO: 23, in which the serine (S) is substituted with amino acid H.

[10] A specific binding member according to any one of [1] to [4], wherein the first sequence consists of a variant of SEQ ID NO: 23, in which the serine (S) is substituted with amino acid I.

[11] A specific binding member according to any one of [1] to [4], wherein the first sequence consists of a variant of SEQ ID NO: 23, in which the serine (S) is substituted with amino acid L.

[12] A specific binding member according to any one of [1] to [4], wherein the first sequence consists of a variant of SEQ ID NO: 23, in which the serine (S) is substituted with amino acid P.

[13] A specific binding member according to any one of [1] to [4], wherein the first sequence consists of a variant of SEQ ID NO: 23, in which the serine (S) is substituted with amino acid R.

[14] A specific binding member according to any one of [1] to [4], wherein the first sequence consists of a variant of SEQ ID NO: 23, in which the serine (S) is substituted with amino acid T.

[15] A specific binding member according to any one of [1] to [4], wherein the first sequence consists of a variant of SEQ ID NO: 23, in which the serine (S) is substituted with amino acid V.

[16] A specific binding member according to any one of [1] to [4], wherein the first sequence consists of a variant of SEQ ID NO: 23, in which the serine (S) is substituted with amino acid Y.

[17] A specific binding member according to any one of [1] to [16], wherein the first sequence consists of a variant of SEQ ID NO: 23, in which the glycine (G) is substituted with amino acid A.

[18] A specific binding member according to any one of [1] to [16], wherein the first sequence consists of a variant of SEQ ID NO: 23, in which the glycine (G) is substituted with amino acid D.

[19] A specific binding member according to any one of [1] to [16], wherein the first sequence consists of a variant of SEQ ID NO: 23, in which the glycine (G) is substituted with amino acid E.

[20] A specific binding member according to any one of [1] to [16], wherein the first sequence consists of a variant of SEQ ID NO: 23, in which the glycine (G) is substituted with amino acid F.

[21] A specific binding member according to any one of [1] to [16], wherein the first sequence consists of a variant of SEQ ID NO: 23, in which the glycine (G) is substituted with amino acid H.

[22] A specific binding member according to any one of [1] to [16], wherein the first sequence consists of a variant of SEQ ID NO: 23, in which the glycine (G) is substituted with amino acid K.

[23] A specific binding member according to any one of [1] to [16], wherein the first sequence consists of a variant of SEQ ID NO: 23, in which the glycine (G) is substituted with amino acid L.

[24] A specific binding member according to any one of [1] to [16], wherein the first sequence consists of a variant of SEQ ID NO: 23, in which the glycine (G) is substituted with amino acid N.

[25] A specific binding member according to any one of [1] to [16], wherein the first sequence consists of a variant of SEQ ID NO: 23, in which the glycine (G) is substituted with amino acid P.

[26] A specific binding member according to any one of [1] to [16], wherein the first sequence consists of a variant of SEQ ID NO: 23, in which the glycine (G) is substituted with amino acid R.

[27] A specific binding member according to any one of [1] to [16], wherein the first sequence consists of a variant of SEQ ID NO: 23, in which the glycine (G) is substituted with amino acid T.

[28] A specific binding member according to any one of [1] to [16], wherein the first sequence consists of a variant of SEQ ID NO: 23, in which the glycine (G) is substituted with amino acid V.

[29] A specific binding member according to any one of [1] to [16], wherein the first sequence consists of a variant of SEQ ID NO: 23, in which the glycine (G) is substituted with amino acid Y.

[30] A specific binding member according to any one of [1] to [29], wherein the second sequence consists of a variant of SEQ ID NO: 11, in which the glutamic acid (E) is substituted with amino acid A.

[31] A specific binding member according to any one of [1] to [29], wherein the second sequence consists of a variant of SEQ ID NO: 11, in which the glutamic acid (E) is substituted with amino acid G.

[32] A specific binding member according to any one of [1] to [29], wherein the second sequence consists of a variant of SEQ ID NO: 11, in which the glutamic acid (E) is substituted with amino acid H.

[33] A specific binding member according to any one of [1] to [29], wherein the second sequence consists of a variant of SEQ ID NO: 11, in which the glutamic acid (E) is substituted with amino acid I.

[34] A specific binding member according to any one of [1] to [29], wherein the second sequence consists of a variant of SEQ ID NO: 11, in which the glutamic acid (E) is substituted with amino acid L.

[35] A specific binding member according to any one of [1] to [29], wherein the second sequence consists of a variant of SEQ ID NO: 11, in which the glutamic acid (E) is substituted with amino acid N.

[36] A specific binding member according to any one of [1] to [29], wherein the second sequence consists of a variant of SEQ ID NO: 11, in which the glutamic acid (E) is substituted with amino acid Q.

[37] A specific binding member according to any one of [1] to [29], wherein the second sequence consists of a variant of SEQ ID NO: 11, in which the glutamic acid (E) is substituted with amino acid R.

[38] A specific binding member according to any one of [1] to [29], wherein the second sequence consists of a variant of SEQ ID NO: 11, in which the glutamic acid (E) is substituted with amino acid S.

[39] A specific binding member according to any one of [1] to [29], wherein the second sequence consists of a variant of SEQ ID NO: 11, in which the glutamic acid (E) is substituted with amino acid W.

[40] A specific binding member according to any one of [1] to [39], wherein the second sequence consists of a variant of SEQ ID NO: 11, in which the proline (P) is substituted with amino acid A.

[41] A specific binding member according to any one of [1] to [39], wherein the second sequence consists of a variant of SEQ ID NO: 11, in which the proline (P) is substituted with amino acid D.

[42] A specific binding member according to any one of [1] to [39], wherein the second sequence consists of a variant of SEQ ID NO: 11, in which the proline (P) is substituted with amino acid E.

[43] A specific binding member according to any one of [1] to [39], wherein the second sequence consists of a variant of SEQ ID NO: 11, in which the proline (P) is substituted with amino acid G.

[44] A specific binding member according to any one of [1] to [39], wherein the second sequence consists of a variant of SEQ ID NO: 11, in which the proline (P) is substituted with amino acid H.

[45] A specific binding member according to any one of [1] to [39], wherein the second sequence consists of a variant of SEQ ID NO: 11, in which the proline (P) is substituted with amino acid N.

[46] A specific binding member according to any one of [1] to [39], wherein the second sequence consists of a variant of SEQ ID NO: 11, in which the proline (P) is substituted with amino acid Q.

[47] A specific binding member according to any one of [1] to [39], wherein the second sequence consists of a variant of SEQ ID NO: 11, in which the proline (P) is substituted with amino acid W.

[48] A specific binding member according to any one of [1] to [39], wherein the second sequence consists of a variant of SEQ ID NO: 11, in which the proline (P) is substituted with amino acid Y.

[49] A specific binding member according to any one of [1] to [48], wherein the second sequence consists of a variant of SEQ ID NO: 11, in which the glutamine (Q) is substituted with amino acid H.

[50] A specific binding member according to any one of [1] to [48], wherein the second sequence consists of a variant of SEQ ID NO: 11, in which the glutamine (Q) is substituted with amino acid N.

[51] A specific binding member according to any one of [1] to [50], wherein the second sequence consists of a variant of SEQ ID NO: 11, in which the tyrosine (Y) is substituted with amino acid A.

[52] A specific binding member according to any one of [1] to [50], wherein the second sequence consists of a variant of SEQ ID NO: 11, in which the tyrosine (Y) is substituted with amino acid D.

[53] A specific binding member according to any one of [1] to [50], wherein the second sequence consists of a variant of SEQ ID NO: 11, in which the tyrosine (Y) is substituted with amino acid H.

[54] A specific binding member according to any one of [1] to [50], wherein the second sequence consists of a variant of SEQ ID NO: 11, in which the tyrosine (Y) is substituted with amino acid T.

[55] A specific binding member according to any one of [1] to [50], wherein the second sequence consists of a variant of SEQ ID NO: 11, in which the tyrosine (Y) is substituted with amino acid V.

[56] A specific binding member according to any one of [1] to [55], wherein the second sequence consists of a variant of SEQ ID NO: 11, in which the alanine (A) is substituted with amino acid D.

[57] A specific binding member according to any one of [1] to [55], wherein the second sequence consists of a variant of SEQ ID NO: 11, in which the alanine (A) is substituted with amino acid E.

[58] A specific binding member according to any one of [1] to [55], wherein the second sequence consists of a variant of SEQ ID NO: 11, in which the alanine (A) is substituted with amino acid G.

[59] A specific binding member according to any one of [1] to [55], wherein the second sequence consists of a variant of SEQ ID NO: 11, in which the alanine (A) is substituted with amino acid L.

[60] A specific binding member according to any one of [1] to [55], wherein the second sequence consists of a variant of SEQ ID NO: 11, in which the alanine (A) is substituted with amino acid R.

[61] A specific binding member according to any one of [1] to [55], wherein the second sequence consists of a variant of SEQ ID NO: 11, in which the alanine (A) is substituted with amino acid S.

[62] A specific binding member according to any one of [1] to [55], wherein the second sequence consists of a variant of SEQ ID NO: 11, in which the alanine (A) is substituted with amino acid W.

[63] A specific binding member according to any one of [1] to [62], wherein the third sequence consists of a variant of SEQ ID NO: 19, in which the serine (S) at position 92 of the CH3 domain is substituted with amino acid A.

[64] A specific binding member according to any one of [1] to [62], wherein the third sequence consists of a variant of SEQ ID NO: 19, in which the serine (S) at position 92 of the CH3 domain is substituted with amino acid G.

[65] A specific binding member according to any one of [1] to [64], wherein the third sequence consists of a variant of SEQ ID NO: 19, in which the asparagine (N) at position 93 of the CH3 domain is substituted with amino acid A.

[66] A specific binding member according to any one of [1] to [64], wherein the third sequence consists of a variant of SEQ ID NO: 19, in which the asparagine (N) at position 93 of the CH3 domain is substituted with amino acid E.

[67] A specific binding member according to any one of [1] to [64], wherein the third sequence consists of a variant of SEQ ID NO: 19, in which the asparagine (N) at position 93 of the CH3 domain is substituted with amino acid F.

[68] A specific binding member according to any one of [1] to [64], wherein the third sequence consists of a variant of SEQ ID NO: 19, in which the asparagine (N) at position 93 of the CH3 domain is substituted with amino acid G.

[69] A specific binding member according to any one of [1] to [64], wherein the third sequence consists of a variant of SEQ ID NO: 19, in which the asparagine (N) at position 93 of the CH3 domain is substituted with amino acid H.

[70] A specific binding member according to any one of [1] to [64], wherein the third sequence consists of a variant of SEQ ID NO: 19, in which the asparagine (N) at position 93 of the CH3 domain is substituted with amino acid I.

[71] A specific binding member according to any one of [1] to [64], wherein the third sequence consists of a variant of SEQ ID NO: 19, in which the asparagine (N) at position 93 of the CH3 domain is substituted with amino acid K.

[72] A specific binding member according to any one of [1] to [64], wherein the third sequence consists of a variant of SEQ ID NO: 19, in which the asparagine (N) at position 93 of the CH3 domain is substituted with amino acid L.

[73] A specific binding member according to any one of [1] to [64], wherein the third sequence consists of a variant of SEQ ID NO: 19, in which the asparagine (N) at position 93 of the CH3 domain is substituted with amino acid Q.

[74] A specific binding member according to any one of [1] to [64], wherein the third sequence consists of a variant of SEQ ID NO: 19, in which the asparagine (N) at position 93 of the CH3 domain is substituted with amino acid R.

[75] A specific binding member according to any one of [1] to [64], wherein the third sequence consists of a variant of SEQ ID NO: 19, in which the asparagine (N) at position 93 of the CH3 domain is substituted with amino acid S.

[76] A specific binding member according to any one of [1] to [64], wherein the third sequence consists of a variant of SEQ ID NO: 19, in which the asparagine (N) at position 93 of the CH3 domain is substituted with amino acid T.

[77] A specific binding member according to any one of [1] to [64], wherein the third sequence consists of a variant of SEQ ID NO: 19, in which the asparagine (N) at position 93 of the CH3 domain is substituted with amino acid Y.

[78] A specific binding member according to any one of [1] to [77], wherein the third sequence consists of a variant of SEQ ID NO: 19, in which the glutamine (Q) at position 97 of the CH3 domain is substituted with amino acid A.

[79] A specific binding member according to any one of [1] to [77], wherein the third sequence consists of a variant of SEQ ID NO: 19, in which the glutamine (Q) at position 97 of the CH3 domain is substituted with amino acid D.

[80] A specific binding member according to any one of [1] to [77], wherein the third sequence consists of a variant of SEQ ID NO: 19, in which the glutamine (Q) at position 97 of the CH3 domain is substituted with amino acid E.

[81] A specific binding member according to any one of [1] to [77], wherein the third sequence consists of a variant of SEQ ID NO: 19, in which the glutamine (Q) at position 97 of the CH3 domain is substituted with amino acid F.

[82] A specific binding member according to any one of [1] to [77], wherein the third sequence consists of a variant of SEQ ID NO: 19, in which the glutamine (Q) at position 97 of the CH3 domain is substituted with amino acid G.

[83] A specific binding member according to any one of [1] to [77], wherein the third sequence consists of a variant of SEQ ID NO: 19, in which the glutamine (Q) at position 97 of the CH3 domain is substituted with amino acid H.

[84] A specific binding member according to any one of [1] to [77], wherein the third sequence consists of a variant of SEQ ID NO: 19, in which the glutamine (Q) at position 97 of the CH3 domain is substituted with amino acid K.

[85] A specific binding member according to any one of [1] to [77], wherein the third sequence consists of a variant of SEQ ID NO: 19, in which the glutamine (Q) at position 97 of the CH3 domain is substituted with amino acid L.

[86] A specific binding member according to any one of [1] to [77], wherein the third sequence consists of a variant of SEQ ID NO: 19, in which the glutamine (Q) at position 97 of the CH3 domain is substituted with amino acid N.

[87] A specific binding member according to any one of [1] to [77], wherein the third sequence consists of a variant of SEQ ID NO: 19, in which the glutamine (Q) at position 97 of the CH3 domain is substituted with amino acid R.

[88] A specific binding member according to any one of [1] to [77], wherein the third sequence consists of a variant of SEQ ID NO: 19, in which the glutamine (Q) at position 97 of the CH3 domain is substituted with amino acid S.

[89] A specific binding member according to any one of [1] to [77], wherein the third sequence consists of a variant of SEQ ID NO: 19, in which the glutamine (Q) at position 97 of the CH3 domain is substituted with amino acid V.

[90] A specific binding member according to any one of [1] to [89], wherein the third sequence consists of a variant of SEQ ID NO: 19, in which the methionine (M) at position 98 of the CH3 domain is substituted with amino acid F.

[91] A specific binding member according to any one of [1] to [89], wherein the third sequence consists of a variant of SEQ ID NO: 19, in which the methionine (M) at position 98 of the CH3 domain is substituted with amino acid I.

[92] A specific binding member according to any one of [1] to [89], wherein the third sequence consists of a variant of SEQ ID NO: 19, in which the methionine (M) at position 98 of the CH3 domain is substituted with amino acid L.

[93] A specific binding member according to any one of [1] to [89], wherein the third sequence consists of a variant of SEQ ID NO: 19, in which the methionine (M) at position 98 of the CH3 domain is substituted with amino acid V.

[94] A specific binding member according to any one of [1] to [89], wherein the third sequence consists of a variant of SEQ ID NO: 19, in which the methionine (M) at position 98 of the CH3 domain is substituted with amino acid W.

[95] A specific binding member according to any one of [1] to [89], wherein the third sequence consists of a variant of SEQ ID NO: 19, in which the methionine (M) at position 98 of the CH3 domain is substituted with amino acid Y.

[96] A specific binding member according to any one of [1] to [95], wherein the third sequence consists of a variant of SEQ ID NO: 19, in which the aspartic acid (D) at position 99 of the CH3 domain is substituted with amino acid E.

[97] A specific binding member according to any one of [1] to [95], wherein the third sequence consists of a variant of SEQ ID NO: 19, in which the aspartic acid (D) at position 99 of the CH3 domain is substituted with amino acid A.

[98] A specific binding member according to any one of [1] to [95], wherein the third sequence consists of a variant of SEQ ID NO: 19, in which the aspartic acid (D) at position 99 of the CH3 domain is substituted with amino acid I.

[99] A specific binding member according to any one of [1] to [95], wherein the third sequence consists of a variant of SEQ ID NO: 19, in which the aspartic acid (D) at position 99 of the CH3 domain is substituted with amino acid L.

[100] A specific binding member according to any one of [1] to [95], wherein the third sequence consists of a variant of SEQ ID NO: 19, in which the aspartic acid (D) at position 99 of the CH3 domain is substituted with amino acid R.

[101] A specific binding member according to any one of [1] to [95], wherein the third sequence consists of a variant of SEQ ID NO: 19, in which the aspartic acid (D) at position 99 of the CH3 domain is substituted with amino acid S.

[102] A specific binding member according to any one of [1] to [95], wherein the third sequence consists of a variant of SEQ ID NO: 19, in which the aspartic acid (D) at position 99 of the CH3 domain is substituted with amino acid T.

[103] A specific binding member according to any one of [1] to [95], wherein the third sequence consists of a variant of SEQ ID NO: 19, in which the aspartic acid (D) at position 99 of the CH3 domain is substituted with amino acid V.

[104] A specific binding member according to any one of [1] to [95], wherein the third sequence consists of a variant of SEQ ID NO: 19, in which the aspartic acid (D) at position 99 of the CH3 domain is substituted with amino acid W.

[105] A specific binding member according to any one of [1] to [95], wherein the third sequence consists of a variant of SEQ ID NO: 19, in which the aspartic acid (D) at position 99 of the CH3 domain is substituted with amino acid Y.

[106] A specific binding member according to any one of [1] to [105], wherein the third sequence consists of a variant of SEQ ID NO: 19, in which the aspartic acid (D) at position 100 of the CH3 domain is substituted with amino acid A.

[107] A specific binding member according to any one of [1] to [105], wherein the third sequence consists of a variant of SEQ ID NO: 19, in which the aspartic acid (D) at position 100 of the CH3 domain is substituted with amino acid E.

[108] A specific binding member according to any one of [1] to [105], wherein the third sequence consists of a variant of SEQ ID NO: 19, in which the aspartic acid (D) at position 100 of the CH3 domain is substituted with amino acid F.

[109] A specific binding member according to any one of [1] to [105], wherein the third sequence consists of a variant of SEQ ID NO: 19, in which the aspartic acid (D) at position 100 of the CH3 domain is substituted with amino acid I.

[110] A specific binding member according to any one of [1] to [105], wherein the third sequence consists of a variant of SEQ ID NO: 19, in which the aspartic acid (D) at position 100 of the CH3 domain is substituted with amino acid K.

[111] A specific binding member according to any one of [1] to [105], wherein the third sequence consists of a variant of SEQ ID NO: 19, in which the aspartic acid (D) at position 100 of the CH3 domain is substituted with amino acid L.

[112] A specific binding member according to any one of [1] to [105], wherein the third sequence consists of a variant of SEQ ID NO: 19, in which the aspartic acid (D) at position 100 of the CH3 domain is substituted with amino acid N.

[113] A specific binding member according to any one of [1] to [105], wherein the third sequence consists of a variant of SEQ ID NO: 19, in which the aspartic acid (D) at position 100 of the CH3 domain is substituted with amino acid R.

[114] A specific binding member according to any one of [1] to [105], wherein the third sequence consists of a variant of SEQ ID NO: 19, in which the aspartic acid (D) at position 100 of the CH3 domain is substituted with amino acid V.

[115] A specific binding member according to any one of [1] to [105], wherein the third sequence consists of a variant of SEQ ID NO: 19, in which the aspartic acid (D) at position 100 of the CH3 domain is substituted with amino acid W.

[116] A specific binding member according to any one of [1] to [105], wherein the third sequence consists of a variant of SEQ ID NO: 19, in which the aspartic acid (D) at position 100 of the CH3 domain is substituted with amino acid Y.

[117] A specific binding member according to any one of [1] to [116], wherein the amino acid at position 101 of the CH3 domain is valine (V).

[118] A specific binding member according to any one of [1] to [116], wherein the amino acid at position 101 of the CH3 domain is absent.

[119] A specific binding member according to any one of [1] to [118], wherein the amino acid at position 38 of the CH3 domain is valine (V).

[120] A specific binding member according to any one of [1] to [118], wherein the amino acid at position 38 of the CH3 domain is alanine (A).

Amino acids may be referred to by their one letter or three letter codes, or by their full name. The one and three letter codes, as well as the full names, of each of the twenty standard amino acids are set out below.

| Amino acid | One letter code | Three letter code |
|---|---|---|
| alanine | A | ala |
| arginine | R | arg |
| asparagine | N | asn |
| aspartic acid | D | asp |
| cysteine | C | cys |
| glutamic acid | E | glu |
| glutamine | Q | gln |
| glycine | G | gly |
| histidine | H | his |
| isoleucine | I | ile |
| leucine | L | leu |
| lysine | K | lys |
| methionine | M | met |
| phenylalanine | F | phe |
| proline | P | pro |
| serine | S | ser |
| threonine | T | thr |
| tryptophan | W | trp |
| tyrosine | Y | tyr |
| valine | V | val |

The PD-L1 binding site of the specific binding member of the invention preferably comprises a first sequence, second sequence and third sequence, wherein:

the first sequence consists of:
  (a) amino acid sequence SGYW (SEQ ID NO: 23), or
  (b) a variant of SEQ ID NO: 23, wherein the serine (S) is substituted with amino acid E, or T;

the second sequence consists of amino acid sequence EPQYWA (SEQ ID NO: 11); and the third sequence consists of:
  (a) amino acid sequence SNWRWQMDD (SEQ ID NO: 19), or
  (b) a variant of SEQ ID NO: 19, wherein the methionine (M) at position 98 is substituted with amino acid I, L, or V; and/or wherein the amino acid at position 101 of the CH3 domain is valine (V) or is absent.

In a preferred embodiment, the binding site of the specific binding member of the invention comprises the first sequence, second sequence and third sequence of Fcab FS17-33-116, wherein the first sequence has the sequence set forth in SEQ ID NO: 23, the second sequence has the sequence set forth in SEQ ID NO: 11, and the third sequence has the sequence set forth in SEQ ID NO: 19.

In another preferred embodiment, the binding site of the specific binding member of the invention comprises the first sequence, second sequence and third sequence of Fcab FS17-33-288, wherein the first sequence has the sequence set forth in SEQ ID NO: 23, the second sequence has the sequence set forth in SEQ ID NO: 11, and the third sequence has the sequence set forth in SEQ ID NO: 27.

In another preferred embodiment, the binding site of the specific binding member of the invention comprises the first sequence, second sequence and third sequence of Fcab FS17-33-289 and Fcab FS17-33-334, wherein the first sequence has the sequence set forth in SEQ ID NO: 23, the second sequence has the sequence set forth in SEQ ID NO: 11, and the third sequence has the sequence set forth in SEQ ID NO: 31.

In another preferred embodiment, the binding site of the specific binding member of the invention comprises the first sequence, second sequence and third sequence of Fcab FS17-33-296, wherein the first sequence has the sequence set forth in SEQ ID NO: 23, the second sequence has the sequence set forth in SEQ ID NO: 11, and the third sequence has the sequence set forth in SEQ ID NO: 35.

In another preferred embodiment, the binding site of the specific binding member of the invention comprises the first sequence, second sequence and third sequence of Fcab FS17-33-449, wherein the first sequence has the sequence set forth in SEQ ID NO: 42, the second sequence has the sequence set forth in SEQ ID NO: 11, and the third sequence has the sequence set forth in SEQ ID NO: 43.

In another preferred embodiment, the binding site of the specific binding member of the invention comprises the first sequence, second sequence and third sequence of Fcab FS17-33-451, wherein the first sequence has the sequence set forth in SEQ ID NO: 47, the second sequence has the sequence set forth in SEQ ID NO: 11, and the third sequence has the sequence set forth in SEQ ID NO: 43.

In addition to the experimental work described above, the present inventors performed a further mutagenesis programme in order to identify specific binding members comprising a non-native binding site for PD-L1 in the CH3 domain of the specific binding member which had an enhanced melting temperature and thus are expected to be more stable. This enhanced stability is expected to be beneficial in the manufacture and storage of the specific binding members.

Specifically, the present inventors surprisingly found that reversion of the aspartic acid (D) residue at position 99 of the CH3 domain of a specific binding member of the invention to the wild-type glycine (G) residue increased the melting temperature of the specific binding member.

In addition to increasing the melting temperature, this amino acid reversion has the added advantage that it reduces the mutational burden of the resulting specific binding member. The present inventors further found that substitution of the histidine (H) residue at position 113 of the CH3 domain of the specific binding member with an arginine (R) residue, in addition to the reversion at position 99, also resulted in a specific binding member with an increased melting temperature of the specific binding members. Both of these mutations arose independently twice, indicating that these amino acid changes may be important for the increase in the melting temperature of the specific binding members.

Thus, in a preferred embodiment the specific binding member of the invention comprises a PD-L1 binding site comprising a first, second and third sequence as disclosed herein, wherein the third sequence is located in the EF structural loop, preferably at positions 92 to 100 of the CH3 domain, and consists of a variant of SEQ ID NO: 19, wherein the aspartic acid (D) at position 99 is substituted with glycine (G), more preferably, where the aspartic acid (D) at position 99 is substituted with glycine (G) and the methionine (M) at position 98 is substituted with leucine (L).

In addition, the histidine (H) at position 113 of the CH3 domain of a specific binding member of the invention may be substituted with arginine (R). The specific binding member may further comprise the following additional mutations in the CH3 domain:
  (i) the leucine (L) at position 84.1 may be substituted with proline (P); and/or
  (ii) the serine (S) at position 85.3 may be substituted with threonine (T); and/or
  (iii) the amino acid at position 101 may be alanine (A).

The present invention thus further provides:

[121] A specific binding member according to any one of [1] to [95] or [106] to [120] above, wherein the third sequence consists of a variant of SEQ ID NO: 19, in which the aspartic acid (D) at position 99 of the CH3 domain is substituted with amino acid G.

[122] A specific binding member according to any one of [1] to [116] or [119] to [121] above, wherein the amino acid at position 101 of the CH3 domain is alanine (A).

[123] A specific binding member according to any one of [1] to [122] above, wherein the amino acid at position 113 of the CH3 domain is arginine (R).

[124] A specific binding member according to any one of [1] to [123] above, wherein the amino acid at position 84.1 of the CH3 domain is proline (P).

[125] A specific binding member according to any one of [1] to [124] above, wherein the amino acid at position 85.3 of the CH3 domain is threonine (T).

In a preferred embodiment, the PD-L1 binding site of the specific binding member of the invention comprises the first sequence, second sequence and third sequence of Fcab FS17-33-488, wherein the first sequence has the sequence set forth in SEQ ID NO: 47, the second sequence has the sequence set forth in SEQ ID NO: 11, and the third sequence has the sequence set forth in SEQ ID NO: 70, wherein the residues at positions 84.1, 85.3, 101 and 113 of the CH3 domain of the specific binding member are proline (P), threonine (T), alanine (A) and arginine (R), respectively.

In a further preferred embodiment, the PD-L1 binding site of the specific binding member of the invention comprises the first sequence, second sequence and third sequence of Fcab FS17-33-539, wherein the first sequence has the sequence set forth in SEQ ID NO: 42, the second sequence has the sequence set forth in SEQ ID NO: 11, and the third sequence has the sequence set forth in SEQ ID NO: 74 and the residue at position 113 of the CH3 domain of the specific binding member is arginine (R).

In a yet further preferred embodiment, the specific binding member comprises the first sequence, second sequence and third sequence of Fcab FS17-33-548, wherein the first sequence has the sequence set forth in SEQ ID NO: 47, the second sequence has the sequence set forth in SEQ ID NO: 11, and the third sequence has the sequence set forth in SEQ ID NO: 78.

The binding site of the specific binding member of the invention may comprise a total of up to twelve, up to eleven, up to ten, up to nine, up to eight, up to seven, up to six, up to five, up to four, up to three, up to two, or one (further) amino acid modifications(s) in a first, second and third sequence, as disclosed herein. In a preferred embodiment, the specific binding member may comprise a total of up to three, up to two, or one (further) amino acid modifications(s) in a first, second and third sequence, as disclosed herein. In a more preferred embodiment, the specific binding member may comprise a total of up to two, or one (further) amino acid modification(s) in a first, second and third sequence, as disclosed herein. The total number of modifications in a first, second and third sequence refers to the total number of modifications made in these sequences combined.

The binding site of the specific binding member of the invention may comprise up to two, or one (further) amino acid modification(s) in a first sequence, as disclosed herein. In addition, or alternatively, the specific binding member may comprise up to five, up to four, up to three, up to two, or one (further) amino acid modification(s) in a second sequence, as disclosed herein. In addition, or alternatively, the binding site of the specific binding member of the invention may comprise up to six, up to five, up to four, up to three, up to two, or one (further) amino acid modification(s) in a third sequence, as disclosed herein.

In a preferred embodiment, the binding site of the specific binding member of the invention may comprise up to two, or one (further) amino acid modification(s) in a first sequence and/or up to two, or one (further) amino acid modification(s) in a third sequence, as disclosed herein. In a more preferred embodiment, the binding member may comprise one (further) amino acid modification in a first sequence and/or one (further) amino acid modification in a third sequence, as disclosed herein.

In a preferred embodiment, the binding site of the specific binding member of the invention comprises one (further) amino acid modification in a first, second or third sequence, as disclosed herein.

The binding site of the specific binding member of the invention may comprise a third sequence in which the methionine (M) at position 98 is substituted with amino acid L. In addition, the binding site of the specific binding member of the invention may comprise one, two or three, preferably one or two, more preferably one, further amino acid modification(s) in the first, second or third sequence.

Where the specific binding member of the invention comprises one or more additional modifications in a first sequence, the amino acid deletion at position 14, 15 or 16 of the CH3 domain is preferably maintained and/or the amino acids at positions 17, 18 of the CH3 domain are preferably unmodified compared with the parent sequence.

Where the specific binding member of the invention comprises one or more additional modifications in a second sequence, the amino acid(s) at position 77, and optionally position 45.3, of the CH3 domain is (are) preferably unmodified compared with the parent sequence.

Where the specific binding member of the invention comprises one or more additional modifications in a third sequence, the amino acid(s) at position 94, and optionally position 92, of the CH3 domain is (are) preferably unmodified compared with the parent sequence.

A modification may be an amino acid substitution, deletion or insertion. Preferably, the modification is a substitution.

In a preferred embodiment, the amino acid at position 101 of the CH3 domain of the specific binding member is valine (V).

In an alternative preferred embodiment, the amino acid at position 101 of the CH3 domain of the specific binding member is alanine (A).

The present inventors showed that certain residues in the AB and EF loops, as well as the framework region could be converted back to the wild-type (WT) residue (see FIG. 1) with a minimal effect on the off-rate (koff) of the specific binding member when bound to PD-L1, while reducing the mutational burden of the specific binding member.

Thus, in a preferred embodiment, the binding site of the specific binding member of the invention comprises a first sequence with:
  a substitution of the serine (S) with amino acid T and/or
  a substitution the glycine (G) with amino acid K.

In another preferred embodiment, the binding site of the specific binding member of the invention comprises a third sequence with:
  a substitution of the asparagine (N) at position 93 with amino acid K, and/or
  a substitution of the aspartic acid (D) at position 100 with amino acid N.

The amino acid at position 38 of the CH3 domain of the specific binding member may be a valine or alanine residue, preferably an alanine residue.

The sequence of the CH3 domain of the specific binding member, other than the sequences of the PD-L1 antigen-binding site, is not particularly limited. Preferably, the CH3 domain is a human immunoglobulin G domain, such as a human IgG1, IgG2, IgG3, or IgG4 CH3 domain, most preferably a human IgG1 CH3 domain. The sequences of human IgG1, IgG2, IgG3, or IgG4 CH3 domains are known in the art.

In a preferred embodiment, the specific binding member comprises the CH3 domain set forth in SEQ ID NO: 24, 28, 32, 36, 39, 44, or 48, more preferably the CH3 domain set forth in SEQ ID NO: 28, 32, 36, 39, 44, or 48, most preferably the CH3 domain set forth in SEQ ID NO: 32, 44, or 48.

In a further most preferred embodiment, the specific binding member comprises the CH3 domain set forth in SEQ ID NO: 71, 75 or 79.

Alternatively, the specific binding member may comprise a CH3 domain with an amino acid sequence which has at least 70%, at least 75%, at least 80%, at least 85%, at least 90%, at least 95%, at least 96%, at least 97%, at least 98%, or at least 99% sequence identity to the sequence set forth in SEQ ID NO: 24, 28, 32, 36, 39, 44, or 48, preferably SEQ ID NO: 28, 32, 36, 39, 44, or 48, most preferably the CH3 domain set forth in SEQ ID NO: 32, 44, or 48.

As a further most preferred embodiment, the specific binding member comprises a CH3 domain with an amino acid sequence which has at least 70%, at least 75%, at least 80%, at least 85%, at least 90%, at least 95%, at least 96%, at least 97%, at least 98%, or at least 99% sequence identity to the sequence set forth in SEQ ID NO: 71, 75 or 79.

The specific binding member may further comprise a CH2 domain. The CH2 domain is preferably located at the N-terminus of the CH3 domain, as in the case in a human IgG molecule. The CH2 domain of the specific binding member is preferably the CH2 domain of human IgG1, IgG2, IgG3, or IgG4, more preferably the CH2 domain of human IgG1. The sequences of human IgG domains are known in the art. In a preferred embodiment, the specific binding member comprises an IgG CH2 domain with the sequence set forth in SEQ ID NO: 5 or 6, or a CH2 domain with an amino acid sequence which has at least 70%, at least 75%, at least 80%, at least 85%, at least 90%, at least 95%, at least 96%, at least 97%, at least 98%, or at least 99% sequence identity to the sequence set forth in SEQ ID NO: 5 or 6. Alternatively, the specific binding member comprises an IgG CH2 domain with the sequence set forth in SEQ ID NO: 82, or a CH2 domain with an amino acid sequence which has at least 70%, at least 75%, at least 80%, at least 85%, at least 90%, at least 95%, at least 96%, at least 97%, at least 98%, or at least 99% sequence identity to the sequence set forth in SEQ ID NO: 82.

In a preferred embodiment, the specific binding member comprises (i) the CH3 domain set forth in SEQ ID NO: 24, 28, 32, 36, 39, 44, 48, 71, 75 or 79 more preferably the CH3 domain set forth in SEQ ID NO: 28, 32, 36, 39, 44, 48, 71, 75 or 79 most preferably the CH3 domain set forth in SEQ ID NO: 32, 44, 48, 71, 75 or 79, and (ii) the CH2 domain set forth in SEQ ID NO: 5.

In an alternative preferred embodiment, the specific binding member comprises (i) the CH3 domain set forth in SEQ ID NO: 24, 28, 32, 36, 39, 44, 48, 71, 75 or 79 more preferably the CH3 domain set forth in SEQ ID NO: 28, 32, 36, 39, 44, 48, 71, 75 or 79 most preferably the CH3 domain set forth in SEQ ID NO: 32, 44, 48, 71, 75 or 79, and (ii) the CH2 domain set forth in SEQ ID NO: 6.

Preferably, the specific binding member comprises an immunoglobulin hinge region, or part thereof, at the N-terminus of the CH2 domain. The immunoglobulin hinge region allows the two CH2-CH3 domain sequences to associate and form a dimer. Preferably, the hinge region, or part thereof, is a human IgG1, IgG2, IgG3 or IgG4 hinge region, or part thereof. More preferably, the hinge region, or part thereof, is an IgG1 hinge region, or part thereof. The sequence of the human IgG1 hinge region is shown in SEQ ID NO: 69. A suitable truncated hinge region which may form part of specific binding member is shown in SEQ ID NO: 7. This hinge region was present in the Fcab molecules tested in the Examples, whereas a full-length hinge region was present in mock mAb$^2$ format. Thus, the specific binding member preferably comprises an immunoglobulin hinge region, or part thereof, at the N-terminus of the CH2 domain, wherein the hinge region has the sequence set forth in SEQ ID NO: 69 or SEQ ID NO: 7, or wherein the hinge region has an amino acid sequence which has at least 70%, at least 75%, at least 80%, at least 85%, at least 90%, at least 95%, at least 96%, at least 97%, at least 98%, or at least 99% sequence identity to the sequence set forth in SEQ ID NO: 69 or 7. Alternatively, the specific binding member may comprises an immunoglobulin hinge region, or part thereof, at the N-terminus of the CH2 domain, wherein the hinge region comprises the sequence set forth in SEQ ID NO: 69, or a fragment thereof, wherein said fragment comprises at least five, at least six, at least seven, at least eight, at least nine or more, at least ten, at least eleven, at least twelve, at least thirteen, or at least fourteen of the amino acid residues of SEQ ID NO: 69.

In a preferred embodiment, the specific binding member comprises (i) the CH3 domain set forth in SEQ ID NO: 24, 28, 32, 36, 39, 44, 48, 71, 75 or 79 more preferably the CH3 domain set forth in SEQ ID NO: 28, 32, 36, 39, 44, 48, 71, 75 or 79 most preferably the CH3 domain set forth in SEQ ID NO: 32, 44, 48, 71, 75 or 79, (ii) the CH2 domain set forth in SEQ ID NO: 5, and (ii) an immunoglobulin hinge region, or part thereof, at the N-terminus of the CH2 domain, wherein the immunoglobulin hinge region has the sequence set forth in SEQ ID NO: 69.

In an alternative preferred embodiment, the specific binding member comprises (i) the CH3 domain set forth in SEQ ID NO: 24, 28, 32, 36, 39, 44, 48, 71, 75 or 79 more preferably the CH3 domain set forth in SEQ ID NO: 28, 32, 36, 39, 44, 48, 71, 75 or 79 most preferably the CH3 domain set forth in SEQ ID NO: 32, 44, 48, 71, 75 or 79, (ii) the CH2 domain set forth in SEQ ID NO: 6, and (iii) an immunoglobulin hinge region, or part thereof, at the N-terminus of the CH2 domain, wherein the immunoglobulin hinge region has the sequence set forth in SEQ ID NO: 69.

In a preferred embodiment, the specific binding member comprises the sequence set forth in SEQ ID NO: 25, 26, 29, 30, 33, 34, 37, 38, 40, 41, 45, 46, 49, or 50, or a sequence which has at least 70%, at least 75%, at least 80%, at least 85%, at least 90%, at least 95%, at least 96%, at least 97%, at least 98%, or at least 99% sequence identity to the sequence set forth in SEQ ID NO: 25, 26, 29, 33, 34, 30, 37, 38, 40, 41, 45, 46, 49, or 50. More preferably, the specific binding member comprises the sequence set forth in SEQ ID NO: 29, 30, 33, 34, 37, 38, 40, 41, 45, 46, 49, or 50, or a sequence which has at least 70%, at least 75%, at least 80%, at least 85%, at least 90%, at least 95%, at least 96%, at least 97%, at least 98%, or at least 99% sequence identity to the sequence set forth in SEQ ID NO: 29, 30, 33, 34, 37, 38, 40, 41, 45, 46, 49, or 50. Most preferably, the specific binding member comprises the sequence set forth in SEQ ID NO: 45, 46, 49, or 50, or a sequence which has at least 70%, at least 75%, at least 80%, at least 85%, at least 90%, at least 95%, at least 96%, at least 97%, at least 98%, or at least 99% sequence identity to the sequence set forth in SEQ ID NO: 45, 46, 49, or 50. In an alternative most preferred embodiment, the specific binding member comprises the sequence set forth in SEQ ID NO: 33, or 34, or a sequence which has at least 70%, at least 75%, at least 80%, at least 85%, at least 90%, at least 95%, at least 96%, at least 97%, at least 98%, or at least 99% sequence identity to the sequence set forth in SEQ ID NO: 33, or 34

In a further most preferred embodiment, the specific binding member comprises the sequence set forth in SEQ ID NO: 72, 73, 76, 77, 80, or 81, or a sequence which has at least 70%, at least 75%, at least 80%, at least 85%, at least 90%, at least 95%, at least 96%, at least 97%, at least 98%, or at least 99% sequence identity to the sequence set forth in SEQ ID NO: 72, 73, 76, 77, 80, or 81.

Monoclonal antibody-based cancer immunotherapies, such as anti-CTLA-4 or anti-PD-1/PD-L1 antibodies, have made a significant impact in the treatment of cancer patients in recent years. However, despite the remarkable clinical efficacy of these monotherapies in a number of malignancies, only a small subset of cancer patients responds to these treatments. Recently, combined inhibition of PD-1 and CTLA-4 in melanoma and non-small cell lung cancer, has highlighted the potential to further enhance the clinical benefits of such monotherapies by combining them with other agents which have a complementary mechanism of action. In addition, the inventors surprisingly found that when specific binding members of the invention were prepared which comprised the CDR-based antigen binding site for CTLA-4 from ipilimumab, in addition to a PD-L1 antigen-binding site located in the CH3 domain of the specific binding member, and these were tested in a Staphylococcal Enterotoxin B assay (SEB assay), the specific binding members showed greater T cell activation than (i) a specific binding member comprising the same PD-L1 antigen-binding site in the CH3 domain and a CDR-based antigen binding site for an irrelevant antigen, (ii) ipilimumab, or a combination of (i) and (ii). This demonstrates that the incorporation of both an anti-PD-L1 antigen binding site into the CH3 domain and a CDR-based antigen binding site for a second antigen into the same specific binding member can result in a synergistic increase in the activity of the specific binding member compared with the combined use of two separate molecules comprising the same antigen-binding sites.

Thus, in addition to the PD-L1 antigen binding site in the CH3 domain of the specific binding member, the specific binding member may further comprise one or more additional antigen-binding sites to create a bi- or multi-specific molecule. Preferably, the specific binding member comprises a CDR-based antigen-binding site. CDR-based antigen binding sites are found in naturally-occurring immunoglobulin molecules and their structure is well-known in the art. Where the specific binding member comprises a CDR-based antigen binding site, the specific binding member is preferably an antibody molecule. The antibody molecule is not particularly limited, provided that it comprises a CH3 domain as herein defined and a CDR-based antigen binding site. In a preferred embodiment, the antibody molecule is a human immunoglobulin G molecule, such as a human IgG1, IgG2, IgG3 or IgG4 molecule, more preferably a human IgG1 molecule.

The sequences of human immunoglobulin G molecules are known in the art and introducing a CH3 domain or a CH3 domain sequence, as disclosed herein, into such a molecule would not present any difficulty for the skilled person.

In a preferred embodiment, the specific binding member of the invention comprises (i) the sequence set forth in SEQ ID NO: 45, 46, 49, 50, 72, 73, 76, 77, 80, 81, 33, 34, 25, 26, 29, 30, 37, 38, 40, or 41, preferably the sequence set forth in SEQ ID NO: 45, 46, 49, 50, 72, 73, 76, 77, 80, 81, 33, or 34, and (ii) a CDR-based antigen-binding site.

The CDR-based antigen binding site may bind an antigen, where the binding of said antigen is expected to be beneficial in the context of cancer treatment.

In one embodiment, where the specific binding member comprises a CDR-based antigen binding site, the CDR-based antigen binding site may bind to a non-redundant and complementary checkpoint inhibitor, such as CTLA-4, LAG-3, TIGIT, TIM-3, VISTA, CD73, CSF-1R, KIR. B7-H3, B7-H4, 2B4, NKG2A, CD47, SIRPα, BTLA, CCR4, CD200R, or TGFbeta.

The inhibition of the PD-1/PD-L1 axis and the stimulation of costimulatory molecules represent complementary strategies to enhance immune responses in human patients. The reversal of T cell exhaustion through checkpoint blockade may allow these cells to be more potently activated and to develop full anti-tumour activity. Thus, in another embodiment, a specific binding member of the invention may comprise a CDR-based antigen-binding site which binds to, and is an agonist for, a costimulatory molecule expressed by T cells such as OX40, ICOS, CD40, HVEM, NKG2D, or TNFR2.

In a further embodiment, the specific binding member of the invention may comprise a CDR-based antigen binding site which binds to a tumour associated antigen (TAA). Such specific binding members are expected to result in tumour-specific T cell responses through localised immune activation. Examples of TAAs are c-Met, B7-H3, B7-H4, EGFR, HER-2, EPCAM, CEACAM, FAP, VEGF, MSLN, GPC3, CD38, CD19, and CD20.

As detailed above, infectious diseases show many parallels with oncology. The role of PD-L1 in immune regulation could be harnessed to maximise the immune response against pathogens.

Immunomodulation in the context of treatment of infectious diseases is an emerging area of medicine and early reviews suggest that PD-L1 blockade may improve biological responses to infection, in particular, helping to counteract T-cell exhaustion, manage immune-mediated clearance, and generate long-term immunity (Wykes and Lewin, 2018).

In some infectious diseases, exaggerated pro-inflammatory responses and suboptimal antigen-specific T-cell activity are the causes of severe tissue damage (Rao M. et al., 2017). Without wishing to be bound by theory, it is thought that the use of a specific binding member of the invention comprising a CDR-based antigen-binding site may find application in the treatment of these diseases by localising beneficial immunomodulatory activity to the pathogen environment.

Alternatively, use of a specific binding member of the invention comprising a CDR-based antigen-binding site which binds to an immune cell target, either for agonism or antagonism, may result in increased T-cell specificity and activity.

Thus, in one embodiment, where the specific binding member comprises a CDR-based antigen binding site, the CDR-based antigen binding site may bind to an immune cell target, such as PD-1, PD-L2, CTLA-4, LAG-3, TIGIT, TIM3, OX40, CD40, ICOS, CD28, or CD80.

Alternatively, where the specific binding member comprises a CDR-based antigen binding site, the CDR-based antigen binding site may bind to a pathogenic target, namely an antigen expressed by a human pathogen. The pathogen may be a virus, bacterium, fungus, or parasite. Preferably the pathogen is a virus, bacterium or fungus. More preferably, the pathogen is a virus or bacterium. Most preferably, the pathogen is a virus. Examples of viral antigens include proteins p24, gp120, and gp41 expressed by human immunodeficiency virus (HIV), hepatitis B surface antigen (HBsAg) expressed by hepatitis B virus (HBV), and hemagglutinin and neuraminidase expressed by influenza virus. Examples of bacterial antigens include Rv1733, Rv2389 and Rv2435n expressed by *Mycobacterium tuberculosis*.

In some embodiments, the CDR-based antigen-binding site of the specific binding member of the invention may not bind to OX40. In addition, or alternatively, the CDR-based antigen-binding site of the specific binding member of the invention may not bind to CD137. In addition, or alternatively, the CDR-based antigen-binding site of the specific binding member of the invention may not bind to CD27. In addition, or alternatively, the CDR-based antigen-binding site of the specific binding member of the invention may not bind to glucocorticoid-induced TNFR-related protein (GITR). In addition, or alternatively, the CDR-based antigen-binding site of the specific binding member of the invention may not bind to lymphocyte-activation gene 3 (LAG-3). In addition, or alternatively, the CDR-based antigen-binding site of the specific binding member of the invention may not bind to Inducible T-cell COStimulator (ICOS). For example, the CDR-based antigen-binding site of the specific binding member of the invention may not bind to ICOS where (i) the PD-L1 binding site of the specific binding member comprises a first sequence located in the AB structural loop at positions 14 to 18 of the CH3 domain, wherein the specific binding member comprises an amino acid deletion at position 14, 15 or 16 of the CH3 domain, and wherein the first sequence consists of the sequence set forth in SEQ ID NO: 23, a second sequence located in the CD structural loop at positions 45.1 to 78 of the CH3 domain, wherein the second sequence consists of the sequence set forth in SEQ ID NO: 11, and a third sequence located in the EF structural loop at positions 92 to 100 of the CH3 domain, wherein the third sequence consists of the sequence set forth in SEQ ID NO: 31; (ii) the CH3 domain of the specific binding member comprises the sequence set forth in SEQ ID NO: 32; and/or (iii) where the specific binding member comprises the sequence set forth in SEQ ID NO: 33 or 34.

The specific binding member may further be conjugated to an immune system modulator, cytotoxic molecule, radio-isotope, or detectable label. The immune system modulator may be a cytotoxic molecule, such as a cytokine.

The present invention also provides a nucleic acid encoding a specific binding member or antibody molecule of the invention, as well as a vector comprising such a nucleic acid.

A recombinant host cell comprising a nucleic acid or the vector of the invention is also provided. Such a recombinant host cell may be used to produce a specific binding member of the invention. Thus, also provided is a method of producing a specific binding member or antibody molecule of the invention, the method comprising culturing the recombinant host cell under conditions for production of the specific binding member or antibody molecule. The method may further comprise a step of isolating and/or purifying the specific binding member or antibody molecule.

The specific binding members and antibodies of the present invention are expected to find application in therapeutic applications, in particular therapeutic applications in humans, such as cancer treatment, the treatment of infectious diseases, and the treatment of inflammation, diseases and conditions associated with inflammation, and inflammatory diseases. Thus, also provided is a pharmaceutical composition comprising a specific binding member or antibody molecule according to the invention and a pharmaceutically acceptable excipient.

The present invention further provides a specific binding member or antibody molecule of the invention, for use in a method of treatment. Also provided is a method of treating a patient, wherein the method comprises administering to the patient a therapeutically effective amount of a specific binding member or antibody molecule according to the invention. Further provided is the use of a specific binding member or antibody molecule according to the invention for use in the manufacture of a medicament. A patient, as referred to herein, is preferably a human patient.

The present invention also provides a specific binding member or antibody molecule of the invention, for use in a method of treating cancer in a patient. Also provided is a method of treating cancer in a patient, wherein the method comprises administering to the patient a therapeutically effective amount of a specific binding member or antibody molecule according to the invention. Further provided is the use of a specific binding member or antibody molecule according to the invention for use in the manufacture of a medicament for the treatment of cancer in a patient. The treatment may further comprise administering to the patient a second anti-cancer agent and/or therapy, such as an anti-tumour vaccine and/or a chemotherapeutic agent. The second anti-cancer agent and/or therapy may be administered to the patient simultaneously, separately, or sequentially to the specific binding member or antibody molecule of the invention.

The present invention also provides a specific binding member or antibody molecule of the invention, for use in a method of treating an infectious disease in a patient. Also provided is a method of treating an infectious disease in a patient, wherein the method comprises administering to the patient a therapeutically effective amount of a specific binding member or antibody molecule according to the invention. Further provided is the use of a specific binding member or antibody molecule according to the invention for use in the manufacture of a medicament for the treatment of an infectious disease in a patient. The treatment may further comprise administering to the patient a second agent and/or therapy for the treatment of the infectious disease. The second agent and/or therapy may be administered to the patient simultaneously, separately, or sequentially to the specific binding member or antibody molecule of the invention.

The present invention also provides a specific binding member or antibody molecule of the invention, for use in a method of treating inflammation, a disease or condition associated with inflammation, or an inflammatory disease in a patient. Also provided is a method of treating inflammation, a disease or condition associated with inflammation, or an inflammatory disease in a patient, wherein the method comprises administering to the patient a therapeutically effective amount of a specific binding member or antibody molecule according to the invention. Further provided is the use of a specific binding member or antibody molecule according to the invention for use in the manufacture of a medicament for the treatment of inflammation, a disease or condition associated with inflammation, or an inflammatory disease in a patient. The treatment may further comprise administering to the patient a second agent and/or therapy for the treatment of the inflammation, disease or condition associated with inflammation, or inflammatory disease. The second agent and/or therapy may be administered to the patient simultaneously, separately, or sequentially to the specific binding member or antibody molecule of the invention.

BRIEF DESCRIPTION OF THE FIGURES

FIG. 1A shows the sequences of the AB, CD and EF loops and framework position 38, 84.1, 85.3 and 113 of the CH3 domain of Fcabs FS17-33, FS17-33-37, FS17-33-116; FS17-33-288, FS17-33-289, FS17-33-296, FS17-33-334, FS17-33-449, FS17-33-451, FS17-33-488, FS17-33-539 and FS17-33-548, as well as the wild-type (WT) Fcab. The numbering of the residues according to the IMGT numbering system is indicated. FIGS. 1B and C show a concordance of antibody residue numbering systems, including the IMGT, consecutive numbering (IMGT exon numbering), EU numbering, and Kabat numbering systems for the CH3 domain residues of an IgG1 CH3 domain, as well as the wild-type IgG1 CH3 domain amino acid sequence. FIG. 1D shows an alignment of the CH3 domain sequences of the Fcabs FS17-33, FS17-33-37, FS17-33-116; FS17-33-288, FS17-33-289, FS17-33-296, FS17-33-334, FS17-33-449, FS17-33-451, FS17-33-488, FS17-33-539 and FS17-33-548, as well as the wild-type (WT) Fcab.

FIG. 5C shows that the presence of the LALA mutation (AA) in the Fcabs did not interfere with their activities in the SEB assay.

DETAILED DESCRIPTION

Figure 2:
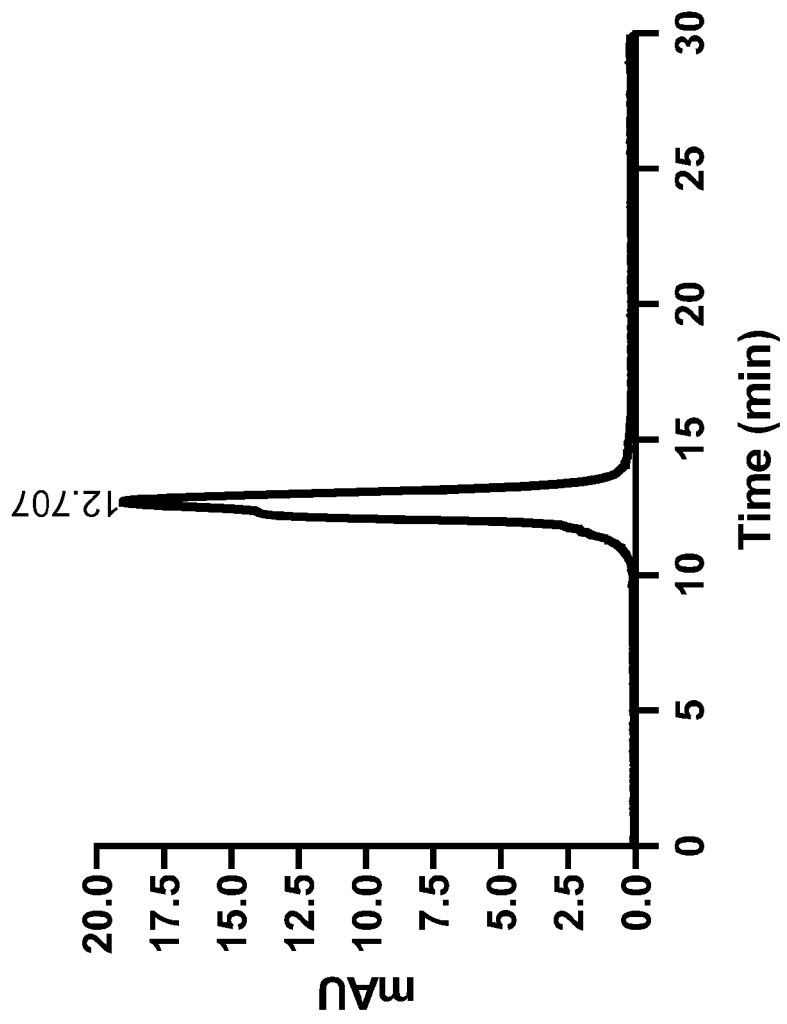
FIG. 2 shows size exclusion chromatography (SEC) profiles of two Fcabs (A and B) and a mAb$^2$ (C). The parental Fcab FS17-33 shows a single peak with a shoulder (A). Fcab FS17-33-116 shows a split peak (B). SEC analysis shows the mAb$^2$ FS17-33-116/4420 (C) had a small amount of aggregation, typical of what is seen with the parental 4420 mAb. Unlike the Fcabs, there is no apparent split peak or shoulder.
Figure 2:
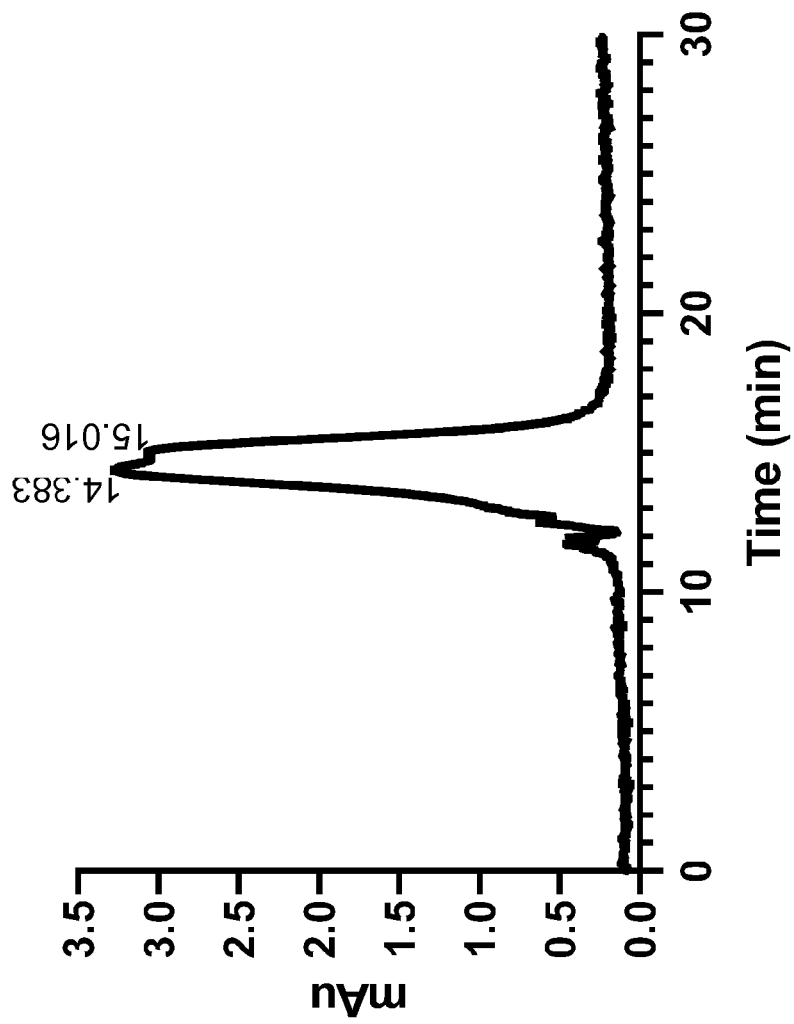
Figure 2:
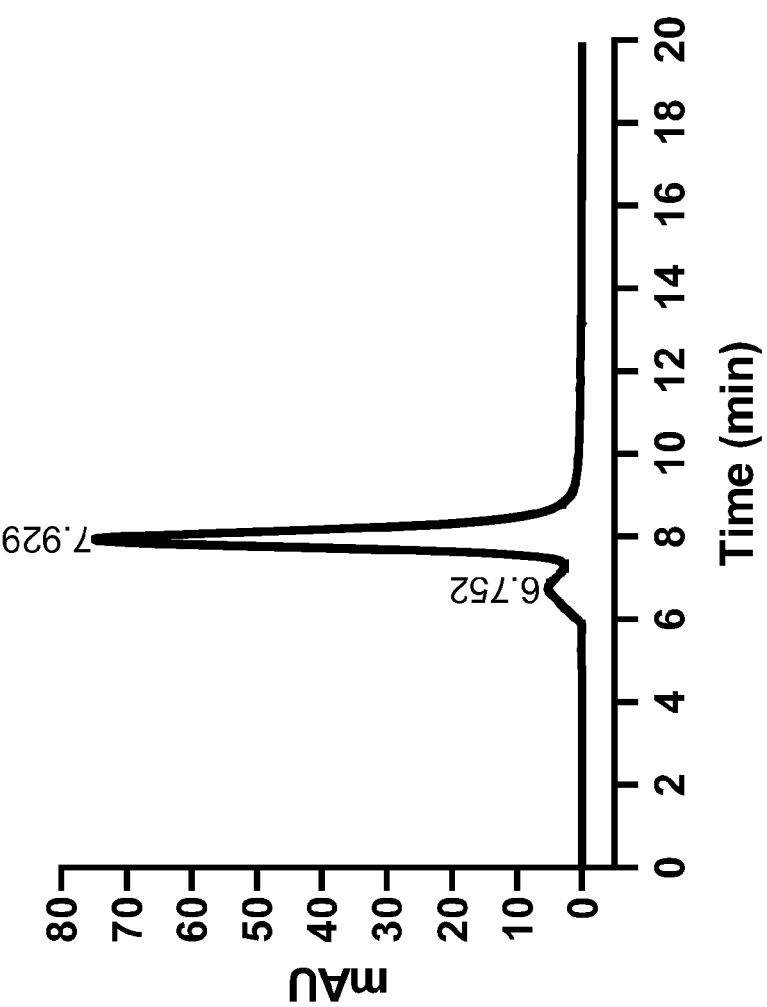

The present invention relates to specific binding members which bind to PD-L1. Specifically, the specific binding members of the present invention comprise a PD-L1 antigen binding site located in a constant domain of the specific binding member. The term "PD-L1" may refer to human PD-L1, and/or cynomolgus monkey PD-L1, unless the context requires otherwise. Preferably, the term "PD-L1" refers to human PD-L1.

The term "specific binding member" describes an immunoglobulin, or fragment thereof, comprising a constant domain, preferably a CH3 domain, comprising a PD-L1 antigen-binding site. Preferably, the specific binding member comprises a CH2 and CH3 domain, wherein the CH2 or CH3 domain, preferably the CH3 domain, comprises a PD-L1 antigen-binding site. In a preferred embodiment, the specific binding member further comprises an immunoglobulin hinge region, or part thereof, at the N-terminus of the CH2 domain. Such a molecule is also referred to herein as an antigen-binding Fc fragment, or Fcab™. The specific binding member may be partly, or wholly, synthetically produced.

The term "specific binding member", as used herein, thus includes fragments, provided said fragments comprise a PD-L1 antigen binding site located in a constant domain, such as a CL, CH1, CH2, or CH3 domain, preferably a CH1, CH2, or CH3 domain, most preferably a CH3 domain, of the specific binding member. Unless the context requires otherwise, the term "specific binding member", as used herein, is thus equivalent to "specific binding member or fragment thereof".

In a preferred embodiment, the specific binding member is an antibody molecule. The term "antibody molecule" encompasses fragments of antibody molecules, provided such fragments comprise a constant domain, such as a CH1, CH2, or CH3 domain, preferably a CH3 domain, comprising a PD-L1 antigen-binding site. The antibody molecule may be human or humanised. The antibody molecule is preferably a monoclonal antibody molecule. Examples of antibody molecules are the immunoglobulin isotypes, such as immunoglobulin G, and their isotypic subclasses, such as IgG1, IgG2, IgG3 and IgG4, as well as fragments thereof.

It is possible to take monoclonal and other antibodies and use techniques of recombinant DNA technology to produce other antibodies or chimeric molecules which retain the specificity of the original antibody. Such techniques may involve introducing the CDRs, or variable regions, into a different immunoglobulin. Introduction of the CDRs of one immunoglobulin into another immunoglobulin is described, for example, in EP-A-184187, GB 2188638A and EP-A-239400. Similar techniques could be employed for the relevant constant domain sequences by introducing the PD-L1 antigen binding site into another constant domain, such as a different CH3 domain, or a CH1 or CH2 domain.

As antibodies can be modified in a number of ways, the term "specific binding member" should be construed as covering antibody fragments, derivatives, functional equivalents and homologues of antibodies, whether natural or wholly or partially synthetic. An example of an antibody fragment comprising a CH3 domain is an Fc domain of an antibody. An example of an antibody fragment comprising both CDR sequences and CH3 domain is a minibody, which comprises an scFv joined to a CH3 domain (Hu et al., 1996).

The specific binding member of the present invention binds to PD-L1. Binding in this context may refer to specific binding. The term "specific" may refer to the situation in which the specific binding member will not show any significant binding to molecules other than its specific binding partner(s), here PD-L1. The term "specific" is also applicable where the specific binding member is specific for particular epitopes, such as epitopes on PD-L1, that are carried by a number of antigens, in which case the specific binding member will be able to bind to the various antigens carrying the epitope. The specific binding member may not bind, or may not show any significant binding, to programmed death-ligand 1 (PD-1) and CD80, such as human and mouse CD80, and human and mouse PD-1.

A specific binding member of the invention preferably comprises a PD-L1 antigen binding site. The PD-L1 antigen binding site is located in a constant domain of the specific binding member, such as a CH1, CH2, CH3 or CH4 domain. Preferably, the PD-L1 antigen binding site is located in the CH3 domain of the specific binding member.

The PD-L1 binding site preferably comprises:
(i) a first sequence located in the AB structural loop, wherein the specific binding member comprises an amino acid deletion at position 14, 15 or 16 of the constant domain, and wherein the first sequence consists of:
  (a) amino acid sequence SGYW (SEQ ID NO: 23), or
  (b) a variant of SEQ ID NO: 23, wherein
    the serine (S) is substituted with amino acid A, E, F, G, H, I, L, P, R, T, V, or Y, and/or
    the glycine (G) is substituted with amino acid A, D, E, F, H, K, L, N, P, R, T, V, or Y;
(ii) a second sequence located in the CD structural loop, wherein the second sequence consist of:
  (a) amino acid sequence EPQYWA (SEQ ID NO: 11), or
  (b) a variant of SEQ ID NO: 11, wherein
    the glutamic acid (E) is substituted with amino acid A, G, H, I, L, N, Q, R, S, or W, and/or
    the proline (P) is substituted with amino acid A, D, E, G, H, N, Q, W, or Y, and/or
    the glutamine (Q) is substituted with amino acid H, or N, and/or
    the tyrosine (Y) is substituted with amino acid A, D, H, T, or V, and/or
    the alanine (A) is substituted with amino acid D, E, G, L, R, S, or W; and
(iii) a third sequence located in the EF structural loop, wherein the third sequence consists of:
  (a) amino acid sequence SNWRWQMD$_1$D$_2$ (SEQ ID NO: 19), or
  (b) a variant of SEQ ID NO: 19, wherein
    the serine (S) is substituted with amino acid A, or G, and/or
    the asparagine (N) is substituted with amino acid A, E, F, G, H, I, K, L, Q, R, S, T, or Y, and/or
    the glutamine (Q) is substituted with amino acid A, D, E, F, G, H, K, L, N, R, S, or V, and/or
    the methionine (M) is substituted with amino acid H, S, F, I, L, V, W, or Y, and/or
    the aspartic acid (D$_1$) is substituted with amino acid E, A, I, L, R, S, T, V, W, Y, or G, and/or
    the aspartic acid (D$_2$) is substituted with amino acid A, E, F, I, K, L, N, R, V, W, or Y; and
  wherein the amino acid at position 101 of the CH3 domain is valine (V), alanine (A), or is absent.

In an alternative preferred embodiment, the PD-L1 binding site comprises:

(i) a first sequence located in the AB structural loop, wherein the specific binding member comprises an amino acid deletion at position 14, 15 or 16 of the constant domain, and wherein the first sequence consists of:
  (a) amino acid sequence SGYW (SEQ ID NO: 23), or
  (b) a variant of SEQ ID NO: 23, wherein
    the serine (S) is substituted with amino acid A, E, F, G, H, I, L, P, R, T, V, or Y, and/or
    the glycine (G) is substituted with amino acid A, D, E, F, H, K, L, N, P, R, T, V, or Y;
(ii) a second sequence located in the CD structural loop, wherein the second sequence consist of:
  (a) amino acid sequence EPQYWA (SEQ ID NO: 11), or
  (b) a variant of SEQ ID NO: 11, wherein
    the glutamic acid (E) is substituted with amino acid A, G, H, I, L, N, Q, R, S, or W, and/or
    the proline (P) is substituted with amino acid A, D, E, G, H, N, Q, W, or Y, and/or
    the glutamine (Q) is substituted with amino acid H, or N, and/or
    the tyrosine (Y) is substituted with amino acid A, D, H, T, or V, and/or
    the alanine (A) is substituted with amino acid D, E, G, L, R, S, or W; and
(iii) a third sequence located in the EF structural loop, wherein the third sequence consists of:
  (a) amino acid sequence SNWRWQMD$_1$D$_2$ (SEQ ID NO: 19), or
  (b) a variant of SEQ ID NO: 19, wherein
    the serine (S) is substituted with amino acid A, or G, and/or
    the asparagine (N) is substituted with amino acid A, E, F, G, H, I, K, L, Q, R, S, T, or Y, and/or
    the glutamine (Q) is substituted with amino acid A, D, E, F, G, H, K, L, N, R, S, or V, and/or
    the methionine (M) is substituted with amino acid H, S, F, I, L, V, W, or Y, and/or
    the aspartic acid (D$_1$) is substituted with amino acid E, A, I, L, R, S, T, V, W, or Y, and/or
    the aspartic acid (D$_2$) is substituted with amino acid A, E, F, I, K, L, N, R, V, W, or Y; and
  wherein the amino acid at position 101 of the CH3 domain is valine (V), or is absent.

The specific binding member of the invention may further comprise an arginine (R) at position 113 of the CH3 domain of the specific binding member. In addition, or alternatively, the specific binding member of the invention may comprise the following additional mutations:
(i) the amino acid at position 84.1 of the CH3 domain may be proline (P); and/or
(ii) the amino acid at position 85.3 of the CH3 domain may be threonine (T); and/or
(iii) the amino acid at position 101 of the CH3 domain may be alanine (A).

Amino acid residues are numbered herein according to the ImMunoGeneTics (IMGT) numbering scheme unless otherwise indicated. The IMGT numbering scheme is described in Lefranc et al., 2005.

Preferably, the first sequence is located at residues 14 to 18 of the CH3 domain, the second sequence is located at positions 45.1 to 78 of the CH3 domain, and/or the third sequence is located at positions 92 to 100 or 92 to 101, of the CH3 domain, wherein the amino acid residue numbering is according to the ImMunoGeneTics (IMGT) numbering scheme.

As an alternative to IMGT numbering, the position of the residues of the CH3 domain, including the modifications described herein, may alternatively be indicated according to consecutive numbering, also referred to as IMGT exon numbering, EU numbering, or Kabat numbering of the residues in the wild-type IgG1 CH3 domain sequence set forth in SEQ ID NO: 4.

The concordance between IMGT numbering, consecutive numbering (IMGT exon numbering), EU numbering, and Kabat numbering of the residues of the WT IgG1 CH3 domain (SEQ ID NO: 4) are shown in FIGS. 1B and C.

The concordance between IMGT numbering and consecutive numbering of the residue positions modified in the CH3 domain of Fcabs FS17-33, FS17-33-37, FS17-33-116; FS17-33-288, FS17-33-289, FS17-33-296, FS17-33-334, FS17-33-449, FS17-33-451, FS17-33-488, FS17-33-539 and FS17-33-548 relative to the wild-type CH3 domain sequence set forth in SEQ ID NO: 4, is shown in FIG. 1A.

Thus, for example, where the present application refers to modification of the AB structural loop at positions 14 to 18, the CD structural loop at positions 45.1 to 78, and/or the EF structural loop at positions 92 to 100 of the CH3 domain, where the residue numbering is according to the IMGT numbering scheme, the positions modified in accordance with consecutive numbering of the amino acid residues of SEQ ID NO: 4 are positions 18 to 22, 46 to 51, and 73 to 81 of the CH3 domain, respectively, as shown in FIG. 1A.

In preferred embodiments, the PD-L1 binding site comprises a first sequence located in the AB loop, a second sequence located in CD loop and a third sequence located in the EF loop,
wherein the first sequence has the sequence set forth in SEQ ID NO: 23, the second sequence has the sequence set forth in SEQ ID NO: 11, and the third sequence has the sequence set forth in SEQ ID NO: 19;
the first sequence has the sequence set forth in SEQ ID NO: 23, the second sequence has the sequence set forth in SEQ ID NO: 11, and the third sequence has the sequence set forth in SEQ ID NO: 27;
the first sequence has the sequence set forth in SEQ ID NO: 23, the second sequence has the sequence set forth in SEQ ID NO: 11, and the third sequence has the sequence set forth in SEQ ID NO: 31;
the first sequence has the sequence set forth in SEQ ID NO: 23, the second sequence has the sequence set forth in SEQ ID NO: 11, and the third sequence has the sequence set forth in SEQ ID NO: 35;
the first sequence has the sequence set forth in SEQ ID NO: 42, the second sequence has the sequence set forth in SEQ ID NO: 11, and the third sequence has the sequence set forth in SEQ ID NO: 43;
the first sequence has the sequence set forth in SEQ ID NO: 47, the second sequence has the sequence set forth in SEQ ID NO: 11, and the third sequence has the sequence set forth in SEQ ID NO: 43;
the first sequence has the sequence set forth in SEQ ID NO: 47, the second sequence has the sequence set forth in SEQ ID NO: 11, and the third sequence has the sequence set forth in SEQ ID NO: 78; or
the first sequence has the sequence set forth in SEQ ID NO: 42, the second sequence has the sequence set forth in SEQ ID NO: 11, and the third sequence has the sequence set forth in SEQ ID NO: 74 and the residue at position 113 of the CH3 domain of the specific binding member is arginine (R).

Most preferably, the PD-L1 binding site comprises a first sequence located in the AB loop, a second sequence located in CD loop and a third sequence located in the EF loop, wherein
the first sequence has the sequence set forth in SEQ ID NO: 23, the second sequence has the sequence set forth in SEQ ID NO: 11, and the third sequence has the sequence set forth in SEQ ID NO: 31;
the first sequence has the sequence set forth in SEQ ID NO: 42, the second sequence has the sequence set forth in SEQ ID NO: 11, and the third sequence has the sequence set forth in SEQ ID NO: 43; or
the first sequence has the sequence set forth in SEQ ID NO: 47, the second sequence has the sequence set forth in SEQ ID NO: 11, and the third sequence has the sequence set forth in SEQ ID NO: 43.

In an alternative most preferred embodiment, the PD-L1 binding site of the specific binding member of the invention may comprise a first sequence located in the AB loop, a second sequence located in CD loop and a third sequence located in the EF loop,
wherein the first sequence has the sequence set forth in SEQ ID NO: 47, the second sequence has the sequence set forth in SEQ ID NO: 11, and the third sequence has the sequence set forth in SEQ ID NO: 78; or
the first sequence has the sequence set forth in SEQ ID NO: 42, the second sequence has the sequence set forth in SEQ ID NO: 11, and the third sequence has the sequence set forth in SEQ ID NO: 74 and the residue at position 113 of the CH3 domain of the specific binding member is arginine (R); or
the first sequence has the sequence set forth in SEQ ID NO: 47, the second sequence has the sequence set forth in SEQ ID NO: 11, and the third sequence has the sequence set forth in SEQ ID NO: 70, wherein the residues at positions 84.1, 85.3, 101 and 113 of the CH3 domain of the specific binding member are proline (P), threonine (T), alanine (A) and arginine (R), respectively.

The first, second and third sequences are preferably located in structural loops of the constant domain of the specific binding member. The introduction of sequences into the structural loop regions of antibody constant domains to create new antigen-binding sites is described, for example, in WO2006/072620 and WO2009/132876.

The structural loops of antibody constant domains include the AB, CD and EF loops. In the CH3 domain, the AB, CD, and EF loops are located at residues 11-18, 43-78 and 92-101 of the CH3 domain. Preferably, the first sequence is located at residues 14 to 18 of the CH3 domain, the second sequence is located at positions 45.1 to 78 of the CH3 domain, and/or the third sequence is located at positions 92 to 100 or 92 to 101, of the CH3 domain.

A specific binding member of the invention may further comprise an alanine or valine residue at position 38, preferably an alanine residue. In particular, a specific binding member which comprises a first, second and third sequence, wherein
the first sequence has the sequence set forth in SEQ ID NO: 23, the second sequence has the sequence set forth in SEQ ID NO: 11, and the third sequence has the sequence set forth in SEQ ID NO: 31;
the first sequence has the sequence set forth in SEQ ID NO: 42, the second sequence has the sequence set forth in SEQ ID NO: 11, and the third sequence has the sequence set forth in SEQ ID NO: 43;
the first sequence has the sequence set forth in SEQ ID NO: 47, the second sequence has the sequence set forth in SEQ ID NO: 11, and the third sequence has the sequence set forth in SEQ ID NO: 43;

the first sequence has the sequence set forth in SEQ ID NO: 47, the second sequence has the sequence set forth in SEQ ID NO: 11, and the third sequence has the sequence set forth in SEQ ID NO: 78;

the first sequence has the sequence set forth in SEQ ID NO: 42, the second sequence has the sequence set forth in SEQ ID NO: 11, and the third sequence has the sequence set forth in SEQ ID NO: 74, and the residue at position 113 of the CH3 domain of the specific binding member is arginine (R); or the first sequence has the sequence set forth in SEQ ID NO: 47, the second sequence has the sequence set forth in SEQ ID NO: 11, and the third sequence has the sequence set forth in SEQ ID NO: 70, wherein the residues at positions 84.1, 85.3, 101 and 113 of the CH3 domain of the specific binding member are proline (P), threonine (T), alanine (A) and arginine (R), respectively;

may further comprise an alanine residue at position 38.

Similarly, a specific binding member which comprises a first, second and third sequence, wherein the first sequence has the sequence set forth in SEQ ID NO: 23, the second sequence has the sequence set forth in SEQ ID NO: 11, and the third sequence has the sequence set forth in SEQ ID NO: 19;

the first sequence has the sequence set forth in SEQ ID NO: 23, the second sequence has the sequence set forth in SEQ ID NO: 11, and the third sequence has the sequence set forth in SEQ ID NO: 27;

the first sequence has the sequence set forth in SEQ ID NO: 23, the second sequence has the sequence set forth in SEQ ID NO: 11, and the third sequence has the sequence set forth in SEQ ID NO: 31; or the first sequence has the sequence set forth in SEQ ID NO: 23, the second sequence has the sequence set forth in SEQ ID NO: 11, and the third sequence has the sequence set forth in SEQ ID NO: 35, may further comprise a valine residue at position 38.

In addition, or alternatively, the specific binding member of the invention may further comprise a valine residue, or an amino acid deletion, at position 101 of the CH3 domain (as shown in FIG. 1A). In particular, a specific binding member which comprises a first, second and third sequence, wherein the first sequence has the sequence set forth in SEQ ID NO: 23, the second sequence has the sequence set forth in SEQ ID NO: 11, and the third sequence has the sequence set forth in SEQ ID NO: 19;

the first sequence has the sequence set forth in SEQ ID NO: 23, the second sequence has the sequence set forth in SEQ ID NO: 11, and the third sequence has the sequence set forth in SEQ ID NO: 27;

the first sequence has the sequence set forth in SEQ ID NO: 23, the second sequence has the sequence set forth in SEQ ID NO: 11, and the third sequence has the sequence set forth in SEQ ID NO: 31;

the first sequence has the sequence set forth in SEQ ID NO: 23, the second sequence has the sequence set forth in SEQ ID NO: 11, and the third sequence has the sequence set forth in SEQ ID NO: 35;

may comprise an amino acid deletion at position 101 of the CH3 domain.

Alternatively, the specific binding member of the invention may further comprise an alanine residue (A) at position 101 of the CH3 domain (as shown in FIG. 1A). In particular, a specific binding member which comprises a first, second and third sequence, wherein the first sequence has the sequence set forth in SEQ ID NO: 47, the second sequence has the sequence set forth in SEQ ID NO: 11, and the third sequence has the sequence set forth in SEQ ID NO: 70, wherein the residues at positions 84.1, 85.3, and 113 of the CH3 domain of the specific binding member are proline (P), threonine (T), and arginine (R), respectively, may comprise an alanine residue (A) at position 101 of the CH3 domain.

In a preferred embodiment, the specific binding member of the invention comprises a CH3 domain which comprises, has, or consists of the sequence set forth in SEQ ID NO: 24, 28, 32, 36, 39, 44, 48, 71, 75 or 79, preferably a CH3 domain with the sequence set forth in SEQ ID NO: 28, 32, 36, 39, 44, 48, 75 or 79.

The specific binding member of the invention may comprise a CH3 domain which comprises, has, or consists of the sequence set forth in SEQ ID NO: 24, 28, 32, 36, 39, 44, 48, 71, 75 or 79, wherein the lysine residue (K) at the immediate C-terminus of the sequence shown in SEQ ID NO: 24, 28, 32, 36, 39, 44, 48, 71, 75 or 79 has been deleted.

In addition, the specific binding member of the invention may comprise a CH2 domain of an immunoglobulin G molecule, such as a CH2 domain of an IgG1, IgG2, IgG3, or IgG4 molecule. Preferably the specific binding member of the invention comprises a CH2 domain of an IgG1 molecule. The CH2 domain may have the sequence set forth in SEQ ID NO: 6.

The CH2 domain of the specific binding member may comprise one or more mutations that reduce or abrogate binding of the CH2 domain to one or more Fcγ receptors, such as FcγRI, FcγRIIa, FcγRIIb, FcγRIII and/or to complement. The inventors postulate that reducing or abrogating binding to Fcγ receptors will decrease or eliminate antibody-dependent cell-mediated cytotoxicity (ADCC) mediated by the antibody molecule. Similarly, reducing or abrogating binding to complement is expected to reduce or eliminate complement-dependent cytotoxicity (CDC) mediated by the antibody molecule. Mutations to reduce or abrogate binding of the CH2 domain to one or more Fcγ receptors and/or complement are known in the art (Wang et al., 2018). These mutations include the "LALA mutation" described in Bruhns, et al., 2009 and Hezareh et al., 2001, which involves substitution of the leucine residues at IMGT positions 1.3 and 1.2 of the CH2 domain with alanine (L1.3A and L1.2A). Alternatively, the generation of aglycosylated antibodies through mutation of the conserved N-linked glycosylation site by mutating the asparagine (N) at IMGT position 84.4 of the CH2 domain to alanine, glycine or glutamine (N84.4A, N84.4G or N84.4Q) is also known to decrease IgG1 effector function (Wang et al., 2018). As a further alternative, complement activation (C1q binding) and ADCC are known to be reduced through mutation of the proline at IMGT position 114 of the CH2 domain to alanine or glycine (P114A or P114G) (Idusogie et al., 2000; Klein et al., 2016). These mutations may also be combined in order to generate antibody molecules with further reduced or no ADCC or CDC activity.

Thus, the specific binding member may comprise a CH2 domain, wherein the CH2 domain comprises:
  (i) alanine residues at positions 1.3 and 1.2; and/or
  (ii) an alanine or glycine at position 114; and/or
  (iii) an alanine, glutamine or glycine at position 84.4;
  wherein the amino acid residue numbering is according to the IMGT numbering scheme.

In a preferred embodiment, the specific binding member comprises a CH2 domain, wherein the CH2 domain comprises:
(i) an alanine residue at position 1.3; and
(ii) an alanine residue at position 1.2;
wherein the amino acid residue numbering is according to the IMGT numbering scheme.

For example, the CH2 domain may have the sequence set forth in SEQ ID NO: 5.

In an alternative preferred embodiment, the antibody molecule comprises a CH2 domain, wherein the CH2 domain comprises:
(i) an alanine residue at position 1.3;
(ii) an alanine residue at position 1.2; and
(iii) an alanine at position 114;
wherein the amino acid residue numbering is according to the IMGT numbering scheme.

For example, the CH2 domain may have the sequence set forth in SEQ ID NO: 82.

In a preferred embodiment, the specific binding member may comprise one or more further antigen-binding sites that bind one or more further antigens, in addition to the PD-L1 antigen-binding site located in the constant domain of the specific binding member. The one or more further antigen-binding sites preferably bind their cognate antigens specifically.

The one or more further antigen-binding sites may bind PD-L1 or another antigen. The specific binding member may thus be a multispecific, for example a bispecific, trispecific, or tetraspecific molecule, preferably a bispecific molecule. In a preferred embodiment, the specific binding member is capable of simultaneously binding to PD-L1 and the one or more further antigens.

Antibody molecules are known to have a modular architecture comprising discrete domains, which can be combined in a multitude of different ways to create multispecific, e.g. bispecific, trispecific, or tetraspecific antibody formats. Exemplary multispecific antibody formats are described in Spiess et al. (2015) and Kontermann (2012), for example. The specific binding members of the present invention may be employed in such multispecific antibody formats. This has the additional advantage of introducing a further antigen-binding site into such multispecific antibody format through the presence of the antigen-binding site in the constant domain, e.g. the CH3 domain, of the specific binding member.

For example, the specific binding member of the invention may be a heterodimeric antibody molecule, such as a heterodimeric complete immunoglobulin molecule, or a fragment thereof. In this case, one part of the antibody molecule will have a sequence or sequences as described herein. For example, where the specific binding member of the invention is a bispecific heterodimeric antibody molecule, the specific binding member may comprise a heavy chain comprising a CH3 domain as described herein paired with a heavy chain which binds an antigen other than PD-L1. Techniques for preparing heterodimeric antibodies are known in the art and include knobs-into-holes (KIHs) technology, which involves engineering the CH3 domains of an antibody molecule to create either a "knob" or a "hole" to promote chain heterodimerization. Alternatively, heterodimeric antibodies can be prepared through the introduction of charge pairs into the antibody molecule to avoid homodimerization of CH3 domains by electrostatic repulsion and to direct heterodimerization by electrostatic attraction. Examples of heterodimeric antibody formats include CrossMab, mAb-Fv, SEED-body, and KIH IgG.

Alternatively, a multispecific specific binding member of the invention may comprise a complete immunoglobulin molecule or a fragment thereof and an additional antigen-binding moiety or moieties. The antigen-binding moiety may for example be an Fv, scFv or single domain antibody, and may be fused to the complete immunoglobulin molecule or a fragment thereof. Examples of multispecific antibody molecules comprising additional antigen-binding moieties fused to a complete immunoglobulin molecule include DVD-IgG, DVI-IgG, scFv4-IgG, IgG-scFv, and scFv-IgG molecules (Spiess et al., 2015; FIG. 1). Examples of multispecific antibody molecules comprising additional antigen-binding moieties fused to an immunoglobulin fragment comprising a CH3 domain include scDiabody-CH3, Diabody-CH3, and scFv-CH3 KIH, for example (Spiess et al., 2015; FIG. 1).

Other suitable multispecific formats would be readily apparent to the skilled person.

In a preferred embodiment, the specific binding member according to the present invention comprises a second antigen-binding site, wherein the second antigen-binding site preferably is a CDR-based antigen binding site. The term "CDR-based antigen binding site" refers to the antigen-binding site of a specific binding member variable region which is composed of six CDR residues.

The second antigen-binding site is preferably specific to a checkpoint inhibitor, costimulatory molecule or tumour associated antigen.

The antibody molecules against a given antigen, such as a tumour associated antigen, and determination of the CDR sequences of such an antibody molecule, is well within the capabilities of the skilled person and many suitable techniques are known in the art. Furthermore, antibodies, including the CDR sequences, against various immune system modulators are known in the art. Thus, the skilled person would have no difficulty in preparing a specific binding member comprising, in addition to a PD-L1 binding site as described herein, a CDR-based antigen-binding site for a second antigen.

In certain examples, the specific binding member of the invention does not comprise a CDR-based antigen binding site.

The specific binding members of the present invention may also comprise variants of the structural loop, CH3 domain, CH2 domain, CH2 and CH3 domain, CDR, VH domain, VL domain, light chain or heavy chain sequences disclosed herein. Suitable variants can be obtained by means of methods of sequence alteration, or mutation, and screening. In a preferred embodiment, a specific binding member comprising one or more variant sequences retains one or more of the functional characteristics of the parent specific binding member, such as binding specificity and/or binding affinity for PD-L1. For example, a specific binding member comprising one or more variant sequences preferably binds to PD-L1 with the same affinity as, or a higher affinity than, the (parent) specific binding member. The parent specific binding member is a specific binding member which does not comprise the amino acid substitution(s), deletion(s), and/or insertion(s) which has (have) been incorporated into the variant specific binding member.

For example, a specific binding member of the invention may comprise a structural loop, CH3 domain, CH2 domain, CH2 and CH3 domain, CDR, VH domain, VL domain, light chain or heavy chain sequence which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to a structural loop, CH3 domain, CH2 domain, CH2 and CH3 domain, CDR, VH domain, VL domain, light chain or heavy chain sequence disclosed herein.

In a preferred embodiment, the specific binding member of the invention comprises a CH3 domain sequence which has at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH3 domain sequence set forth in SEQ ID NO: 24, 28, 32, 36, 39, 44, 48, 71, 75 or 79, preferably SEQ ID NO: 28, 32, 36, 39, 44, 48, 71, 75 or 79, most preferably 32, 44, 48, 71, 75 or 79. In particular, the specific binding member of the invention comprises a CH3 domain having at least 96% sequence identity to the CH3 domain sequence set forth in SEQ ID NO: 24.

In a further preferred embodiment, the specific binding member of the invention comprises a CH2 domain sequence, which has at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH2 domain sequence set forth in SEQ ID NO: 5 or 6.

In another preferred embodiment, the specific binding member of the invention comprises, or consists of, a sequence, which has at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to sequence set forth in SEQ ID NO: 25, 26, 29, 30, 33, 34, 37, 38, 40, 41, 45, 46, 49, 50, 72, 73, 76, 77, 80, or 81, most preferably SEQ ID NO: 45, 46, 49, 50, 72, 73, 76, 77, 80, or 81. In an alternative most preferred embodiment, the specific binding member of the invention comprises, or consists of, a sequence, which has at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to sequence set forth in SEQ ID NO: 33 or 34.

Tables 9A, B and C show that in the context of the molecules prepared in the examples, certain residues in the structural loops could not be modified without an increase in the off-rate of the Fcab when bound to PD-L1 as compared with the off-rate of the parent molecule.

Thus, where the specific binding member:

(i) comprises a CH3 domain sequence defined by its sequence identity to the (parent) sequence set forth in SEQ ID NO: 24, 28, 32, 36, 39, 44, 48, 71, 75 or 79; or (ii) comprises, or consist of, a sequence defined by its sequence identity to the (parent) sequence set forth in SEQ ID NO: 25, 26, 29, 30, 33, 34, 37, 38, 40, 41, 45, 46, 49, 50, 72, 73, 76, 77, 80, or 81, as set out in the preceding paragraphs and elsewhere herein,

- the amino acid deletion at position 14, 15 or 16 of the CH3 domain is preferably maintained and/or the amino acids at positions 17, 18 of the CH3 domain are preferably unmodified compared with the parent sequence;
- the amino acids at position 77, and optionally position 45.3 of the CH3 domain are preferably unmodified compared with the parent sequence; and/or
- the amino acid(s) at position 94, and optionally position 92, of the CH3 domain is(are) preferably unmodified compared with the parent sequence.

Sequence identity is commonly defined with reference to the algorithm GAP (Wisconsin GCG package, Accelerys Inc, San Diego USA). GAP uses the Needleman and Wunsch algorithm to align two complete sequences, maximising the number of matches and minimising the number of gaps. Generally, default parameters are used, with a gap creation penalty equaling 12 and a gap extension penalty equaling 4. Use of GAP may be preferred but other algorithms may be used, e.g. BLAST (which uses the method of Altschul et al., 1990), FASTA (which uses the method of Pearson and Lipman, 1988), or the Smith-Waterman algorithm (Smith and Waterman, 1981), or the TBLASTN program, of Altschul et al., 1990 supra, generally employing default parameters. In particular, the psi-Blast algorithm (Altschul et al., 1997) may be used.

A specific binding member of the invention may also comprise a structural loop, CH3 domain, CH2 domain, CH2 and CH3 domain, CDR, VH domain, VL domain, light chain or heavy chain sequence which has one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with a structural loop, CH3 domain, CH2 domain, CH2 and CH3 domain, CDR, VH domain, VL domain, light chain or heavy chain sequence disclosed herein. In particular, alterations may be made in one or more framework regions of the specific binding member.

In a preferred embodiment, the specific binding member of the invention may comprise a CH3 domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH3 domain sequence set forth in SEQ ID NO: 24, 28, 32, 36, 39, 44, 48, 71, 75 or 79.

In a further preferred embodiment, the specific binding member of the invention comprises a CH2 domain sequence, with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH2 domain sequence set forth in SEQ ID NO: 5 or 6.

In a further preferred embodiment, the specific binding member of the invention comprises or consists of a sequence, with one or more amino acid sequence alterations (addition, deletion, substitution and/or insertion of an amino acid residue), preferably 40 alterations or fewer, 30 alterations or fewer, 20 alterations or fewer, 15 alterations or fewer, 10 alterations or fewer, 5 alterations or fewer, 4 alterations or fewer, 3 alterations or fewer, 2 alterations or fewer, or 1 alteration compared with the sequence set forth in SEQ ID NO: 25, 26, 29, 30, 33, 34, 37, 38, 40, 41, 45, 46, 49, 50, 72, 73, 76, 77, 80, or 81.

Also contemplated is a specific binding member which competes with a specific binding member of the invention for binding to PD-L1, or which binds to the same epitope on PD-L1 as a specific binding member of the invention, wherein the specific binding member preferably comprises a PD-L1 antigen binding site located in a CH3 domain of the specific binding member. Methods for determining competition for an antigen by two antibodies are known in the art.

For example, competition of binding to an antigen by two antibodies can be determined using surface plasmon resonance, such as Biacore. Methods for mapping the epitope bound by an antibody are similarly known in the art.

The specific binding member of the invention may bind to human PD-L1, and/or cynomolgus monkey PD-L1. Preferably, the specific binding member of the invention binds to human PD-L1.

The specific binding member of the present invention is preferably capable of binding to PD-L1 expressed on the surface of a cell. The cell is preferably a cancer cell.

Where the specific binding member comprises a second antigen-binding site, such as a CDR-based antigen binding site, specific for a second antigen, the specific binding member is preferably capable of simultaneously binding to PD-L1 and the second antigen. Preferably, the specific binding member is capable of simultaneously binding to PD-L1 and the second antigen, wherein the PD-L1 and the second antigen are expressed on the surface of a single cell, or on the surface of two separate cells.

The specific binding member of the invention preferably binds to monomeric PD-L1, preferably human monomeric PD-L1, with an affinity ($K_D$) of 5 nM, 4 nM, 3 nM, or 2 nM, or an affinity which is greater. Preferably, the specific binding member of the invention binds to PD-L1, preferably human PD-L1, with an affinity ($K_D$) of 2 nM, or an affinity which is greater.

The specific binding member of the invention preferably binds to PD-L1, preferably human PD-L1 expressed on the surface of a cell, with an affinity ($K_D$) of 20 nM, 19 nM, 18 nM, 17 nM, or 16 nM, or an affinity which is greater. Preferably, the specific binding member of the invention binds to PD-L1, preferably human PD-L1, expressed on the surface of a cell, with an affinity ($K_D$) of 16 nM, or an affinity which is greater.

The binding affinity of a specific binding member to a cognate antigen, such as PD-L1 can be determined by surface plasmon resonance (SPR), such as Biacore, for example. The binding affinity of a specific binding member to a cognate antigen, such as PD-L1, expressed on a cell surface can be determined by flow cytometry.

Fcabs have a smaller binding interface than monoclonal antibodies as the binding sites of Fcabs form a relatively compact antibody fragment with two binding sites situated in close proximity. In contrast, the Fab arms of a typical mAb are separated by a flexible hinge region. The two antigen binding sites of an Fcab are also spatially close to each other, as compared with those of a typical mAb. Based on this smaller binding interface and reduced flexibility of the two binding sites it was surprising that the anti-PD-L1 Fcabs were able to bind to and inhibit PD-L1 with similar affinity and potency as a monoclonal antibody specific for PD-L1.

The specific binding member may have an $EC_{50}$ in a T cell activation assay, such as a DO11.10 assay, of 9 nM or less, 8 nM or less, 7 nM or less, 6 nM or less, 5 nM or less, 4 nM or less, 3 nM or less, or 2 nM or less, preferably 2 nM or less, when the specific binding member is in the form of a complete immunoglobulin molecule, also referred to herein as a $mAb^2$.

The specific binding member may have an $EC_{50}$ in a T cell activation assay, such as a DO11.10 assay, of 2 nM or less, 1 nM or less, or 0.5 nM or less, preferably 0.5 nM or less, when the specific binding member is in the form of an Fcab, consisting of a CH3 domain, CH2 domain and truncated immunoglobulin hinge region located at the N-terminus of the CH2 domain.

The DO11.10 assay is an IL-2 release assay based on the T-lymphocyte and B-lymphocyte hybridoma cell lines and may be use for functional screening of the specific binding members of the invention. IL-2 release is a marker of T cell activation. The DO11.10 assay may be a DO11.10 assay as described in Example 6 herein.

For example, the DO11.10 assay may comprise preparing dilutions of the specific binding member of interest, for example in experimental media, such as complete DO11.10 culture medium without puromycin. The specific binding member may be mixed 1:1 with $4\times10^5$/ml B cell hybridoma cells transduced with a lentiviral vector containing human PD-L1 to overexpress human PD-L1 (referred to as "B cell hybridoma cells") (e.g. LK35.2 hPD-L1 cells) in experimental media in presence of 2.46 μM OVA peptide (e.g. 100 μL B cell hybridoma cells/specific binding member) mix per well, for example in a 96-round bottom plate, and may be incubated at 37° C., 5% $CO_2$ for 1 hour. $2\times10^5$ DO11.10 T cell hybridoma cells transduced with an empty lentiviral vector (referred to as "DO11.10 T cells"; (e.g. DO11.10 pLVX cells) per ml in 100 μl volume experimental media may be added to 100 μl of the B cell hybridoma cells/specific binding member mix. The cells may then be mixed before being incubated at 37° C., 5% $CO_2$ for 24 hours. Supernatants may be collected and assayed with a mouse IL-2 ELISA kit (e.g. from eBioscience, 88-7024-88 or R&D systems, SM2000). Plates may be read at 450 nm using a plate reader, such as a plate reader with the Gen5 Software, BioTek. Absorbance values of 570 nm may be subtracted from those of 450 nm for correction purposes. The standard curve for calculation of cytokine concentration may be based on four parameter logistic curve fit (such as Gen5 Software, BioTek). The concentration of mouse IL-2 may be plotted versus the log concentration of the specific binding member. The resulting curves may be fitted using the log (agonist) versus response equation, for example using GraphPad Prism.

In the context of a DO11.10 T cell activation assay, DO11.10 T cell hybridoma cells transduced with an empty lentiviral vector may be prepared using lentiviral transduction methodology, for example to generate DO11.10 cells containing the empty lentiviral vector pLVX using the Lenti-X HTX Packaging System. Lenti-X expression vector (pLVX) may be co-transfected with a Lenti-X HTX Packaging Mix into the Lenti-X 293T Cell Line to generate virus. The DO11.10 cell line may be transduced using the lentiviral particles produced with the Lenti-X HTX Packaging System.

In the context of a DO11.10 T cell activation assay, B cell hybridoma cells, such as LK35.2 B cell lymphoma cells (ATCC, HB-98), transduced with a lentiviral vector containing human PD-L1 to overexpress human PD-L1 may be prepared using lentiviral transduction methodology, e.g. using the Lenti-X HTX Packaging System. A Lenti-X expression vector (pLVX), containing human PD-L1 cDNA, may be co-transfected with a Lenti-X HTX Packaging Mix into the Lenti-X 293T Cell Line to generate virus. The B cell hybridoma cell line may be transduced using the lentiviral vectors produced with the Lenti-X HTX Packaging System.

The specific binding member may have an $EC_{50}$ in a Staphylococcal Enterotoxin B (SEB) assay, of 5 nM or less, 4 nM or less, 3 nM or less, or 2 nM or less, preferably 2 nM or less, when the specific binding member is in the form of a complete immunoglobulin molecule, also referred to as a $mAb^2$ herein.

The specific binding member may have an $EC_{50}$ in a Staphylococcal Enterotoxin B (SEB) assay, of 5 nM or less, 4 nM or less, 3 nM or less, 2 nM or less, 1 nM or less, 0.5 nM or less, 0.3 nM or less, or 0.2 nM or less, preferably 0.2 nM or less, when the specific binding member is in the form of an Fcab, consisting of a CH3 domain, CH2 domain and truncated immunoglobulin hinge region located at the N-terminus of the CH2 domain.

Staphylococcal Enterotoxin B is a superantigen, and binds to MHC class II molecules on antigen presenting cells (APCs) and the vβ chain of the T cell receptor (TCR), causing non-specific activation of T cells and cytokine release. There is no requirement for antigen-specific TCRs to be present for T cell activation. The SEB assay uses stimulated human peripheral blood mononuclear cells (PBMCs) with physiological levels of checkpoint inhibitors, and can be used to confirm that T cell activation is enhanced by the specific binding member in a human system.

The SEB assay may be an SEB assay as described in Example 7 herein.

For example, the SEB assay may comprise:
(i) isolating PBMCs from leukocyte cones, e.g. by Ficoll gradient separation. CD4+ T cells may be isolated, e.g. using a human CD4+ T Cell Isolation Kit (e.g. from Miltenyi Biotec Ltd, 130-096-533). Human T-Activator CD3/CD28 Dynabeads (e.g. from Life technologies, 11131D) may be resuspended by vortexing. Beads may be transferred to a sterile 15 ml tube and 10 ml RPMI (e.g. from Life Technologies, 61870044) with 10% FBS (e.g. from Life Technologies, 10270106) and 1× Penicillin Streptomycin (e.g. from Life Technologies, 15140122) may be added to wash the Dynabeads. The supernatant may be discarded. The required amount of CD4+ T cells at $1.0 \times 10^6$ cells/ml in RPMI with 10% FBS and 1× Penicillin Streptomycin Solution and 50 IU/ml recombinant human IL2 (e.g. from Peprotech, 200-02-50 μg) with 3:1 bead to cell ratio may be transferred to T75 flask (e.g. from Greiner Bio-one, 690195) and incubated at 37° C.+5% $CO_2$. After 3 days the cells may be gently resuspended and counted. The cell density may be maintained between $0.8-1 \times 10^6$ cells/ml by adding fresh media (e.g. RPMI-10% FBS+ Penicillin Streptomycin Solution 1×+50 IU/ml rhuIL2). On day 7 or 8, the CD3/28 beads may be removed. CD4+ T cells may be rested overnight at $1 \times 10^6$ cells/ml fresh media RPMI-10% FBS+Penicillin Streptomycin Solution 1× with reduced 10 IU/ml rhuIL2;
(ii) isolating untouched monocytes from human PBMCs, e.g. using human Pan Monocyte Isolation Kit (such as from Miltenyi Biotec Ltd, 130-096-537) e.g. using the method described in (i). Monocytes may be differentiated to iDCs, e.g. using human Mo-DC Differentiation Medium (such as from Miltenyi Biotec Ltd, 130-094-812); and/or
(iii) preparation of dilutions of the specific binding member of interest, e.g. in AIM medium (such as from Gibco, 12055-091). MoiDCs, e.g. prepared as set out in (ii), may be mixed with T cells from the same donor at a 1:10 ratio (5 ml of iDCs at $2 \times 10^5$ cells/ml may be combined with 5 ml of T cells at $2 \times 10^6$ cells/ml). 20 μl of SEB (e.g. from Sigma, S4881) at 0.1 μg/ml may be added to 10 ml of the cells. In a round bottom 96 well plate, 100 μl of the cell/SEB mixture may be added to 100 μl of the specific binding member dilution, giving a ratio of $10^4$ iDC cells to $10^5$ T cells with 0.1 ng/ml SEB in 200 μl of media (e.g. AIM media) per well. Cells may be incubated at 37° C., 5% $CO_2$ for 4 days. Supernatants may be assayed for $IFN_\gamma$ using an ELISA, such as the human $IFN_\gamma$ ELISA kit (e.g. from R&D Systems, PDIF50). The assay may be performed using supernatants diluted 1:30 with PBA (DPBS, 2% BSA (such as from Sigma, A7906-100G)). The concentration of human $IFN_\gamma$ may be plotted versus the log concentration of the specific binding member. The resulting curves may be fitted using the log (agonist) versus response equation, e.g. in GraphPad Prism software.

The specific binding member may be capable of blocking the interaction between PD-L1 and PD-1, preferably human PD-L1 and human PD-1, with an $EC_{50}$ of 30 nM or less, 20 nM or less, 15 nM or less, 14 nM or less, 13 nM or less, 12 nM or less, or 11 nM or less, preferably 11 nM or less.

The specific binding member may be capable of blocking the interaction between PD-L1 and CD80, preferably human PD-L1 and human CD80, with an $EC_{50}$ of 50 nM or less, 45 nM or less, 40 nM or less, or 30 nM or less, preferably 30 nM or less, when the specific binding member is in the form of a complete immunoglobulin molecule, also referred to herein as a $mAb^2$.

The specific binding member may be capable of blocking the interaction between PD-L1 and CD80, preferably human PD-L1 and human CD80, with an $EC_{50}$ of 20 nM or less, 15 nM or less, 14 nM or less, 13 nM or less, 12 nM or less, 11 nM or less, or 10 nM or less, preferably 10 nM or less, when the specific binding member is in the form of an Fcab, consisting of a CH3 domain, CH2 domain and truncated immunoglobulin hinge region located at the N-terminus of the CH2 domain.

Methods for testing the ability of a specific binding member of the invention to block the interaction between human PD-L1 and human PD-1 or human CD80 are known in the art and are described herein. For example, blocking of the interaction between human PD-L1 and human PD-1 or human CD80 may be tested using a cell-based Receptor Binding Assay. 2 μg/mL biotinylated human PD-L1 may be incubated for 1 hour with titrating concentrations of Fcabs ranging from 400 nM to 3 μM. The mix may be incubated for another hour with cells, such as HEK293 cells, overexpressing either human PD-1 or human CD80. The level of bound biotinylated human PD-L1 on the cells may be detected using streptavidin 647 and fluorescence levels may be measured using FACS, whereby the level of fluorescence detected indicates the level of binding of PD-L1 to PD-1 or human CD80 expressed on the cells.

The specific binding member may have a melting temperature of 60° C. or higher, 61° C. or higher, 62° C. or higher, 63° C. or higher, 64° C. or higher, 65° C. or higher, 66° C. or higher, 67° C. or higher, or 68° C. or higher, preferably 65° C. or higher, 66° C. or higher, 67° C. or higher, or 68° C. or higher, more preferably 66° C. or higher, 67° C. or higher, or 68° C. or higher. When the melting temperature is measured, the specific binding member may be in the form of a complete immunoglobulin molecule, also referred to herein as a $mAb^2$.

The melting temperature of a specific binding member of the invention may be measured by known methods. For example, the melting temperature of a specific binding member of the invention may be measured by differential scanning colorimetry (DSC) or differential scanning fluorimetry (DSF).

Aggregation of therapeutic antibodies may result results in the loss of drug potency and may cause unnecessary immunogenicity. Antibodies which show little or no aggregation are therefore preferred for this purpose. The specific binding member may show no more than 5%, 4%, or 3%, preferably 3% aggregation, when the specific binding member is in an aqueous solution. Aggregation of the specific binding member in an aqueous solution can be determined using size exclusion chromatography (SEC), for example.

The specific binding member of the present invention may be conjugated to a bioactive agent, therapeutic agent or detectable label. In this case, the specific binding member may be referred to as a conjugate. Such conjugates find application in the treatment of diseases and conditions as described herein.

For example, the specific binding member may be conjugated to an immune system modulator, cytotoxic molecule, radioisotope, or detectable label. The immune system modulator or cytotoxic molecule may be a cytokine. The immune system modulator may also be a cell-surface receptor, or a biologically active fragment thereof, e.g. a fragment comprising or consisting of the ligand-binding domain of the receptor. Alternatively, the immune system modulator may be a ligand, e.g. a peptide ligand, of a cell-surface receptor, or a biologically active fragment of the ligand, e.g. a fragment comprising or consisting of the receptor-binding domain of the ligand. The detectable label may be a radioisotope, e.g. a non-therapeutic radioisotope.

The specific binding member may be conjugated to the bioactive agent, therapeutic agent or detectable label by means of a peptide bond or linker, i.e. within a fusion polypeptide comprising said bioactive agent, therapeutic agent or detectable label and the specific binding member or a polypeptide chain component thereof. Other means for conjugation include chemical conjugation, especially cross-linking using a bifunctional reagent (e.g. employing DOUBLE-REAGENTS™ Cross-linking Reagents Selection Guide, Pierce).

The specific binding member and the bioactive agent, therapeutic agent or detectable label may thus be connected to each other directly, for example through any suitable chemical bond or through a linker, for example a peptide linker.

The peptide linker may be a short (2-20, preferably 2-15, residue stretch of amino acids). Suitable examples of peptide linker sequences are known in the art. One or more different linkers may be used. The linker may be about 5 amino acids in length.

The chemical bond may be, for example, a covalent or ionic bond. Examples of covalent bonds include peptide bonds (amide bonds) and disulphide bonds. For example, the specific binding member and bioactive agent, therapeutic agent, or detectable label (diagnostic agent) may be covalently linked, for example, by peptide bonds (amide bonds). The bioactive agent, therapeutic agent, or detectable label may be connected by a covalent bond, e.g. a peptide bond (amide bond), directly to the C-terminal or N-terminal end of the specific binding member. In a particular embodiment, the bioactive agent, therapeutic agent, or detectable label is connected by a peptide bond (amide bond) directly to the N-terminal end of the specific binding member. Thus, the specific binding member and bioactive agent, therapeutic agent, or detectable label (diagnostic agent) may be produced (secreted) as a single chain polypeptide.

The invention also provides isolated nucleic acids encoding the antibody molecules of the invention. The skilled person would have no difficulty in preparing such nucleic acids using methods well-known in the art. An isolated nucleic acid may be used to express the specific binding member of the invention, for example, by expression in a bacterial, yeast, insect or mammalian host cell. A preferred host cell is a mammalian cell such as a CHO, HEK or NS0 cell. The nucleic acid will generally be provided in the form of a recombinant vector for expression.

In vitro host cells comprising such nucleic acids and vectors are part of the invention, as is their use for expressing the specific binding members of the invention, which may subsequently be purified from cell culture and optionally formulated into a pharmaceutical composition. The present invention thus further provides a method of producing the specific binding member of the invention, comprising culturing the recombinant host cell of the invention under conditions for production of the specific binding member. Methods for culturing suitable host cells as mentioned above are well-known in the art. The method may further comprise isolating and/or purifying the specific binding member. The method may also comprise formulating the specific binding member into a pharmaceutical composition, optionally with a pharmaceutically acceptable excipient or other substance as described below.

PD-L1 is known to be expressed on many cancer cells, as well as cells of the immune system.

Thus, a specific binding member of the invention may be used in a method of treating cancer in a patient. The patient is preferably a human patient.

Cells of the cancer to be treated using the specific binding member of the invention may express PD-L1, e.g. on their cell surface. In one embodiment, cells of the cancer to be treated may have been determined to express PD-L1, e.g. on their cell surface. Methods for determining the expression of an antigen on a cell surface are known in the art and include, for example, flow cytometry.

Treatment against various types of cancer using anti-PD-L1 or anti-PD-1 antibodies has been investigated in clinical trials and shown promising results. These include solid tumours such as ovarian cancer, prostate cancer, colorectal cancer, fibrosarcoma, renal cell carcinoma, melanoma (advanced and metastatic melanoma), pancreatic cancer, breast cancer, glioblastoma multiforme, lung cancer (such as non-small cell lung cancer and small cell lung cancer), head and neck cancer (such as head and neck squamous cell carcinoma), stomach cancer (gastric cancer), bladder cancer, cervical cancer, uterine cancer (uterine endometrial cancer, uterine cervical cancer), vulvar cancer, testicular cancer, penile cancer, esophageal cancer, hepatocellular carcinoma, nasopharyngeal cancer, Merkel cell carcinoma, mesothelioma, DNA mismatch repair deficient colorectal cancer, DNA mismatch repair deficient endometrial cancer, thyroid cancer, Hodgkin's lymphoma, non-Hodgkin's lymphoma (such as diffuse large B-cell lymphoma, follicular lymphoma, indolent non-Hodgkin's lymphoma, mantle cell lymphoma), leukaemia (such as chronic lymphocytic leukaemia, myeloid leukaemia, acute lymphoblastoid leukaemia, or chronic lymphoblastoid leukaemia), multiple myeloma, and peripheral T-cell lymphoma. The specific binding members of the present invention thus may find application in the treatment of these cancers. Tumours of these cancers are known, or expected, to contain immune cells, such as TILs, expressing PD-L1.

In particular, treatment of melanoma, colorectal cancer, breast cancer, bladder cancer, renal cell carcinoma, gastric cancer, head and neck cancer (such as squamous cell carcinoma of the head and neck), mesothelioma, lung cancer (such as non-small-cell lung cancer), ovarian cancer, Merkel-cell carcinoma, pancreatic cancer, melanoma and hepatocellular carcinoma using anti-PD-L1 antibodies has been investigated in clinical trials and shown promising results. Thus, the cancer to be treated using the antibody molecules of the present invention may be a melanoma, colorectal cancer, breast cancer, bladder cancer, renal cell carcinoma, bladder cancer, gastric cancer, head and neck cancer (such as squamous cell carcinoma of the head and neck), mesothelioma, lung cancer (such as non-small-cell lung cancer), ovarian cancer, Merkel-cell carcinoma, pancreatic cancer, melanoma, or hepatocellular carcinoma.

Where the application refers to a particular type of cancer, such as breast cancer, this refers to a malignant transformation of the relevant tissue, in this case a breast tissue. A cancer which originates from malignant transformation of a different tissue, e.g. ovarian tissue, may result in metastatic lesions in another location in the body, such as the breast, but is not thereby a breast cancer as referred to herein but an ovarian cancer.

The cancer may be a primary or secondary cancer. Thus, the specific binding member of the present invention may be for use in a method of treating cancer in a patient, wherein the cancer is a primary tumour and/or a tumour metastasis.

The specific binding members of the invention are also expected to find application in the treatment of infectious diseases, such as viral, bacterial, fungal and/or parasitic infections. Preferably, the infectious disease is a viral, bacterial or fungal disease, more preferably a viral or bacterial disease, most preferably a viral disease. The infectious disease may be chronic or acute, but is preferably chronic.

Examples of viral diseases which may be treated with a specific binding member according to the present invention include: human immunodeficiency virus (HIV), influenza virus, enterovirus, hepatitis B virus (HBV), hepatitis C virus (HCV), hepatitis A virus (HAV), hepatitis D virus (HDV), and hepatitis E virus (HEV), respiratory syncytial virus (RSV), herpesvirus (such as Epstein-Barr virus, herpes simplex virus 1 (HSV-1), herpes simplex virus 2 (HSV-2), cytomegalovirus (CMV)), and papillomavirus infection.

Examples of bacterial diseases which may be treated with a specific binding member of the invention include: *Mycobacterium tuberculosis*, gram-negative bacteria (such as *Acinetobacter, Klebsiella, Enterobacter*), gram-positive bacteria (such as *Clostridium difficile, Staphylococcus aureus*), and *Listeria* (e.g. *Listeria monocytogenes*) infection.

Examples of fungal diseases which may be treated with a specific binding member of the invention include: *Aspergillus* and Candidia infection.

Examples of parasitic diseases which may be treated with a specific binding member of the invention include: Malaria, *Toxoplasma*, and *Leishmania* infection.

The specific binding members of the invention are also expected to find application in the treatment of inflammation, diseases and conditions associated with inflammation, and inflammatory diseases, such as stroke, stroke-related inflammation, and vascular inflammation or vasculitis, e.g., medium and large vessel vasculitis, or vasculitis of the central and/or peripheral nervous system.

The specific binding members of the invention are designed to be used in methods of treatment of patients, preferably human patients. Specific binding members will usually be administered in the form of a pharmaceutical composition, which may comprise at least one component in addition to the specific binding member, such as a pharmaceutically acceptable excipient. For example, a pharmaceutical composition of the present invention, may comprise, in addition to active ingredient, a pharmaceutically acceptable excipient, carrier, buffer, stabiliser or other materials well-known to those skilled in the art. Such materials should be non-toxic and should not interfere with the efficacy of the active ingredient. The precise nature of the carrier or other material will depend on the route of administration, which may be by injection, e.g. intravenous or subcutaneous. The specific binding member may be administered intravenously, or subcutaneously.

Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the specific binding member, or pharmaceutical composition comprising the specific binding member, is preferably in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be employed, as required. Many methods for the preparation of pharmaceutical formulations are known to those skilled in the art. See, for example, Robinson ed., Sustained and Controlled Release Drug Delivery Systems, Marcel Dekker, Inc., New York, 1978.

A composition comprising a specific binding member according to the present invention may be administered alone or in combination with other treatments, concurrently or sequentially or as a combined preparation with another therapeutic agent or agents, dependent upon the condition to be treated. For example, a specific binding member of the invention may be administered in combination with an existing therapeutic agent for the disease to be treated, e.g. a cancer as mentioned above. For example, a specific binding member of the present invention may be administered to the patient in combination with a second anti-cancer therapy, such as chemotherapy, anti-tumour vaccination (also referred to as a cancer vaccination), radiotherapy, immunotherapy, an oncolytic virus, chimeric antigen receptor (CAR) T-cell therapy, or hormone therapy.

It is expected that the specific binding member of the invention may act as an adjuvant in anti-cancer therapy, such as chemotherapy, anti-tumour vaccination, or radiotherapy. Without wishing to be bound by theory, it is thought that administration of the specific binding member to the patient as part of chemotherapy, anti-tumour vaccination, or radiotherapy will trigger a greater immune response against the cancer associated antigen PD-L1, than is achieved with chemotherapy, anti-tumour vaccination, or radiotherapy alone.

A method of treating cancer in a patient may thus comprise administering to the patient a therapeutically effective amount of a specific binding member according to the present invention in combination with a chemotherapeutic agent, anti-tumour vaccine, radionuclide, immunotherapeutic agent, oncolytic virus, CAR-T cell, or agent for hormone therapy. The chemotherapeutic agent, anti-tumour vaccine, radionuclide, immunotherapeutic agent, oncolytic virus, CAR-T cell, or agent for hormone therapy is preferably a chemotherapeutic agent, anti-tumour vaccine, radionuclide, immunotherapeutic agent, oncolytic virus, CAR-T cell, or agent for hormone therapy for the cancer in question, i.e. a chemotherapeutic agent, anti-tumour vaccine, radionuclide, immunotherapeutic agent, oncolytic virus, CAR-T cell, or agent for hormone therapy which has been shown to be effective in the treatment of the cancer in question. The selection of a suitable chemotherapeutic agent, anti-tumour vaccine, radionuclide, immunotherapeutic agent, oncolytic virus, CAR-T cell, or agent for hormone therapy, which have been shown to be effective for the cancer in question, is well within the capabilities of the skilled practitioner.

For example, where the method comprises administering to the patient a therapeutically effective amount of a specific binding member according to the present invention in combination with a chemotherapeutic agent, the chemotherapeutic agent may be selected from the group consisting of: taxanes, cyctotoxic antibiotics, tyrosine kinase inhibitors, PARP inhibitors, B_RAF enzyme inhibitors, alkylating agents, platinum analogues, nucleoside analogues, thalidomide derivatives, antineoplastic chemotherapeutic agents and others. Taxanes include docetaxel, paclitaxel and nab-paclitaxel; cytotoxic antibiotics include actinomycin, bleomycin, anthracyclines, doxorubicin and valrubicin; tyrosine kinase inhibitors include sunitinib, erlotinib, gefitinib, axitinib, PLX3397, imatinib, cobemitinib and trametinib; PARP inhibitors include piraparib; B-Raf enzyme inhibitors include vemurafenib and dabrafenib; alkylating agents include dacarbazine, cyclophosphamide, temozolomide; platinum analogues include carboplatin, cisplatin and oxaliplatin; nucleoside analogues include gemcitabine and azacitidine; antineoplastics include fludarabine. Other chemotherapeutic agents suitable for use in the present invention include methotrexate, defactinib, entinostat, pemetrexed, capecitabine, eribulin, irinotecan, fluorouracil, and vinblastine.

Vaccination strategies for the treatment of cancers has been both implemented in the clinic and discussed in detail within scientific literature (such as Rosenberg, S., 2000). This mainly involves strategies to prompt the immune system to respond to various cellular markers expressed by autologous or allogenic cancer cells by using those cells as a vaccination method, both with or without granulocyte-macrophage colony-stimulating factor (GM-CSF). GM-CSF provokes a strong response in antigen presentation and works particularly well when employed with said strategies.

Where the method comprises administering to the patient a therapeutically effective amount of a specific binding member according to the present invention in combination with an immunotherapeutic agent, the immunotherapeutic agent may be selected from the group consisting of: antibodies binding to a checkpoint inhibitor, costimulatory molecule or soluble factor, such as antibodies binding to CTLA-4, LAG-3, TIGIT, TIM-3, VISTA, CD73, CSF-1R, KIR, OX40, CD40, HVEM, TGFB, IL-10, CSF-1. Alternatively, the immunotherapeutic agent may one or more cytokines or cytokine-based therapies selected from the group consisting of IL-2, prodrug of conjugated IL2, GM-CSF, IL-7, IL-12, IL-9, IL-15, IL-18, IL-21, and type I interferon.

Administration may be in a "therapeutically effective amount", this being an amount which is sufficient to show benefit to a patient. Such benefit may be at least amelioration of at least one symptom. Thus, "treatment" of a specified disease refers to amelioration of at least one symptom. The actual amount administered, and rate and time-course of administration, will depend on the nature and severity of what is being treated, the particular patient being treated, the clinical condition of the individual patient, the cause of the disorder, the site of delivery of the composition, the type of specific binding member, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of specific binding members are well known in the art (Ledermann et al., 1991; and Bagshawe et al., 1991). Specific dosages indicated herein, or in the Physician's Desk Reference (2003) as appropriate for a specific binding member being administered, may be used. A therapeutically effective amount or suitable dose of a specific binding member can be determined by comparing its in vitro activity and in vivo activity in an animal model. Methods for extrapolation of effective dosages in mice and other test animals to humans are known. The precise dose will depend upon a number of factors, including the size and location of the area to be treated, and the precise nature of the specific binding member. Treatments may be repeated at daily, twice-weekly, weekly or monthly intervals, at the discretion of the physician. Treatment may be given before and/or after surgery, and may be administered or applied directly at the anatomical site of surgical treatment.

Further aspects and embodiments of the invention will be apparent to those skilled in the art given the present disclosure, including the following experimental exemplification.

"and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1—Naïve Selection of Anti-Human PD-L1 Fcabs 1.1 Protein Biotinylation

Recombinant human PD-L1 (R&D Systems, 157-67), human PD-1 (R&D Systems, 1086-PD) and mouse PD-L1 (R&D Systems, 1019-67) with a C-terminal human IgG tag were purchased and biotinylated using the Lightning Link Type A Biotinylation kit (Innova Biosciences, 370-0010). Briefly, 100 μg of lyophilised protein was reconstituted in 100 μl PBS to a final concentration of 1 mg/ml and 10 μl of Modifier Reagent was added to the diluted protein and gently mixed. The solution was added to a vial of Lightning-Link mix and gently resuspended and the mixture was incubated overnight at room temperature. The Quencher solution (10 μl) was added and incubated for 30 minutes at room temperature, before storing the biotinylated protein at −80° C. in 10 μl aliquots.

1.2 Phage Libraries

Naïve phage libraries displaying the CH3 domain of human IgG1 (IMGT numbering 1.4-130) with randomisation within the AB (residues 11-18) and EF (residues 92-101) loops were used for selection with the PD-L1 antigen described above. The libraries were selected in three rounds using Streptavidin Dynabeads (Thermo Fisher, 11205D) and Neutravidin binding protein coupled to Dynabeads (Thermo Fisher, 31000) to isolate the phage bound to biotinylated PD-L1 Fc. In addition, an excess of IgG Fc fragment of human plasma was added to each selection step to avoid the isolation of Fc binders.

The outputs were screened by ELISA for binding to PD-L1 and positive binders sub-cloned and expressed as soluble Fcabs (containing a truncated hinge) in *Pichia*

*pastoris* using EasySelect *Pichia* Expression Kit (Life Technologies, K1740-01). Of the 30 unique Fcab clones selected, 18 clones expressed as soluble proteins when transferred from phage to a soluble expression platform.

1.3 ELISA Based Blocking Assay

The ability of the human PD-L1-binding Fcabs to block the interaction between human PD-L1 Fc and PD-1 or CD80 was studied in an ELISA based Receptor Binding Assay (RBA) using recombinant biotinylated human PD-L1 (described in Example 1.1) and recombinant human PD-1 Fc (R&D Systems, 1086-PD) or CD80 Fc (R&D Systems, 140-61).

Briefly, recombinant human PD-1 Fc or CD80 Fc were coated onto a Maxisorp plate (Thermo Scientific, 439454) at 0.5 or 1.0 µg/ml, respectively. The plates were incubated overnight at 4° C., washed once in PBS and subsequently blocked with 300 µl PBS containing 1% Tween for 2 hours at room temperature. Relevant concentrations of Fcab (0.5 to 500 nM, 2-fold dilutions), control IgG Fc (10-10000 nM, 2-fold dilutions) or control antibodies (0.010 to 10 nM, 2-fold dilutions) were incubated with 250 ng/µl biotinylated PD-L1 Fc in 100 µl PBS for 1 hour at room temperature whilst shaking at 450 rpm. Control IgG Fc was tested up to a concentration of 10000 nM to determine any non-specific blocking activity. The control mAbs used were anti-human PD-L1 mAb (MIH1, Affymetrix eBioscience, 14-5983-82) and PD-L1 mAb YW243.55.570 ("S70") (Patent Pub. No.: US 2013/0045202 A1).

Blocking solution was discarded and the biotinylated PD-L1 Fc/Fcab or control antibody mix was added to the maxisorp plates and incubated for 1 hour at room temperature whilst shaking at 450 rpm. Plates were washed 3× with 300 µl PBS/Tween 0.05%, followed by 3 washes with 1×PBS. Streptavidin conjugated to Horseradish Peroxidase (HRP) was diluted 1:1000 in PBS and 100 µl was added to the wells and incubated for 1 hour at 4° C. whilst shaking at 450 rpm. Plates were washed 3× with 300 µl PBS/Tween 0.05%, followed by 3 washes with 1×PBS. 100 µl TMB substrate (eBioscience, 00-4201-56) was added to each well. The reaction was stopped between 2-10 minutes after addition of TMB by the addition of 50 µl 1M sulphuric acid solution. OD was read at 450-630 nm in a 96-well plate reader within 30 minutes of sulphuric acid addition and analysed using GraphPad Prism software (GraphPad Software, Inc.)

18 clones were tested, three of which, FS17-19, FS17-26 and FS17-33, were able to block the interaction between human PD-L1 Fc and PD-1. For these clones, a full dose response RBA was performed and their ability to block PD-L1 interaction with CD80 was analysed. FS17-19, FS17-26 and FS17-33 all showed potent blocking activity towards both the PD-L1:PD-1 interaction and PD-L1:CD80 interaction (data not shown).

1.4 Binding of Fcabs to Recombinant PD-L1

The binding of FS17-19, FS17-26 and FS17-33 to human and mouse PD-L1 Fc was measured by Surface Plasmon Resonance using BIAcore 3000 (GE Healthcare).

Briefly, a streptavidin sensor chip (GE Healthcare, BR100032) was used to coat human PD-L1 Fc (described in Example 1.1) on flow cell 2, mouse PD-L1 Fc (described in Example 1.1) on flow cell 4, and flow cell 1 was not coated and was used as a reference. Human PD-L1 Fc and mouse PD-L1 Fc were coupled at about 10000 RU. Fcabs diluted in HBS-EP buffer (GE Healthcare, BR100669) were injected at 10 µM or 3.3 µM and 3-fold dilutions for 5 minutes and then allowed to dissociate in buffer for 3 minutes. Regeneration was not required as the Fcabs completely dissociated in buffer. Subtracted data (flow cell 2–flow cell 1 or flow cell 4–flow cell 1) was analysed using BIAevaluation 3.2 to identify binding.

The binding data (not shown) demonstrated that FS17-19, FS17-26 and FS17-33 bound to human PD-L1 Fc. FS17-19 was also found to be weakly cross-reactive to mouse PD-L1 Fc, but FS17-26 and FS17-33 were not.

1.5 Development of HEK 293 Cells Expressing Human PD-L1, Cynomolgus PD-L1, Mouse PD-L1, Human CD80, Mouse CD80 and Human PD-1

Human, mouse, and cynomolgus PD-L1 sequences (SEQ ID Nos 61, 62 and 63) were subcloned into pcDNA5FRT vector (Life Technologies) using KpnI and NotI restriction sites. For human and mouse CD80 and human PD-1 (SEQ ID Nos 65, 66 and 64) HindIII and NotI restriction sites were used. These vectors were then transformed into Flp-In T-REx 293 cell line (Life Technologies, R780-07) using Lipofectamine 2000 (Life Technologies, 11668-019). Cells were grown in DMEM containing 10% FBS, 100 µg/ml Hygromycin B (Melford Laboratories Ltd, Z2475) and 15 µg/ml Blasticidin (Melford Laboratories Ltd, B1105) for 3-4 weeks until colonies of stably transformed cells had formed. These colonies were amplified in the presence of 1 µg/ml Doxycyclin (Sigma Aldrich, D9891) and tested for expression of PD-L1, CD80 or PD-1 using PE conjugated anti-human PD-L1 (MIH1) antibody (BD Biosciences, 557924), PE conjugated anti-mouse PD-L1 (MIH5) antibody (BD Biosciences, 558091), PE conjugated anti-human CD80 antibody (L307.4, BD Biosciences 557227), PE conjugated anti-human PD-1 antibody (MIH4, BD Biosciences, 557946), or FITC-conjugated anti-mouse CD80 antibody (16-10A1, BD Biosciences, 553768). Cells were detached using cell dissociation buffer, washed once with PBS and $2 \times 10^5$ cells were plated in wells of a 96-well plate and then incubated with antibody diluted 1:20 in PBS for 1 hour at 4° C. Cells were washed once in PBS and then measured on an Accuri C6 cytometer (BD Biosciences) and the data was analysed using FlowJoX. Expression of human, cynomolgus and mouse PD-L1, as well as human CD80, mouse CD80 and human PD-1, was detected in the respective cell lines.

1.6 Cell Based Binding Assay

The FS17-19, FS17-26 and FS17-33 Fcab were then tested for binding to HEK 293 cell-expressed human PD-L1, human CD80, human PD-1, mouse CD80 or mouse PD-L1 (see Example 1.5 for details regarding production of these cell lines).

Briefly, HEK 293 cells overexpressing these proteins were grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) and were detached from tissue culture flasks using cell dissociation buffer (Life Technologies, 13151-014) and seeded in V-bottom 96-well plates at $2 \times 10^5$ cells/well. Fcabs were incubated with the cells at 1 µM in a 100 µl volume for 1 hour at 4° C. PE- or FITC conjugated control mAbs were added at concentrations as recommended by the manufacturer in a 100 µl volume for 1 hour at 4° C. The antibodies used in Example 1.5 were used as control antibodies in this experiment. The plates were washed once with PBS by centrifuging the plate at 1500 rpm for 3 minutes at 4° C. and the supernatant was removed. Secondary antibody (Goat anti-human Fc Alexa Fluor 488, Jackson ImmunoResearch, 109-546-098) was diluted 1:1000 in PBS and 100 µl was added to the cells for 30 minutes at 4° C. (plates were kept in the dark). After washing the plates once with PBS, as before, the pellet was resuspended in 100 µl PBS containing 1 µg/ml DAPI (Biotium, 40043). The plate was read on an Accuri C6 cytometer (BD Bioscience) and the data analysed using FlowJoX.

FS17-19, FS17-26 and FS17-33 were found to bind specifically to cell-surface human PD-L1 and not to human PD-1, human CD80, mouse PD-L1 or mouse CD80.

1.7 Cell Based Blocking Assay

The ability of Fcabs FS17-19, FS17-26 and FS17-33 to block the binding of recombinant PD-L1 to cell-bound PD-1 was determined in a cell based blocking assay.

Briefly, HEK 293 cells expressing human PD-1 (see Example 1.5) were seeded at $1 \times 10^5$ cells per well in a V-bottom 96-well plate in PBS. The relevant concentrations of Fcab (78 to 10000 nM, 2-fold dilutions), control IgG Fc (10000 nM) or control antibody (500 nM) were incubated with 250 ng/µl biotinylated PD-L1 Fc in 100 µl 1×PBS for 1 hour at room temperature whilst shaking at 450 rpm. Anti-human PD-L1 mAb (MIH1) was used as control. The plates were centrifuged at 1500 rpm for 3 minutes at 4° C. to pellet the cells. The PBS was discarded and the pre-incubated Fcab or control antibody/biotinylated hPD-L1 Fc mixture was added to the wells for 1 hour at 4° C. The plates were centrifuged at 1500 rpm for 3 minutes at 4° C. to pellet the cells, supernatant was discarded and the cells were resuspended in PBS. Streptavidin conjugated to Alexa 647 was diluted 1:1000 in PBS and 100 µl was added to the wells for 30 minutes at 4° C. The plates were centrifuged, supernatant discarded and the cells resuspended in PBS as performed previously. The plate was read on an Accuri C6 cytometer (BD Bioscience) and the data analysed using FlowJoX.

Consistent with the results of the ELISA based blocking assay, FS17-19, FS17-26 and FS17-33 showed potent blocking activity at the concentrations tested. Fcabs FS17-19 and FS17-33 showed higher blocking activity than FS17-26 and were therefore selected for affinity maturation.

1.8 Summary of Naïve Selection Procedure

From the 30 Fcabs identified by the initial screen of the naïve phage libraries, three anti-human PD-L1 Fcabs (FS17-19, FS17-26 and FS17-33) showed potent PD-L1/PD-1 and PD-L1/CD80 blocking activity. Both Fcabs FS17-19 and FS17-33 showed higher blocking activity in both an ELISA assay and in a cell-based assay than Fcab FS17-26, as well as specific binding to recombinant and cell-surface PD-L1 Fc, and were therefore selected for further affinity maturation as described in Example 2 below.

Example 2—Affinity Maturation and Functional Improvement of Fcab Clones Identified in Example 1

2.1 Affinity Maturation and Functional Improvement of Fcab FS17-19 Fcab FS17-19 underwent multiple rounds of affinity maturation starting with an NNK walk of the AB and EF loops, using a similar method to that described in 2.2.1 below. The NNK walk resulted in clones derived from FS17-19 which had very low functional activity when measured in a DO11 T-cell activation assay (see Example 6 for methodology), with an $EC_{50}$ that was 300-fold less than the positive control anti-PD-L1 antibody S1. With a view to improving functional activity, a randomisation of the AB, CD and EF loops, using a similar method to that described in 3.1 below, was carried out. Clones containing mutations in the AB loop showed improved activity in the DO11 T-cell activation assay to within 80-fold of the control antibody S1. One Fcab clone selected from the AB loop library underwent a further round of affinity maturation, focusing on just the CD and EF loops. Clones from this maturation did not show any improvement in functional activity over the previous round's clones.

Despite the extensive affinity maturation strategy described above, it was not possible to identify clones from the FS17-19 lineage that had an acceptable level of functional activity in a DO11 T-cell activation assay, and work on this lineage was therefore abandoned.

2.2 Affinity Maturation and Functional Improvement of Fcab FS17-33

Anti-human PD-L1 Fcab FS17-33 was isolated from naïve phage selections, as described in Example 1 above. The objective of this study was to gain improvements in FS17-33 activity by randomising individual residues in the binding loops by performing an NNK walk through the AB and EF loops.

2.2.1 NNK Walk of Binding Loop

To identify mutations in Fcab FS17-33 that improved PD-L1/PD-1 blocking activity, parsimonious mutagenesis libraries were generated by diversifying one amino acid residue at a time in the AB or EF loop of Fcab FS17-33, leading to a total of 12 individual libraries (see Table 1 below). The libraries were made with low redundancy NNK codons to represent all possible amino acids in the position of interest. Forward and reverse primers were designed according to the guidelines of Quickchange Lightning Site-Directed Mutagenesis Kit (Agilent, 200518), which was used to create the libraries.

TABLE 1

Amino acid sequence of the AB and EF binding loops of FS17-33. The '~' symbol indicates a deletion in the FS17-33 sequence compared to the wild-type IgG1 Fc. The X indicates the single amino acid scanned at that time in the NNK walk.

| | AB loop | | | | | EF loop | | | | | | | | |
|---|---|---|---|---|---|---|---|---|---|---|---|---|---|---|
| FS17-33 | Q | S | G | Y | W | S | N | W | R | W | Q | M | G | D | ~ |
| Library 1 | X | | | | | | | | | | | | | | |
| Library 2 | | X | | | | | | | | | | | | | |
| Library 3 | | | X | | | | | | | | | | | | |
| Library 4 | | | | X | | | | | | | | | | | |
| Library 5 | | | | | X | | | | | | | | | | |
| Library 6 | | | | | | X | | | | | | | | | |
| Library 7 | | | | | | | X | | | | | | | | |
| Library 8 | | | | | | | | X | | | | | | | |
| Library 9 | | | | | | | | | X | | | | | | |

TABLE 1-continued

Amino acid sequence of the AB and EF binding loops of FS17-33. The '~' symbol indicates a deletion in the FS17-33 sequence compared to the wild-type IgG1 Fc. The X indicates the single amino acid scanned at that time in the NNK walk.

| | AB loop | | | | | EF loop | | | | | | | | |
|---|---|---|---|---|---|---|---|---|---|---|---|---|---|---|
| FS17-33 | Q | S | G | Y | W | S | N | W | R | W | Q | M | G | D | ~ |
| Library 10 | | | | | | | | | | | | X | | | |
| Library 11 | | | | | | | | | | | | | X | | |
| Library 12 | | | | | | | | | | | | | | X | |

Briefly, the FS17-33 Fcab sequence (CH3, CH2 and truncated hinge, additionally containing a LALA mutation in the CH2 domain) was cloned into the pTT5 expression vector (National Research Council of Canada) resulting in vector pTT5-FS17-33AA. The introduction of the LALA mutation in the CH2 domain of human IgG1 is known to reduce Fc γ receptor binding (Bruhns, P., et al., 2009 and Hezareh et al., 2001). This was used as template for the mutagenesis libraries. PCR reactions were treated with DpnI for 5 min at 37° C. to remove any parental DNA before being transformed into *E. coli* (Mix and Go, Zymo research, T3009) and plated on ampicillin-containing LB plates. Transformants were picked the following day and sequenced to confirm the mutations.

DNA for transfection was prepared using standard DNA isolation methods and the parsimonious libraries were expressed in HEK Expi293 cells (DNA transfected using ExpiFectamine 293 Transfection Kit (Life Technologies, A14524) into Expi293F cells (Life technologies, A14527). The Fcab concentration in transfected HEK supernatants was determined by BLI using Octet (ForteBio). Fcabs were purified using mAb Select SuRe protein A columns.

The HEK 293 supernatants were subsequently analysed in an ELISA-based RBA at two concentrations (10 nM and 50 nM, see Example 1.3 for methodology). Fcabs with potentially improved PD-L1/PD-1 blocking activity compared to FS17-33 protein in this assay were selected and sequenced. This identified particular positions in the sequence of FS17-33 that were critical for binding PD-L1, i.e. where few or no alternative amino acids were identified as suitable substitutions (see Table 2), as well as well as positions at which several potential alternative amino acids were possible. Several mutants were identified multiple times, enforcing confidence in the assay results.

TABLE 2

Number of amino acid substitutions identified for each position mutated within the AB and EF loop of FS17-33. Residue numbering according to IMGT numbering.

| | AB loop (14-18) | | | | | EF loop (92-100) | | | | | | | | |
|---|---|---|---|---|---|---|---|---|---|---|---|---|---|---|
| FS17-33 | Q | S | G | Y | W | S | N | W | R | W | Q | M | G | D |
| Mutants (#) | 4 | 15 | 7 | 4 | 0 | 0 | 4 | 1 | | | | 9 | 1 | 7 | 10 |

The twenty-seven Fcabs with the highest activity in the ELISA based blocking assay were expressed, purified and tested in a cell-based blocking assay (see Example 2.2.2 for methodology). Four AB loop and three EF loop clones were then shuffled by splice overlap extension PCR to generate new combinations (Horton et al., 2013). Shuffled Fcabs were cloned into the pTT5 expression vector, expressed and tested again for PD-L1/PD-1 blocking in both ELISA based blocking (as described in 1.3) and cell based blocking assays (as described in 2.2.2 below).

One of the clones identified following loop shuffling was FS17-33-37, which, compared to FS17-33, had a single change in the AB loop (S15V) and a single change in the EF loop (G99D). The AB and EF loops of clone FS17-33-37 are shown in Table 3.

TABLE 3

Comparison of residues within AB and EF loops for the FS17-33-37 and FS17-33 Fcabs. Residue numbering according to IMGT numbering. The '~' symbol indicates a deletion in the FS17-33 sequenced compared to the wild-type IgG1 Fc.

| | AB loop (14-18) | | | | | EF loop (92-101) | | | | | | | | |
|---|---|---|---|---|---|---|---|---|---|---|---|---|---|---|
| FS17-33 | Q | S | G | Y | W | S | N | W | R | W | Q | M | G | D | ~ |
| FS17-33-37 | Q | V | G | Y | W | S | N | W | R | W | Q | M | D | D | ~ |

2.2.2 Blocking Activity

The blocking activity of the clones produced in Example 2.2.1 was analysed in a cell-based assay using HEK 293 cells overexpressing human PD-L1 (see 1.5 for development of the cell line). Briefly, HEK 293 cells expressing human PD-L1 were seeded at $1 \times 10^5$ cells per well in a V-bottom 96-well plate in PBS. The relevant concentrations of Fcab or positive control anti-PD-L1 mAb YW243.55.S1 ("S1") (Patent Pub. No. US 2013/0045202 A1) were incubated with 500 ng/ml biotinylated PD-1 Fc in 100 µl 1×PBS for 45 minutes whilst shaking at 450 rpm. The plates were centrifuged at 1500 rpm for 3 minutes at 4° C. to pellet the cells. PBS was discarded and the pre-incubated Fcab or positive control/biotinylated hPD-1 Fc mixture was added to the wells for 1 hour at 4° C. The plates were centrifuged at 1500 rpm for 3 minutes at 4° C. to pellet the cells, supernatant was discarded and the cells were resuspended in PBS. Streptavidin conjugated to Alexa 488 was diluted 1:1000 in PBS and 100 µl was added to the wells for 30 minutes at 4° C. The plates were centrifuged at 1500 rpm for 3 minutes at 4° C. to pellet the cells, supernatant discarded and the cells were resuspended in PBS with DAPI. The plate was read on FACS Canto (BD Bioscience) and the data analysed using FlowJoX.

Fcab clones with improved activity compared with FS17-33 were identified. An example of this is illustrated in Table 4, below, which shows the improved blocking activity for FS17-33-37 compared to the parent FS17-33 clone. This binding activity was similar to the positive control S1 mAb.

TABLE 4

PD-L1/PD-1 blocking activity of the FS17-33-37 Fcab compared to the parent FS17-33 Fcab.

| Clone | PD-L1/PD-1 blocking activity ($IC_{50}$) |
|---|---|
| FS17-33 | 17.7 nM |
| FS17-33-37 | 8.1 nM |

2.2.3 Cell Binding to Human and Cynomolgus PD-L1

To test binding to cell-surface human and cynomolgus PD-L1, the 11 Fcab clones with the highest activity in the cell based blocking assays, including FS17-33-37, were tested for binding to HEK 293 cells overexpressing human or cynomolgus PD-L1 (see Example 1.5 for methodology). All Fcabs showed dose-dependent binding to human PD-L1 with $EC_{50}$ values around 5-10 nM and bound to cynomolgus PD-L1 with $EC_{50}$ values around 100-200 nM.

2.2.4 DO11.10 T Cell Activation Assay

Inhibition of the PD-L1/PD-1 interaction is known to lead to increased T cell activation (Stewart et al., 2015). As FS17-33-derived Fcabs showed potent blocking activity of the PD-L1/PD-1 interaction, they were expected to also increase T cell activation. In order to test this, 20 FS17-33 derived Fcabs were tested using a DO11.10 T cell activation assay and compared with anti-PD-L1 mAb S1 as a positive control. The assay is described in more detail in Example 6.

The results showed that the FS17-33 derived clones were able to enhance T cell activation in this assay but the activity was very weak compared to the anti-PD-L1 positive control antibody 51 (data not shown). This was unexpected, as the difference in the PD-L1/PD-1 blocking activity of the Fcab clones tested was within 3-10 fold of the positive control.

2.2.5 Characterisation of FS17-33-37

Fcab clone FS17-33-37 was chosen for further affinity maturation based on its low/minimal non-specific activity (without OVA peptide) in the DO11.10 T cell activation assay and based on its size exclusion (SE)-HPLC profile. Size exclusion chromatography (SEC) profiles were assessed on percentage monomeric protein and the elution time, favoring clones with an elution time closer to that of wild type IgG Fc (see FIG. 2). A full dose titration of FS17-33-37 in the cell binding, cell based blocking assay and DO11.10 T cell activation assays were performed to further characterise FS17-33-37 (data not shown). The results confirmed that FS17-33-37 showed potent cell binding and blocking activity but weak activity in the DO11.10 T cell activation assay.

2.2.6 Summary of the Affinity Maturation and Functional Improvement of Fcab FS17-33

The NNK walk mutagenesis of the FS17-33 Fcab led to the identification of multiple clones with increased PD-L1:PD-1 blocking activity, to a level that is similar to the anti-PD-L1 positive control S1 mAb. Additionally, the anti-human PD-L1 binding FS17-33 derived Fcabs were cross-reactive to cynomolgus PD-L1.

However, surprisingly activity of the FS17-33 lineage in the DO11.10 T cell activation assay was very weak compared with the positive control S1 mAb. This data seemed inconsistent with the blocking data. As the DO11.10 T cell activation assay is a more physiologically-relevant potency assay than the blocking assay, FS17-33 derived Fcabs clones were over 1000-fold lower in functional activity compared to the positive control antibodies.

Without wishing to be bound by theory, it was hypothesized that the FS17-33-derived Fcabs may be unable to bind to monomeric PD-L1 with a high enough affinity to result in functional activity when measured by the DO11.10 T cell activation assay. The results obtained from the blocking and binding assays may have been influenced by an avidity effect that was a result of the high levels of human PD-L1 used in these assays.

More substantial randomisation of the binding loops was therefore conducted with the aim of identifying Fcabs with higher affinity for PD-L1 and functional activity. Based on its specific activity and SEC-HPLC profile, FS17-33-37 was selected as the parental clone for further affinity maturations, as described in Example 3 below.

Example 3—Affinity Maturation and Functional Improvement of Fcab Clone FS17-33-37

3.1 Affinity Maturation

In order to obtain an Fcab with improved activity, FS17-33-37 was affinity matured to introduce the maximum diversity. Specifically, the FS17-33-37 PTTS plasmid DNA (see 2.2.1) was used as a template to prepare libraries containing randomized loops. A portion of the AB loop (residues 14-18), the CD loop (residues 45.1-78), and the EF loop (residues 92-94, and 97-101) was randomized using NNK primers (AB loop) or ELLA primers (CD and EF loop). ELLA primers specify the codons used for each amino acid and their relative abundance within the mix. Only cysteine was excluded from the mix and no bias was given to any other amino acid. The individual loop libraries (one library for each of the AB, CD and EF loops) went through several rounds of selection to enrich for Fcab clones with improved binding to biotinylated hPD-L1-his (comprising a his-tag) compared to the parent clone FS17-33-37.

To further improve the affinity of the matured clones for PD-L1, the outputs from each single loop library were shuffled in an unbiased manner to identify the loop combinations with the highest affinity for hPD-L1. The outputs from the selections were shuffled by isolating DNA from selected cells from each of the single loop libraries and shuffling DNA by splice overlap extension PCR to generate unbiased loop recombinations. This DNA was then used to create a new yeast display library. Yeast cells (EBY100, Invitrogen V835-01) were transformed using the amplified PCR product along with a yeast vector (pYD1dem, Invitrogen V835-01). The shuffled library then underwent multiple rounds of selection to enrich for the clones with the highest affinity for monomeric PD-L1.

Selected Fcabs were screened for binding to recombinant protein both monomeric and dimeric PD-L1 antigen. Monomeric His-tagged antigen (Acro biosystems Cat #PD1-H5229) was biotinylated using the Pierce LC-LC biotinylation kit (Thermo Fisher Scientific 21338) whilst the biotinylated dimeric antigen is available commercially (BPS Bioscience #71105)

From the screening, 104 Fcab clones were chosen for soluble expression. Soluble Fcabs were expressed in HEK cells from the pTT5 Fcab expression vector and purified using mAb Select SuRe protein A columns.

3.2 SEC Profiles

Size exclusion chromatography (SEC) was carried out to determine whether any of the affinity matured Fcabs identified in 3.1 showed aggregation. All purified Fcabs were analysed by SE-HPLC using an Agilent 1100 series HPLC with a Zorbax GF-250 column (Agilent). All clones containing an MFYGP motif in the EF loop showed excessive aggregation or did not enter the column at all. As a result, these clones were not considered to represent suitable candidate Fcabs and were not tested further. The remaining 40 clones did not show aggregate peaks, but they did have split peaks or shoulders. For example, as shown in FIG. 2, clone FS17-33-116 showed a split peak (B) that wasn't present in the parent FS17-33-37 clone (A). The potential cause of these deviations will be discussed later, but was not considered a reason to remove these Fcab clones from the candidate selection process.

3.3 Off-Rate Screening of Expressed Fcabs

Following soluble expression in HEK cells, the Fcabs from the selection using the monomeric, His-tagged antigen were screened for their off-rate when bound to human PD-L1 using BIAcore. Briefly, biotinylated antigen was coated on the chip at 10 µg/mL to 585 RU and supernatant from the expressed clones was flowed over the chip at 30 µL/minute. This assay was carried out with both monomeric and dimeric PD-L1 antigen. The dissociation was carried out for 6 minutes. Analysis was carried out using the BIAevaluate software. Curves were double subtracted from the blank flow cell and from a run with no Fcab. Curves were then aligned and normalized for comparison. It was hypothesised that clones with slower off-rates when bound to PD-L1 would have enhanced T cell activation activity due to continuous blocking of PD-L1 binding to its ligands. 33 of the 40 Fcab clones tested showed a significantly improved (slower) dissociation (off) rate compared with the parent clone FS17-33-37 when bound to PD-L1 and were selected for further functional screening as described in 3.4 below.

3.4 Functional Screening

In order to determine whether the affinity maturation described in 3.1 resulted in an improvement in functional activity, the 33 Fcab clones identified in 3.3 were tested for activity using the DO11.10 T cell activation assay and compared with the anti-PD-L1 antibody S70 as a positive control (see Example 6.1 for experimental details). A titration of each Fcab was used to calculate the $EC_{50}$ values for each Fcab in this assay to facilitate comparison. Five clones (FS17-33-85, FS17-33-87, FS17-33-114 and FS17-33-116) all had $EC_{50}$ values between 0.28 to 0.5 nM, which is comparable to the positive control, the S70 antibody.

Clones FS17-33-85, FS17-33-87, FS17-33-114 and FS17-33-116 had very similar sequences with only 1 or 2 amino acid differences, none of which are in the AB or CD loops (see Table 5, which identifies the differences in sequence between these clones, all of which are located in the EF loop or the framework region). Surprisingly, the AB loop sequence present in all clones from the shuffle library (see 3.1) had not been identified in the screening of the individual AB loop library and contained an amino acid deletion, with the result that the AB loop sequence between residues 14 to 18 was only four amino acids in length, rather than five. The exact location of the deletion was not known. As the residues at positions 17 and 18 of the AB loop could not be substituted with another amino acid without a significant worsening in the off-rate (faster) when the Fcab was bound to PD-L1 (see Table 9A below), the deletion had to be located at either residue 14, 15 or 16 of the AB loop. The deletion is thought to be an artefact in the shuffle library resulting from accidentally truncated mutagenesis primers. Fcab clones comprising such deletions in their loop regions are usually removed during the selection process, as deletions rarely result in Fcabs which retain antigen-binding activity. Even though an AB sequence with a deletion was not identified from screening of the AB clones, this sequence must have been present in the output pool from the selections as a rare clone or lower affinity binder. However, when this truncated AB sequence was shuffled with the other loops, it became the dominant AB loop, suggesting a strong contribution of this deletion to the antigen-binding activity and/or structure of the shuffled Fcab clones, in the context of Fcabs containing the new CD loop sequences. Fcab clones comprising such a deletion in their AB loop would not have been identified if a more directed shuffle approach had been implemented, where the best sequences identified from the AB loop selections would have been combined with the best sequences from the CD loop selections. The deletion in the AB loop of the representative FS17-33-116 clone compared with the wild-type Fcab sequence is shown in FIG. 1. Furthermore, as described in more detail in 4.3 below, restoring this deleted residue in the AB loop produced a significant loss in binding affinity. The presence of this deletion in the AB loop was therefore important for binding of the Fcabs to PD-L1.

TABLE 5

| | EF loop (92-101) | | | | | | | | Other mutations | DO11.10 T cell activity assay $EC_{50}$ (nM) |
|---|---|---|---|---|---|---|---|---|---|---|
| FS17-33-85 | S | N | W | R | W | Q | M | E | Q | ~ A38V | 0.47 |
| FS17-33-87 | S | N | W | R | W | Q | M | D | D | ~ | 0.32 |
| FS17-33-114 | S | N | W | R | W | R | M | D | D | ~ | 0.39 |
| FS17-33-116 | S | N | W | R | W | Q | M | D | D | ~ A38V | 0.28 |

3.5 Further Characterisation of Fcab FS17-33-116

Since all of the Fcab clones identified in 3.4 had contained very similar sequences, a representative clone (FS17-33-116) was chosen for further characterisation. Any of the other Fcab clones listed in Table 5 could equally be chosen for further characterisation given that all of these Fcab clones had $EC_{50}$ comparable to that of the positive control, the S70 antibody, in the DO11.10 T cell activation assay. Affinity of FS17-33-116 for PD-L1 was measured using Biacore, employing protein A to capture the Fcab. The monomeric PD-L1-his human antigen was flowed over the chip in titrating concentrations at a high flow rate to minimise mass transport limitations. The $K_D$s were measured using a 1:1 fitting analysis with no refractive index correction and $R_{max}$ set to local. Fcab clone FS17-33-116 showed a strong improvement in affinity compared to the parental clone, FS17-33-37, as well as an improved affinity compared with the positive control antibody, S70 (see Table 6). This is primarily due to a slower off-rate of the Fcab when bound to PD-L1.

TABLE 6

| Clone ID | $K_D$ (nM) | $K_d$ (1/s) | $K_a$ (1/Ms) |
|---|---|---|---|
| FS17-33-37 | 270 | 0.02 | $7.6 \times 10^4$ |
| FS17-33-116 | 0.49 | $4.4 \times 10^{-4}$ | $1.5 \times 10^6$ |
| S70 mAb | 1.1 | $3.0 \times 10^{-4}$ | $2.7 \times 10^5$ |

To test the specificity of clone FS17-33-116 for PD-L1, PD-1 (R&D systems 1086-PD) and PD-L2 (R&D systems 1224-PL) were coated onto a Biacore chip along with PD-L1. The Fcab was then flowed over the chip at a 1000-fold concentration range. No binding was observed to either PD-1 or PD-L2 at these concentrations. However, the Fcab did bind to PD-L1. This indicates that Fcab FS17-33-116 binds specifically to PD-L1.

To further assess the functional activity of FS17-33-116, the Fcab was tested in an SEB assay (see Example 7.1 for experimental details). Since this assay uses cells donated from patients, the cells are expressing endogenous levels of PD-L1. These expression levels are considerably lower than the LK35.2 cells used in the DO11.10 assay. In the SEB assay, the FS17-33-116 Fcab matched the positive control S70 antibody in both potency and efficacy (see Table 7). No activity was seen with the anti-FITC antibody, 4420, which served as a negative control. Since the S70 antibody has been shown to have efficacy in the clinic, it is expected that the FS17-33-116 Fcab will similarly have clinical efficacy

TABLE 7

| SEB Assay | |
|---|---|
| Clone ID | $EC_{50}$ (nM) |
| Negative control 4420 mAb | No activity |
| FS17-33-116 | 0.07527 |
| Positive control S70 mAb | 0.07605 |

3.6 Construction and Expression of FS17-33-116 in a mAb² Format

Fcabs may be incorporated into conventional immunoglobulin molecules to provide bispecific antibodies, comprising both the CDR-based antigen-binding site of the immunoglobulin molecule and an additional binding site in a constant domain of the immunoglobulin as a result of the incorporation of the Fcab. Such molecules are also referred to as mAb² molecules. "mock" mAb² may also be prepared. A "mock" mAb² is a mAb² where the Fcab of interest has been incorporated into an immunoglobulin molecule comprising a CDR-based antigen binding site for an antigen which is not expected to bind in the context in which the "mock" mAb² is to be used. This allows the Fcab to be tested in a format which is comparable to an intact immunoglobulin molecule without any effect from the CDR-based antigen binding site of the molecule.

A "mock" mAb² consisting of an IgG1 comprising the FS17-33-116 anti-human PD-L1 Fcab described above was prepared in order to allow the characterisation of this Fcab in mAb² format. This mock mAb² was prepared by substituting part of the CH3 domain of the FS17-33-116 Fcab, comprising the AB, CD and EF loops, for the corresponding region of the CH3 domain of the anti-FITC antibody 4420, and also comprised the LALA mutation in the CH2 domain of the heavy chain of the antibody. The heavy and light chain sequences of antibody 4420 are shown in SEQ ID NOS 51 and 52, respectively (Bedzyk, W. D., et al., 1989 and Bedzyk, W. D., et al., 1990). The mock mAb² was called FS17-33-116/4420 mAb². The mock mAb² was produced by transient expression in HEK293-6E cells and purified using mAb Select SuRe protein A columns.

The "mock" FS17-33-116/4420 mAb² was compared to Fcab FS17-33-116 to ensure the desired qualities were maintained. A SEC profile for the mAb² showed that the mAb² no longer had a split peak or shoulder (see FIG. 2C). A small amount of aggregation was observed, as expected for the 4420 mAb, as this antibody is known to aggregate. The FS17-33-116/4420 mAb² was then tested for binding and functional activity.

The FS17-33-116/4420 mAb² was tested in a DO11.10 T cell activation assay (see Example 6 for methodology). The FS17-33-116/4420 mAb² showed a drop in activity in this assay compared with the FS17-33-116 Fcab. This drop in activity was significant, but small. The $EC_{50}$ for FS17-33-116/4420 mAb² remained below 1 nM. Since the intrinsic affinity of FS17-33-116/4420 mAb² and FS17-33-116 for PD-L1 was the same, it is thought that the most likely cause for the drop in activity observed with FS17-33-116/4420 mAb² in the DO11.10 assay was due to a higher avidity of the FS17-33-116 Fcab compared with the S17-33-116/4420 mAb². Since the Fcab, but not the mAb², showed a split peak when analysed using SEC, it is postulated that the Fcab was forming dimers that, in the context of a cell based assay such as the DO11.10 assay, could boost the activity of the Fcab via avidity. To address this, the molecules were analysed via analytical ultracentrifugation using a Beckman Optima XL-1 instrument.

Data from this experiment showed two peaks for the Fcab and only a single peak for the mAb². The calculated masses for the Fcab were consistent with a monomer for the first peak and a dimer for the second peak. The amount of dimerization was concentration dependent and the $K_D$ for the interaction was estimated to be 2 µM. Although this interaction is weak, these data support the notion that the Fcab was boosted in activity in the cell-based functional assay via avidity on the cell surface mediated through self-interactions. In addition, the positive control antibody S70 had an intrinsic affinity for PD-L1 similar to FS17-33-116 and activity in a Mixed Lymphocyte Reaction (MLR) assay equivalent to FS17-33-116. As antibodies are bivalent, it is postulated that a monovalent Fab would have similar activity to the mAb² as a result of the loss of avidity. To test this hypothesis the S70 Fab arms were digested away from the Fc portion above the hinge resulting in monovalent Fab domains. These domains were then purified using protein A to remove Fc domains, anti-his to remove enzymes and finally subjected to SEC to purify the monomeric fraction. These Fab arms were then tested in an MLR assay and showed a loss of activity equivalent to the drop in activity observed between the Fcab and mAb² in this assay, providing additional support for the hypothesis that the reduction in activity between the Fcab and mAb² was due to the avidity of the Fcab.

3.7 Summary of Affinity Maturation and Functional Improvement of Fcab Clone FS17-33-37

The affinity maturation of FS17-33-37 produced Fcab clones with significant improvements in off-rate and functional activity. One of these clones, FS17-33-116, showed similar activity to the clinically-verified positive control S70 antibody in both the DO11.10 and SEB assays. Since the positive control mAb has been shown to have efficacy in the clinic, it is expected that the FS17-33-116 Fcab and molecules comprising this Fcab, such as mAb$^2$ molecules, will also have clinical efficacy.

The FS17-33-116 Fcab was also inserted into a "mock" mAb$^2$ format and similar results were observed as reported for the Fcab format, albeit with a slight reduction in activity when measured in the DO11.10 T cell activation assay. Without wishing to be bound by theory, it is believed that the Fcabs, but not the mAb$^2$, self-associate and form dimers in the context of a cell-based assay and that this could account for the difference in activity between the Fcab and mock mAb$^2$ formats of FS17-33-116.

Example 4—Further Improvement of Fcab Clone FS17-33-116

Whilst the FS17-33-116 Fcab described in Example 3 displayed a high affinity for PD-L1 and high activity in a DO11.10 T cell activation assay, it was considered that further improvements could be made to the Fcab to remove potential manufacturing sequence liabilities and to improve biophysical properties. In particular, the FS17-33-116 Fcab contained a methionine in the EF loop and showed a small degree of dimerization. Therefore, the FS17-33-116 clone was further engineered to address these issues.

4.1 Methionine Substitution

A methionine appeared in the EF loop of the FS17-33 lineage at the naïve selection stage. Since this may be a sequence liability and this residue was retained through multiple rounds of affinity maturation, the likelihood of finding a substitution that would improve activity was therefore very small. Instead the goal was to find a residue that could replace the methionine with minimal loss in activity and worsening in the binding of the resulting Fcab to PD-L1.

Site directed mutagenesis was carried out using primers that contain the degenerate codon NNK at IMGT position M98 in the EF loop of FS17-33-116. The primers did not include codons that code for cysteine and glycine, as these amino acids are also considered potential sequence liabilities.

The Met substitution clones were expressed and tested as Fcabs in an off-rate screen to identify clones that had similar binding kinetics to human PD-L1 as clone FS17-33-116. From this experiment it was seen that hydrophobic residues replaced the Met with a minimal increase in the off-rate of the Fcab when bound to PD-L1 (within two fold of the off-rate of the parental clone FS17-33-116). The only exception was proline, which showed the fastest off-rate of all of the Fcab clones tested.

All of the Fcab clones were then purified on Protein A columns for further testing. Ten of the Fcab clones did not elute off the Protein A column and were therefore not included in further analysis. This included the Fcab in which tryptophan was substituted for methionine, which had shown an off-rate within two-fold of the parental clone.

The purified Fcab clones were then put onto a SEC column to assess aggregation. From this analysis, Fcabs in which the methionine was substituted with phenylalanine or tyrosine showed significant aggregation and retention on the column. Thus, these clones were excluded from further analysis. Three Fcab clones were identified with an off-rate within two-fold of the parental clone. These contained leucine, isoleucine or valine in place of the methionine at position 98. These were Fcabs FS17-33-289, FS17-33-288, and FS17-33-296, respectively, as shown in FIG. 1 and SEQ ID Nos 31, 27 and 35 below.

In addition, an Fcab clone was prepared in which the framework mutation A38V was reverted back to the wild-type alanine to reduce the mutational load of the Fcab. The A38V mutation was observed in clone FS17-33-116 but not in sibling clones with similar activity (see Table 5). This reverse mutation was made based on the FS17-33-289 Fcab, and the resulting Fcab termed FS17-33-334. A summary of sequences for the AB, CD and EF loops and the residue at position 38 for these clones is provided in FIG. 1.

FS17-33-289, FS17-33-288, FS17-33-296, and FS17-33-334 were then tested for their binding affinity to PD-L1, ability to block the PD-1/PD-L1 interaction and activity in a DO11.10 T cell activation assay in both a Fcab and mock mAb$^2$ formats (see 4.2 for details regarding generation of the mock mAb$^2$), as further described in Examples 6 and 7 below.

4.2 Construction and Expression of Fcabs FS17-33-289, FS17-33-288, FS17-33-296, FS17-33-334, FS17-33-449 and FS17-33-451 in mAb$^2$ format In order to test the PD-L1 binding affinity, PD-1/PD-L1 blocking activity, and functional activity in a DO11.10 T-cell activation assay of Fcabs in the format of a complete immunoglobulin molecule, various mAb$^2$ comprising the Fcabs were constructed and expressed as described below.

4.2.1 "Mock" mAb$^2$ Construction and Expression

"Mock" mAb$^2$ consisting of an IgG1 comprising Fcabs, including Facbs FS17-33-289, FS17-33-288, FS17-33-296, FS17-33-334, described in 4.1 above, and FS17-33-449 and FS17-33-451 described in 4.3 below, were prepared in order to allow the characterisation of these Fcabs in mAb$^2$ format. These mock mAb$^2$ were prepared by substituting part of the CH3 domain of the Fcabs, comprising the AB, CD and EF loops, for the corresponding region of the CH3 domain of the anti-hen egg white lysozyme antibody HelD1.3, either with or without the LALA mutation in the CH2 domain of the heavy chain of the antibody. The heavy and light chain sequences of antibody HelD1.3 with the LALA mutation are shown in SEQ ID Nos 53 and 54, respectively. Generation of the HelD1.3 antibody is described in Tello et al. 1993. The mock mAb$^2$ were produced by transient expression in HEK293-6E cells and purified using mAb Select SuRe protein A columns. The mock mAb$^2$ produced are listed in Table 8.

Additionally, "mock" mAb$^2$ comprising the FS17-33-449 and FS17-33-451 anti-human PD-L1 Fcabs described in 4.3 below were prepared as described in the preceding paragraph but using the anti-Cytomegalovirus (CMV) gH glycoprotein antibody MSL109. Generation of the MSL109 antibody is described in WO1994/016730 A1. These mAb$^2$ were prepared with the LALA mutation in the CH2 domain. The heavy and light chain sequences of antibody MSL109 with the LALA mutation are shown in SEQ ID Nos 55 and 56. The mAb$^2$ were produced by transient expression in HEK293-6E cells and purified using mAb Select SuRe protein A columns.

4.2.2 Anti-CTLA-4 mAb$^2$ Construction and Expression mAb$^2$ comprising the FS17-33-289, FS17-33-449 and FS17-33-451 anti-human PD-L1 Fcabs described in 4.1 and 4.3 were prepared as described above but using the anti-CTLA-4 mAb ipilimumab. These mAb$^2$ were prepared without the LALA mutation in the CH2 domain. The heavy and light chain sequences of ipilimumab are shown in SEQ ID Nos 67 and 68. The CTLA-4 containing mAb$^2$ were produced by transient expression in HEK293-6E cells and purified using mAb Select SuRe protein A columns.

A summary of the mAb² generated and expressed is provided in Table 8.

TABLE 8

| mAb² name | Fcab clone | Fab clone | Contains LALA? |
|---|---|---|---|
| F17-33-288AA/HelD1.3 | F17-33-288 | HelD1.3 | Yes |
| F17-33-289AA/HelD1.3 | F17-33-289 | HelD1.3 | Yes |
| F17-33-296AA/HelD1.3 | F17-33-296 | HelD1.3 | Yes |
| FS17-33-296/HelD1.3 | F17-33-296 | HelD1.3 | No |
| F17-33-334AA/HelD1.3 | F17-33-334 | HelD1.3 | Yes |
| F17-33-449AA/HelD1.3 | F17-33-449 | HelD1.3 | Yes |
| FS17-33-449/HelD1.3 | F17-33-449 | HelD1.3 | No |
| F17-33-451AA/HelD1.3 | F17-33-451 | HelD1.3 | Yes |
| FS17-33-449AA/MSL | F17-33-449 | MSL109 | Yes |
| FS17-33-451AA/MSL | F17-33-451 | MSL109 | Yes |
| FS17-33-289/CTLA-4 | F17-33-289 | CTLA-4 | No |
| FS17-33-449/CTLA-4 | F17-33-449 | CTLA-4 | No |
| FS17-33-451/CTLA-4 | F17-33-451 | CTLA-4 | No |

4.3 NNK Walk of Binding Loops

To identify Fcabs with improved biophysical properties, reduced mutational load, and optimized affinity for PD-L1, each position in the AB, CD and EF loops of the parent Fcab clones (Fcab FS17-33-116 for the AB and EF loops, and mock mAb² F17-33-334AA/HelD1.3 for the CD loop) was mutated to all possible amino acid substitutions and the resulting Fcabs screened for binding to PD-L1 and functional activity followed by an assessment of their biophysical properties.

Tables 9A-C list the number of different amino acid substitutions at each position of the AB, CD and EF loops, as well as the specific amino acid substitutions at the relevant positions, which resulted in no reduction in the off-rate of the Fcab/mAb² on PD-L1 greater than two-fold compared with the parent Fcabs, Fcab FS17-33-116 for the AB and EF loop mutants and mock mAb² F17-33-334AA/HelD1.3 for the CD loop mutants. Note that residues at positions 95 and 96 in the EF loop were not mutated in the naïve or affinity maturation libraries, as the residues at these positions are known to be important for the structural integrity of the EF loop (Hasenhindl et al., 2013).

Binding to PD-L1 was measured using an Octet system. Binding of the AB and EF loop mutants to PD-L1 was tested in Fcab format, while the CD loop mutants were tested in mock mAb² format based on antibody HelD1.3. These mock mAb² were constructed as described in Example 4.2.1 above.

The Fcabs and mock mAb² were captured via a protein A tip and then exposed to monomeric PD-L1-his. The off-rates of the Fcabs/mock mAb² when bound to PD-L1 were then calculated using the Octet analysis software and compared to the parental clone, FS17-33-116 or F17-33-334AA/HelD1.3. Generally, a two-fold difference in the off-rate is within the error of this type of assay and therefore clones that fell within this range were considered to have an equivalent off-rate when bound to PD-L1 as the parent clone, FS17-33-116 or F17-33-334AA/HelD1.3.

Two positions in the AB loop, two in the CD loop and three in the EF loop (residues 15, 16, 45.1, 45.2, 93, 97 and 100) could be substituted with more than half of the tested amino acids, resulting in no worsening (faster) in the off-rate when the Fcab/mock mAb² was bound to PD-L1 greater than two-fold compared with the relevant parent Fcab/mock mAb². These positions are therefore considered permissive. Fewer substitutions were tolerated at other positions, with some positons not tolerating any substitutions at all (Table 9A-C). No mutations were found that improved binding to PD-L1, or functional activity, compared with the relevant parent clone.

TABLE 9A

|  | AB loop (14-18) | | | | |
|---|---|---|---|---|---|
| Residue position (IMGT) | 14 | 15 | 16 | 17 | 18 |
| Sequence of parent Fcab FS17-33-116 | ~ | S | G | Y | W |
| Number of substitutions resulting in expressed Fcabs | 1 | 13 | 17 | 16 | 17 |
| Number of substitutions resulting in an Fcab retaining binding to PD-L1 within 2-fold of the parent Fcab | 0 | 13 | 13 | 0 | 0 |
| Identity of substitutions resulting in an Fcab retaining binding to PD-L1 within 2-fold of the parent Fcab |  | AEFGHILPRTVY | ADEFHKLNPRTVY |  |  |

TABLE 9B

|  | CD loop (45.1-78) | | | | | |
|---|---|---|---|---|---|---|
| Residue position (IMGT) | 45.1 | 45.2 | 45.3 | 45.4 | 77 | 78 |
| Sequence of parent mock mAb² F17-33-334AA/HelD1.3 | E | P | Q | Y | W | A |
| Number of substitutions resulting in expressed Fcabs | 16 | 17 | 17 | 15 | 17 | 17 |

TABLE 9B-continued

|  | CD loop (45.1-78) | | | | | |
| --- | --- | --- | --- | --- | --- | --- |
| Residue position (IMGT) | 45.1 | 45.2 | 45.3 | 45.4 | 77 | 78 |
| Number of substitutions resulting in an Fcab retaining binding to PD-L1 within 2-fold of the parent Fcab | 10 | 9 | 2 | 5 | 0 | 7 |
| Identity of substitutions resulting in an Fcab retaining binding to PD-L1 within 2-fold of the parent Fcab | AGHILNQRSW | ADEGHNQWY | HN | ADHTV |  | DEGLRSW |

TABLE 9C

|  | EF loop (92-101) | | | | | | | |
| --- | --- | --- | --- | --- | --- | --- | --- | --- |
| Residue position (IMGT) | 92 | 93 | 94 | 97 | 98 | 99 | 100 | 101 |
| Sequence of parent Fcab FS17-33-116 | S | N | W | Q | M | D | D | ~ |
| Number of substitutions resulting in expressed Fcabs | 17 | 16 | 14 | 16 | 19 | 16 | 14 | 1 |
| Number of substitutions resulting in an Fcab retaining binding to PD-L1 within 2-fold of the parent Fcab | 2 | 13 | 0 | 12 | 6 | 9 | 11 | 1 |
| Identity of substitutions resulting in an Fcab retaining binding to PD-L1 within 2-fold of the parent Fcab | AG | AEFGHIKLQRSTY |  | ADEFGHKLNRSV | FILVWY | AILRSTVWY | AEFIKLNRVWY | V |

Next, at each permissive position where the parent clones did not already comprise the wild-type (WT) amino acid (residues 15, 16, 45.1, 93 and 100; see FIG. 1 for the sequence of the "WT Fcab"), the Fcab clones with a WT amino acid at that position were tested in mock mAb² format to determine their off-rate when bound to PD-L1. The mock mAb² were constructed based on the HelD1.3 antibody as described in Example 4.2.1 above. The off-rate was determined using a Biacore 3000 instrument, where the mock mAb² were captured on a protein A chip and monomeric hPD-L1 was flowed over the captured antibodies. Off-rates were then calculated using the Biaevaluate software from GE. It was found that WT reversions at positions 15 and 16 of the AB loop and 93 and 100 of the EF loop had minimal impact on the off-rate of the mock mAb² when bound to PD-L1 compared with the parent clone in the same mock mAb² format.

In addition, Fcabs were prepared in which the deleted residues 14 and 101 in the AB and EF loops were restored to the WT residue and tested. Fcabs with WT reversions showing minimal to no worsening in the off-rate of the mock mAb² when bound to PD-L1 (faster) were also combined with deletions at residues 14 and 101 in the AB and EF loops. Surprisingly, restoring the deleted residue at position 14 in the AB loop resulted a significant worsening in the off-rate when the mock mAb² was bound to PD-L1 (faster) and no further studies were done with these Fcab clones. However, restoring the deleted residue in the EF loop had no impact on PD-L1 binding by itself but, combining this with any other WT reversion in the EF loop did result in a significant drop in affinity. Finally, the WT reversions in the AB loop at positions 15 and 16 were recombined with the restoration of the deletion in position 101 of the EF loop. One of these clones FS17-33-449 comprising the WT reversions at position 15 in the AB loop and position 101 of the EF loop showed binding to PD-L1 comparable to the parent clone and was further analysed as described below.

A subset of the Fcab clones in mock $mAb^2$ format (the mock $mAb^2$ were prepared based on FS17-33-334AA/HELD1.3) was selected from the NNK walk mutagenesis screen described above on the basis that the clones showed no loss in activity greater than 2-fold as measured in the DO11.10 T cell activation assay (see Example 6 for experimental details) compared with the parent clone FS17-33-334AA/HELD1.3 (see 4.2.1 for preparation of this mock $mAb^2$). A two-fold difference in activity is within the error of this assay and therefore mock $mAb^2$ that fell within this range were considered to have comparable activity in the DO11.10 T cell activation assay to the parent clone FS17-33-334AA/HELD1.3. This subset of mock $mAb^2$ clones also showed no indication of aggregation greater than 3% of total protein, as measured by SEC analysis (see 3.2 for experimental details). The results are shown in Table 9D.

The subset of Fcabs, comprised Fcabs with mutations at position 15 of the AB loop and positions 93, 97 and 100 of the EF loop, whereby S could be changed to E, H, L, F or Y at position 15, N could be changed to A, Q or H at position 93, Q could be changed to R, H or S at position 97, and D could be changed to A at position 100.

TABLE 9D

| Clone ID | Residue modified | Amino acid substitution | Kd (1/s) | DO11.10 EC$_{50}$ (nM) | SEC % monomer |
|---|---|---|---|---|---|
| FS17-33-334AA/HELD1.3 | N/A | | 3.72E−04 | 0.4027 | 99% |
| FS17-33-157AA/HELD1.3 | 15 | E | 5.59E−04 | 0.4813 | 98% |
| FS17-33-159AA/HELD1.3 | 15 | H | 4.27E−04 | 0.2632 | 98% |
| FS17-33-161AA/HELD1.3 | 15 | L | 5.78E−04 | 0.4528 | 99% |
| FS17-33-163AA/HELD1.3 | 15 | F | 3.72E−04 | 0.3704 | 99% |
| FS17-33-166AA/HELD1.3 | 15 | Y | 5.23E−04 | 0.2382 | 99% |
| FS17-33-235AA/HELD1.3 | 93 | A | 7.09E−04 | 0.5613 | 100% |
| FS17-33-239AA/HELD1.3 | 93 | Q | 6.93E−04 | 0.5875 | 100% |
| FS17-33-241AA/HELD1.3 | 93 | H | 5.92E−04 | 0.3038 | 100% |
| FS17-33-266AA/HELD1.3 | 97 | R | 3.77E−04 | 0.4342 | 97% |
| FS17-33-271AA/HELD1.3 | 97 | H | 5.18E−04 | 0.254 | 99% |
| FS17-33-277AA/HELD1.3 | 97 | S | 4.15E−04 | 0.3192 | 100% |
| FS17-33-316AA/HELD1.3 | 100 | A | 5.66E−04 | 0.5633 | 97% |

The subset of mock mAb[2] described above was then further modified by replacing the deleted amino acid at position 101 in the EF loop, thereby creating a second panel of mock mAb[2] molecules which comprised a reduced number of mutations compared with the WT Fcab (see FIG. 1) and thus had a reduced mutational burden. This second panel of mock mAb[2], including FS17-33-449AA/HELD1.3 that contains a wild-type reversion at permissive position 15, were tested for function in a DO11.10 T cell activation assay (see Example 6 for experimental set-up) and binding to hPD-L1. The results are shown in Table 9E. All clones showed equivalent functional activity in the DO11.10 assay to the parent mAb[2] FS17-33-334AA/HELD1.3 (except for FS17-33-456AA/HELD1.3, FS17-33-457AA/HELD1.3 and FS17-33-462AA/HELD1.3, which were excluded from further analysis), demonstrating that the introduction of a valine at position 101 of the EF loop in the CH3 domain was well tolerated. Two clones exhibited improved biophysical characteristics when analysed by dynamic light scattering (DLS), protein A purification and solubility analysis. These clones were FS17-33-449AA/HELD1.3 and FS17-33-451AA/HELD1.3, which were therefore chosen as the lead candidates from this final panel.

TABLE 9E

| Clone ID | Residues modified | Amino acid substitution | DO11 EC$_{50}$ | Kd 1/s |
|---|---|---|---|---|
| FS17-33-334AA/HELD1.3 | N/A | N/A | 0.6721 | 2.91E−04 |
| FS17-33-449AA/HELD1.3 | 15/101 | T/V | 0.7665 | 3.11E−04 |
| FS17-33-451AA/HELD1.3 | 15/101 | E/V | 0.9079 | 2.53E−04 |
| FS17-33-452AA/HELD1.3 | 15/101 | H/V | 0.5646 | 3.38E−04 |
| FS17-33-453AA/HELD1.3 | 15/101 | L/V | 0.6323 | 3.03E−04 |
| FS17-33-454AA/HELD1.3 | 15/101 | F/V | 0.5094 | 2.69E−04 |
| FS17-33-455AA/HELD1.3 | 15/101 | Y/V | 0.6801 | 3.43E−04 |
| FS17-33-456AA/HELD1.3 | 93/101 | A/V | 1.891 | 6.19E−04 |
| FS17-33-457AA/HELD1.3 | 93/101 | Q/V | 1.005 | 5.89E−04 |
| FS17-33-458AA/HELD1.3 | 93/101 | H/V | 0.741 | 4.56E−04 |
| FS17-33-459AA/HELD1.3 | 97/101 | R/V | 0.6632 | 3.80E−04 |
| FS17-33-460AA/HELD1.3 | 97/101 | H/V | 0.5217 | 2.02E−04 |
| FS17-33-461AA/HELD1.3 | 97/101 | S/V | 0.593 | 3.59E−04 |
| FS17-33-462AA/HELD1.3 | 100/101 | N/V | 2.025 | 8.99E−04 |

Example 5—Binding Affinity and PD-1/PD-L1 Blocking Activity of Fcabs and mAb[2]

The FS17-33-288, FS17-33-289, FS17-33-296, FS17-33-334, FS17-33-449 and FS17-33-451 Fcab clones, in both an Fcab (see 4.1 and 4.2 for details) and mAb[2] format (see Example 4 for details), were then tested for their ability to bind human PD-L1 and block PD-1/PD-L1 interaction. As described in Example 4, the aim behind generating these Fcabs and mAb[2] was to remove sequence liabilities and to improve biophysical properties, whilst maintaining the binding, blocking and functional properties of Fcab FS17-33-116.

5.1 Binding to PD-L1

Fcab and mAb[2] binding to human PD-L1 was assessed by both BIAcore and in a cell binding assay. To measure the affinity of the clones to monomeric hPD-L1-his, the mAb[2] were captured using an anti-Fab antibody coated on a CM5 chip (GE 28-9582-20 AC) and Fcabs were captured using a Protein A chip (GE 29127556) using a Biacore T200 (GE). To minimize mass transport effects, the capture level was minimized to 200RU and a fast flow rate of 75 μl/min was used. Both the human (Acro biosciences PD1-H5229) and cynomolgus (Acro Biosciences PD1-052H4) monomeric antigens were titrated and flowed over the captured mAb[2]. The analysis of the data was done using the Biacore T200 evaluation software. Curves subtracted against a blank flow cell and a run with no antigen were analysed using a 1:1 fitting model with no bulk analysis and Rmax analysed locally.

Cell binding assays were performed by incubating Fcabs or mAb[2] proteins with either control HEK293 cells or HEK293 cells overexpressing hPD-L1 or cynomolgus PD-L1 cells for 1 hour at 4° C. Fcab/mAb binding was subsequently detected using an anti-human Fc 488 detection antibody. Fluorescent signal intensities were measured using a FACS canto.

The results of these binding experiments are summarised in Table 10. Table 10 shows that all of the clones tested had a high affinity for monomeric and cell-expressed human and cynomolgus PD-L1.

TABLE 10

| | | Binding affinity - K$_D$ (nM) | | | |
|---|---|---|---|---|---|
| Clone ID | Format | Human monomeric PD-L1 | Cynomolgus monomeric PD-L1 | Cell binding human PD-L1 | Cell binding cynomolgus PD-L1 |
| FS17-33-116 | Fcab | 0.33 | 0.42 | 1.68 | 0.6651 |
| FS17-33-288 | Fcab | 1.6 | 2.1 | 2.5 | 2.6 |
| FS17-33-288AA/HelD1.3 | mAb[2] | 1.43 | 2.0 | 15.2 | 7.8 |
| FS17-33-289 | Fcab | 0.54 | 0.66 | 1.0 | 0.44 |
| FS17-33-289AA/HelD1.3 | mAb[2] | not tested | not tested | 3.9 | 2.2 |

TABLE 10-continued

| Clone ID | Format | Binding affinity - $K_D$ (nM) | | | |
| --- | --- | --- | --- | --- | --- |
| | | Human monomeric PD-L1 | Cynomolgus monomeric PD-L1 | Cell binding human PD-L1 | Cell binding cynomolgus PD-L1 |
| FS17-33-296 | Fcab | 0.73 | 0.87 | 1.0 | 0.50 |
| FS17-33-296AA/HelD1.3 | $mAb^2$ | not tested | not tested | 2.7 | 2.0 |
| FS17-33-334 | Fcab | 1.93 | 2.18 | 2.06 | 0.68 |
| FS17-33-334AA/HelD1.3 | $mAb^2$ | 1.45 | 1.9 | 8.9 | 0.91 |
| FS17-33-449AA/MSL | $mAb^2$ | 0.38 | 0.6 | 7.88 | 3.6 |
| FS17-33-449AA/HELD1.3 | $mAb^2$ | 0.49 | 0.9 | | |
| FS17-33-451AA/MSL | $mAb^2$ | 0.34 | 0.5 | 11.7 | 4.52 |
| FS17-33-451AA/HELD1.3 | $mAb^2$ | 0.45 | 0.63 | | |
| S70 comprising LALA mutation | mAb | 0.11 | 7.8 | 1.74 | 0.75 |

5.2 Blocking Activity

The ability of the Fcabs and mock $mAb^2$ to block hPD-1/hPD-L1 and hPD-L1/hCD80 interactions was tested in cell-based Receptor Binding Assays (RBA). In brief, biotinylated hPD-L1-Fc-Avi was incubated for 1 hour with titrating concentrations of Fcabs ranging from 400 nM to 3 μM. The mix was incubated for another hour with HEK293 cells overexpressing either hPD-1 or hCD80. The level of bound biotinylated hPD-L1-Fc-Avi on the HEK293 cells was detected using streptavidin 647 and fluorescence levels were measured using the FACS Canto (BD Biosciences).

The results of these blocking experiments are shown in Table 11. Table 11 shows that all of the clones tested were able to potently block hPD-1/hPD-L1 and hPD-L1/hCD80 interactions.

TABLE 11

| Clone ID | Format | Blocking activity - $EC_{50}$ (nM) | |
| --- | --- | --- | --- |
| | | PD-L1/PD-1 | PD-L1/CD80 |
| FS17-33-116 | Fcab | 9.5 | 8.4 |
| FS17-33-288 | Fcab | 2.8 | 0.79 |
| FS17-33-289 | Fcab | 10.1 | 9.2 |
| FS17-33-296 | Fcab | 9.0 | 8.8 |
| FS17-33-334 | Fcab | 0.99 | 0.55 |
| FS17-33-449AA/MSL | $mAb^2$ | 1.96 | 194* |
| FS17-33-451AA/MSL | $mAb^2$ | 0.92 | 190* |
| S70 | mAb | 0.63 | 9.6 (74.5*) |

*The PD-L1 concentration was increased from 2 μg/mL to 50 μg/mL in these experiments resulting in higher $EC_{50}$ values.

Example 6—Activity of Fcab Molecules in DO11.10 T Cell Activation Assays

6.1 Activity of the Fcabs in a Human PD-L1 DO11.10 T Cell Activation Assay

The panel of Fcabs containing the LALA mutation was tested in a DO11.10 based T cell activation assay in Fcab and $mAb^2$ format. $mAb^2$ were produced as described in Example 4 and tested in a DO11.10 T cell assay as described below.

An IL-2 release assay based on the DO11.10 OVA-specific T-lymphocyte and LK35.2 B-lymphocyte hybridoma cell lines was used for functional screening of the $mAb^2$. IL-2 release is a marker of T cell activation. T cells, expressing endogenous murine PD-1, were transfected with empty vector (pLVX). B-cells were transfected with human PD-L1 construct.

The $mAb^2$ were tested with and without the LALA mutation (AA), depending on the $mAb^2$ in question. The Fab portion of the $mAb^2$ was either the variable region of a monoclonal antibody directed against hen egg white lysozyme (HelD1.3), the FITC molecule (4420), the human CTLA-4 (ipilimumab). Details regarding the construction of these $mAb^2$ are provided in Example 4.

6.1.1 Production of T Cell Lines with an Empty Vector

Lentiviral transduction methodology was used to generate DO11.10 cells (National Jewish Health) containing the empty lentiviral vector pLVX using the Lenti-X HTX Packaging System (Cat. No 631249). Lenti-X expression vector (pLVX) (Cat. No 631253) was co-transfected with a Lenti-X HTX Packaging Mix into the Lenti-X 293T Cell Line (Cat. No 632180) to generate virus. The DO11.10 cell line was transduced using the lentiviral particles produced with the Lenti-X HTX Packaging System.

6.1.2 Production of Antigen Presenting Cells Over-Expressing PD-L1

Lentiviral transduction methodology was used to generate LK35.2 B cell lymphoma cells (ATCC, HB-98) over-expressing human PD-L1 using the Lenti-X HTX Packaging System (Cat. No 631249). Lenti-X expression vector (pLVX) (Cat. No 631253), containing, human PD-L1 cDNA, was co-transfected with a Lenti-X HTX Packaging Mix into the Lenti-X 293T Cell Line (Cat. No 632180) to generate virus. The LK35.2 cell line was transduced using the lentiviral vectors produced with the Lenti-X HTX Packaging System.

6.1.3 Media and Peptide

Cell culture medium: DMEM (Gibco, 61965-026) 10% FBS (Gibco, 10270-106), 1 mM Sodium Pyruvate (Gibco, 11360-070), 1 μg/ml puromycin (Gibco, A11138-03) Experimental medium: complete DO11.10 culture medium without puromycin.

OVA peptide (MW=1773.9 Da): H-ISQAVHAA-HAEINEAGR-OH (Pepscan)

Cells:

DO11.10 pLVX: DO11.10 T cell hybridoma transduced with an empty lentiviral vector;

LK 35.2 hPD-L1: B cell hybridoma transduced with a lentiviral vector containing hPD-L1 to overexpress human PD-L1

Dilutions of Fcabs, $mAb^2$, anti-human positive control mAb (S1 or S70) or the human IgG1 isotype control mAb (anti-HELD1.3 or MSL) were prepared in experimental media. Fcabs, $mAb^2$ or control mAbs were mixed 1:1 with $4\times10^5$/ml LK35.2 hPD-L1 cells in experimental media in presence of 2.46 μM OVA peptide (100 μL LK35.2 hPD-L1/(Fcab, $mAb^2$ or control mAbs) mix per well in 96-round bottom plate) and incubated at 37° C., 5% $CO_2$ for 1 hour. $2\times10^5$ DO11.10 pLVX cells/ml in 100 μl volume experimental media were added to 100 μl of the LK35.2 hPD-L1/(Fcab, $mAb^2$ or control mAbs) mix. The cells were then mixed before being incubated at 37° C., 5% $CO_2$ for 24 hours. Supernatants were collected and assayed with mouse IL-2 ELISA kit (eBioscience, 88-7024-88 or R&D systems, SM2000) following the manufacturer's instructions. Plates were read at 450 nm using the plate reader with the Gen5 Software, BioTek. Absorbance values of 570 nm were subtracted from those of 450 nm (Correction). The standard curve for calculation of cytokine concentration was based on four parameter logistic curve fit (Gen5 Software, BioTek). The concentration of mouse IL-2 was plotted vs the log concentration of Fcab, mAb$^2$ or positive control mAb and the resulting curves were fitted using the log (agonist) vs response equation in GraphPad Prism.

Figure 3:
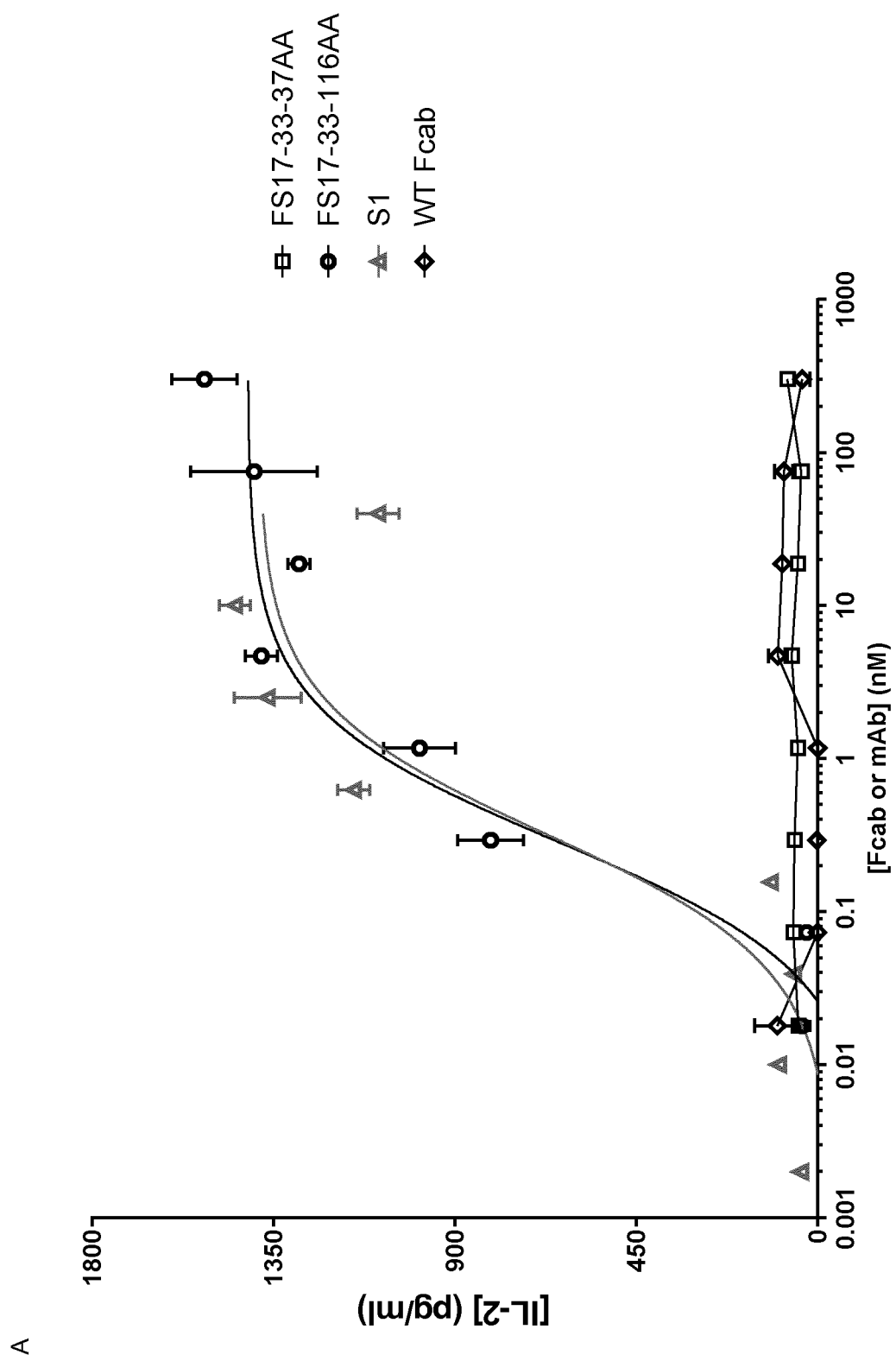
FIG. 3A shows that the anti-PD-L1 Fcab, FS17-33-116AA, inhibits human PD-L1 activity leading to release of IL-2 in a DO11.10 T cell activation assay. This release was comparable to the positive control anti-PD-L1 mAb, YW243.55.S1 (S1). The anti-PD-L1 Fcab, FS17-33-37AA, and a wild-type (WT) Fcab showed no significant T cell activation in this assay.
FIG. 3B shows that the anti-PD-L1 Fcabs, FS17-33-288AA, FS17-33-289AA and FS17-33-296AA, all showed IL-2 release in the DO11.10 T cell activation assay that was comparable to that of the positive control mAb, S1. All Fcabs tested contained the LALA mutation in the CH2 domain, as indicated by "AA" in the clone name.
Figure 3:
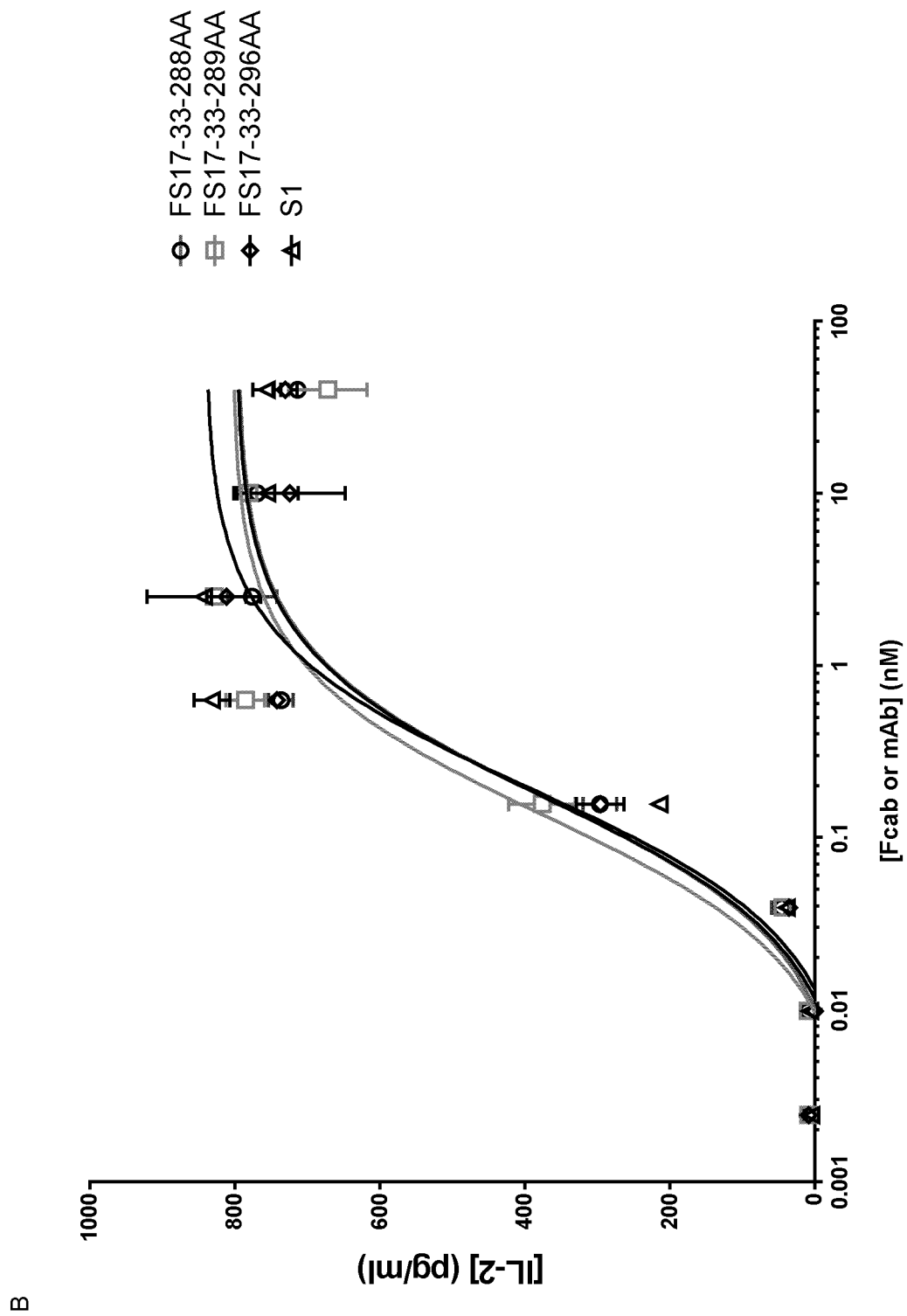
Figure 4:
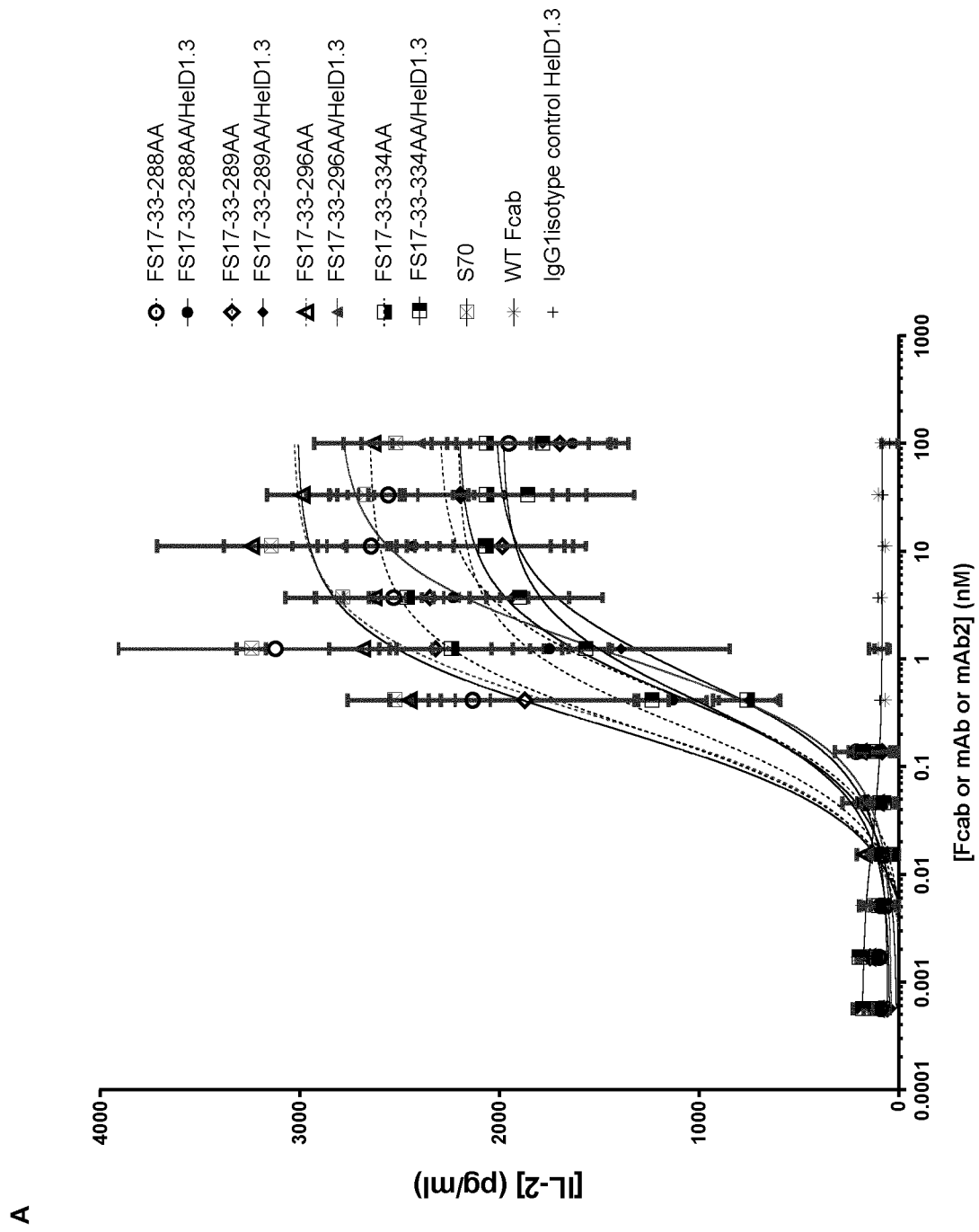
FIG. 4A shows that the anti-PD-L1 Fcabs, FS17-33-288AA, FS17-33-289AA and FS17-33-296AA and FS17-33-334AA, in Fcab and mock mAb$^2$ format inhibit human PD-L1, leading to release of IL-2 in a DO11.10 T cell activation assay. The conversion of the Fcab into a mock mAb$^2$ format resulted in a partial reduction in IL-2 release in this assay.
FIG. 4B shows that the anti-PD-L1 Fcabs, FS17-33-449 and FS17-33-451, in a mock mAb$^2$ format were also able to inhibit PD-L1 and release IL-2 in a DO11.10 T cell activation assay.
Figure 4:
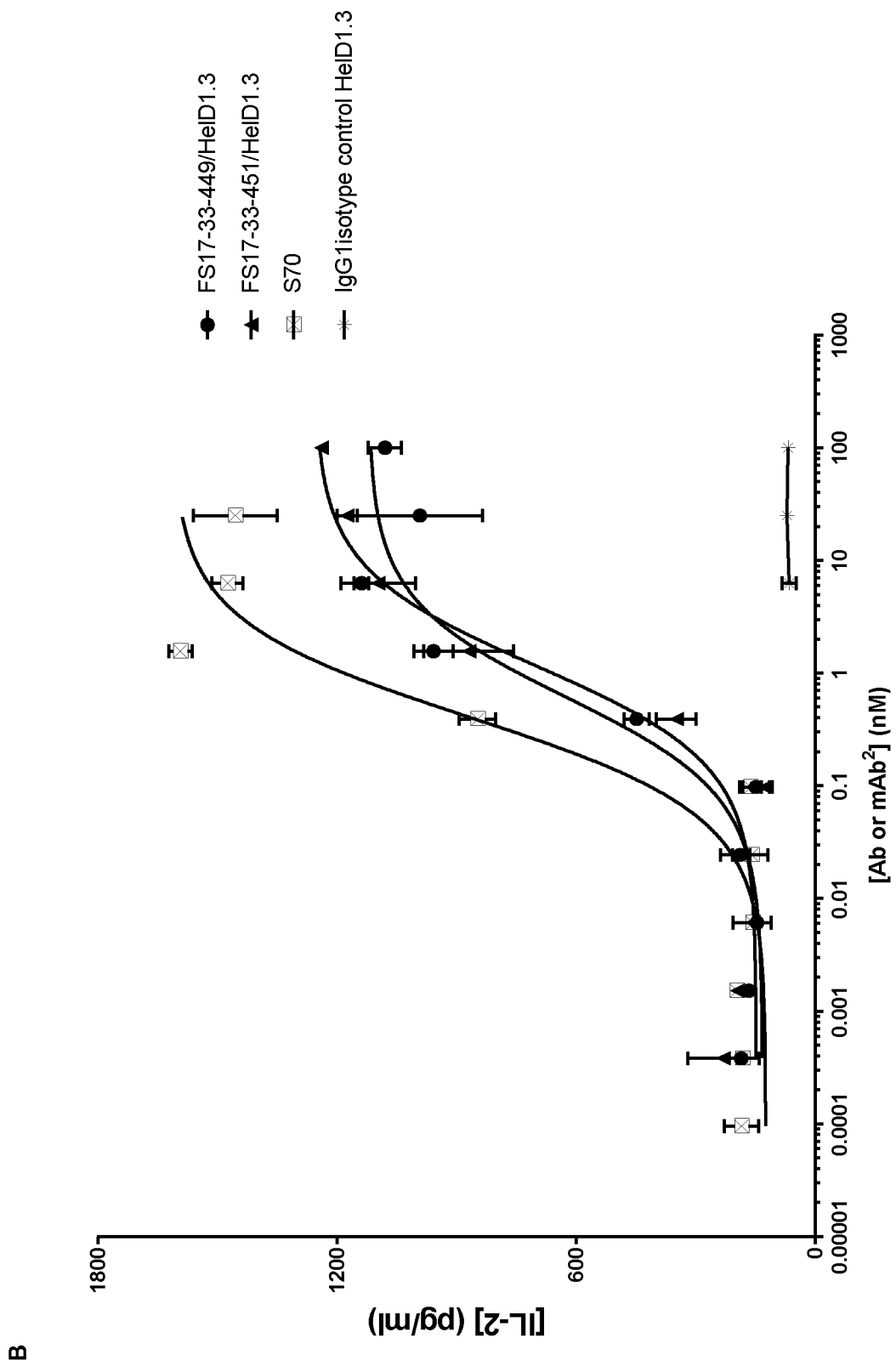

The results are shown in FIGS. 3 and 4 and Table 12. The human Fcabs showed significant activity in the T cell activation assay with potencies (E050) in the range of 0.2 nM comparable to the positive control mAbS1 antibody. Both the Fcab and the mock mAb$^2$ released the PD-L1 mediated inhibition of the T cells. However, the conversion of the Fcab into a mock mAb$^2$ format resulted in a partial reduction of the IL-2 release.

TABLE 12

$EC_{50}$ values of anti-human PD-L1 Fcabs and mock mAb$^2$ in DO11.10 T cell activation assay

| Anti-human PD-L1 Fcabs (with LALA mutation) and positive control anti-human PD-L1 mAb, S1 and S70 | $EC_{50}$ (nM) | Std Dev |
|---|---|---|
| FS17-33-37AA | — | — |
| FS17-33-116AA | 0.28 (n = 1) | — |
| FS17-33-288AA | 0.137 (n = 2) | 0.116 |
| FS17-33-289AA | 0.228 (n = 3) | 0.032 |
| FS17-33-296AA | 0.166 (n = 2) | 0.119 |
| F17-33-334AA | 0.381 (n = 2) | 0.128 |
| F17-33-288AA/HELD1.3 | 0.428 (n = 2) | 0.029 |
| F17-33-289AA/HELD1.3 | 1.555 (n = 2) | 1.209 |
| F17-33-296AA/HELD1.3 | 1.122 (n = 2) | 0.027 |
| F17-33-334AA/HELD1.3 | 0.934 (n = 2) | 0.741 |
| F17-33-449AA/HELD1.3 | 0.95 (n = 2) | 0.467 |
| F17-33-451AA/HELD1.3 | 1.035 (n = 2) | 0.177 |
| S1 | 0.257 (n = 2) | 0.092 |
| S70 | 0.323 (n = 2) | 0.118 |

Example 7—Activity of mAb$^2$ Molecules in an SEB Assay

Next, the activity of these Fcabs in a mAb$^2$ format was tested in an SEB assay. mAb$^2$ were produced as described in Example 4.

7.1 Staphylococcal Enterotoxin B assay

Fcab, PD-L1 mock mAb$^2$ and PD-L1/CTLA-4 mAb$^2$ were tested in the human-PBMC based Staphylococcal Enterotoxin B assay (SEB assay). Staphylococcal Enterotoxin B is a superantigen, and binds to MHC class II molecules on antigen presenting cells (APCs) and the vβ chain of the T cell receptor (TCR), causing non-specific activation of T cells and cytokine release. There is no requirement for antigen to be present to see T cell activation. The SEB assay uses stimulated human cells (PBMCs) with physiological levels of checkpoint inhibitors, and can be used to confirm that T cell activation is enhanced by the mAb$^2$ in a human system.

7.1.1 Generation of Expanded T Cells

PBMCs were isolated from leukocyte cones by Ficoll gradient separation. CD4+ T cells were isolated using human CD4+ T Cell Isolation Kit (Miltenyi Biotec Ltd, 130-096-533) according to the manufacturer's instruction. Human T-Activator CD3/CD28 Dynabeads (Life technologies, 11131D) were resuspended by vortexing. Beads were transferred to a sterile 15 ml tube and 10 ml RPMI (Life Technologies, 61870044) with 10% FBS (Life Technologies, 10270106) and 1× Penicillin Streptomycin (Life Technologies, 15140122) was added to wash Dynabeads. The supernatant was discarded. The required amount of CD4+ T cells at 1.0×10$^6$ cells/ml in RPMI with 10% FBS and 1× Penicillin Streptomycin Solution and 50 IU/ml recombinant human IL2 (Peprotech, 200-02-50 µg) with 3:1 bead to cell ratio were transferred to T75 flask (Greiner Bio-one, 690195) and incubated at 37° C.+5% CO$_2$. After 3 days the cells were gently resuspended and counted. The cell density was maintained between 0.8-1×10$^6$ cells/ml by adding fresh media (RPMI-10% FBS+Penicillin Streptomycin Solution 1×+50 IU/ml rhuIL2) as needed. On day 7 or 8, the CD3/28 beads were removed and CD4+ T cells were rested overnight at 1×10$^6$ cells/ml fresh media RPMI-10% FBS+Penicillin Streptomycin Solution 1× with reduced 10 IU/ml rhuIL2. The cells were stored frozen until required.

7.1.2 Generation of MoiDCs

Untouched monocytes were isolated from human PBMCs using human Pan Monocyte Isolation Kit, (Miltenyi Biotec Ltd, 130-096-537) following the manufacturer's instructions. Monocytes were differentiated to iDCs using human Mo-DC Differentiation Medium (Miltenyi Biotec Ltd, 130-094-812) following the manufacturer's instructions.

7.1.3 SEB Assay

Expanded T cells and MoiDCs were thawed before the experiment, washed with AIM medium (Gibco, 12055-091) and incubated at 37° C., 5% CO$_2$ in AIM medium.

Figure 5:
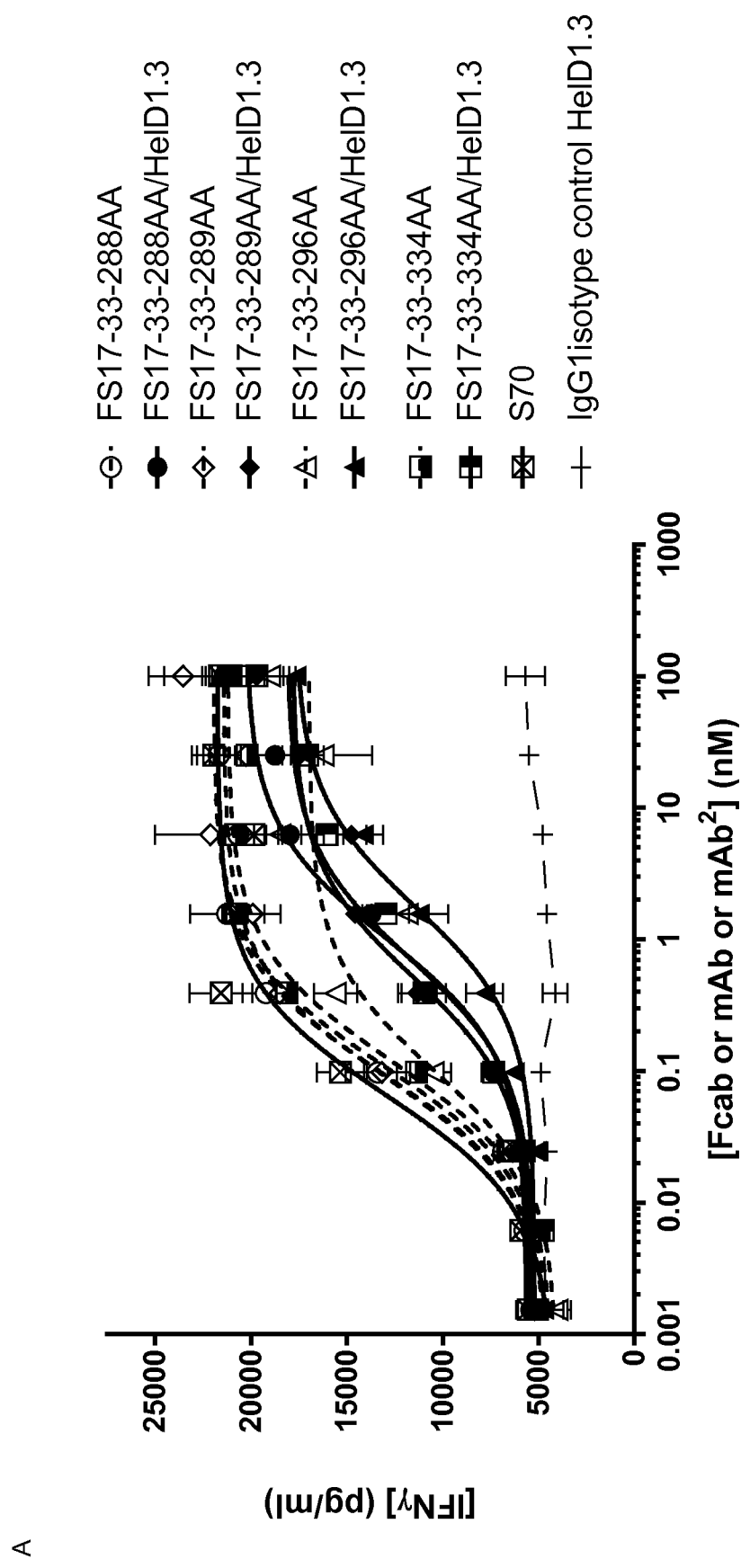
FIG. 5 shows representative plots from the SEB assay. Both the Fcabs and the mock mAb$^2$ showed enhanced IFNγ release by the T cells as compared to the IgG1 isotype control mAb HelD1.3 (A and B). The activities of the Fcabs were close or comparable to the anti-PD-L1 positive control mAb, YW243.55.570 (S70). The Fcabs in a mock mAb$^2$ format showed a slight reduction in IFNγ release in this assay.
Figure 5:
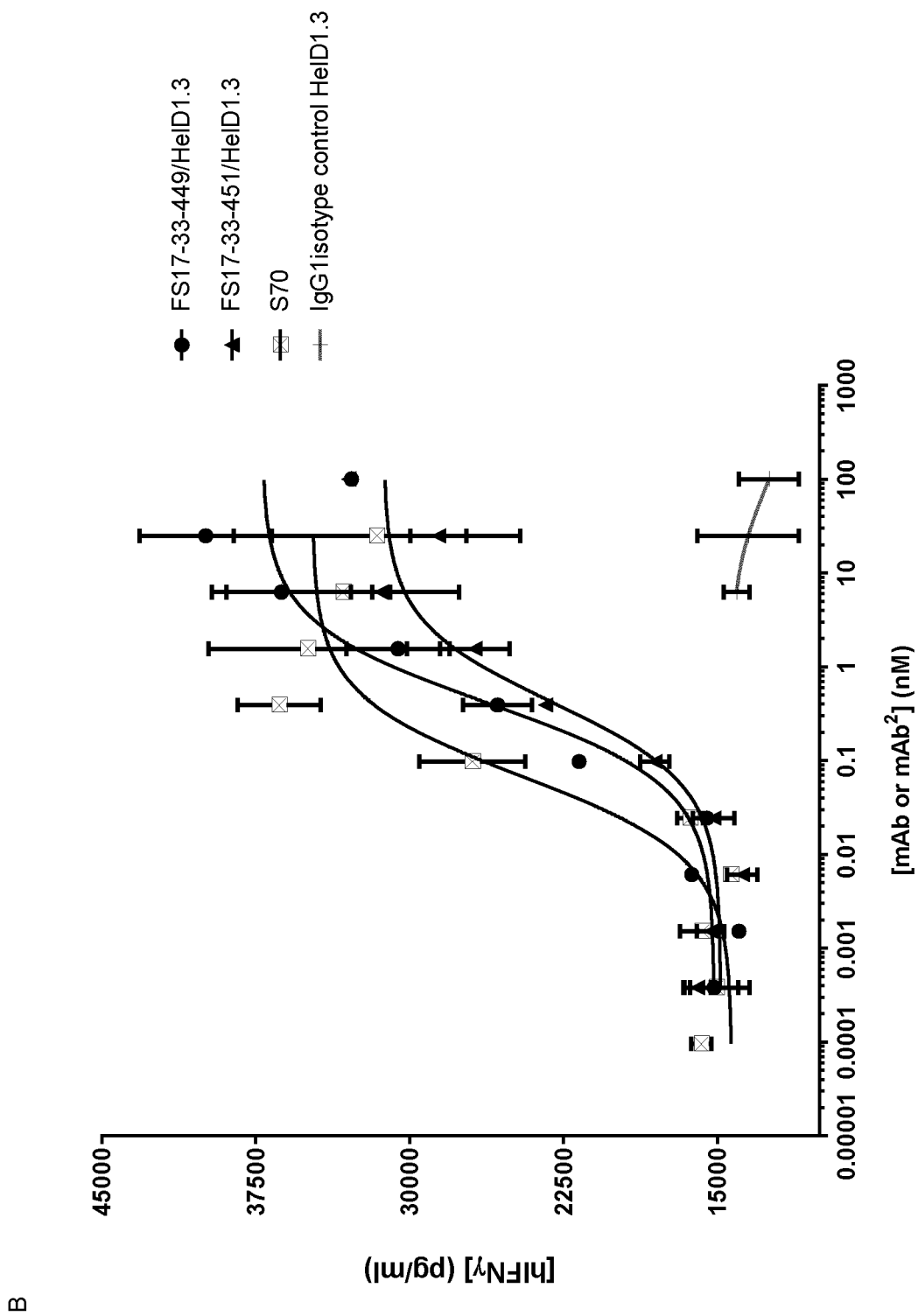
Figure 5:
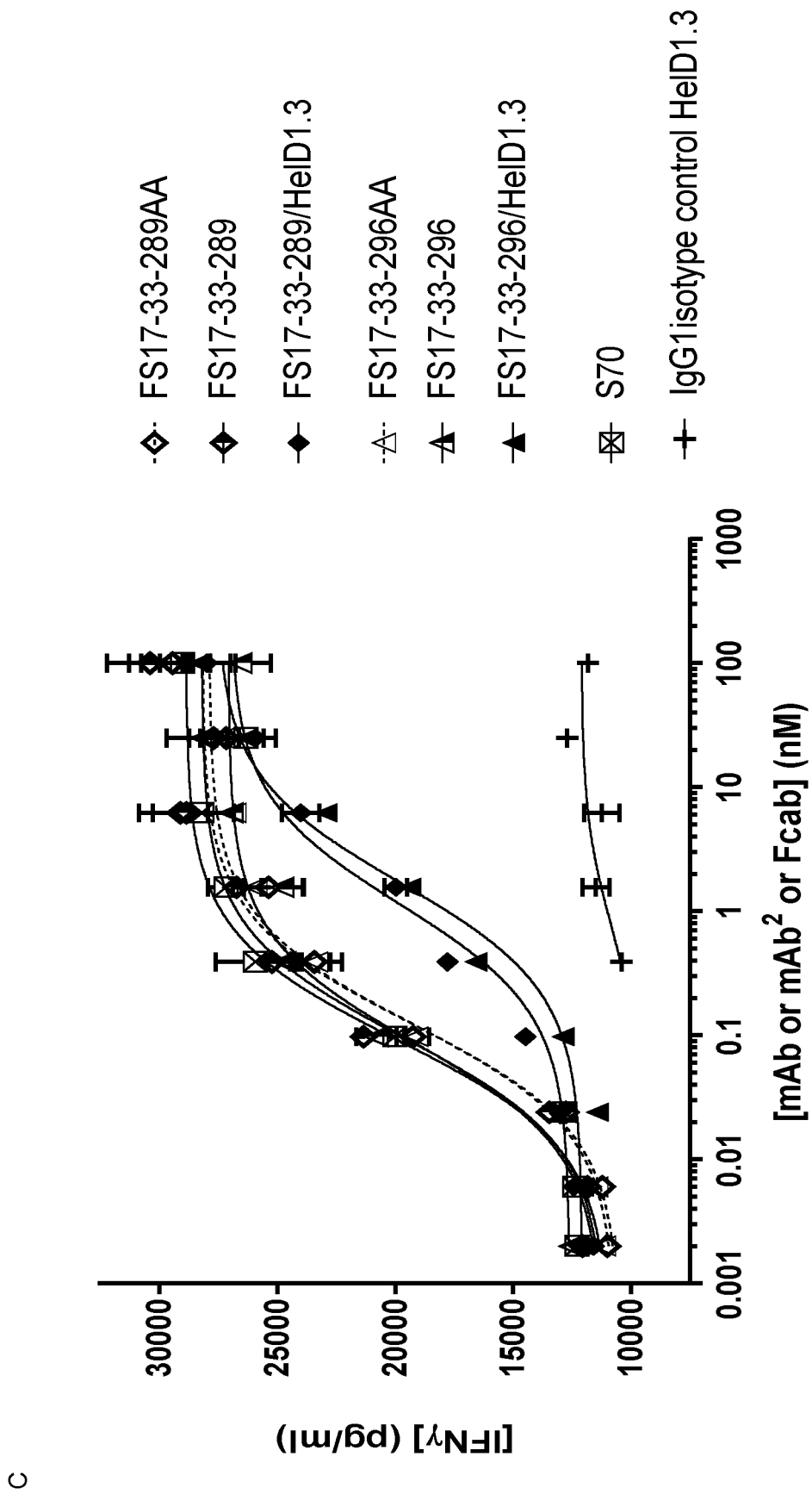

Dilutions of Fcabs, mAb$^2$, anti-human positive control mAb (S1 (with or without LALA mutation) or S70) or the human IgG1 isotype control mAb (anti-HELD1.3 or anti-FITC clone 4420) were prepared in AIM medium. MoiDCs were mixed with T cells from the same donor at a 1:10 ratio (5 ml of iDCs at 2×10$^5$ cells/ml were combined with 5 ml of T cells at 2×10$^6$ cells/ml). 20 µl of SEB (Sigma, S4881) at 0.1 µg/ml was added to 10 ml of the cells. In a round bottom 96 well plate, 100 µl of the cell/SEB mixture was added to 100 µl of the antibody dilution, giving a ratio of 10$^4$ iDC cells to 10$^5$T cells with 0.1 ng/ml SEB in 200 µl of AIM media per well. Cells were incubated at 37° C., 5% CO$_2$ for 4 days. Supernatants were collected and assayed immediately with human IFN$_\gamma$ ELISA kit (R&D Systems, PDIF50) or frozen down at -20° C. for further analysis. The assay was performed according to the kit manufacturer's instructions using supernatants diluted 1:30 with PBA (DPBS, 2% BSA (Sigma, A7906-100G)). The concentration of human IFN$_\gamma$ was plotted vs the log concentration of mAb$^2$ or mAb and the resulting curves were fitted using the log (agonist) vs response equation in GraphPad Prism software. Table 13 shows the $EC_{50}$ values and the span of the IFNγ release in the SEB assay with cells from individual cell donors. FIG. 5 shows representative plot of the SEB assay with a single donor. As shown in the DO11.10 T cell activation assay, some of the Fcab clones showed activity close to the anti-PD-L1 positive control (S70). However, the conversion of the Fcab into a mock mAb$^2$ format resulted in a partial reduction of the IFNγ release. In addition, the results demonstrate that the presence of the LALA mutation in the Fcabs did not interfere with their activities, as shown in FIG. 5C. As explained in 3.6 above, the Fcab self-associate, leading to the formation of dimers. In the mock mAb$^2$ format, this self-association is abrogated. Without wishing to be bound by theory, it is thought that the formation of dimeric Fcabs could boost the activity of the Fcabs in cell-based assays, such as the SEB assay, via avidity.

TABLE 13

| Fcab/mAb²/control mAbs | EC$_{50}$ (nM) | Std Dev |
|---|---|---|
| FS17-33-116AA | 0.100 (n = 3) | 0.0383 |
| FS17-33-288AA | 0.08987 (n = 1) | — |
| FS17-33-288AA/HelD1.3 | 1.016 (n = 1) | — |
| FS17-33-289AA | 0.108385 (n = 4) | 0.045634 |
| FS17-33-289AA/HelD1.3 | 0.56615 (n = 2) | 0.054801 |
| FS17-33-289/HelD1.3 | 0.969 (n = 3) | 0.423315 |
| FS17-33-289 | 0.08855 (n = 2) | 0.00487 |
| FS17-33-289/CTLA-4 | 0.444 (n = 3) | 0.202808 |
| FS17-33-296AA | 0.1242 (n = 3) | 0.032628 |
| FS17-33-296AA/HelD1.3 | 1.772 (n = 1) | — |
| FS17-33-296/HelD1.3 | 1.714 (n = 3) | 0.081132 |
| FS17-33-296 | 0.08692 (n = 1) | — |
| FS17-33-334AA | 0.14385 (n = 2) | 0.032173 |
| FS17-33-334AA/HelD1.3 | 0.761067 (n = 3) | 0.204171 |
| FS17-33-449AA/HelD1.3 | 0.55 (n = 2) | 0.19799 |
| FS17-33-449/HelD1.3 | 0.644 (n = 4) | 0.353366 |
| FS17-33-451AA/HelD1.3 | 1.125 (n = 2) | 0.997021 |
| FS17-33-451/HelD1.3 | 0.852 (n = 3) | 0.732615 |
| FS17-33-449/CTLA-4 | 0.975 (n = 3) | 0.338388 |
| FS17-33-451/CTLA-4 | 0.662 (n = 2) | 0.164897 |
| S70 | 0.100 (n = 8) | 0.033012 |

Figure 6:
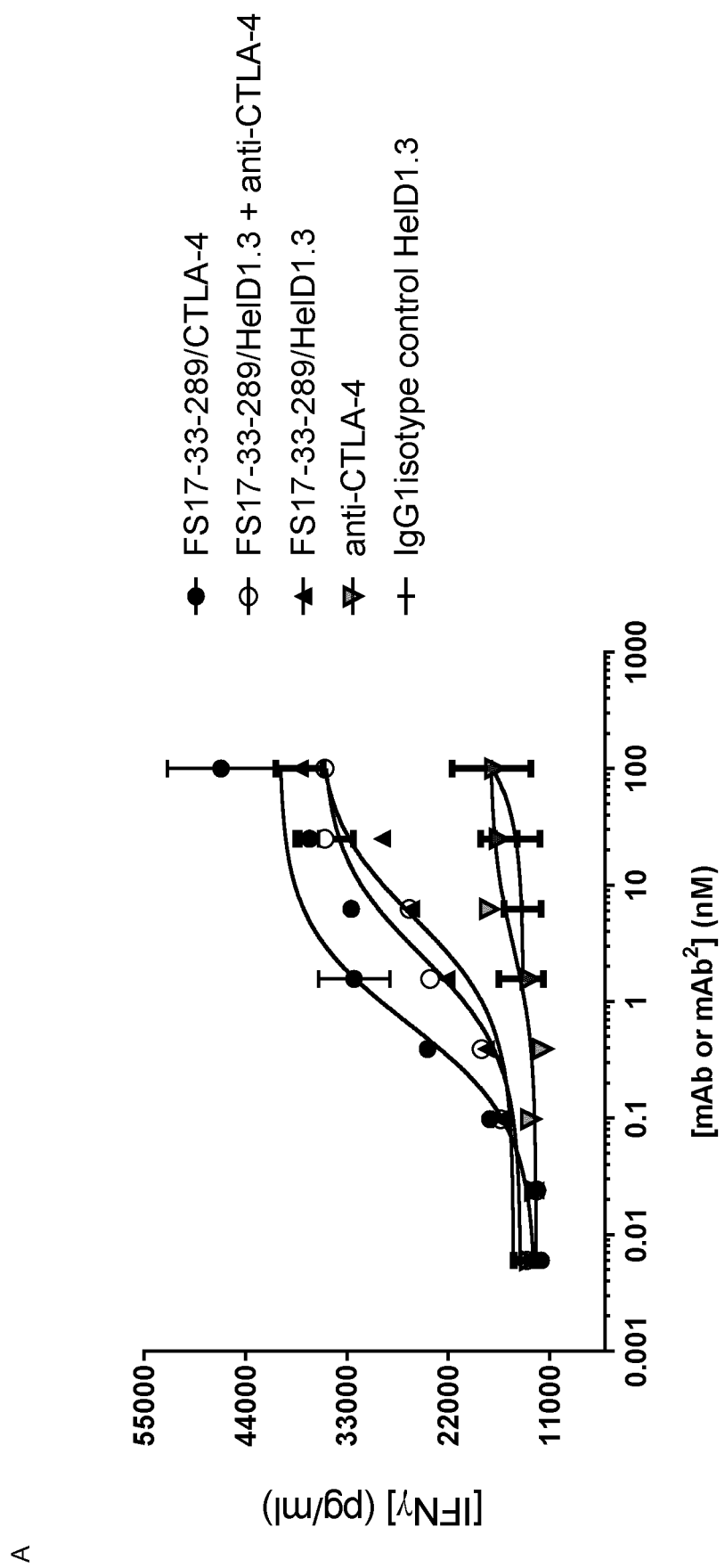
FIGS. 6A and B show representative plots from the SEB assay. As compared to ipilimumab (anti-CTLA-4), both the mock mAb$^2$ and the PD-L1/CTLA-4 mAb$^2$ showed an enhanced IFNγ release by the T cells.
Figure 6:
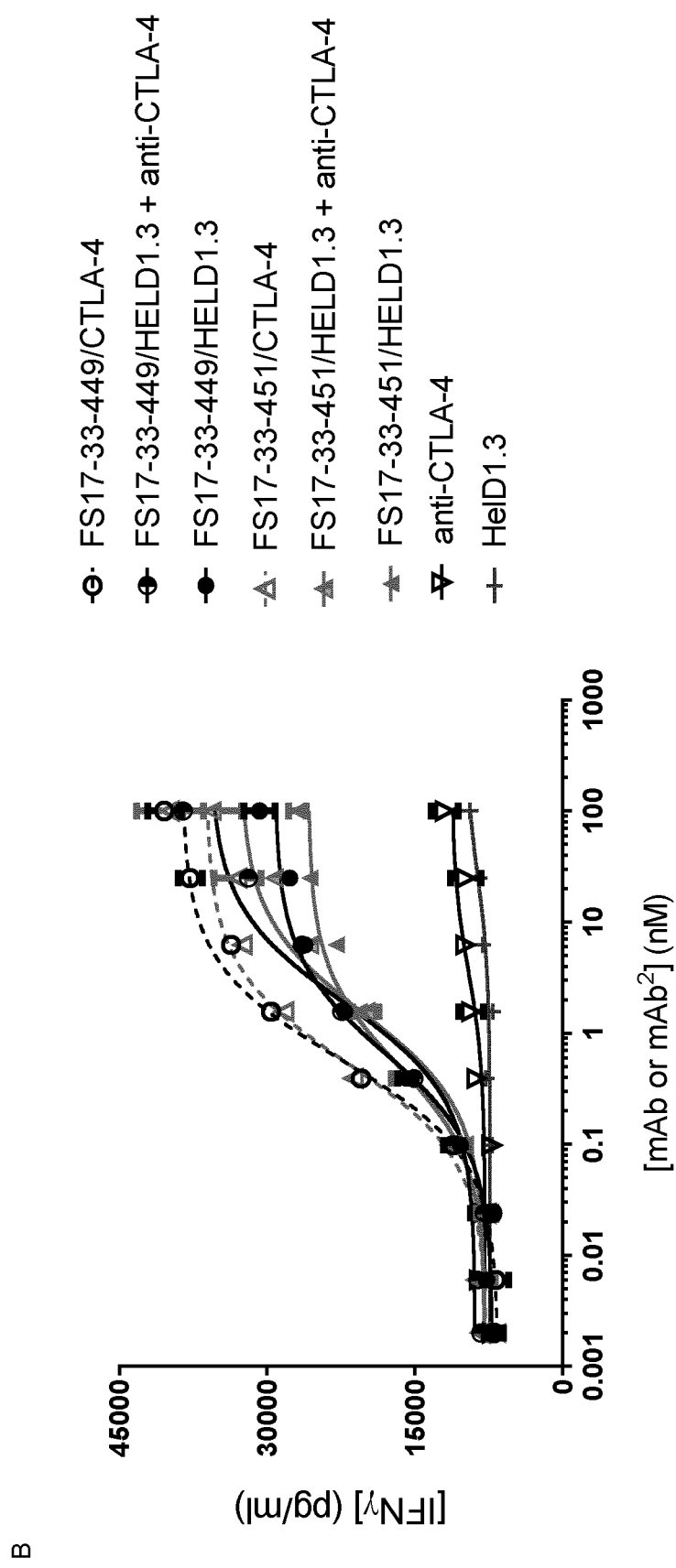

The PD-L1 Fcabs, FS17-33-449 and FS17-33-451, were also paired with the anti-CTLA-4 Fab ipilimumab (see Example 4 for construction details) and the activity of the mAb² were assessed in the SEB assay in comparison to the mock mAb² (with FS17-33-449/HELD1.3 or FS17-33-451/HELD1.3) and ipilimumab alone or to the combination of the mock mAb² and ipilimumab. The PD-L1/CTLA-4 mAb² showed greater activation than the mock mAb² and ipilimumab as single agent or in combination. In one assay out of three, the FS17-33-449/CTLA-4 mAb² did show an activity not greater but comparable to the combination of the mock mAb² and ipilimumab. This result showed that a better synergistic activity can be achieved with the mAb². A representative plot of the SEB assay illustrating these results is provided as FIG. 6B.

Example 8—Selection of Anti-PD-L1 Fcab Molecules with Improved Stability

The Fcab molecules, FS17-33-449 and FS17-33-451, have improved biophysical properties as determined by dynamic light scattering (DLS), protein A purification and solubility analysis (see Example 4.3). However, the melting temperature (T$_m$) of the Fc domain of these molecules is lower than that of the wild-type Fc domain. The reduced melting temperature suggests that these molecules may be less stable than the wild-type Fc domain which might potentially impact the integrity and solubility of these molecules during manufacture and/or the stability of these molecules during long-term storage.

To identify molecules with increased melting temperatures, Fcabs FS17-33-449 and FS17-33-451, were thermally stressed during selection of an error prone phage display library as described below. The aim of this selection campaign was to identify mutations that increase the melting temperature of the Fcab molecules and therefore their thermal stability without reducing target binding and activity of the Fcabs.

8.1 Selection of Anti-PD-L1 Fcab Molecules with Improved Stability from Error Prone Libraries Since mutations in the binding loops and the framework could potentially improve the stability of the clones, error prone PCR (Diversify® PCR Random Mutagenesis Kit (Takara Clontech, 630703) was performed across the entire CH3 domain to generate a CH3 domain library from each of the Fcab clones, FS17-33-449 and FS17-33-451. Two consecutive rounds of PCR were performed to achieve an average 6±2 mutations per CH3 fragment. The mutated CH3 domains were then ligated into the phagemid vector pADL-23c (licensed from Antibody Design Laboratories) and transformed into E. Coli (TG1, Lucigen, 60502-PQ997-A). The CH3 domain library was then subjected to selection for CH3 domains with higher melting temperatures, by first heating the phage to 80° C. for 10 minutes, followed by selection for binding to human PD-L1 (hPD-L1) antigen at a concentration of 20 nM. Human PD-L1-his (Acro biosciences, PD1-H5229), biotinylated as described in Example 3.1, was used as antigen source for the selections. After one round of selection, the output was screened for binding to hPD-L1 in a phage ELISA and hits were sequenced. 86 unique CH3 domain sequences were identified. One mutation, the change of the aspartic acid residue (D) at position 99 of the CH3 domain (in the EF loop) to a glycine residue (G), was overrepresented in the resulting clone population. Interestingly, this mutation represents a reversion to the wild-type sequence at position 99 of the CH3 domain (see, for example, FIG. 1A).

The selected CH3 domain sequences were subcloned and expressed in "mock" (MSL109) mAb² format with the LALA mutation in the CH2 domain, as described in Example 4.2.1, for further screening. The parent FS17-33-449 and FS17-33-451 clones in "mock" (MSL109) mAb² format with the LALA mutation in the CH2 domain were used as controls. The supernatants were then tested for binding to hPD-L1 antigen using the Octet system and 29 clones were shown to retain binding to this antigen. These clones were then expressed on a larger scale and 21 of the clones could be purified following expression. The K$_D$ values for these 21 clones were then measured as described in Example 5.1, and the results are summarised in Table 14. 17 of the 21 clones were chosen on the basis that they had K$_D$ values for binding to hPD-L1 below 1 nM and tested for their activity in a DO11.10 T cell activation assay using the method described in Example 6 (see Table 14 for the assay results). The thermal stability of the six Fcab clones with the highest activity based on their E050 values in the DO11.10 assay was then assessed by determining the melting temperatures of these Fcabs using differential scanning calorimetry (DSC) (see Table 14 for results). As the Tm of the CH2 and CH3 domains of the Fcab clones show only small differences, it is not possible to determine from the profiles which peak represents the CH2 domain and which represents the CH3 domain, respectively. Table 14 therefore reports the Tms for Peak 1 and Peak 2, with the lowest transition temperature being most representative of the Tm of the overall molecule. Three of the Fcabs showed a significant increase in melting temperature compared with the parent Fcab, namely Fcabs FS17-33-488, FS17-33-539 and FS17-33-548. Table 15 shows the EF loop sequences of these three Fcabs and any additional framework mutation in the CH3 domain that these Fcabs contained. All three of the Fcabs contained the reversion of the aspartic acid (D) at position 99 of the CH3 domain to the wild-type glycine (G). In addition, Fcabs FS17-33-488 and FS17-33-539 both contained a mutation of the histidine (H) at position 113 of the CH3 domain to an arginine (R) residue. As these two Fcabs have different parental clones (see Table 15 for details), this mutation, and also the D99G reversion, arose independently twice, indicating that these mutations may play an important role in increasing the melting temperature, and therefore stability, of these Fcabs. Fcab FS17-33-488 also comprised an alanine residue at position 101, as well as additional mutations in the CH3 domain framework (see Table 15 for details).

Fcab clones FS17-33-539 and FS17-33-548 were chosen for further analysis from the panel of Fcabs tested, as these combined an improved melting temperature with a low mutational burden, compared with the FS17-33-488 Fcab which included a larger number of mutations. In addition, a greater improvement in the melting temperature was observed for these two clones (an increase of 3-4° C.) than for the FS17-33-488 clone (an increase of about 2° C.), as compared to the melting temperate of the relevant parental clone (FS17-33-449 or FS17-33-451; see Table 15 for details) (Table 14).

TABLE 14

| Mock mAb² | DO11.10 KD, nM | Kd, 1/s | EC$_{50}$ (nM) | $T_m$ (° C.) measured by DSC Peak 1 CH2/3 | Peak 2 |
|---|---|---|---|---|---|
| FS17-33-449AA/MSL109 (parent 1) | | | | 63.8 | 65.9 |
| FS17-33-451AA/MSL109 (parent 2) | 0.30 | 3.29E−04 | 4.83 | 63.4 | 65.5 |
| FS17-33-469AA/MSL109 | 6.0 | 6.27E−03 | | | |
| FS17-33-475AA/MSL109 | 0.77 | 9.87E−04 | 12.87 | | |
| FS17-33-477AA/MSL109 | 0.26 | 3.41E−04 | 12.81 | | |
| FS17-33-488AA/MSL109 | 0.36 | 3.60E−04 | 3.253 | 65.7 | 67.8 |
| FS17-33-491AA/MSL109 | 0.27 | 3.21E−04 | 11.31 | | |
| FS17-33-492AA/MSL109 | 0.51 | 6.60E−04 | 76.46 | | |
| FS17-33-498AA/MSL109 | 2.2 | 2.22E−03 | | | |
| FS17-33-499AA/MSL109 | 0.75 | 8.63E−04 | 18.69 | | |
| FS17-33-501AA/MSL109 | 3.8 | 3.81E−03 | | | |
| FS17-33-507AA/MSL109 | 0.28 | 3.50E−04 | 8.576 | 62.1 | 64.2 |
| FS17-33-514AA/MSL109 | 0.35 | 4.16E−04 | 3.326 | | |
| FS17-33-515AA/MSL109 | 0.35 | 4.78E−04 | 10.62 | | |
| FS17-33-517AA/MSL109 | 0.32 | 3.72E−04 | 11.1 | | |
| FS17-33-523AA/MSL109 | 0.63 | 8.28E−04 | 23.18 | | |
| FS17-33-532AA/MSL109 | 3.7 | 4.66E−03 | | | |
| FS17-33-533AA/MSL109 | 0.30 | 4.49E−04 | 67.65 | | |
| FS17-33-537AA/MSL109 | 0.28 | 3.31E−04 | 5.179 | 64.1 | 66.4 |
| FS17-33-539AA/MSL109 | 0.39 | 4.27E−04 | 3.14 | 66.9 | 69.0 |
| FS17-33-540AA/MSL109 | 0.45 | 5.60E−04 | 8.481 | | |
| FS17-33-543AA/MSL109 | 0.24 | 3.34E−04 | 8.355 | 63.1 | 65.5 |
| FS17-33-548AA/MSL109 | 0.43 | 4.37E−04 | 8.513 | 67.1 | 69.4 |

TABLE 15

| Mock mAb² | Parent Clone | EF loop (92-101) | | | | | | | | | CH3 domain framework mutations |
|---|---|---|---|---|---|---|---|---|---|---|---|
| FS17-33-488AA/ MSL109 | FS17-33-451 | S | N | W | R | W | Q | L | G | D | A | L84.1P, S85.3T, H113R |
| FS17-33-539AA/ MSL109 | FS17-33-449 | S | N | W | R | W | Q | L | G | D | V | H113R |
| FS17-33-548AA/ MSL109 | FS17-33-451 | S | N | W | R | W | Q | L | G | D | V | none |

8.2 Binding to PD-L1 of Fcab Molecules with Improved Stability

The Fcabs identified in Example 8.1, FS17-33-539AA/MSL109 and FS17-33-548AA/MSL109, were produced on a larger scale and purified as described in Example 4.2.1. Binding of the mock mAb² to hPD-L1 was assessed by both SPR, using a Biacore T200 system (GE Healthcare), and in a cell binding assay as described in Example 5.1. To measure the affinity of the clones to monomeric hPD-L1-his, the mock mAb² were captured using an anti-Fab antibody coated on a CM5 chip (GE 28-9582-20 AC) using a Biacore T200 system. To minimise mass transport effects, the capture level was minimised to 200 RU and a fast flow rate of 75 μl/min was used. Both the human (Acro biosciences, PD1-H5229) and cynomolgus (Acro Biosciences, PD1-052H4) monomeric antigens were titrated and flowed over the captured mock mAb². The analysis of the data was done using the Biacore T200 evaluation software. Curves subtracted against a blank flow cell and a run with no antigen were analysed using a 1:1 fitting model with no bulk analysis and $R_{max}$ analysed locally.

Cell binding assays were performed by incubating the mock mAb² with either control HEK293 cells or HEK293 cells overexpressing hPD-L1 or cynomolgus PD-L1 cells for 1 hour at 4° C. Mock mAb² binding was subsequently detected using an anti-human Fc 488 detection antibody. Fluorescent signal intensities were measured using a FACS Canto flow cytometer (BD Biosciences).

The results of these binding experiments are summarised in Table 16. Table 16 shows that all of the mock mAb² tested had a high affinity for monomeric and cell-expressed human and cynomolgus PD-L1.

TABLE 16

| | Binding affinity - K$_D$ (nM) | | Binding EC$_{50}$ (nM) | |
|---|---|---|---|---|
| Mock mAb² | Human monomeric PD-L1 | Cynomolgus monomeric PD-L1 | Cell-expressed human PD-L1 | Cell-expressed cynomolgus PD-L1 |
| FS17-33-539AA/ MSL109 | 0.90 | 0.95 | 4.8 | 10 |
| FS17-33-548AA/ MSL109 | 0.6 | 0.45 | 1.5 | 2.1 |

8.3 Blocking Activity of Fcab Molecules with Improved Stability

The ability of the mock mAb² to block hPD-1/hPD-L1 and hPD-L1/hCD80 interactions was tested in cell-based Receptor Blocking Assays (RBA). The anti-PD-L1 antibody S70 in an IgG1 framework and comprising the LALA mutation (G1AA/S70) was used as a positive control. In brief, biotinylated hPD-L1-Fc-Avi was incubated for 1 hour with titrating concentrations of mock mAb² ranging from 2000 nM to 3 μM. The mix was incubated for another hour with HEK293 cells overexpressing either hPD-1 or hCD80. The level of bound biotinylated hPD-L1-Fc-Avi on the HEK293 cells was detected using streptavidin 647 and fluorescence levels were measured using the FACS Canto flow cytometer.

The results of these blocking experiments are shown in Table 17. Table 17 shows that all the clones tested were able to fully block hPD-1/hPD-L1 and hPD-L1/hCD80 interactions.

TABLE 17

| Mock mAb²/mAb | Blocking activity - $EC_{50}$ (nM) | |
|---|---|---|
| | PD-L1/PD-1 | PD-L1/CD80 |
| FS17-33-539AA/MSL109 | 49.67 | 118.6 |
| FS17-33-548AA/MSL109 | 43.17 | 129.9 |
| G1AA/S70 | 42.93 | 477.1 |

8.4 Activity of Fcabs with Improved Stability in Human T Cell Activation Assays

The activity of the mock mAb² was tested in a DO11.10 cell-based T cell activation assay as described in Example 6.1, and in an SEB assay as described in Example 7.1. The results are shown in Table 18. Due to the potential for variability to be seen between assays, e.g. depending on the donor source of the stimulated PBMCs used in the SEB assay, one of the parental clones, FS17-33-451 (in "mock" MSL109 mAb² format and comprising the LALA mutation), was also included in both assays as a direct comparator. Both of the mock mAb² tested retained T cell activation activity in both assays. The $EC_{50}$ of the mock mAb² in these assays was either improved, or comparable, to that of the parental clone FS17-33-451AA/MSL109.

TABLE 18

| mAb² | DO11.10 $EC_{50}$ (nM) | SEB $EC_{50}$ (nM) |
|---|---|---|
| FS17-33-539AA/MSL109 | 2.91 | 0.97 |
| FS17-33-548AA/MSL109 | 7.59 | 3.21 |
| FS17-33-451AA/MSL109 (parent) | 8.28 | 1.11 |

8.5 Assessment of Thermal Stability by Differential Scanning Colorimetry (DSC)

The melting temperature ($T_m$) of the FS17-33-539 and FS1733-548 Fcabs (in mock MSL109 mAb² format and with the LALA mutation) was measured using a Microcal VP-capillary differential scanning calorimeter. The G1AA/MSL109 mAb² was included as positive control in this analysis as it contains wild-type CH3 domain and a LALA containing CH2 domain. Samples were measured in sample buffer at a concentration of 0.2 mg/ml. The scan rate was set at 60° C./hr and data collected between 35° C. and 100° C. Data analysis was performed with Origin 7.0 software. The results are shown in Table 19. As was seen when the clones were produced at smaller scale (see Table 14), the FS17-33-539 and FS1733-548 Fcab molecules in mock mAb² format exhibited an improvement in the melting temperature of the Fc domain by 3-4° C. compared with the relevant parental clone.

TABLE 19

| mAb²/control mAb | $T_m$ (° C.) of CH2/CH3 domain measured by DSC | |
|---|---|---|
| | Peak 1 | Peak 2 |
| FS17-33-449AA/MSL109 (parent 1) | 63.8 | 65.9 |
| FS17-33-451AA/MSL109 (parent 2) | 63.4 | 65.5 |
| FS17-33-539AA/MSL109 | 67.3 | 68.9 |
| FS17-33-548AA/MSL109 | 67.2 | 68.9 |
| G1AA/MSL109 | 73.6 | 84.8 |

REFERENCES

All documents mentioned in this specification are incorporated herein by reference in their entirety.

Altschul et al., Basic local alignment search tool. J. Mol. Biol. 215(3), 403-10 (1990).

Altschul et al., Gapped BLAST and PSI-BLAST: a new generation of protein database search programs. Nucleic Acids Res. 25(17), 3389-402 (1997).

Bagshawe et al., Antibody-enzyme conjugates can generate cytotoxic drugs from inactive precursors at tumor sites. Antibody, Immunoconjugates and Radiopharmaceuticals 4, 915-22 (1991).

Bedzyk et al., Comparison of variable region primary structures within an anti-fluorescein idiotype family. J. Biol. Chem. 264(3), 1565-69 (1989).

Bedzyk et al., Immunological and structural characterization of a high affinity anti-fluorescein single-chain antibody. J. Biol. Chem. 265(30), 18615-20 (1990).

Bodhankar et al., PD-L1 Monoclonal Antibody Treats Ischemic Stroke by Controlling Central Nervous System Inflammation. Stroke 46(10), 2926-2934 (2015).

Bruhns et al., Specificity and affinity of human Fcγ receptors and their polymorphic variants for human IgG subclasses. Blood 113(16), 3716-25 (2009).

Curran et al., PD-1 and CTLA-4 combination blockade expands infiltrating T cells and reduces regulatory T and myeloid cells within B16 melanoma tumors. Proc. Natl. Acad. Sci. U.S.A. 107(9), 4275-80 (2010).

Daxini et al., Vasculitis associated with immune checkpoint inhibitors—a systematic review. Clin. Rheumatol. 37(9), 2579-2584 (2018).

Grosso et al., Programmed death-ligand 1 (PD-L1) expression in various tumor types. Journal for Immunotherapy of Cancer. 1(Suppl 1):P53. (2013).

Hasenhindl et al., Stability assessment on a library scale: a rapid method for the evaluation of the commutability and insertion of residues in C-terminal loops of the CH3 domains of IgG1-Fc., Protein Eng. Des. Sel., 26(10), 675-82 (2013).

Herbst et al., Predictive correlates of response to the anti-PD-L1 antibody MPDL3280A in cancer patients. Nature. 515(7528), 563-7 (2014).

Hezareh et al., Effector function activities of a panel of mutants of a broadly neutralizing antibody against human immunodeficiency virus type 1. J. Virol. 75(24), 12161-8 (2001).

Hid Cadena et al., Checks and Balances in Autoimmune Vasculitis. Front. Immunol. 9, 315 (2018).

Horton et al., Gene splicing by overlap extension: tailor-made genes using the polymerase chain reaction. Bio-Techniques 8(5):528-535 (November 1990). BioTechniques 54(3), 129-33 (2013).

Hu et al., Minibody: A novel engineered anti-carcinoembryonic antigen antibody fragment (single-chain Fv-CH3) which exhibits rapid, high-level targeting of xenografts. Cancer Res. 56(13), 3055-61 (1996).

Idusogie et al., Mapping of the C1q binding site on rituxan, a chimeric antibody with a human IgG1 Fc. J. Immunol. 164(8), 4178-84 (2000).

Iwai et al., Involvement of PD-L1 on tumor cells in the escape from host immune system and tumor immunotherapy by PD-L1 blockade. Proc. Natl. Acad. Sci. U.S.A. 99(19), 12293-7 (2002).

Klein et al., The use of CrossMAb technology for the generation of bi- and multispecific antibodies. MAbs. 8(6), 1010-20 (2016).

Kontermann, Dual targeting strategies with bispecific antibodies. MAbs 4(2):182-97 (2012).

Larkin et al., Combined Nivolumab and Ipilimumab or Monotherapy in Untreated Melanoma. N. Engl. J. Med. 373(13), 1270-1 (2015).

Ledermann et al., A phased study of repeated therapy with radiolabelled antibody to carcinoembryonic antigen using intermittent or continuous administration of cyclosporin A to suppress the immune response. Int. J. Cancer 47(5), 659-64 (1991).

Lefranc et al., IMGT unique numbering for immunoglobulin and T cell receptor constant domains and Ig superfamily C-like domains. Dev. Comp. Immunol. 29(3), 185-203 (2005).

Pearson and Lipman, Improved tools for biological sequence comparison. Proc. Natl. Acad. Sci. U.S.A. 85(8), 2444-8 (1988).

Rao M. et al., Anti-PD-1/PD-L1 therapy for infectious diseases: learning from the cancer paradigm. Int. J. Infect. Dis. 56, 221-228 (2017.)

Rosenberg, S., Development of Cancer Vaccines, ASCO Educational Book Spring: 60-62 (2000).

Smith and Waterman, Identification of common molecular subsequences. J. Mol. Biol. 147(1), 195-197 (1981).

Spiess et al., Alternative molecular formats and therapeutic applications for bispecific antibodies. Molecular Immunology. 67:95-106 (2015).

Stewart et al., Identification and Characterization of MED14736, an Antagonistic Anti-PD-L1 Monoclonal Antibody. Cancer Immunol. Res. 3(9), 1052-62 (2015).

Tello et al., Three-dimensional structure and thermodynamics of antigen binding by anti-lysozyme antibodies. Biochem. Soc. Trans. 21(4), 943-6 (1993).

Wang et al., IgG Fc engineering to modulate antibody effector functions. Protein Cell. 9(1), 63-73 (2018).

Wolchok J et al., Nivolumab plus ipilimumab in advanced melanoma. N. Engl. J. Med. 369(2), 122-33 (2013).

Wykes and Lewin, Immune checkpoint blockade in infectious diseases. Nat. Rev. Immunol. 18(2), 91-104 (2018).

```
Sequence Listing
Amino acid sequences of WT Fcab CH3 domain structural loops
WT Fcab AB loop
                                                        (SEQ ID NO: 1)
LTKNQ WT Fcab CD loop
                                                        (SEQ ID NO: 2)
QPENNY WT Fcab EF loop
                                                        (SEQ ID NO: 3)
DKSRWQQGNV Amino acid sequence of WT Fcab CH3 domain
                                                        (SEQ ID NO: 4)
GQPREPQVYTLPPSRDELTKNQVSLTCLVKGFYPSDIAVEWESNGQPENNYKTTPPVLDSDGSFFLYSK

LTVDKSRWQQGNVFSCSVMHEALHNHYTQKSLSLSPGK

Amino acid sequence of the CH2 domain of the WT Fcab, FS17-33, and
FS17-33-37/116/288/289/296/334/449/451/488/539/548 with LALA mutation
The location of the LALA mutation is underlined
                                                        (SEQ ID NO: 5)
APEAAGGPSVFLFPPKPKDTLMISRTPEVTCVVVDVSHEDPEVKFNWYVDGVEVHNAKTKPREEQYNST

YRVVSVLTVLHQDWLNGKEYKCKVSNKALPAPIEKTISKAK

Consensus sequences of Fcab FS17-33-116/288/289/296/334/449/451
CH3 domain structural loops
AB loop
                                                        (SEQ ID NO: 10)
X₁GYW CD loop
                                                        (SEQ ID NO: 11)
EPQYWA EF loop
                                                        (SEQ ID NO: 12)
SNWRWQX₂DDX₃
X₁ = V, S, T, or E
X₂ = M, I, L, V
X₃ = V or absent
```

Amino acid sequences of Fcab FS17-33 CH3 domain structural loops
FS17-33 AB loop (SEQ ID NO: 13)
QSGYW FS17-33 CD loop (SEQ ID NO: 2)
QPENNY FS17-33 EF loop (SEQ ID NO: 14)
SNWRWQMGD Amino acid sequence of Fcab FS17-33 CH3 domain (SEQ ID NO: 15)
GQPREPQVYTLPPSRDEQSGYWVSLTCLVKGFYPSDIAVEWESNGQPENNYKTTPPVLDSDGSFFLYSK

LTVSNWRWQMGDFSCSVMHEALHNHYTQKSLSLSPGK

Amino acid sequence of Fcab FS17-33 with LALA mutation
Hinge region (underlined), CH2 domain (bold) and CH3 domain (italics)

(SEQ ID NO: 16)
TCPPCPAPEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPSRDEQSG

YWVSLTCLVKGFYPSDIAVEWESNGQPENNYKTTPPVLDSDGSFFLYSKLTVSNWRWQMGDFSCSVMH

EALHNHYTQKSLSLSPGK

Amino acid sequence of Fcab FS17-33 without LALA mutation
Hinge region (underlined), CH2 domain (bold) and CH3 domain (italics)

(SEQ ID NO: 17)
TCPPCPAPELLGGPSVFLFPPKPKDTLMISRTPEVTCVVVDVSHEDPEVKFNVVYVDGVEVHNAKTKPR

EEQYNSTYRVVSVLTVLHQDWLNGKEYKCKVSNKALPAPIEKTISKAKGQPREPQVYTLPPSRDEQSG

YWVSLTCLVKGFYPSDIAVEWESNGQPENNYKTTPPVLDSDGSFFLYSKLTVSNWRWQMGDFSCSVMH

EALHNHYTQKSLSLSPGK

Amino acid sequence of the CH2 domain of the WT Fcab, FS17-33, and FS17-33-
37/116/288/289/296/334/449/451/488/539/548 without LALA mutation (SEQ ID NO: 6)
APELLGGPSVFLFPPKPKDTLMISRTPEVTCVVVDVSHEDPEVKFNWYVDGVEVHNAKTKPREEQYNST

YRVVSVLTVLHQDWLNGKEYKCKVSNKALPAPIEKTISKAK

Amino acid sequence of the truncated hinge region of the WT Fcab,
FS17-33, and FS17-33-37/116/288/289/296/334/449/451/488/539/548

(SEQ ID NO: 7)
TCPPCP

Amino acid sequence of WT Fcab with LALA mutation
Hinge region (underlined), CH2 domain (bold) and CH3 domain (italics)

(SEQ ID NO: 8)
TCPPCPAPEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPSRDELTKN

QVSLTCLVKGFYPSDIAVEWESNGQPENNYKTTPPVLDSDGSFFLYSKLTVDKSRWQQGNVFSCSVMH

EALHNHYTQKSLSLSPGK

Amino acid sequence of WT Fcab without LALA mutation
Hinge region (underlined), CH2 domain (bold) and CH3 domain (italics)

(SEQ ID NO: 9)
TCPPCPAPELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPSRDELTKN

QVSLTCLVKGFYPSDIAVEWESNGQPENNYKTTPPVLDSDGSFFLYSKLTVDKSRWQQGNVFSCSVMH

EALHNHYTQKSLSLSPGK

Amino acid sequences of Fcab FS17-33-37 CH3 domain structural loops
FS17-33 AB loop (SEQ ID NO: 18)
QVGYW FS17-33 CD loop (SEQ ID NO: 2)
QPENNY FS17-33 EF loop (SEQ ID NO: 19)
SNWRWQMDD Amino acid sequence of Fcab FS17-33-37 CH3 domain (SEQ ID NO: 20)
GQPREPQVYTLPPSRDEQVGYWVSLTCLVKGFYPSDIAVEWESNGQPENNYKTTPPVLDSDGSFFLYSK

LTVSNWRWQMDDFSCSVMHEALHNHYTQKSLSLSPGK

Amino acid sequence of Fcab FS17-33-37 with LALA mutation
Hinge region (underlined), CH2 domain (bold) and CH3 domain (italics)

(SEQ ID NO: 21)
<u>TCPPCP</u>APEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK*GQPREPQVYTLPPSRDEQVG*

*YWVSLTCLVKGFYPSDIAVEWESNGQPENNYKTTPPVLDSDGSFFLYSKLTVSNWRWQMDDFSCSVMH*

*EALHNHYTQKSLSLSPGK*

Amino acid sequence of Fcab FS17-33-37 without LALA mutation
Hinge region (underlined), CH2 domain (bold) and CH3 domain (italics)

(SEQ ID NO: 22)
<u>TCPPCP</u>APELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK*GQPREPQVYTLPPSRDEQVG*

*YWVSLTCLVKGFYPSDIAVEWESNGQPENNYKTTPPVLDSDGSFFLYSKLTVSNWRWQMDDFSCSVMH*

*EALHNHYTQKSLSLSPGK*

Amino acid sequences of Fcab FS17-33-116 CH3 domain structural loops
FS17-33-116 AB loop (SEQ ID NO: 23)
SGYW FS17-33-116 CD loop (SEQ ID NO: 11)
EPQYWA FS17-33-116 EF loop (SEQ ID NO: 19)
SNWRWQMDD Amino acid sequence of Fcab FS17-33-116 CH3 domain (SEQ ID NO: 24)
GQPREPQVYTLPPSRDESGYWVSLTCLVKGFYPSDIVVEWESNGEPQYWAKTTPPVLDSDGSFFLYSKL

TVSNWRWQMDDFSCSVMHEALHNHYTQKSLSLSPGK

Amino acid sequence of Fcab FS17-33-1 16 with LALA mutation
Hinge region (underlined), CH2 domain (bold) and CH3 domain (italics)

(SEQ ID NO: 25)
<u>TCPPCP</u>APEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK*GQPREPQVYTLPPSRDESGY*

*WVSLTCLVKGFYPSDIVVEWESNGEPQYWAKTTPPVLDSDGSFFLYSKLTVSNWRWQMDDFSCSVMH*

*EALHNHYTQKSLSLSPGK*

Amino acid sequence of Fcab FS17-33-1 16 without LALA mutation
Hinge region (underlined), CH2 domain (bold) and CH3 domain (italics)

(SEQ ID NO: 26)
<u>TCPPCP</u>APELLGGPSVFLFPPKPKDTLMISRTPEVTCVVVDVSHEDPEVKFNVVYVDGVEVHNAKTKPR

EEQYNSTYRVVSVLTVLHQDWLNGKEYKCKVSNKALPAPIEKTISKAK*GQPREPQVYTLPPSRDESGY*

```
WVSLTCLVKGFYPSDIVVEWESNGEPQYWAKTTPPVLDSDGSFFLYSKLTVSNWRWQMDDFSCSVMH

EALHNHYTQKSLSLSPGK
```

Amino acid sequences of Fcab FS17-33-288 CH3 domain structural loops
FS17-33-288 AB loop (SEQ ID NO: 23)
```
SGYW
```

FS17-33-288 CD loop (SEQ ID NO: 11)
```
EPQYWA
```

FS17-33-288 EF loop (SEQ ID NO: 27)
```
SNWRWQIDD
```

Amino acid sequence of FS17-33-288 CH3 domain (SEQ ID NO: 28)
```
GQPREPQVYTLPPSRDESGYWVSLTCLVKGFYPSDIVVEWESNGEPQYWAKTTPPVLDSDGSFFLYSKL

TVSNWRWQIDDFSCSVMHEALHNHYTQKSLSLSPGK
```

Amino acid sequence of Fcab FS17-33-288 with LALA mutation
Hinge region (underlined), CH2 domain (bold) and CH3 domain (italics)

(SEQ ID NO: 29)
<u>TCPPCP</u>APEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDESGY_

_WVSLTCLVKGFYPSDIVVEWESNGEPQYWAKTTPPVLDSDGSFFLYSKLTVSNWRWQIDDFSCSVMHE_

_ALHNHYTQKSLSLSPGK_

Amino acid sequence of Fcab FS17-33-288 without LALA mutation
Hinge region (underlined), CH2 domain (bold) and CH3 domain (italics)

(SEQ ID NO: 30)
<u>TCPPCP</u>APELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDESGY_

_WVSLTCLVKGFYPSDIVVEWESNGEPQYWAKTTPPVLDSDGSFFLYSKLTVSNWRWQIDDFSCSVMHE_

_ALHNHYTQKSLSLSPGK_

Amino acid sequences of Fcab FS17-33-289 CH3 domain structural loops
FS17-33-289 AB loop (SEQ ID NO: 23)
```
SGYW
```

FS17-33-289 CD loop (SEQ ID NO: 11)
```
EPQYWA
```

FS17-33-289 EF loop (SEQ ID NO: 31)
```
SNWRWQLDD
```

Amino acid sequence of Fcab FS17-33-289 CH3 domain (SEQ ID NO: 32)
```
GQPREPQVYTLPPSRDESGYWVSLTCLVKGFYPSDIVVEWESNGEPQYWAKTTPPVLDSDGSFFLYSKL

TVSNWRWQLDDFSCSVMHEALHNHYTQKSLSLSPGK
```

Amino acid sequence of Fcab FS17-33-289 with LALA mutation
Hinge region (underlined), CH2 domain (bold) and CH3 domain (italics)

(SEQ ID NO: 33)
<u>TCPPCP</u>APEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDESGY_

_WVSLTCLVKGFYPSDIVVEWESNGEPQYWAKTTPPVLDSDGSFFLYSKLTVSNWRWQLDDFSCSVMHE_

_ALHNHYTQKSLSLSPGK_

Amino acid sequence of Fcab FS17-33-289 without LALA mutation
Hinge region (underlined), CH2 domain (bold) and CH3 domain (italics)
(SEQ ID NO: 34)

<u>TCPPCP</u>APELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDESGY_

_WVSLTCLVKGFYPSDIVVEWESNGEPQYWAKTTPPVLDSDGSFFLYSKLTVSNWRWQLDDFSCSVMHE_

_ALHNHYTQKSLSLSPGK_

Amino acid sequences of Fcab FS17-33-296 CH3 domain structural loops
FS17-33-296 AB loop
(SEQ ID NO: 23)
SGYW FS17-33-296 CD loop
(SEQ ID NO: 11)
EPQYWA FS17-33-296 EF loop
(SEQ ID NO: 35)
SNWRWQVDD Amino acid sequence of Fcab FS17-33-296 CH3 domain
(SEQ ID NO: 36)
GQPREPQVYTLPPSRDESGYWVSLTCLVKGFYPSDIVVEWESNGEPQYWAKTTPPVLDSDGSFFLYSKL

TVSNWRWQVDDFSCSVMHEALHNHYTQKSLSLSPGK

Amino acid sequence of Fcab FS17-33-296 with LALA mutation
Hinge region (underlined), CH2 domain (bold) and CH3 domain (italics)
(SEQ ID NO: 37)

<u>TCPPCP</u>APEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDESGY_

_WVSLTCLVKGFYPSDIVVEWESNGEPQYWAKTTPPVLDSDGSFFLYSKLTVSNWRWQVDDFSCSVMHE_

_ALHNHYTQKSLSLSPGK_

Amino acid sequence of Fcab FS17-33-296 without LALA mutation
Hinge region (underlined), CH2 domain (bold) and CH3 domain (italics)
(SEQ ID NO: 38)

<u>TCPPCP</u>APELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDESGY_

_WVSLTCLVKGFYPSDIVVEWESNGEPQYWAKTTPPVLDSDGSFFLYSKLTVSNWRWQVDDFSCSVMHE_

_ALHNHYTQKSLSLSPGK_

Amino acid sequences of Fcab FS17-33-334 CH3 domain structural loops
FS17-33-334 AB loop
(SEQ ID NO: 23)
SGYW FS17-33-334 CD loop
(SEQ ID NO: 11)
EPQYWA FS17-33-334 EF loop
(SEQ ID NO: 31)
SNWRWQLDD Amino acid sequence of Fcab FS17-33-334 CH3 domain
(SEQ ID NO: 39)
GQPREPQVYTLPPSRDESGYWVSLTCLVKGFYPSDIAVEWESNGEPQYWAKTTPPVLDSDGSFFLYSKL

TVSNWRWQLDDFSCSVMHEALHNHYTQKSLSLSPGK

Amino acid sequence of Fcab FS17-33-334 with LALA mutation
Hinge region (underlined), CH2 domain (bold) and CH3 domain (italics)
(SEQ ID NO: 40)

<u>TCPPCP</u>APEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDESGY_

```
WVSLTCLVKGFYPSDIAVEWESNGEPQYWAKTTPPVLDSDGSFFLYSKLTVSNWRWQLDDFSCSVMHE

ALHNHYTQKSLSLSPGK
```

Amino acid sequence of Fcab FS17-33-334 without LALA mutation
Hinge region (underlined), CH2 domain (bold) and CH3 domain (italics)
(SEQ ID NO: 41)

<u>TCPPCP</u>APELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK*GQPREPQVYTLPPSRDESGY*

*WVSLTCLVKGFYPSDIAVEWESNGEPQYWAKTTPPVLDSDGSFFLYSKLTVSNWRWQLDDFSCSVMHE*

*ALHNHYTQKSLSLSPGK*

Amino acid sequences of Fcab FS17-33-449 CH3 domain structural loops
FS17-33-449 AB loop
(SEQ ID NO: 42)
TGYW FS17-33-449 CD loop
(SEQ ID NO: 11)
EPQYWA FS17-33-449 EF loop
(SEQ ID NO: 43)
SNWRWQLDDV Amino acid sequence of Fcab FS17-33-449 CH3 domain
(SEQ ID NO: 44)
GQPREPQVYTLPPSRDETGYWVSLTCLVKGFYPSDIAVEWESNGEPQYWAKTTPPVLDSDGSFFLYSKL

TVSNWRWQLDDVFSCSVMHEALHNHYTQKSLSLSPGK

Amino acid sequence of Fcab FS17-33-449 with LALA mutation
Hinge region (underlined), CH2 domain (bold) and CH3 domain (italics)
(SEQ ID NO: 45)

<u>TCPPCP</u>APEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK*GQPREPQVYTLPPSRDETGY*

*WVSLTCLVKGFYPSDIAVEWESNGEPQYWAKTTPPVLDSDGSFFLYSKLTVSNWRWQLDDVFSCSVMH*

*EALHNHYTQKSLSLSPGK*

Amino acid sequence of Fcab FS17-33-449 without LALA mutation
Hinge region (underlined), CH2 domain (bold) and CH3 domain (italics)
(SEQ ID NO: 46)

<u>TCPPCP</u>APELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK*GQPREPQVYTLPPSRDETGY*

*WVSLTCLVKGFYPSDIAVEWESNGEPQYWAKTTPPVLDSDGSFFLYSKLTVSNWRWQLDDVFSCSVMH*

*EALHNHYTQKSLSLSPGK*

Amino acid sequences of Fcab FS17-33-451 CH3 domain structural loops
FS17-33-451 AB loop
(SEQ ID NO: 47)
EGYW FS17-33-451 CD loop
(SEQ ID NO: 11)
EPQYWA FS17-33-451 EF loop
(SEQ ID NO: 43)
SNWRWQLDDV Amino acid sequence of Fcab FS17-33-451 CH3 domain
(SEQ ID NO: 48)
GQPREPQVYTLPPSRDEEGYWVSLTCLVKGFYPSDIAVEWESNGEPQYWAKTTPPVLDSDGSFFLYSKL

TVSNWRWQLDDVFSCSVMHEALHNHYTQKSLSLSPGK

Amino acid sequence of Fcab FS17-33-451 with LALA mutation
Hinge region (underlined), CH2 domain (bold) and CH3 domain (italics)
(SEQ ID NO: 49)
<u>TCPPCP</u>APEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDEEGY_

_WVSLTCLVKGFYPSDIAVEWESNGEPQYWAKTTPPVLDSDGSFFLYSKLTVSNWRWQLDDVFSCSVMH_

_EALHNHYTQKSLSLSPGK_

Amino acid sequence of Fcab FS17-33-451 without LALA mutation
Hinge region (underlined), CH2 domain (bold) and CH3 domain (italics)
(SEQ ID NO: 50)
<u>TCPPCP</u>APELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDEEGY_

_WVSLTCLVKGFYPSDIAVEWESNGEPQYWAKTTPPVLDSDGSFFLYSKLTVSNWRWQLDDVFSCSVMH_

_EALHNHYTQKSLSLSPGK_

Amino acid sequence of the heavy chain of the IgG1 4420 antibody with
LALA mutation
In the below heavy chain sequence, as well as the heavy chain sequences
for antibodies HelD1.3, MSL109, S70, and S1 listed below, the sequence
of the variable domain is shown in italics, the sequence of the CH1
domain is underlined, the sequence of the hinge region is doubly
underlined, the sequence of the CH2 domain is shown in bold, and the
sequence of the CH3 domain is shown in plain font.
(SEQ ID NO: 51)
_EVKLDETGGGLVQPGRPMKLSCVASGFTFSDYWMNWVRQSPEKGLEWVAQIRNKPYNYETYYSDSVK_

_GRFTISRDDSKSSVYLQMNNLRVEDMGIYYCTGSYYGMDYWGQGTSVTVSS_<u>ASTKGPSVFPLAPSSKST</u>

<u>SGGGTAALGCLVKDYFPEPVTVSWNSGALTSGVHTFPAVLQSSGLYSLSSVVTVPSSSLGTQTYICNVNHK</u>

<u>PSNTKVDKKV</u><u><u>EPKSCDKTHTCPPCP</u></u>APEAAGGPSVFLFPPKPKDTLMISRTPEVTCVVVDVSHEDPEVK

FNVVYVDGVEVHNAKTKPREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTPPVLDSDGSFFLYSKLTV

DKSRWQQGNVFSCSVMHEALHNHYTQKSLSLSPGK

Amino acid sequence of the light chain of the IgG1 4420 antibody with
LALA mutation
In the below light chain sequence, as well as the light chain sequences
for antibodies HelD1.3, MSL109, S70, and S1 listed below, the sequence
of the variable domain is shown in italics, and the sequence of the
constant domain is underlined.
(SEQ ID NO: 52)
_DVVMTQTPLSLPVSLGDQASISCRSSQSLVHSNGNTYLRWYLQKPGQSPKVLIYKVSNRFSGVPDRFSG_

_SGSGTDFTLKISRVEAEDLGVYFCSQSTHVPWTFGGGTKLEIK_<u>RTVAAPSVFIFPPSDEQLKSGTASVVCL</u>

<u>LNNFYPREAKVQWKVDNALQSGNSQESVTEQDSKDSTYSLSSTLTLSKADYEKHKVYACEVTHQGLSSP</u>

<u>VTKSFNRGEC</u>

Amino acid sequence of the heavy chain of the HelD1.3 antibody with
LALA mutation
(SEQ ID NO: 53)
_QVQLQESGPGLVRPSQTLSLTCTVSGSTFSGYGVNWVRQPPGRGLEWIGMIWGDGNTDYNSALKSRVT_

_MLVDTSKNQFSLRLSSVTAADTAVYYCARERDYRLDYWGQGSLVTVSS_<u>ASTKGPSVFPLAPSSKSTSGG</u>

<u>TAALGCLVKDYFPEPVTVSWNSGALTSGVHTFPAVLQSSGLYSLSSVVTVPSSSLGTQTYICNVNHKPSN</u>

<u>TKVDKKV</u><u><u>EPKSCDKTHTCPPCP</u></u>APEAAGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK

Amino acid sequence of the light chain of the HelD1.3 antibody with LALA mutation (SEQ ID NO: 54)

DIQMTQSPASLSASVGETVTITCRASGNIHNYLAWYQQKQGKSPQLLVYNAKTLADGVPSRFSGSGSGT

QYSLKINSLQPEDFGSYYCQHFWSTPRTFGGGTKLEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSPVTKSF

NRGEC

Amino acid sequence of the heavy chain of the MSL109 antibody with LALA mutation (SEQ ID NO: 55)

EEQVLESGGGLVKPGGSLRLSCAASGFTFSPYSVFWVRQAPGKGLEWVSSINSDSTYKYYADSVKGRF

TISRDNAENSIFLQMNSLRAEDTAVYYCARDRSYYAFSSGSLSDYYYGLDVWGQGTTVIVSSASTKGPSV

FPLAPSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Amino acid sequence of the light chain of the MSL109 antibody with LALA mutation (SEQ ID NO: 56)

DIVMTQSPLSLSVTPGEPASISCRSSQSLLHTNGYNYLDWYVQKPGQSPQLLIYLASNRASGVPDRFSGS

GSGTDFTLKISRVETEDVGVYYCMQALQIPRTFGQGTKVEIKRTVAAPSVFIFPPSDEQLKSGTASVVCLL

NNFYPREAKVQWKVDNALQSGNSQESVTEQDSKDSTYSLSSTLTLSKADYEKHKVYACEVTHQGLSSP

VTKSFNRGEC

Amino acid sequence of the heavy chain of the S70 antibody with LALA mutation (SEQ ID NO: 57)

EVQLVESGGGLVQPGGSLRLSCAASGFTFSDSWIHWVRQAPGKGLEWVAWISPYGGSTYYADSVKGRF

TISADTSKNTAYLQMNSLRAEDTAVYYCARRHWPGGFDYWGQGTLVTVSAASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCDKTHTCPPCPAPEAAGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKTTPPVLDSDGSFFLYSKLTVD

KSRWQQGNVFSCSVMHEALHNHYTQKSLSLSPGK

Amino acid sequence of the light chain of the S70 antibody with LALA mutation (SEQ ID NO: 58)

DIQMTQSPSSLSASVGDRVTITCRASQDVSTAVAWYQQKPGKAPKLLIYSASFLYSGVPSRFSGSGSGTD

FTLTISSLQPEDFATYYCQQYLYHPATFGQGTKVEIKRTVAAPSVFIFPPSDEQLKSGTASVVCLLNNFYP

REAKVQWKVDNALQSGNSQESVTEQDSKDSTYSLSSTLTLSKADYEKHKVYACEVTHQGLSSPVTKSFN

RGEC

Amino acid sequence of the heavy chain of the S1 antibody with LALA mutation (SEQ ID NO: 59)

EVQLVESGGGLVQPGGSLRLSCAASGFTFSDSWIHWVRQAPGKGLEWVAWISPYGGSTYYADSVKGRF

TISADTSKNTAYLQMNSLRAEDTAVYYCARRHWPGGFDYWGQGTLVTVSAASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCDKTHTCPPCPAPEAAGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALPAPIEKTISKAKGQP

-continued

REPQVYTLPPSRDELTKNQVSLTCLVKGFYPSDIAVEWESNGQPENNYKTTPPVLDSDGSFFLYSKLTVD

KSRWQQGNVFSCSVMHEALHNHYTQKSLSLSPGK

Amino acid sequence of the light chain of the S1 antibody with
LALA mutation
(SEQ ID NO: 60)

*DIQMTQSPSSLSASVGDRVTITCRASQDVSTAVAWYQQKPGKAPKLLIYSASFLYSGVPSRFSGSGSGTD*

*FTLTISSLQPEDFATYYCQQYLFTPPTFGQGTKVEIK*RTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNR

GEC

Amino acid sequence of human PD-L1
(SEQ ID NO: 61)

MRIFAVFIFMTYWHLLNAFTVTVPKDLYVVEYGSNMTIECKFPVEKQLDLAALIVYWEMEDKNIIQFVHG

EEDLKVQHSSYRQRARLLKDQLSLGNAALQITDVKLQDAGVYRCMISYGGADYKRITVKVNAPYNKINQ

RILVVDPVTSEHELTCQAEGYPKAEVIWTSSDHQVLSGKTTTTNSKREEKLFNVTSTLRINTTTNEIFYCT

FRRLDPEENHTAELVIPELPLAHPPNERTHLVILGAILLCLGVALTFIFRLKGRMMDVKKCGIQDTNSKK

QSDTHLEET

Amino acid sequence of murine PD-L1
(SEQ ID NO: 62)

MRIFAGIIFTACCHLLRAFTITAPKDLYVVEYGSNVTMECRFPVERELDLLALVVYWEKEDEQVIQFVAGE

EDLKPQHSNFRGRASLPKDQLLKGNAALQITDVKLQDAGVYCCIISYGGADYKRITLKVNAPYRKINQRI

SVDPATSEHELICQAEGYPEAEVIWTNSDHQPVSGKRSVTTSRTEGMLLNVTSSLRVNATANDVFYCT

FWRSQPGQNHTAELIIPELPATHPPQNRTHWVLLGSILLFLIVVSTVLLFLRKQVRMLDVEKCGVEDTSS

KNRNDTQFEET

Amino acid sequence of cynomolgus PD-L1
(SEQ ID NO: 63)

MRIFAVFIFTIYWHLLNAFTVTVPKDLYVVEYGSNMTIECKFPVEKQLDLTSLIVYWEMEDKNIIQFVHGE

EDLKVQHSNYRQRAQLLKDQLSLGNAALRITDVKLQDAGVYRCMISYGGADYKRITVKVNAPYNKINQR

ILVVDPVTSEHELTCQAEGYPKAEVIWTSSDHQVLSGKTTTTNSKREEKLLNVTSTLRINTTANEIFYCIF

RRLDPEENHTAELVIPELPLALPPNERTHLVILGAIFLLLGVALTFIFYLRKGRMMDMKKCGIRVTNSKKQ

RDTQLEET

Amino acid sequence of human PD-1
(SEQ ID NO: 64)

MQIPQAPWPVVWAVLQLGWRPGWFLDSPDRPWNPPTFSPALLVV

TEGDNATFTCSFSNTSESFVLNWYRMSPSNQTDKLAAFPEDRSQPGQDCRFRVTQLPN

GRDFHMSVVRARRNDSGTYLCGAISLAPKAQIKESLRAELRVTERRAEVPTAHPSPSP

RPAGQFQTLVVGVVGGLLGSLVLLVWVLAVICSRAARGTIGARRTGQPLKEDPSAVPV

FSVDYGELDFQWREKTPEPPVPCVPEQTEYATIVFPSGMGTSSPARRGSADGPRSAQP

LRPEDGHCSWPL

Amino acid sequence of human CD80
(SEQ ID NO: 65)

MGHTRRQGTSPSKCPYLNFFQLLVLAGLSHFCSGVIHVTKEVKE

VATLSCGHNVSVEELAQTRIYWQKEKKMVLTMMSGDMNIWPEYKNRTIFDITNNLSIV

ILALRPSDEGTYECVVLKYEKDAFKREHLAEVTLSVKADFPTPSISDFEIPTSNIRRI

ICSTSGGFPEPHLSWLENGEELNAINTTVSQDPETELYAVSSKLDFNMTTNHSFMCLI

KYGHLRVNQTFNWNTTKQEHFPDNLLPSWAITLISVNGIFVICCLTYCFAPRCRERRR

NERLRRESVRPV

-continued

Amino acid sequence of mouse CD80
(SEQ ID NO: 66)
MACNCQLMQDTPLLKFPCPRLILLFVLLIRLSQVSSDVDEQLSK

SVKDKVLLPCRYNSPHEDESEDRIYWQKHDKVVLSVIAGKLKVWPEYKNRTLYDNTTY

SLIILGLVLSDRGTYSCVVQKKERGTYEVKHLALVKLSIKADFSTPNITESGNPSADT

KRITCFASGGFPKPRFSWLENGRELPGINTTISQDPESELYTISSQLDFNTTRNHTIK

CLIKYGDAHVSEDFTWEKPPEDPPDSKNTLVLFGAGFGAVITVVVIVVIIKCFCKHRS

CFRRNEASRETNNSLTFGPEEALAEQTVFL

Amino acid sequence of the heavy chain of the Ipilimumab antibody without LALA mutation
The CDRs are underlined. The CH3 sequence is shown in bold
(SEQ ID NO: 67)
QVQLVESGGGVVQPGRSLRLSCAAS<u>GFTFSSY</u>TMHWVRQAPGKGLEWV<u>TFISYDGNNK</u>YYADSVKGR FTISRDNSKNTLYLQMNSLRAEDTAIYYC<u>ARTGWLGPFDY</u>WGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGK

Amino acid sequence of the light chain of the Ipilimumab antibody without LALA mutation
The CDR sequences are underlined
(SEQ ID NO: 68)
EIVLTQSPGTLSLSPGERATLSCRAS<u>QSVGSSY</u>LAWYQQKPGQAPRLLIY<u>GAFS</u>RATGIPDRFSGSGSGT DFTLTISRLEPEDFAVYYC<u>QQYGSSPWT</u>FGQGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSPVTKSF

NRGEC

Amino acid sequence of the human IgG1 hinge region
(SEQ ID NO: 69)
EPKSCDKTHTCPPCP Amino acid sequences of Fcab FS17-33-488 CH3 domain structural loops
FS17-33-488 AB loop
(SEQ ID NO: 47)
EGYW FS17-33-488 CD loop
(SEQ ID NO: 11)
EPQYWA FS17-33-488 EF loop
(SEQ ID NO: 70)
SNWRWQLGDA Amino acid sequence of Fcab FS17-33-488 CH3 domain
(SEQ ID NO: 71)
GQPREPQVYTLPPSRDEEGYWVSLTCLVKGFYPSDIAVEWESNGEPQYWAKTTPPVPDSDGTFFLYSKL

TVSNWRWQLGDAFSCSVMHEALRNHYTQKSLSLSPGK

Amino acid sequence of Fcab FS17-33-488 with LALA mutation
Hinge region (underlined), CH2 domain (bold) and CH3 domain (italics)
(SEQ ID NO: 72)
<u>TCPPCP</u>APEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK*GQPREPQVYTLPPSRDEEGY*

*WVSLTCLVKGFYPSDIAVEWESNGEPQYWAKTTPPVPDSDGTFFLYSKLTVSNWRWQLGDAFSCSVMH*

*EALRNHYTQKSLSLSPGK*

-continued

Amino acid sequence of Fcab FS17-33-488 without LALA mutation
Hinge region (underlined), CH2 domain (bold) and CH3 domain (italics)
(SEQ ID NO: 73)
TCPPCPAPELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDEEGY_

_WVSLTCLVKGFYPSDIAVEWESNGEPQYWAKTTPPVPDSDGTFFLYSKLTVSNWRWQLGDAFSCSVMH_

_EALRNHYTQKSLSLSPGK_

Amino acid sequences of Fcab FS17-33-539 CH3 domain structural loops
FS17-33-539 AB loop
(SEQ ID NO: 42)
TGYW FS17-33-539 CD loop
(SEQ ID NO: 11)
EPQYWA FS17-33-539 EF loop
(SEQ ID NO: 74)
SNWRWQLGDV Amino acid sequence of Fcab FS17-33-539 CH3 domain
(SEQ ID NO: 75)
GQPREPQVYTLPPSRDETGYWVSLTCLVKGFYPSDIAVEWESNGEPQYWAKTTPPVLDSDGSFFLYSKL

TVSNWRWQLGDVFSCSVMHEALRNHYTQKSLSLSPGK

Amino acid sequence of Fcab FS17-33-539 with LALA mutation
Hinge region (underlined), CH2 domain (bold) and CH3 domain (italics)
(SEQ ID NO: 76)
TCPPCPAPEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDETGY_

_WVSLTCLVKGFYPSDIAVEWESNGEPQYWAKTTPPVLDSDGSFFLYSKLTVSNWRWQLGDVFSCSVMH_

_EALRNHYTQKSLSLSPGK_

Amino acid sequence of Fcab FS17-33-539 without LALA mutation
Hinge region (underlined), CH2 domain (bold) and CH3 domain (italics)
(SEQ ID NO: 77)
TCPPCPAPELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDETGY_

_WVSLTCLVKGFYPSDIAVEWESNGEPQYWAKTTPPVLDSDGSFFLYSKLTVSNWRWQLGDVFSCSVMH_

_EALRNHYTQKSLSLSPGK_

Amino acid sequences of Fcab FS17-33-548 CH3 domain structural loops
FS17-33-548 AB loop
(SEQ ID NO: 47)
EGYW FS17-33-548 CD loop
(SEQ ID NO: 11)
EPQYWA FS17-33-548 EF loop
(SEQ ID NO: 78)
SNWRWQLGDV Amino acid sequence of Fcab FS17-33-548 CH3 domain
(SEQ ID NO: 79)
GQPREPQVYTLPPSRDEEGYWVSLTCLVKGFYPSDIAVEWESNGEPQYWAKTTPPVLDSDGSFFLYSKL

TVSNWRWQLGDVFSCSVMHEALHNHYTQKSLSLSPGK

Amino acid sequence of Fcab FS17-33-548 with LALA mutation
Hinge region (underlined), CH2 domain (bold) and CH3 domain (italics)
(SEQ ID NO: 80)
TCPPCPAPEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK_GQPREPQVYTLPPSRDEEGY_

-continued

WVSLTCLVKGFYPSDIAVEWESNGEPQYWAKTTPPVLDSDGSFFLYSKLTVSNWRWQLGDVFSCSVMH

*EALHNHYTQKSLSLSPGK*

Amino acid sequence of Fcab FS17-33-548 without LALA mutation
Hinge region (underlined), CH2 domain (bold) and CH3 domain (italics)

(SEQ ID NO: 81)

<u>TCPPCP</u>APELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAK*GQPREPQVYTLPPSRDEEGY*

*WVSLTCLVKGFYPSDIAVEWESNGEPQYWAKTTPPVLDSDGSFFLYSKLTVSNWRWQLGDVFSCSVMH*

*EALHNHYTQKSLSLSPGK*

Amino acid sequence of the CH2 domain with LALA mutation and P114A mutation
LALA mutation underlined; P114A mutation bold and underlined (SEQ ID NO: 82)

APE<u>AA</u>GGPSVFLFPPKPKDTLMISRTPEVTCVVVDVSHEDPEVKFNWYVDGVEVHNAKTKPREEQYNST

YRVVSVLTVLHQDWLNGKEYKCKVSNKAL<u>A</u>APIEKTISKAK

---

The invention claimed is:

1. An antibody molecule, or fragment thereof, which binds to programmed death-ligand 1 (PD-L1), comprising a PD-L1 antigen-binding site located in a CH3 domain of the antibody molecule, or fragment thereof, wherein the PD-L1 binding site comprises:

(i) a first sequence located in the AB structural loop at positions 14 to 18 of the CH3 domain, wherein the antibody molecule, or fragment thereof comprises an amino acid deletion at position 14, 15 or 16 of the CH3 domain, and wherein the first sequence consists of:

(a) amino acid sequence SGYW (SEQ ID NO: 23), or (b) a variant of SEQ ID NO: 23, wherein the serine (S) is substituted with amino acid A, E, F, G, H, I, L, P, R, S, T, V, or Y, and/or the glycine (G) is substituted with amino acid A, D, E, F, H, K, L, N, P, R, T, V, or Y;

(ii) a second sequence located in the CD structural loop at positions 45.1 to 78 of the CH3 domain, wherein the second sequence consists of:
(a) amino acid sequence EPQYWA (SEQ ID NO: 11), or
(b) a variant of SEQ ID NO: 11, wherein
the glutamic acid (E) is substituted with amino acid A, G, H, I, L, N, Q, R, S, or W, and/or
the proline (P) is substituted with amino acid A, D, E, G, H, N, Q, W, or Y, and/or
the glutamine (Q) is substituted with amino acid H, or N, and/or
the tyrosine (Y) is substituted with amino acid A, D, H, T, or V, and/or
the alanine (A) is substituted with amino acid D, E, G, L, R, S, or W; and
(iii) a third sequence located in the EF structural loop at positions 92 to 100 of the CH3 domain, wherein the third sequence consists of:
(a) amino acid sequence SNWRWQMDD (SEQ ID NO: 19), or
(b) a variant of SEQ ID NO: 19, wherein
the serine (S) at position 92 is substituted with amino acid A, or G, and/or
the asparagine (N) at position 93 is substituted with amino acid A, E, F, G, H, I, K, L, Q, R, S, T, or Y, and/or
the glutamine (Q) at position 97 is substituted with amino acid A, D, E, F, G, H, K, L, N, R, S, or V, and/or
the methionine (M) at position 98 is substituted with amino acid F, I, L, V, W, or Y, and/or
the aspartic acid (D) at position 99 is substituted with amino acid E, A, I, L, R, S, T, V, W, Y, or G, and/or
the aspartic acid (D) at position 100 is substituted with amino acid A, E, F, I, K, L, N, R, V, W, or Y; and
wherein the amino acid at position 101 of the CH3 domain is valine (V), alanine (A) or is absent;
wherein the amino acid residue numbering is according to the ImMunoGeneTics (IMGT) numbering scheme; and
wherein the antibody molecule, or antigen-binding fragment thereof, is not an antibody molecule, or antigen-binding fragment thereof which comprises a CDR-based antigen binding site which binds Inducible T-cell COStimulator (ICOS) and a PD-L1 binding site comprising a first sequence located in the AB structural loop at positions 14 to 18 of the CH3 domain, wherein the antibody molecule, or antigen-binding fragment thereof, comprises an amino acid deletion at position 14, 15 or 16 of the CH3 domain, and wherein the first sequence consists of the sequence set forth in SEQ ID NO: 23, a second sequence located in the CD structural loop at positions 45.1 to 78 of the CH3 domain, wherein the second sequence consists of the sequence set forth in SEQ ID NO: 11, and a third sequence located in the EF structural loop at positions 92 to 100 of the CH3 domain, wherein the third sequence consists of the sequence set forth in SEQ ID NO: 31.

2. The antibody molecule, or fragment thereof according to claim 1, wherein:
(i) the first sequence has the sequence set forth in SEQ ID NO: 42, the second sequence has the sequence set forth in SEQ ID NO: 11, and the third sequence has the sequence set forth in SEQ ID NO: 43;
(ii) the first sequence has the sequence set forth in SEQ ID NO: 47, the second sequence has the sequence set forth in SEQ ID NO: 11, and the third sequence has the sequence set forth in SEQ ID NO: 43;
(iii) wherein the first sequence has the sequence set forth in SEQ ID NO: 47, the second sequence has the sequence set forth in SEQ ID NO: 11, and the third sequence has the sequence set forth in SEQ ID NO: 78;
(iv) the first sequence has the sequence set forth in SEQ ID NO: 42, the second sequence has the sequence set forth in SEQ ID NO: 11, and the third sequence has the sequence set forth in SEQ ID NO: 74 and the residue at position 113 of the CH3 domain of the antibody molecule, or fragment thereof is arginine (R);
(v) the first sequence has the sequence set forth in SEQ ID NO: 47, the second sequence has the sequence set forth in SEQ ID NO: 11, and the third sequence has the sequence set forth in SEQ ID NO: 70, wherein the residues at positions 84.1, 85.3, 101 and 113 of the CH3 domain of the antibody molecule, or fragment thereof, are proline (P), threonine (T), alanine (A) and arginine (R), respectively; or
(vi) the first sequence has the sequence set forth in SEQ ID NO: 23, the second sequence has the sequence set forth in SEQ ID NO: 11, and the third sequence has the sequence set forth in SEQ ID NO: 31.

3. The antibody molecule, or fragment thereof according to claim 2, wherein the first sequence has the sequence set forth in SEQ ID NO: 42, the second sequence has the sequence set forth in SEQ ID NO: 11, and the third sequence has the sequence set forth in SEQ ID NO: 43.

4. The antibody molecule, or fragment thereof according to claim 2, wherein the first sequence has the sequence set forth in SEQ ID NO: 47, the second sequence has the sequence set forth in SEQ ID NO: 11, and the third sequence has the sequence set forth in SEQ ID NO: 43.

5. The antibody molecule, or fragment thereof according to claim 2, wherein the first sequence has the sequence set forth in SEQ ID NO: 47, the second sequence has the sequence set forth in SEQ ID NO: 11, and the third sequence has the sequence set forth in SEQ ID NO: 78.

6. The antibody molecule, or fragment thereof according to claim 2, wherein the first sequence has the sequence set forth in SEQ ID NO: 42, the second sequence has the sequence set forth in SEQ ID NO: 11, and the third sequence has the sequence set forth in SEQ ID NO: 74 and the residue at position 113 of the CH3 domain of the antibody molecule, or fragment thereof is arginine (R).

7. The antibody molecule, or fragment thereof according to claim 2, wherein the first sequence has the sequence set forth in SEQ ID NO: 23, the second sequence has the sequence set forth in SEQ ID NO: 11, and the third sequence has the sequence set forth in SEQ ID NO: 31.

8. The antibody molecule, or fragment thereof, according to claim 1, wherein the antibody molecule, or fragment thereof comprises the CH3 domain set forth in SEQ ID NO: 44, 48, 71, 75, 79, or 32.

9. The antibody molecule, or fragment thereof according to claim 1, wherein the antibody molecule, or fragment thereof, further comprises a CH2 domain.

10. The antibody molecule, or fragment thereof according to claim 9, wherein the CH2 domain has the sequence set forth in SEQ ID NO: 5, 6, or 82.

11. The antibody molecule, or fragment thereof according to claim 9, wherein the antibody molecule, or fragment thereof, further comprises an immunoglobulin hinge region, or part thereof, at the N-terminus of the CH2 domain.

12. The antibody molecule, or fragment thereof according to claim 11, wherein the antibody molecule, or fragment thereof, comprises or consists of the sequence set forth in SEQ ID NO: 45, 46, 49, 50, 72, 73, 76, 77, 80, 81, 33, or 34.

13. The antibody molecule, or fragment thereof, according to claim 1, wherein the antibody molecule, or fragment thereof, further comprises a second antigen-binding site, wherein the second antigen-binding site is a CDR-based antigen-binding site.

14. The antibody molecule, or fragment thereof according to claim 13, wherein the CDR-based antigen-binding site binds to a checkpoint inhibitor, costimulatory molecule, or tumour associated antigen.

15. A nucleic acid encoding an antibody molecule, or fragment thereof, according to claim 1.

16. A recombinant host cell comprising the nucleic acid of claim 15.

17. A method of producing an antibody molecule, or fragment thereof, comprising culturing the recombinant host cell of claim 16 under conditions for production of the antibody molecule, or fragment thereof.

18. A pharmaceutical composition comprising an antibody molecule, or fragment thereof, according to claim 1 and a pharmaceutically acceptable excipient.

19. A method of treating cancer, an infectious disease, inflammation, a disease or condition associated with inflammation, or an inflammatory disease in a patient, wherein the method comprises administering to the patient a therapeutically effective amount of an antibody molecule, or fragment thereof, according to claim 1.

20. The antibody molecule, or fragment thereof, according to claim 8, wherein the lysine residue (K) at the immediate C-terminus of the sequence shown in SEQ ID NO: 44, 48, 71, 75, 79, or 32 has been deleted.

21. The antibody molecule, or fragment thereof, according to claim 2, wherein the first sequence has the sequence set forth in SEQ ID NO: 47, the second sequence has the sequence set forth in SEQ ID NO: 11, and the third sequence has the sequence set forth in SEQ ID NO: 70, wherein the residues at positions 84.1, 85.3, 101 and 113 of the CH3 domain of the antibody molecule, or fragment thereof, are proline (P), threonine (T), alanine (A) and arginine (R), respectively.

* * * * *